United States Patent
Mayse et al.

(10) Patent No.: US 12,285,345 B2
(45) Date of Patent: Apr. 29, 2025

(54) ENDOBRONCHIAL IMPLANTS AND RELATED TECHNOLOGY

(71) Applicant: Apreo Health, Inc., Menlo Park, CA (US)

(72) Inventors: Martin L. Mayse, Wayzata, MN (US); Karun D. Naga, Los Altos, CA (US); Hanson S. Gifford, III, Woodside, CA (US); Steven W. Kim, Los Altos, CA (US); Michael Hendricksen, Redwood City, CA (US); Douglas S. Sutton, Pacifica, CA (US); Nifer Beth Goldman, Redwood City, CA (US); Patrick P. Wu, San Carlos, CA (US); Jagannath Padmanabhan, San Carlos, CA (US)

(73) Assignee: Apreo Health, Inc., Menlo Park, CA (US)

( * ) Notice: Subject to any disclaimer, the term of this patent is extended or adjusted under 35 U.S.C. 154(b) by 0 days.

(21) Appl. No.: 18/544,215

(22) Filed: Dec. 18, 2023

(65) Prior Publication Data

US 2024/0139002 A1    May 2, 2024

Related U.S. Application Data

(63) Continuation of application No. PCT/US2022/073962, filed on Jul. 20, 2022.
(Continued)

(51) Int. Cl.
*A61F 2/88* (2006.01)
*A61F 2/04* (2013.01)
(Continued)

(52) U.S. Cl.
CPC .............. *A61F 2/88* (2013.01); *A61F 2/82* (2013.01); *A61F 2/86* (2013.01); *A61F 2002/043* (2013.01); *A61F 2002/825* (2013.01)

(58) Field of Classification Search
CPC ...... A61F 2/82; A61F 2/86; A61F 2/88; A61F 2002/044; A61F 2002/825; A61F 2/04; A61F 2/043
See application file for complete search history.

(56) References Cited

U.S. PATENT DOCUMENTS 4,553,545 A * 11/1985 Maass ................... A61F 2/0105
                                                                267/167
4,886,062 A    12/1989 Wiktor
(Continued)

FOREIGN PATENT DOCUMENTS

AU    2006252347 A1    12/2006
CN       2836753 Y    11/2006
(Continued)

OTHER PUBLICATIONS

AAPM CT Lexicon version 2.0 Mar. 8, 2022; Retrieved from the internet: URL://https://www.aapm.org/pubs/ctprotocols/documents/ctterminologylexicon.pdf [retrieved on Dec. 28, 2023].
(Continued)

*Primary Examiner* — William H Matthews
(74) *Attorney, Agent, or Firm* — Fortem IP LLP

(57) ABSTRACT

An implant in accordance with an embodiment of the present technology includes proximal and distal end portions spaced apart from one another along a longitudinal axis and configured to be deployed at first and second airways, respectively, of a bronchial tree, the second airway being of a greater generation than the first airway. The implant includes a wire extending along a wire path within a tubular region coaxially aligned with the longitudinal axis. The wire includes first and second legs alternatingly disposed along
(Continued)

the wire path and extending distally and proximally, respectively, in a circumferential direction about the longitudinal axis. The implant is configured to transition from a low-profile delivery state to an expanded deployed state at a treatment location and to allow mucociliary clearance from immediately distal to the implant to immediately proximal to the implant while the in deployed at the treatment location.

30 Claims, 52 Drawing Sheets

Related U.S. Application Data

(60) Provisional application No. 63/268,604, filed on Feb. 27, 2022, provisional application No. 63/223,546, filed on Jul. 20, 2021.

(51) Int. Cl.
  A61F 2/82 (2013.01)
  A61F 2/86 (2013.01)

(56) References Cited

U.S. PATENT DOCUMENTS

| | | | |
|---|---|---|---|
| 5,314,472 A | 5/1994 | Fontaine | |
| 5,601,593 A | 2/1997 | Freitag | |
| 5,662,713 A | 9/1997 | Andersen et al. | |
| 6,019,779 A | 2/2000 | Thorud et al. | |
| 6,071,305 A | 6/2000 | Brown et al. | |
| 6,241,718 B1 | 6/2001 | Arless et al. | |
| 6,273,907 B1 | 8/2001 | Laufer | |
| 6,328,689 B1 | 12/2001 | Gonzalez et al. | |
| 6,416,554 B1 | 7/2002 | Alferness et al. | |
| 6,514,290 B1 | 2/2003 | Loomas | |
| 6,527,761 B1 | 3/2003 | Soltesz et al. | |
| 6,575,933 B1 | 6/2003 | Wittenberger et al. | |
| 6,592,594 B2 | 7/2003 | Rimbaugh et al. | |
| 6,599,311 B1 | 7/2003 | Biggs et al. | |
| 6,913,618 B2 | 7/2005 | Denardo et al. | |
| 7,320,697 B2 | 1/2008 | Demond et al. | |
| 7,422,584 B2 | 9/2008 | Loomas et al. | |
| 7,426,929 B2 | 9/2008 | Tanaka | |
| 7,462,162 B2 | 12/2008 | Phan et al. | |
| 7,556,624 B2 | 7/2009 | Laufer et al. | |
| 7,670,373 B1 | 3/2010 | Sabanathan | |
| 8,092,512 B2 | 1/2012 | Rudnick et al. | |
| 8,092,549 B2 | 1/2012 | Hillis et al. | |
| 8,221,491 B1 | 7/2012 | Burmeister et al. | |
| 8,465,551 B1 | 6/2013 | Wijay et al. | |
| 8,801,775 B2 | 8/2014 | Griswold | |
| 8,998,975 B2 | 4/2015 | Rowe | |
| 9,138,336 B2 | 9/2015 | Carman et al. | |
| 9,592,057 B2 | 3/2017 | Perrot et al. | |
| 9,592,138 B1 * | 3/2017 | Mayse | A61F 2/04 |
| 10,159,557 B2 | 12/2018 | Chobotov et al. | |
| 10,182,902 B2 | 1/2019 | Heuser et al. | |
| 10,342,685 B2 | 7/2019 | Bales et al. | |
| 10,463,509 B2 | 11/2019 | Bales et al. | |
| 10,575,973 B2 | 3/2020 | Ta et al. | |
| 10,682,218 B2 | 6/2020 | Mayse | |
| 10,682,222 B2 | 6/2020 | Chobotov et al. | |
| 11,607,303 B2 | 3/2023 | Mayse | |
| 11,759,305 B2 | 9/2023 | Mayse | |
| 2001/0037808 A1 | 11/2001 | Deem et al. | |
| 2002/0042565 A1 | 4/2002 | Cooper et al. | |
| 2003/0024527 A1 | 2/2003 | Ginn | |
| 2005/0056292 A1 | 3/2005 | Cooper | |
| 2005/0096529 A1 | 5/2005 | Cooper et al. | |
| 2006/0074396 A1 | 4/2006 | Stiger | |
| 2006/0106455 A1 | 5/2006 | Furst et al. | |
| 2006/0135947 A1 | 6/2006 | Soltesz et al. | |
| 2007/0073380 A1 | 3/2007 | Vazquez et al. | |
| 2007/0250148 A1 | 10/2007 | Perry et al. | |
| 2008/0132988 A1 | 6/2008 | Jordan | |
| 2008/0195189 A1 | 8/2008 | Asgari | |
| 2009/0182273 A1 | 7/2009 | Johnson | |
| 2010/0122698 A1 | 5/2010 | Shaffer et al. | |
| 2010/0286760 A1 | 11/2010 | Beach et al. | |
| 2011/0040371 A1 | 2/2011 | Hanssen et al. | |
| 2012/0226340 A1 | 9/2012 | Leschinsky | |
| 2012/0316559 A1 | 12/2012 | Mayse et al. | |
| 2013/0103163 A1 | 4/2013 | Krimsky et al. | |
| 2013/0289339 A1 | 10/2013 | Karino | |
| 2014/0105472 A1 | 4/2014 | Yin et al. | |
| 2015/0025629 A1 | 1/2015 | Weber et al. | |
| 2015/0238270 A1 | 8/2015 | Raffy et al. | |
| 2016/0144074 A1 | 5/2016 | Matheny | |
| 2016/0338822 A1 | 11/2016 | Rocha | |
| 2016/0374689 A1 | 12/2016 | Tanaka et al. | |
| 2017/0071765 A1 | 3/2017 | Mayse | |
| 2017/0128186 A1 | 5/2017 | Mayse | |
| 2017/0245977 A1 | 8/2017 | Foster et al. | |
| 2017/0281378 A1 | 10/2017 | Shintaku et al. | |
| 2018/0085240 A1 | 3/2018 | Mower et al. | |
| 2018/0303594 A1 | 10/2018 | Eller et al. | |
| 2019/0224484 A1 | 7/2019 | Pierce et al. | |
| 2020/0315770 A1 | 10/2020 | Dupont et al. | |
| 2021/0049762 A1 | 2/2021 | Mintz et al. | |
| 2021/0077052 A1 | 3/2021 | Radhakrishnan et al. | |
| 2022/0241062 A1 | 8/2022 | Mayse | |
| 2022/0280279 A1 | 9/2022 | Mayse | |
| 2022/0361736 A1 | 11/2022 | Danna et al. | |
| 2022/0387046 A1 | 12/2022 | Mathis et al. | |
| 2023/0000567 A1 | 1/2023 | Flexman et al. | |
| 2023/0075509 A1 | 3/2023 | Mayse | |
| 2023/0200973 A1 | 6/2023 | Mayse | |
| 2023/0233315 A1 | 7/2023 | Mayse | |
| 2023/0363884 A1 | 11/2023 | Mayse | |
| 2024/0180556 A1 | 6/2024 | Fann et al. | |

FOREIGN PATENT DOCUMENTS

| | | |
|---|---|---|
| EP | 1078601 A2 | 2/2001 |
| EP | 3095414 A1 | 11/2016 |
| JP | 2003506132 A | 2/2003 |
| JP | 2011036272 A | 2/2011 |
| WO | 2012103501 A1 | 8/2012 |
| WO | 2012128032 A1 | 9/2012 |
| WO | 2014143898 A1 | 9/2014 |
| WO | 2020081698 A2 | 4/2020 |
| WO | 2020105577 A1 | 5/2020 |
| WO | 2022221691 A1 | 10/2022 |
| WO | 2023004362 A1 | 1/2023 |
| WO | 2024145618 A1 | 7/2024 |
| WO | 2024159054 A2 | 8/2024 |
| WO | 2024159055 A2 | 8/2024 |
| WO | 2024159056 A1 | 8/2024 |

OTHER PUBLICATIONS

International Search Report and Written Opinion mailed Nov. 18, 2022, International Application No. PCT/US2022/073962, 19 pages.
"International Search Report and Written Opinion mailed Dec. 22, 2016, International Application No. PCT/US2016/051512, 9 pages."
Takahashi et al., "Ultraflex Expandable Stents for the Management for Air Leaks", Annals of Thoracic and Cardiovascular Surgery, 2006年02月, vol. 12, No. 1, pp. 50-52, ISSN:1341-1098.
Dotter, Charles T. et al.; Percutaneous Transluminal Treatment of Arteriosclerotic Obstruction; Radiology; vol. 84; Issue 4; Apr. 1965; pp. 631-643.
Jahnke, Thoams; Endovascular Placement of Self-expanding Nitinol Coil Stents for the Treatment of Femoropopliteal Obstructive Disease; JVIR; Mar. 2002; vol. 13; pp. 257-266.
Kozarek, Richard A.; Metallic biliary stents for malignant obstructive jaundice: a review; World J Gastroentero; Oct. 2000; vol. 6; No. 5; 4 pages.
Pan, Chen et al.; Structural Design of Vascular Stents: A Review; Micromachines 2021, 12, 770; 26 pages.

(56) References Cited

OTHER PUBLICATIONS

Stanislawska,, Alicja; Biomaterials and Implants in Cardiac and Vascular Surgery—Review; Advances in Materials Science; vol. 14; No. 3(41); Sep. 2014; 13 pages.
Tanaka, Takehiro et al.; Clinical Results of the Internally Covered Spiral Z Stent for Malignant Esophagogastric Obstruction and the Reduction of Stent Migration; JVIR 2000; vol. 11; No. 6; pp. 771-776.

* cited by examiner

| GENERATION | NAME | LUNG UNIT SUPLIED | DIAMETER | LENGTH (MM) | NUMBER |
|---|---|---|---|---|---|
| 0 | TRACHEA | | 18 | 120 | 1 |
| 1 | MAIN BRONCHUS | LUNG | 14-16# | 20-50# | 2 |
| 2 | LOBAR BRONCHUS | LOBE | 8.0 | 19 | 5 |
| 3 | SEGMENTAL BRONCHUS | SEGMENT | 5.5 | 8 | 18 |
| 4 | SUB SEGMENTAL BRONCHUS | SUB SEGMENT | 4.5 | 13 | 36 |
| 5 | | | 3.5 | 11 | 72 |
| 6 | | | | | 144 |
| 7 | | | | | 288 |
| 8 | | | | | 576 |
| 9 | TERMINAL BRONCHUS | | | | 1152 |
| 10 | BRONCHIOLES | | | | 2304 |
| 11 | | | | | 4608 |
| 12 | | | | | 9216 |
| 13 | | | | | 18432 |
| 14 | LOBULAR BRONCHIOLE | SECONDARY LOBULE | 1.0 | 3 | 36864 |
| 15 | | | | | 73728 |
| 16 | TERMINAL BRONCHIOLE | ACINUS | 0.6 | 1.5 | 147456 |
| 17 | RESPIRATORY BRONCIOLE (PRIMARY) | PRIMARY LOBULE | 0.5 | 1 | 294912 |
| 18 | RESPIRATORY BRONCIOLE (SECONDARY) | | | | 589824 |
| 19 | RESPIRATORY BRONCIOLE (TERTIARY) | | | | 1179648 |
| 20 | ALVEOLAR DUCT (PRIMARY) | | | | 2359296 |
| 21 | ALVEOLAR DUCT (SECONDARY) | | | | 4718592 |
| 22 | ALVEOLAR DUCT (TERTIARY) | | | | 9437184 |
| 23 | ALVEOLAR SACS | ALVEOLUS | 0.4 | 0.5 | 18874368 |

FIG. 4

Normal Acinar

Centriacinar Emphysema

Panacinar Emphysema

Paraseptal Emphysema

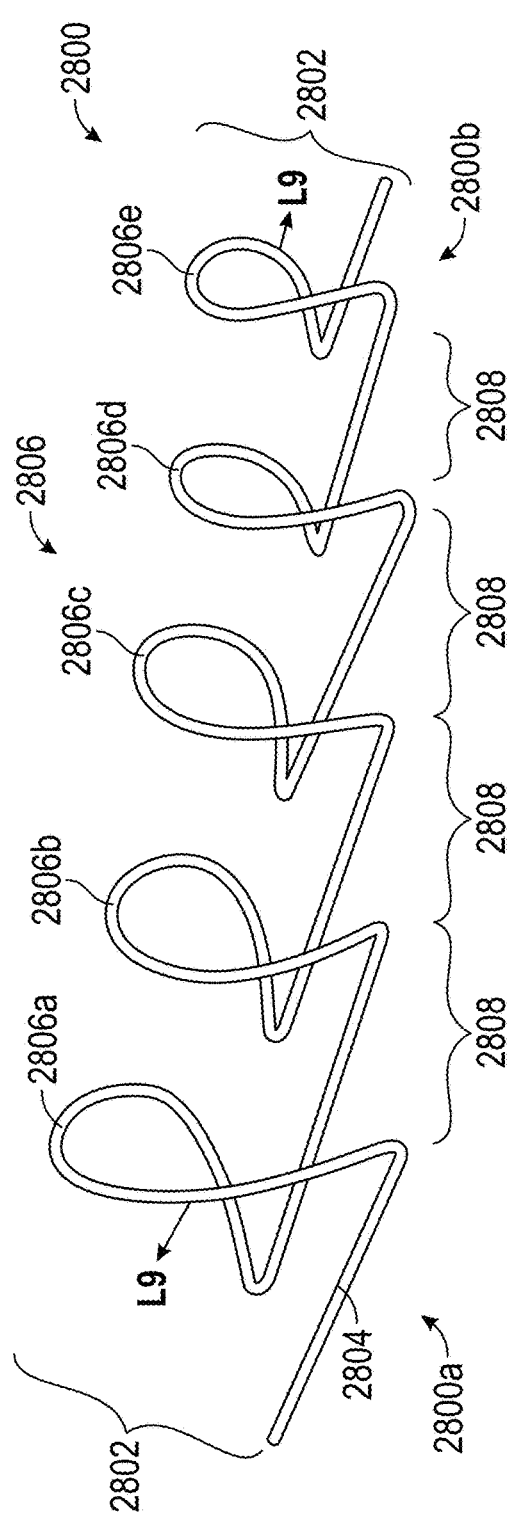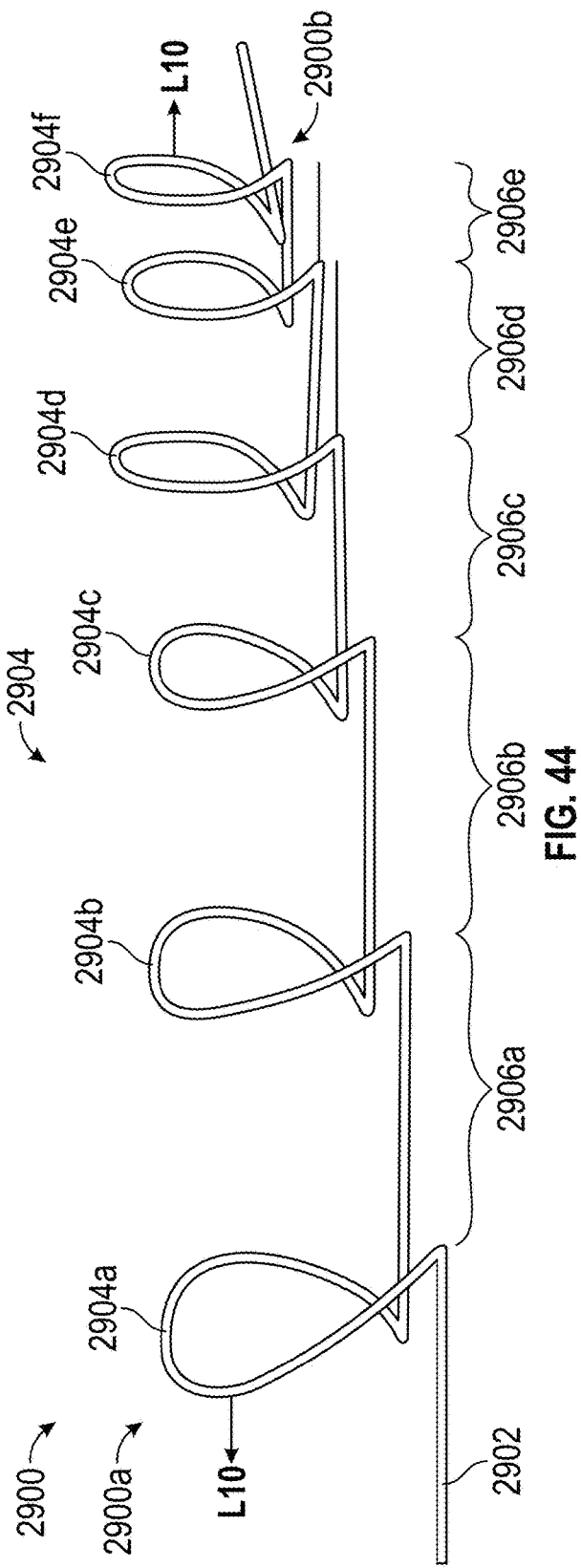

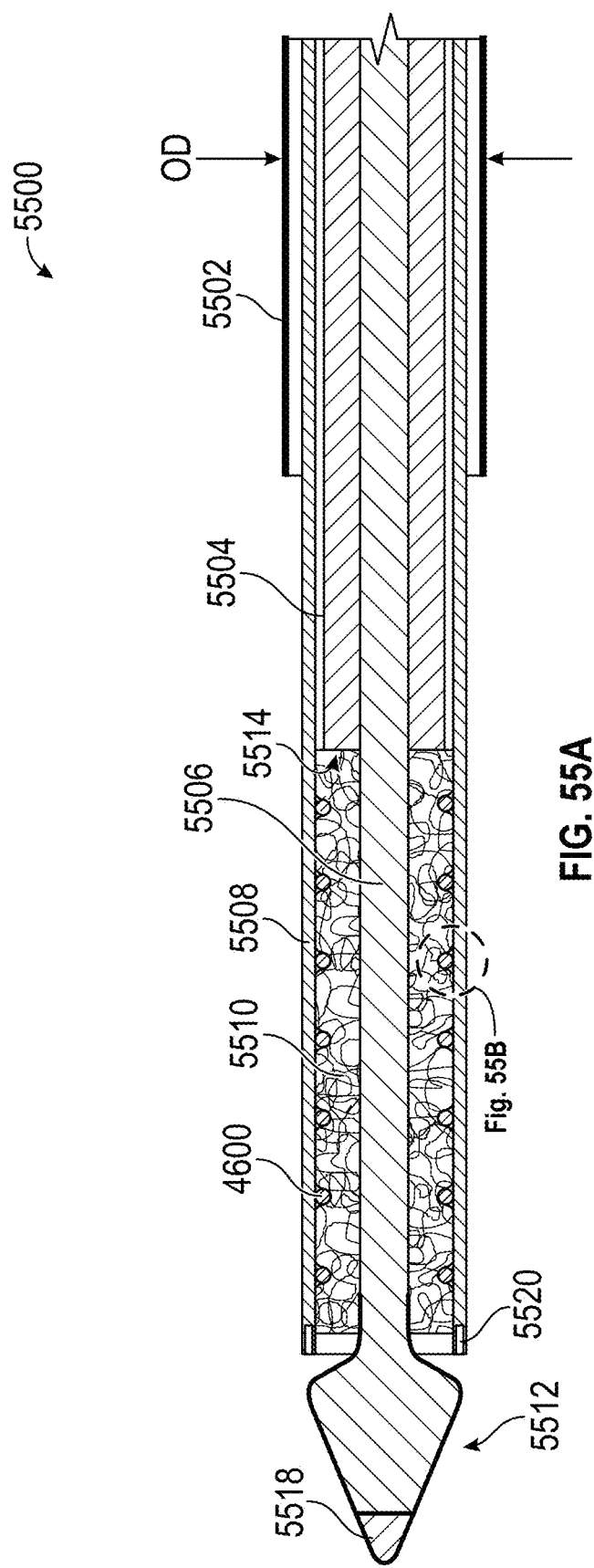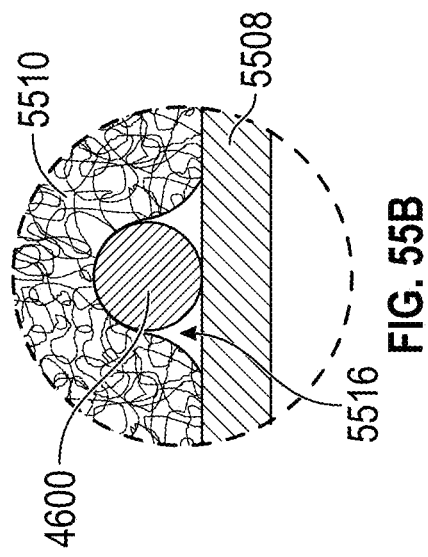
FIG. 55A
FIG. 55B

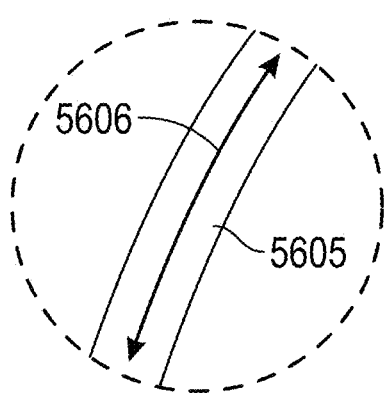
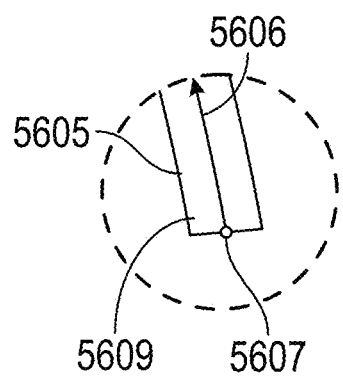
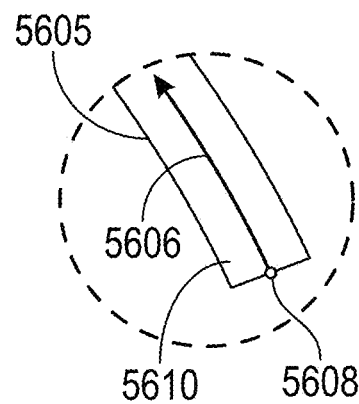
FIG. 56B  FIG. 56C  FIG. 56D
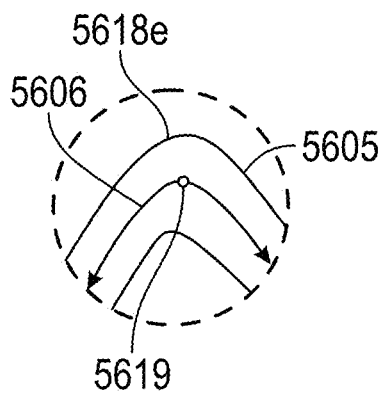
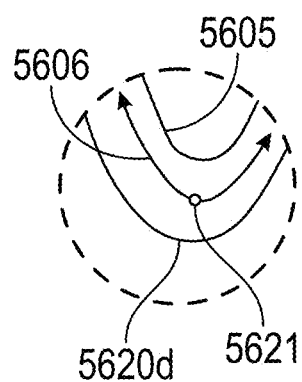
FIG. 56E  FIG. 56F
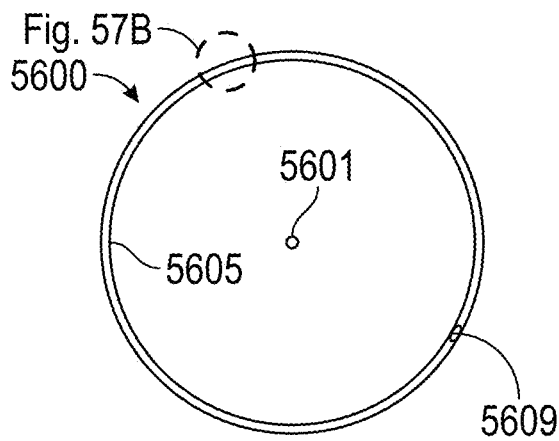
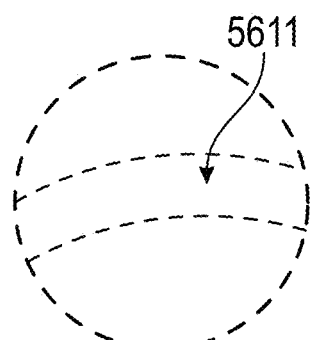
FIG. 57A  FIG. 57B

ENDOBRONCHIAL IMPLANTS AND RELATED TECHNOLOGY

CROSS-REFERENCE TO RELATED APPLICATIONS

This application is a continuation of International Application No. PCT/US2022/073962, filed Jul. 20, 2022, which claims the benefit of priority to U.S. Provisional Patent Application No. 63/223,546, filed Jul. 20, 2021, and U.S. Provisional Patent Application No. 63/268,604, filed Feb. 27, 2022. The foregoing applications are incorporated herein by reference in their entireties.

TECHNICAL FIELD

The present technology relates to implants, such as endobronchial implants for treating chronic obstructive pulmonary disorder.

BACKGROUND

Chronic obstructive pulmonary disorder (COPD) is a disease of impaired lung function. Symptoms of COPD include coughing, wheezing, shortness of breath, and chest tightness. Cigarette smoking is the leading cause of COPD, but long-term exposure to other lung irritants (e.g., air pollution, chemical fumes, dust, etc.) may also cause or contribute to COPD. In most cases, COPD is a progressive disease that worsens over the course of many years. Accordingly, many people have COPD, but are unaware of its progression. COPD is currently a major cause of death and disability in the United States. Severe COPD may prevent a patient from performing even basic activities such as walking, climbing stairs, or bathing. Unfortunately, there is no known cure for COPD. Nor are there known medical techniques capable of reversing the pulmonary damage associated with COPD.

In normal respiration, the act of inhaling draws air into the lungs via the nose or mouth and the trachea. Within each lung, inhaled air moves into a branching network of progressively narrower airways called bronchi, and then into the narrowest airways called bronchioles. The bronchioles end in bunches of tiny round structures called alveoli. Small blood vessels called capillaries run through the walls of the alveoli. When inhaled air reaches the alveoli, oxygen moves from the alveoli into blood in the capillaries. At the same time, carbon dioxide moves in the opposite direction, i.e., from blood in the capillaries into the alveoli. This process is called gas exchange. In a healthy lung, the airways and alveoli are elastic and stretch to accommodate air intake. When a breath is drawn in, the alveoli fill up with air like small balloons. When a breath is expelled, the alveoli deflate. This expansion of the alveoli is an important part of effective gas exchange. Alveoli that are free to expand exchange more gas than alveoli that are inhibited from expanding.

In COPD-affected lung tissue, less air flows through the airways for a variety of reasons. The airways and/or alveoli may be relatively inelastic, the walls between the alveoli may be damaged or destroyed, the walls of the airways may be thick or inflamed, and/or the airways may generate excessive mucus resulting in mucus buildup and airway blockage. In a typical case of COPD, the disease does not equally affect all airways and alveoli in a lung. A lung may have some regions that are significantly more affected than other regions. In severe cases, the airways and alveoli that are unsuitable for effective gas exchange may make up 20 to 30 percent or more of total lung volume.

The effects of COPD are often most pronounced when a patient exercises or engages in other physical exertion that would cause a healthy person to breath heavily. A patient with COPD may not be able to breathe heavily because diseased portions of the patient's lungs trap air, resulting in an inability to exhale completely. This, in turn, inhibits subsequent expansion of healthy lung tissue. Thus, during exercise or other physical exertion, the lungs of a COPD patient may operate in a state of dynamic hyperinflation that impairs respiratory mechanics and increases the work of breathing. Hyperinflation of the lungs may also hinder cardiac filling, lead to dyspnea, and/or reduce a patient's exercise performance. These and/or other detrimental effects of COPD can lead to a cascade of symptoms that eventually impairs a patient's quality of life and increases the risk of severe disability and death.

The term COPD includes both chronic bronchitis and emphysema. About 25% of COPD patients have emphysema. About 40% of these emphysema patients have severe emphysema. Furthermore, it is common for COPD patients to have symptoms of both chronic bronchitis and emphysema. In chronic bronchitis, the lining of the airways is inflamed, generally as a result of ongoing irritation. This inflammation results in thickening of the airway lining and in production of a thick mucus that may coat and eventually congest the airways. Emphysema, in contrast, is primarily a pathological diagnosis concerning abnormal permanent enlargement of air spaces distal to the terminal bronchioles. In emphysematous lung tissue, the small airways and/or alveoli typically have lost their structural integrity and/or their ability to maintain an optimal shape. For example, damage to or destruction of alveolar walls may have resulted in fewer, but larger alveoli. This may significantly impair normal gas exchange. Within the lung, focal or "diseased" regions of emphysematous lung tissue characterized by a lack of discernible alveolar walls may be referred to as pulmonary bullae. These relatively inelastic pockets of dead space are often greater than 1 cm in diameter and do not contribute significantly to gas exchange. Pulmonary bullae tend to retain air and thereby create hyperinflated lung sections that restrict the ability of healthy lung tissue to fully expand upon inhalation. Accordingly, in patients with emphysema, not only does the diseased lung tissue no longer contribute significantly to respiratory function, it impairs the functioning of healthy lung tissue.

Pharmacological treatment is often prescribed for COPD. A treatment algorithm of bronchodilators, B2-agonists, muscarinic agonists, corticosteroids, or combinations thereof may provide short term alleviation of the symptoms of COPD. These treatments, however, do not cure COPD or meaningfully slow the disease progression. Non-pharmaceutical management solutions, such as home oxygen, non-invasive positive pressure ventilation, and pulmonary rehabilitation, are also common but have only modest therapeutic effect. Another treatment option for patients with severe emphysema is lung volume reduction surgery (LVRS). This surgery involves removing poorly functioning portions of a lung (typically up to 20 to 25 percent of lung volume) thereby reducing the overall size of the lung and making more volume within the chest cavity available for expansion of relatively healthy lung tissue. With greater available volume for expansion, the lung tissue remaining after LVRS has an enhanced capacity for effective gas exchange. The obvious drawback of LVRS is its highly invasive nature. Accordingly, LVRS is usually considered to be a last-resort option suitable for only a small percentage of emphysema patients.

Procedures for lung volume reduction without surgical removal of diseased lung tissue also exist. Examples include use coils or clips to seize and physically compact diseased lung tissue. These procedures can reduce the overall volume of a lung for an effect similar to that of LVRS. The potential of these procedures is limited, however, because the proximal positioning of the coils or clips tends to isolate not just diseased portions of the lung, but also healthy portions. Furthermore, these procedures are often associated with serious complications such as pneumothorax and chronic increased risk of respiratory infections.

Another device-based treatment for COPD involves placement of one-directional stent valves in airways proximal to emphysematous tissue. These valves allow air to flow out of but not into overinflated portions of the lung. This approach is only recommended for patients with little to no collateral ventilation (i.e., ventilation of alveoli via pathways that bypass normal airways). Unfortunately, fewer than 20% of patients with emphysema lack collateral ventilation. Accordingly, one-directional stent valves are not suitable for most emphysema patients. Moreover, as with endobronchial coils and clips, the proximal positioning of one-directional stent valves can isolate not just diseased portions of the lung, but also healthy portions.

Bronchoscopic thermal vapor ablation (BTVA) is yet another suboptimal COPD treatment option. BTVA involves introducing heated water vapor into diseased lung tissue. This produces a thermal reaction leading to an initial localized inflammatory response followed by permanent fibrosis and atelectasis. Similar to thermal treatments like BTVA, there are also biochemical treatments that involve injecting glues or sealants into diseased lung tissue. Both thermal and biochemical procedures may precipitate remodeling that results in reduction of tissue and air volume at targeted regions of hyperinflated lung. These procedures, however, are known to cause local toxicity and associated complications that undermine their potential therapeutic benefit.

Although not conventionally used to treat COPD, stents are sometimes used in the lumen of the central airways (i.e., the trachea, main bronchi, lobar bronchi, and/or segmental bronchi) to temporarily improve patency of these airways. For example, stents may be used to temporarily improve patency in a central airway affected by a benign or malignant obstruction. Central airway stenting is not an effective treatment for emphysema because central airways have little or no impact on the overall airway obstruction and/or airway narrowing associated with emphysema. Furthermore, conventional stents, when placed in airways, are plagued by issues of occlusion, including the formation of granulation tissue and mucous impaction.

Some other known COPD treatments involve bypassing an obstructed airway. For example, a perforation through the chest wall into the outer portions of the lung can be used to create a direct communication (i.e., a bypass tract) between diseased alveoli and the outside of the body. If no other steps are taken, these bypass tracts will close by normal healing or by the formation of granulation tissue, thereby eliminating the therapeutic benefit. Placing a tubular prosthetic in the bypass tract can temporarily extend the therapeutic benefit. Such prosthetics, however, eventually induce a foreign body reaction and accelerate the formation of granulation tissue. Moreover, forming bypass tracts tends to be difficult and time intensive. Once formed, bypass tracts can also be uncomfortable, inconvenient, and/or debilitating for the patient.

COPD is a major public health issue. There are over one million patients in the United States alone with severe emphysema and severe hyperinflation. An overwhelming majority of these patients are underserved by currently available treatments. The global unmet clinical need, including in countries with high incidence of respiratory disease due to smoking, is many times greater than in the United States. As discussed above, conventional approaches to treating COPD are associated with serious complications, have limited effectiveness, are only suitable for a small percentage of COPD patients, and/or have other significant disadvantages. Given the prevalence of the disease and the inadequacy of conventional treatments, there is a great need for innovation in this field.

SUMMARY

Certain aspects of the present technology are described in this summary section as Examples numbered (1, 2, 3, etc.) for convenience. These are examples only. They are not intended to limit the present technology.

Example 1: An implant configured to be deployed at a treatment location within a bronchial tree of a human subject, the implant comprising:
  a proximal end portion configured to be deployed at a first airway of the bronchial tree, wherein a generation of the first airway is two or greater;
  a distal end portion spaced apart from the proximal end portion along a longitudinal axis of the implant and configured to be deployed at a second airway of the bronchial tree, wherein a generation of the second airway is greater than the generation of the first airway;
  an intermediate portion between the proximal end portion and the distal end portion along the longitudinal axis; and
  a wire extending along a continuous wire path within a tubular region coaxially aligned with the longitudinal axis, wherein the wire path at the intermediate portion includes at least three complete turns about the longitudinal axis,
  wherein the wire comprises first and second legs alternatingly disposed along the wire path, the first legs extend distally in a circumferential direction about the longitudinal axis, and the second legs extend proximally in the circumferential direction,
  wherein the implant is configured to allow mucociliary clearance from a location immediately distal to the implant to a location immediately proximal to the implant while the implant is deployed at the treatment location, and
  wherein the implant is configured to resiliently transition from a low-profile delivery state in which the implant has a first average diameter perpendicular to the longitudinal axis to an expanded deployed state in which the implant has a second average diameter perpendicular to the longitudinal axis, the second average diameter being at least three times larger than the first average diameter.

Example 2: The implant of claim of any of the preceding or following examples, wherein the intermediate portion consists essentially of the wire.

Example 3: The implant of claim of any of the preceding or following examples, wherein the proximal end portion and the distal end portion consist essentially of the wire.

Example 4: The implant of claim of any of the preceding or following examples, wherein the implant is a single-wire implant.

Example 5: The implant of claim of any of the preceding or following examples, wherein:
the wire path has a first end at the proximal end portion and an opposite second end at the distal end portion;
the wire includes an untethered first terminus at the first end of the wire path; and
the wire includes an untethered second terminus at the second end of the wire path.

Example 6: The implant of claim of any of the preceding or following examples, wherein:
the first terminus is at a proximalmost end of the implant; and
the second terminus is proximal to a distalmost end of the implant.

Example 7: The implant of claim of any of the preceding or following examples, wherein:
the wire includes a first atraumatic tip at the first terminus; and
the wire includes a second atraumatic tip at the second terminus.

Example 8: The implant of claim of any of the preceding or following examples, wherein:
the wire includes a given one of the first legs at the first end of the wire path; and
the wire includes a given one of the second legs at the second end of the wire path.

Example 9: The implant of claim of any of the preceding or following examples, wherein an average length of the first legs at the intermediate portion is different than an average length of the second legs at the intermediate portion.

Example 10: The implant of claim of any of the preceding or following examples, wherein the average length of the first legs at the intermediate portion is greater than the average length of the second legs at the intermediate portion.

Example 11: The implant of claim of any of the preceding or following examples, wherein the average length of the first legs at the intermediate portion is from 20% to 50% greater than the average length of the second legs at the intermediate portion.

Example 12: The implant of claim of any of the preceding or following examples, wherein a ratio of the average length of the first legs at the intermediate portion to the average length of the second legs at the intermediate portion is at least:

$$\frac{n}{n-1}$$

wherein n=an average number of first legs per complete turn of the wire path about the longitudinal axis at the intermediate portion.

Example 13: The implant of claim of any of the preceding or following examples, wherein:
the wire includes first and second apex portions alternatingly disposed along the wire path;
the first apex portions point distally;
the second apex portions point proximally; and
the individual first and second legs are interspersed among the individual first and second apex portions along the wire path.

Example 14: The implant of claim of any of the preceding or following examples, wherein:
the first apex portions at the intermediate portion define a first helix;
the second apex portions at the intermediate portion define a second helix;
the implant defines a helical band between the first and second helixes; and
successive turns of the helical band are spaced apart from one another along the longitudinal axis when the implant is in the deployed state.

Example 15: The implant of claim of any of the preceding or following examples, wherein the successive turns of the helical band are spaced apart from one another along the longitudinal axis when the implant is in the delivery state.

Example 16: The implant of claim of any of the preceding or following examples, wherein the successive turns of the helical band are overlapping when the implant is in the delivery state.

Example 17: The implant of claim of any of the preceding or following examples, wherein an average width of the helical band parallel to the longitudinal axis is within a range from 30% to 75% of an average pitch of the wire path at the intermediate portion when the implant is in the deployed state.

Example 18: The implant of claim of any of the preceding or following examples, wherein the wire occupies from 5% to 30% of a total area of the helical band when the implant is in the deployed state.

Example 19: The implant of claim of any of the preceding or following examples, wherein the wire consists essentially of the first and second legs and the first and second apex portions.

Example 20: The implant of claim of any of the preceding or following examples, wherein an average radius of curvature of the first apex portions and the second apex portions is within a range from 0.35 mm to 0.60 mm.

Example 21: The implant of claim of any of the preceding or following examples, wherein:
a given three of the first apex portions at respective neighboring turns of the wire path at the intermediate portion are within 5 degrees of circumferential alignment with one another; and
a given three of the second apex portions at respective neighboring turns of the wire path at the intermediate portion are within 5 degrees of circumferential alignment with one another.

Example 22: The implant of claim of any of the preceding or following examples, wherein:
the given three of the first apex portions are within 5 degrees of circumferential alignment with one another both when the implant is in the delivery state and when the implant is in the deployed state; and
the given three of the second apex portions are within 5 degrees of circumferential alignment with one another both when the implant is in the delivery state and when the implant is in the deployed state.

Example 23: The implant of claim of any of the preceding or following examples, wherein:
the individual first and second apex portions are at respective apex points along the wire path; and
an average circumferential spacing between successive apex points along the wire path at the intermediate portion is within a range from 35 degrees to 95 degrees.

Example 24: The implant of claim of any of the preceding or following examples, wherein:
the individual first and second apex portions are at respective apex points along the wire path; and an average circumferential spacing between successive apex points along the wire path at the intermediate portion is within a range from 55 degrees to 65 degrees.

Example 25: The implant of claim of any of the preceding or following examples, wherein:
the individual first and second apex portions are at respective apex points along the wire path; and
an average circumferential spacing in degrees between successive apex points along the wire path at the intermediate portion when the implant is in the delivery state is no more than 5% different than when the implant is in the deployed state.

Example 26: The implant of claim of any of the preceding or following examples, wherein:
the individual first apex portions are at respective first apex points along the wire path;
the individual second apex portions are at respective second apex points along the wire path;
a line between a pair of the first apex points neighboring one another along the wire path subtends an angle from an intervening one of the second apex points along the wire path;
the angle is within a range from −20 degrees to 20 degrees when the implant is in the delivery state; and
the angle is within a range from 20 degrees to 90 degrees when the implant is in the deployed state.

Example 27: The implant of claim of any of the preceding or following examples, wherein:
the angle is a first angle;
a line between a pair of the second apex points neighboring one another along the wire path subtends a second angle from an intervening one of the first apex points along the wire path;
the second angle is within a range from −20 degrees to 90 degrees when the implant is in the delivery state; and
the second angle is within a range from 20 degrees to 90 degrees when the implant is in the deployed state.

Example 28: The implant of claim of any of the preceding or following examples, wherein:
the implant is configured to define an unobstructed mucociliary clearance region extending along a continuous mucociliary clearance path from the location immediately distal to the implant to the location immediately proximal to the implant while the implant is deployed at the treatment location; and
an average width of the mucociliary clearance region parallel to the longitudinal axis is at least 10 times greater than an average cross-sectional diameter of the wire perpendicular to the wire path.

Example 29: The implant of claim of any of the preceding or following examples, wherein the implant consists essentially of the wire, and wherein the wire is unbranched throughout the wire path.

Example 30: The implant of claim of any of the preceding or following examples, wherein the wire is untethered throughout the wire path.

Example 31: The implant of claim of any of the preceding or following examples, wherein an average pitch of the wire path at the intermediate portion when the implant is in an unconstrained state is at least 10 times greater than an average cross-sectional diameter of the wire perpendicular to the wire path at the intermediate portion.

Example 32: The implant of claim of any of the preceding or following examples, wherein an average pitch of the wire path at the intermediate portion when the implant is in an unconstrained state is within a range from 50% to 110% of an average diameter of the implant at the intermediate portion perpendicular to the longitudinal axis when the implant is in the unconstrained state.

Example 33: The implant of claim of any of the preceding or following examples, wherein an average pitch of the wire path at the intermediate portion when the implant is in an unconstrained state is greater than an average pitch of the wire path at the distal end portion when the implant is in the unconstrained state.

Example 34: The implant of claim of any of the preceding or following examples, wherein an average pitch of the wire path at the proximal end portion when the implant is in an unconstrained state is greater than an average pitch of the wire path at the distal end portion when the implant is in the unconstrained state.

Example 35: The implant of claim of any of the preceding or following examples, wherein any given plane perpendicular to the longitudinal axis at the intermediate portion intersects at least three circumferentially spaced apart points along the wire path when the implant is in an unconstrained state.

Example 36: The implant of claim of any of the preceding or following examples, wherein any given plane perpendicular to the longitudinal axis at the intermediate portion intersects from three to five circumferentially spaced apart points along the wire path when the implant is in an unconstrained state.

Example 37: The implant of claim of any of the preceding or following examples, wherein:
the wire path has a first end at the proximal end portion and an opposite second end at the distal end portion; and
any given plane perpendicular to a distalmost 5% of a length of the implant along the longitudinal axis intersects at least five circumferentially spaced apart points along the wire path when the implant is in an unconstrained state.

Example 38: The implant of claim of any of the preceding or following examples, wherein:
any given plane perpendicular to a middle 50% of a length of the implant along the longitudinal axis intersects at least a first number of circumferentially spaced apart points along the wire path when the implant is in an unconstrained state;
any given plane perpendicular to a distalmost 5% of the length of the implant along the longitudinal axis intersects at least a second number of circumferentially spaced apart points along the wire path when the implant is in the unconstrained state; and
the second number of circumferentially spaced apart points is greater than the first number of circumferentially spaced apart points.

Example 39: The implant of claim of any of the preceding or following examples, wherein:
the implant has a third average diameter perpendicular to the longitudinal axis when the implant is in an unconstrained state; and
the third average diameter is at least four times larger than the first average diameter.

Example 40: The implant of claim of any of the preceding or following examples, wherein:
the implant has a third average diameter perpendicular to the longitudinal axis when the implant is in an unconstrained state; and
the third average diameter is at least five times larger than the first average diameter.

Example 41: The implant of claim of any of the preceding or following examples, wherein a ratio of a radial spring constant of the implant to a longitudinal spring constant of the implant is within a range from 10:1 to 80:1.

Example 42: The implant of claim of any of the preceding or following examples, wherein a length of the implant along the longitudinal axis when the implant is in an unconstrained state is within a range from 50 mm to 200 mm.

Example 43: The implant of claim of any of the preceding or following examples, wherein a length of the implant along the longitudinal axis when the implant is in an unconstrained state is within a range from 70 mm to 120 mm.

Example 44: The implant of claim of any of the preceding or following examples, wherein an average diameter of the implant perpendicular to the longitudinal axis when the implant is in an unconstrained state is within a range from 5 mm to 15 mm.

Example 45: The implant of claim of any of the preceding or following examples, wherein:
- the implant has a third average diameter perpendicular to the longitudinal axis when the implant is in an unconstrained state; and
- a ratio of the third average diameter to a length of the implant along the longitudinal axis when the implant is in the unconstrained state is within a range from 1:10 to 1:30.

Example 46: The implant of claim of any of the preceding or following examples, wherein:
- the implant has a third average diameter perpendicular to the longitudinal axis when the implant is in an unconstrained state; and
- the third average diameter at the proximal end portion is no more than 10% different than the third average diameter at the distal end portion.

Example 47: The implant of claim of any of the preceding or following examples, wherein:
- the implant has a third average diameter perpendicular to the longitudinal axis when the implant is in an unconstrained state; and
- the third average diameter varies no more than 10% throughout a length of the implant along the longitudinal axis.

Example 48: The implant of claim of any of the preceding or following examples, wherein the wire is uncoated.

Example 49: The implant of claim of any of the preceding or following examples, wherein a ratio of a radial spring constant of the implant in newton-meters to a longitudinal shear modulus of the implant in pascals is within a range from 0.005 to 0.100.

Example 50: The implant of claim of any of the preceding or following examples, wherein a ratio of a longitudinal spring constant of the implant in newton-meters to a longitudinal shear modulus of the implant in pascals is within a range from 0.5 to 5.0.

Example 51: A method for increasing patency at a low-patency or nonpatent treatment location within a bronchial tree of a human subject diagnosed with chronic obstructive pulmonary disorder, the method comprising:
- moving an implant intraluminally within the bronchial tree toward the treatment location while the implant is in a low-profile delivery state, wherein the implant is elongate and has a longitudinal axis, wherein the implant includes springs and connectors interspersed among the springs, and wherein the implant is more resiliently biased at the springs than at the connectors while the implant is in the delivery state;
- transitioning the implant from the delivery state to an expanded deployed state at the treatment location, wherein transitioning the implant includes releasing at least some resilient bias of the implant; and
- maintaining a therapeutically effective increase in patency at the treatment location throughout a continuous maintenance period of at least three months while the implant is in the deployed state at the treatment location.

Example 52: The method of claim of any of the preceding or following examples, wherein:
- the implant in the delivery state while moving within the bronchial tree has a first average diameter perpendicular to the longitudinal axis; and
- the implant in the deployed state during the maintenance period has a second average diameter perpendicular to the longitudinal axis, the second average diameter being at least three times larger than the first average diameter.

Example 53: The method of claim of any of the preceding or following examples, further comprising expanding a wall portion of the bronchial tree coextensive with a length of the implant along the longitudinal axis to an average expanded diameter at least three times larger than an average native diameter of the wall portion.

Example 54: The method of claim of any of the preceding or following examples, wherein:
- transitioning the implant expands a wall portion of the bronchial tree coextensive with a length of the implant along the longitudinal axis to an first average expanded diameter; and
- the method further comprises:
  - expanding a balloon at the treatment location to expand the wall portion and the implant to a second average expanded diameter greater than the first average expanded diameter, and
  - removing the balloon from the treatment location before the continuous maintenance period.

Example 55: The method of claim of any of the preceding or following examples, wherein the second average expanded diameter is greater than an average unconstrained diameter of the implant.

Example 56: The method of claim of any of the preceding or following examples, wherein expanding the wall portion from the first average expanded diameter toward the second average expanded diameter creates and/or enlarges broncho fenestrations in the wall portion.

Example 57: The method of claim of any of the preceding or following examples, wherein maintaining the therapeutically effective increase in patency includes maintaining the therapeutically effective increase in patency without the presence of a drug-eluting material between the connectors and a wall portion of the bronchial tree at the treatment location.

Example 58: The method of claim of any of the preceding or following examples, further comprising:
- expanding a first wall portion of the bronchial tree coextensive with a distalmost 10% of a length of the implant along the longitudinal axis to a first average expanded diameter; and
- expanding a second wall portion of the bronchial tree coextensive with a proximalmost 10% of the length of the implant along the longitudinal axis to a second average expanded diameter, wherein a ratio of the first average expanded diameter to an average native diameter of the first wall portion is greater than a ratio of the second average expanded diameter to an average native diameter of the second wall portion.

Example 59: The method of claim of any of the preceding or following examples, wherein the ratio of the first average expanded diameter to the average native diameter of the first wall portion is at least 8 times greater than the ratio of the second average expanded diameter to the average native diameter of the second wall portion.

Example 60: The method of claim of any of the preceding or following examples, wherein the first average expanded diameter differs from the second average expanded diameter by between 0% and 20%.

Example 61: The method of claim of any of the preceding or following examples, wherein:
during the maintenance period, a first area of a wall portion of the bronchial tree coextensive with a length of the implant along the longitudinal axis is in direct contact with the implant and a second area of the wall portion is out of direct contact with the implant; and
the second area is at least five times larger than the first area.

Example 62: The method of claim of any of the preceding or following examples, wherein the second area is at least eight times larger than the first area.

Example 63: The method of claim of any of the preceding or following examples, further comprising:
expanding the wall portion to an average expanded diameter; and
throughout the maintenance period, maintaining a maximum invagination of the wall portion at the second area of no more than 50% of the average expanded diameter.

Example 64: The method of claim of any of the preceding or following examples, wherein transitioning the implant comprises:
expanding a proximal end portion of the implant at a first airway of the bronchial tree, wherein a generation of the first airway is two or greater; and
expanding a distal end portion of the implant at a second airway of the bronchial tree, wherein a generation of the second airway is greater than the generation of the first airway.

Example 65: The method of claim of any of the preceding or following examples, wherein the generation of the second airway is at least two greater than the generation of the first airway.

Example 66: The method of claim of any of the preceding or following examples, wherein the generation of the second airway is at least three greater than the generation of the first airway.

Example 67: The method of claim of any of the preceding or following examples, wherein the generation of the second airway is at least four greater than the generation of the first airway.

Example 68: The method of claim of any of the preceding or following examples, wherein:
the implant includes a wire extending along a wire path within a tubular region coaxially aligned with the longitudinal axis;
the wire path has a first end at the proximal end portion and an opposite second end at the distal end portion;
expanding the proximal end portion includes contacting a wall of the first airway and an untethered first terminus of the wire; and
expanding the distal end portion includes contacting a wall of the second airway and an untethered second terminus of the wire.

Example 69: The method of claim of any of the preceding or following examples, wherein:
contacting the wall of the first airway and the untethered first terminus of the wire includes contacting the wall of the first airway and the untethered first terminus of the wire at a portion of the wall of the first airway at a proximalmost end of the implant; and
contacting the wall of the second airway and the untethered second terminus of the wire includes contacting the wall of the second airway and the untethered second terminus of the wire at a portion of the wall of the second airway proximal to a distalmost end of the implant.

Example 70: The method of claim of any of the preceding or following examples, wherein:
the wire comprises first and second legs alternatingly disposed along the wire path;
the connectors are at the first and second legs;
the first legs extend distally in a circumferential direction about the longitudinal axis while the implant is in the deployed state at the treatment location;
the second legs extend proximally in the circumferential direction while the implant is in the deployed state at the treatment location;
expanding the proximal end portion includes contacting the wall of the first airway and a given one of the first legs at the first end of the wire path; and
expanding the distal end portion includes contacting a wall of the second airway and a given one of the second legs at the second end of the wire path.

Example 71: The method of claim of any of the preceding or following examples, wherein:
the implant includes a wire extending along a wire path within a tubular region coaxially aligned with the longitudinal axis;
the wire comprises first and second legs alternatingly disposed along the wire path, and apex portions between the first and second legs;
the connectors are at the first and second legs;
the springs are at the apex portions; and
transitioning the implant includes increasing an average degree of curvature of the wire path at the apex portions.

Example 72: The method of claim of any of the preceding or following examples, wherein:
the apex portions include first apex portions that point distally while the implant is in the deployed state at the treatment location and second apex portions that point proximally while the implant is in the deployed state at the treatment location; and
transitioning the implant includes transitioning the implant while a given three of the first apex portions at respective neighboring turns of the wire path remain within 5 degrees of circumferential alignment with one another and while a given three of the second apex portions at the respective neighboring turns of the wire path remain within 5 degrees of circumferential alignment with one another.

Example 73: The method of claim of any of the preceding or following examples, wherein:
the individual apex portions are at respective apex points along the wire path; and
transitioning the implant includes transitioning the implant while an average circumferential spacing between successive apex points along the wire path is within a range from 35 degrees to 95 degrees.

Example 74: The method of claim of any of the preceding or following examples, wherein:
the individual apex portions are at respective apex points along the wire path; and
transitioning the implant includes transitioning the implant while an average circumferential spacing between successive apex points along the wire path is within a range from 55 degrees to 65 degrees.

Example 75: The method of claim of any of the preceding or following examples, wherein:
the individual apex portions are at respective apex points along the wire path; and
transitioning the implant includes transitioning the implant while an average circumferential spacing in degrees between successive apex points along the wire path changes by no more than 5%.

Example 76: The method of claim of any of the preceding or following examples, wherein:
the apex portions include first apex portions that point distally while the implant is in the deployed state at the treatment location and second apex portions that point proximally while the implant is in the deployed state at the treatment location;
the first apex portions define a first helix;
the second apex portions define a second helix;
the implant defines a helical band between the first and second helixes; and
transitioning the implant includes decreasing a width of the helical band parallel to the longitudinal axis while transitioning the implant.

Example 77: The method of claim of any of the preceding or following examples, wherein the wire occupies from 5% to 30% of a total area of the helical band during the maintenance period.

Example 78: The method of claim of any of the preceding or following examples, further comprising maintaining a mucociliary clearance region at the treatment location substantially free of granulation tissue and mucoid impaction throughout the maintenance period, wherein the mucociliary clearance region extends along a continuous mucociliary clearance path from a location immediately distal to the implant to a location immediately proximal to the implant.

Example 79: The method of claim of any of the preceding or following examples, wherein maintaining the mucociliary clearance region includes further maintaining the mucociliary clearance region substantially free of inflammation, inflammatory cells, fibrosis, fibrotic cells, tissue hyperplasia, and tissue necrosis during the maintenance period.

Example 80: The method of claim of any of the preceding or following examples, wherein:
the implant includes a wire extending along a wire path within a tubular region coaxially aligned with the longitudinal axis;
the wire path has a first end at a proximal end portion of the implant and an opposite second end at a distal end portion of the implant; and
transitioning the implant includes transitioning the implant such that no portion of the wire crosses the mucociliary clearance path.

Example 81: The method of claim of any of the preceding or following examples, wherein maintaining the mucociliary clearance region includes maintaining the mucociliary clearance region at an average width parallel to the longitudinal axis at least 10 times greater than an average cross-sectional diameter of the wire perpendicular to the wire path.

Example 82: The method of claim of any of the preceding or following examples, wherein:
the implant in the delivery state while moving within the bronchial tree has a first length; and
the implant in the deployed state immediately after transitioning the implant has a second length no more than 10% different than the first length.

Example 83: The method of claim of any of the preceding or following examples, further comprising, after transitioning the implant, exerting against a wall of the bronchial tree at the treatment location a force per unit area of contact with the implant of at least 0.05 megapascals.

Example 84: The method of claim of any of the preceding or following examples, further comprising, after transitioning the implant, resisting elongation of the implant along the longitudinal axis during a full respiration cycle by the subject with a resisting force less than a force of friction between the implant and a wall of the bronchial tree at the treatment location.

Example 85: The method of claim of any of the preceding or following examples, wherein the bronchial tree distal to the treatment location has collateral ventilation.

Example 86: The method of claim of any of the preceding or following examples, further comprising releasing trapped air within the bronchial tree distal to the treatment location.

Example 87: The method of claim of any of the preceding or following examples, wherein transitioning the implant includes:
expanding a distal end portion of the implant;
expanding an intermediate portion of the implant after expanding the distal end portion, wherein the intermediate portion is proximal to the distal end portion along the longitudinal axis; and
expanding a proximal end portion of the implant after expanding the intermediate portion, wherein the proximal end portion is proximal to the intermediate portion along the longitudinal axis.

Example 88: The method of claim of any of the preceding or following examples, wherein transitioning the implant includes simultaneously increasing contact between the implant and a wall of the bronchial tree at three or more circumferentially spaced apart portions of the wall while expanding the intermediate portion.

Example 89: The method of claim of any of the preceding or following examples, wherein transitioning the implant includes simultaneously increasing contact between the implant and a wall of the bronchial tree at five or more circumferentially spaced apart portions of the wall while expanding the distal end portion.

Example 90: The method of claim of any of the preceding or following examples, wherein transitioning the implant includes:
simultaneously increasing contact between the implant and a wall of the bronchial tree at a first number of circumferentially spaced apart portions of the wall while expanding the intermediate portion; and
simultaneously increasing contact between the implant and the wall at a second number of circumferentially spaced apart portions of the wall while expanding the distal end portion, wherein the second number of circumferentially spaced apart portions of the wall is greater than the first number of circumferentially spaced apart portions of the wall.

Example 91: The method of claim of any of the preceding or following examples, wherein a ratio of an average diameter of the implant perpendicular to the longitudinal axis immediately after transitioning the implant and a length of the implant immediately after transitioning the implant is within a range from 1:10 to 1:30.

Example 92: The method of claim of any of the preceding or following examples, further comprising constraining radial expansion of the implant within a sheath extending around the implant while moving the implant, wherein transitioning the implant includes causing relative movement between the implant and the sheath.

Example 93: The method of claim of any of the preceding or following examples, further comprising constraining longitudinal expansion of the implant via a shaft extending longitudinally through the implant while moving the implant.

Example 94: The method of claim of any of the preceding or following examples, wherein:
constraining longitudinal expansion of the implant includes constraining longitudinal expansion of the implant via a pad of the shaft;
the pad is disposed between the implant and a core of the shaft while moving the implant; and
the pad is more resilient than the core.

Example 95: A method for improving pulmonary function in a human subject, the method comprising:
moving an implant intraluminally within a bronchial tree of the subject toward a treatment location within the bronchial tree while the implant is in a low-profile delivery state, wherein a portion of the bronchial tree distal to the treatment location is emphysematous and has collateral ventilation;
transitioning the implant from the delivery state to an expanded deployed state at the treatment location, wherein transitioning the implant includes expanding expandable structures within a helical band extending around a longitudinal axis of the implant, and wherein expanding the expandable structures increases a helical length of the helical band; and
increasing one-second forced expiratory volume of the subject after deploying the implant relative to before deploying the implant by at least 5%.

Example 96: The method of claim of any of the preceding or following examples, wherein:
the implant is a first implant;
the treatment location is a first treatment location;
the delivery state is a first delivery state;
the deployed state is a first deployed state;
the expandable structures are first expandable structures;
the helical band is a first helical band; and
the method further comprises:
moving a second implant intraluminally within the bronchial tree toward a second treatment location within the bronchial tree while the second implant is in a low-profile second delivery state, wherein a portion of the bronchial tree distal to the second treatment location is emphysematous and has collateral ventilation, and
transitioning the second implant from the second delivery state to an expanded second deployed state at the second treatment location, wherein transitioning the second implant includes expanding second expandable structures within a second helical band extending around a longitudinal axis of the second implant, and wherein expanding the second expandable structures increases a helical length of the second helical band; and
increasing one-second forced expiratory volume of the subject includes increasing one-second forced expiratory volume of the subject after deploying the first and second implants relative to before deploying the first and second implants.

Example 97: The method of claim of any of the preceding or following examples, further comprising:
moving a third implant intraluminally within the bronchial tree toward a third treatment location within the bronchial tree while the third implant is in a low-profile third delivery state, wherein a portion of the bronchial tree distal to the third treatment location is emphysematous and has collateral ventilation; and
transitioning the third implant from the third delivery state to an expanded third deployed state at the third treatment location, wherein transitioning the third implant includes expanding third expandable structures within a third helical band extending around a longitudinal axis of the third implant, and wherein expanding the third expandable structures increases a helical length of the third helical band,
wherein increasing one-second forced expiratory volume of the subject includes increasing one-second forced expiratory volume of the subject after deploying the first, second, and third implants relative to before deploying the first, second, and third implants.

Example 98: The method of claim of any of the preceding or following examples, wherein increasing one-second forced expiratory volume of the subject includes increasing one-second forced expiratory volume of the subject by at least 10%.

Example 99: The method of claim of any of the preceding or following examples, wherein transitioning the implant includes releasing at least some resilient bias on the implant at the expandable structures.

Example 100: The method of claim of any of the preceding or following examples, wherein:
the implant in the delivery state while moving within the bronchial tree has a first average diameter perpendicular to the longitudinal axis; and
the implant in the deployed state after transitioning the implant has a second average diameter perpendicular to the longitudinal axis, the second average diameter being at least three times larger than the first average diameter.

Example 101: The method of claim of any of the preceding or following examples, further comprising expanding a wall portion of the bronchial tree coextensive with a length of the implant along the longitudinal axis to an average expanded diameter at least three times larger than an average native diameter of the wall portion.

Example 102: The method of claim of any of the preceding or following examples, further comprising:
expanding a first wall portion of the bronchial tree coextensive with a distalmost 10% of a length of the implant along the longitudinal axis to a first average expanded diameter; and
expanding a second wall portion of the bronchial tree coextensive with a proximalmost 10% of the length of the implant along the longitudinal axis to a second average expanded diameter, wherein a ratio of the first average expanded diameter to an average native diameter of the first wall portion is greater than a ratio of the second average expanded diameter to an average native diameter of the second wall portion.

Example 103: The method of claim of any of the preceding or following examples, wherein the ratio of the first average expanded diameter to the average native diameter of the first wall portion is at least 8 times greater than the ratio of the second average expanded diameter to the average native diameter of the second wall portion.

Example 104: The method of claim of any of the preceding or following examples, wherein the first average expanded diameter differs from the second average expanded diameter by between 0% and 20%.

Example 105: The method of claim of any of the preceding or following examples, wherein:
  after transitioning the implant, a first area of a wall portion of the bronchial tree coextensive with a length of the implant along the longitudinal axis is in direct contact with the implant and a second area of the wall portion is out of direct contact with the implant; and
  the second area is at least five times larger than the first area.

Example 106: The method of claim of any of the preceding or following examples, wherein the second area is at least eight times larger than the first area.

Example 107: The method of claim of any of the preceding or following examples, wherein transitioning the implant includes:
  expanding a proximal end portion of the implant at a first airway of the bronchial tree, wherein a generation of the first airway is two or greater; and
  expanding a distal end portion of the implant at a second airway of the bronchial tree, wherein a generation of the second airway is greater than the generation of the first airway.

Example 108: The method of claim of any of the preceding or following examples, wherein the generation of the second airway is at least two greater than the generation of the first airway.

Example 109: The method of claim of any of the preceding or following examples, wherein the generation of the second airway is at least three greater than the generation of the first airway.

Example 110: The method of claim of any of the preceding or following examples, wherein:
  the implant includes a wire extending along a wire path within a tubular region coaxially aligned with the longitudinal axis;
  the wire path has a first end at the proximal end portion and an opposite second end at the distal end portion;
  expanding the proximal end portion includes contacting a wall of the first airway and an untethered first terminus of the wire; and
  expanding the distal end portion includes contacting a wall of the second airway and an untethered second terminus of the wire.

Example 111: The method of claim of any of the preceding or following examples, wherein:
  contacting the wall of the first airway and the untethered first terminus of the wire includes contacting the wall of the first airway and the untethered first terminus of the wire at a portion of the wall of the first airway at a proximalmost end of the implant; and
  contacting the wall of the second airway and the untethered second terminus of the wire includes contacting the wall of the second airway and the untethered second terminus of the wire at a portion of the wall of the second airway proximal to a distalmost end of the implant.

Example 112: The method of claim of any of the preceding or following examples, wherein:
  the wire comprises first and second legs alternatingly disposed along the wire path;
  the first legs extend distally in a circumferential direction about the longitudinal axis while the implant is in the deployed state at the treatment location;
  the second legs extend proximally in the circumferential direction while the implant is in the deployed state at the treatment location;
  expanding the proximal end portion includes contacting the wall of the first airway and a given one of the first legs at the first end of the wire path; and
  expanding the distal end portion includes contacting a wall of the second airway and a given one of the second legs at the second end of the wire path.

Example 113: The method of claim of any of the preceding or following examples, wherein:
  the implant includes a wire extending along a wire path within a tubular region coaxially aligned with the longitudinal axis;
  the wire comprises first and second legs alternatingly disposed along the wire path, and apex portions between the first and second legs;
  the expandable structures are at the apex portions; and
  transitioning the implant includes increasing an average degree of curvature of the wire path at the apex portions.

Example 114: The method of claim of any of the preceding or following examples, wherein:
  the apex portions include first apex portions that point distally while the implant is in the deployed state at the treatment location and second apex portions that point proximally while the implant is in the deployed state at the treatment location; and
  transitioning the implant includes transitioning the implant while a given three of the first apex portions at respective neighboring turns of the wire path remain within 5 degrees of circumferential alignment with one another and while a given three of the second apex portions at the respective neighboring turns of the wire path remain within 5 degrees of circumferential alignment with one another.

Example 115: The method of claim of any of the preceding or following examples, wherein:
  the individual apex portions are at respective apex points along the wire path; and
  transitioning the implant includes transitioning the implant while an average circumferential spacing between successive apex points along the wire path is within a range from 35 degrees to 95 degrees.

Example 116: The method of claim of any of the preceding or following examples, wherein:
  the individual apex portions are at respective apex points along the wire path; and
  transitioning the implant includes transitioning the implant while an average circumferential spacing between successive apex points along the wire path is within a range from 55 degrees to 65 degrees.

Example 117: The method of claim of any of the preceding or following examples, wherein:
  the individual apex portions are at respective apex points along the wire path; and
  transitioning the implant includes transitioning the implant while an average circumferential spacing in degrees between successive apex points along the wire path changes by no more than 5%.

Example 118: The method of claim of any of the preceding or following examples, wherein:
  the apex portions include first apex portions that point distally while the implant is in the deployed state at the treatment location and second apex portions that point proximally while the implant is in the deployed state at the treatment location;

the first apex portions define a first helix;
the second apex portions define a second helix;
the first and second helixes define the helical band; and
transitioning the implant includes decreasing a width of the helical band parallel to the longitudinal axis while transitioning the implant.

Example 119: The method of claim of any of the preceding or following examples, wherein the wire occupies from 5% to 15% of a total area of the helical band after transitioning the implant.

Example 120: The method of claim of any of the preceding or following examples, further comprising maintaining a mucociliary clearance region at the treatment location substantially free of granulation tissue and mucoid impaction throughout a continuous maintenance period of at least three months while the implant is in the deployed state at the treatment location, wherein the mucociliary clearance region extends along a continuous mucociliary clearance path from a location immediately distal to the implant to a location immediately proximal to the implant.

Example 121: The method of claim of any of the preceding or following examples, wherein maintaining the mucociliary clearance region includes further maintaining the mucociliary clearance region substantially free of inflammation, inflammatory cells, fibrosis, fibrotic cells, tissue hyperplasia, and tissue necrosis during the maintenance period.

Example 122: The method of claim of any of the preceding or following examples, wherein:
the implant includes a wire extending along a wire path within a tubular region coaxially aligned with the longitudinal axis;
the wire path has a first end at a proximal end portion of the implant and an opposite second end at a distal end portion of the implant; and
transitioning the implant includes transitioning the implant such that no portion of the wire crosses the mucociliary clearance path.

Example 123: The method of claim of any of the preceding or following examples wherein maintaining the mucociliary clearance region includes maintaining the mucociliary clearance region at an average width parallel to the longitudinal axis at least 10 times greater than an average cross-sectional diameter of the wire perpendicular to the wire path.

Example 124: The method of claim of any of the preceding or following examples, wherein maintaining the mucociliary clearance region includes maintaining the mucociliary clearance region without the presence of a drug-eluting material between the expandable structures and a wall portion of the bronchial tree at the treatment location.

Example 125: The method of claim of any of the preceding or following examples, wherein:
the implant in the delivery state while moving within the bronchial tree has a first length; and
the implant in the deployed state immediately after transitioning the implant has a second length no more than 10% different than the first length.

Example 126: The method of claim of any of the preceding or following examples, further comprising, after transitioning the implant, exerting against a wall of the bronchial tree at the treatment location a force per unit area of contact with the implant of at least 0.05 megapascals.

Example 127: The method of claim of any of the preceding or following examples, further comprising, after transitioning the implant, resisting elongation of the implant along the longitudinal axis during a full respiration cycle by the subject with a resisting force less than a force of friction between the implant and a wall of the bronchial tree at the treatment location.

Example 128: The method of claim of any of the preceding or following examples, further comprising releasing trapped air within the portion of the bronchial tree distal to the treatment location.

Example 129: The method of claim of any of the preceding or following examples, wherein transitioning the implant includes:
expanding a distal end portion of the implant;
expanding an intermediate portion of the implant after expanding the distal end portion, wherein the intermediate portion is proximal to the distal end portion along the longitudinal axis; and
expanding a proximal end portion of the implant after expanding the intermediate portion, wherein the proximal end portion is proximal to the intermediate portion along the longitudinal axis.

Example 130: The method of claim of any of the preceding or following examples, wherein transitioning the implant includes simultaneously increasing contact between the implant and a wall of the bronchial tree at three or more circumferentially spaced apart portions of the wall while expanding the intermediate portion.

Example 131: The method of claim of any of the preceding or following examples, wherein transitioning the implant includes simultaneously increasing contact between the implant and a wall of the bronchial tree at five or more circumferentially spaced apart portions of the wall while expanding the distal end portion.

Example 132: The method of claim of any of the preceding or following examples, wherein transitioning the implant includes:
simultaneously increasing contact between the implant and a wall of the bronchial tree at a first number of circumferentially spaced apart portions of the wall while expanding the intermediate portion; and
simultaneously increasing contact between the implant and the wall at a second number of circumferentially spaced apart portions of the wall greater than the first number of circumferentially spaced apart portions of the wall while expanding the intermediate portion.

Example 133: The method of claim of any of the preceding or following examples, wherein a ratio of an average diameter of the implant perpendicular to the longitudinal axis immediately after transitioning the implant and a length of the implant immediately after transitioning the implant is within a range from 1:10 to 1:30.

Example 134: The method of claim of any of the preceding or following examples, further comprising constraining radial expansion of the implant within a sheath extending around the implant while moving the implant, wherein transitioning the implant includes causing relative movement between the implant and the sheath.

Example 135: The method of claim of any of the preceding or following examples, further comprising constraining longitudinal expansion of the implant via a shaft extending longitudinally through the implant while moving the implant.

Example 136: The method of claim of any of the preceding or following examples, wherein:
constraining longitudinal expansion of the implant includes constraining longitudinal expansion of the implant via a pad of the shaft;
the pad is disposed between the implant and a core of the shaft while moving the implant; and the pad is more resilient than the core.

Example 137: The method of claim of any of the preceding or following examples, wherein:
transitioning the implant expands a wall portion of the bronchial tree coextensive with a length of the implant along the longitudinal axis to an first average expanded diameter; and
the method further comprises:
expanding a balloon at the treatment location to expand the wall portion and the implant to a second average expanded diameter greater than the first average expanded diameter, and
removing the balloon from the treatment location.

Example 138: The method of claim of any of the preceding or following examples, wherein the second average expanded diameter is greater than an average unconstrained diameter of the implant.

Example 139: The method of claim of any of the preceding or following examples, wherein expanding the wall portion from the first average expanded diameter toward the second average expanded diameter creates and/or enlarges broncho fenestrations in the wall portion.

Example 140: An implant configured to be deployed at a treatment location within a bronchial tree of a human subject, the implant comprising:
expanding means for expanding the implant from a low-profile delivery state to an expanded deployed state at the treatment location; and
stabilizing means for stabilizing the implant in the deployed state at the treatment location during respiration by the subject.

Example 141: The implant of claim of any of the preceding or following examples, further comprising placing means for increasing placement accuracy of a distal end portion of the implant during deployment of the implant at the treatment location.

Example 142: The implant of claim of any of the preceding or following examples, further comprising retrieving means for retrieving the implant after deployment of the implant at the treatment location.

Example 143: A system for deploying an implant at a treatment location within a bronchial tree of a human subject, the system comprising:
an implant configured to be deployed at the treatment location;
radial constraining means for constraining radial expansion of the implant while the implant moves intraluminally within the bronchial tree toward the treatment location; and
longitudinal constraining means for constraining longitudinal expansion of the implant while the implant moves intraluminally within the bronchial tree toward the treatment location.

Example 144: An implantable device for placement in a bronchial airway lumen for treatment of an obstructive pulmonary disease, the implantable device comprising:
a first end portion, a second end portion, and a longitudinal axis extending therebetween, wherein the first end portion is configured to be positioned in a distal region of the bronchial airway and the second end portion is configured to be positioned in a proximal region of the bronchial airway, the distal region comprising a greater generation than the proximal region,
wherein the device comprises an elongated member comprising a resilient material and wound about the longitudinal axis of the device in a series of contiguous loops, each of the loops comprising a plurality of peaks and a plurality of valleys, and wherein the device comprises a continuous opening extending between the loops from the first end portion to the second end portion, and
wherein the implantable device has a compressed state and an expanded state and is configured to be delivered in the compressed state through a catheter to the bronchial airway lumen at the distal region and allowed to self-expand into apposition with an inner surface of a wall at the bronchial airway lumen, thereby pressing radially outwardly on the wall and dilating the distal region to a diameter that is no less than two times a diameter of the bronchial airway lumen at the distal region prior to expansion of the device.

Example 145: An implant configured to be deployed at a treatment location within a body lumen of a human subject, the implant comprising:
a proximal end portion configured to be deployed at a proximal location in the body lumen;
a distal end portion spaced apart from the proximal end portion along a longitudinal axis of the implant and configured to be deployed at a distal location in the body lumen;
an intermediate portion between the proximal end portion and the distal end portion along the longitudinal axis; and
a wire extending along a continuous wire path within a tubular region coaxially aligned with the longitudinal axis, wherein the wire path at the intermediate portion includes at least three complete turns about the longitudinal axis,
wherein the wire comprises first and second legs alternatingly disposed along the wire path, the first legs extend distally in a circumferential direction about the longitudinal axis, and the second legs extend proximally in the circumferential direction,
wherein the wire path further comprises a series of contiguous loops, each of the loops comprising a plurality of peaks and a plurality of valleys, and a continuous opening extending between the loops from the proximal end portion to the distal end portion, and
wherein the implant is configured to resiliently transition from a low-profile delivery state in which the implant has a first average diameter perpendicular to the longitudinal axis to an expanded deployed state in which the implant has a second average diameter perpendicular to the longitudinal axis, the second average diameter being at least three times larger than the first average diameter.

Example 146: The implant of claim of any of the preceding or following examples, wherein the implant is configured for placement in a bronchial airway of the human subject for the treatment of emphysema.

Example 147: The implant of claim of any of the preceding or following examples, wherein the implant is configured for placement in a central airway of the human subject for the treatment of tracheobronchomalacia (TBM).

Example 148: The implant of claim of any of the preceding or following examples, wherein the implant is configured for placement in a urethra of the human subject for the treatment of benign prostatic hyperplasia (BPH).

Example 149: The implant of claim of any of the preceding or following examples, wherein the implant is configured to maintain a at least a portion of the treatment location substantially free of granulation tissue, mucoid impaction, inflammation, inflammatory cells, fibrosis, fibrotic cells, tissue hyperplasia, and tissue necrosis.

BRIEF DESCRIPTION OF THE DRAWINGS

Many aspects of the present technology can be better understood with reference to the following drawings. The relative dimensions in the drawings may be to scale with respect to some embodiments of the present technology. With respect to other embodiments, the drawings may not be to scale. The drawings may also be enlarged arbitrarily. For clarity, reference-number labels for analogous components or features may be omitted when the appropriate reference-number labels for such analogous components or features are clear in the context of the specification and all of the drawings considered together. Furthermore, the same reference numbers may be used to identify analogous components or features in multiple described embodiments.

FIG. 4 is a table showing examples of dimensions and generation numbers of different portions of a bronchial tree of a human subject.

FIGS. 42-46 are perspective views of respective implants in accordance with at least some embodiments of the present technology.

FIG. 47 is a side view of a bend of the implant shown in FIG. 46.

FIG. 55A is a cross-sectional view of a delivery system in accordance with at least some embodiments of the present technology.

FIG. 55B is a callout corresponding to FIG. 55A.

FIGS. 56B-56F are callouts corresponding to FIG. 56A.

FIG. 57A is an end view of the implant shown in FIG. 56A in the unconstrained state.

FIG. 57B is a callout corresponding to FIG. 57A.

FIG. 65 is a profile view of the implant shown in FIG. 63 in a deployed state within an airway region.

DETAILED DESCRIPTION

Figure 1:
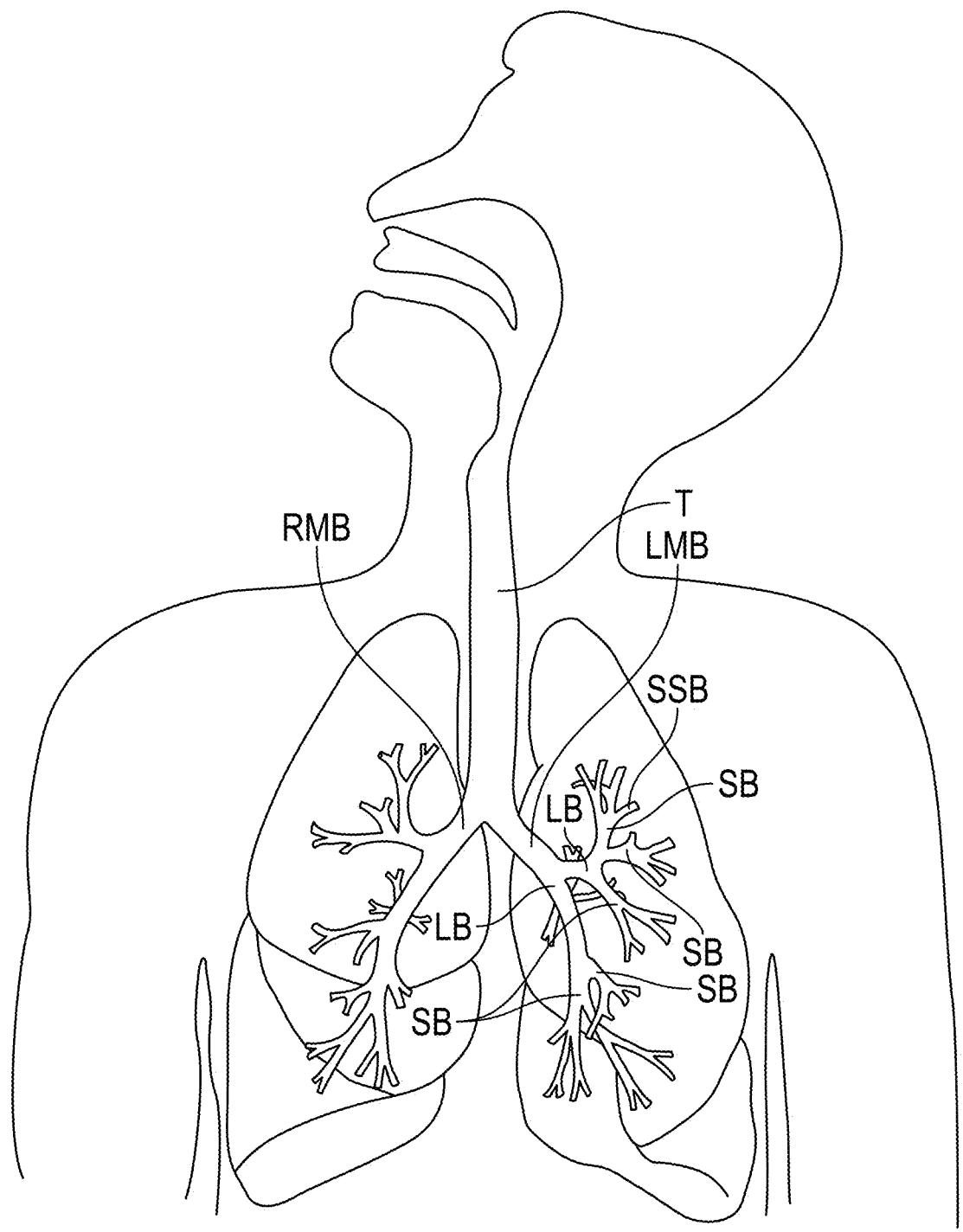
FIG. 1 is a schematic illustration of a bronchial tree of a human subject within a chest cavity of the subject.

As discussed above, existing approaches to treating COPD are either highly invasive (e.g., lung volume reduction surgery), ineffective for most patients (e.g., one-directional stent valves), have an undue impact on gas exchange by healthy lung tissue (e.g., endobronchial coils and clips), carry a high risk of complications (e.g., bronchoscopic thermal vapor ablation), have poor long-term efficacy (e.g., bypass tract prosthetics), and/or suffer from one or more other major limitations. Overcoming these limitations is a significant technical challenge. As discussed in detail below, the inventors have developed new approaches to treating COPD that address at least some of the deficiencies of conventional approaches. In at least some cases, these new approaches are surprisingly effective at establishing and maintaining airway patency. Moreover, this is expected to be the case both in emphysema patients without collateral ventilation and in emphysema patients with collateral ventilation. Approaches to treating COPD in accordance with at least some embodiments of the present technology include the use of innovative endobronchial implants. Aside from the potential clinical benefits, these implants may have better deliverability, retrievability, and/or safety characteristics relative to conventional devices. Given the prevalence and severity of COPD, the innovative endobronchial implants and other aspects of the treatment of COPD in accordance with various embodiments of the present technology have great potential to have a meaningful positive impact on worldwide public health.

At least some embodiments of the present technology are directed to establishing and maintaining patency in obstructed and/or narrowed portions of one or more airways of a lung. This can have a therapeutic benefit for patients diagnosed with COPD, including patients diagnosed with emphysema and/or chronic bronchitis. At least some of this therapeutic benefit may be associated with facilitating the release of air from hyperinflated and/or diseased lung portions along with a corresponding increase in intrathoracic volume available for gas exchange by other lung portions. Implants in accordance with at least some embodiments of the present technology are configured to be intraluminally positioned within an airway and expanded against the airway wall, thereby distending and/or dilating the airway and increasing the cross-sectional area of the airway lumen. In at least some cases, the implants are configured to enlarge the airway beyond its normal size.

In at least some cases, implants in accordance with embodiments of the present technology are configured to have relatively little (e.g., minimal) surface contact with an airway wall and/or to maintain stable contact with an airway wall during respiration. These and other features disclosed herein may reduce or eliminate the gradual airway occlusion by biological processes (e.g., inflammation, fibrosis, granulation, mucous impaction, etc.) that would otherwise limit the effectiveness of implants for the treatment of COPD. An overview of the relevant anatomy and physiology of the lungs as well as additional details regarding implants in accordance with embodiments of the present technology are discussed below.

Many specific details of devices, systems, and methods in accordance with various embodiments of the present technology are disclosed herein. Although these devices, systems, and methods may be disclosed primarily or entirely in the context of treating COPD (sometimes emphysema in particular) other contexts in addition to those disclosed herein are within the scope of the present technology. For example, suitable features of described devices, systems, and methods can be implemented in the context of treating tracheobronchomalacia (TBM) or benign prostatic hyperplasia (BPH) among other examples. Furthermore, it should understood in general that other devices, systems, and methods in addition to those disclosed herein are within the scope of the present technology. For example, devices, systems, and methods in accordance with embodiments of the present technology can have different and/or additional configurations, components, and procedures than those disclosed herein. Moreover, a person of ordinary skill in the art will understand that devices, systems, and methods in accordance with embodiments of the present technology can be without one or more of the configurations, components, and/or procedures disclosed herein without deviating from the present technology.

Anatomy and Physiology

Figure 2:
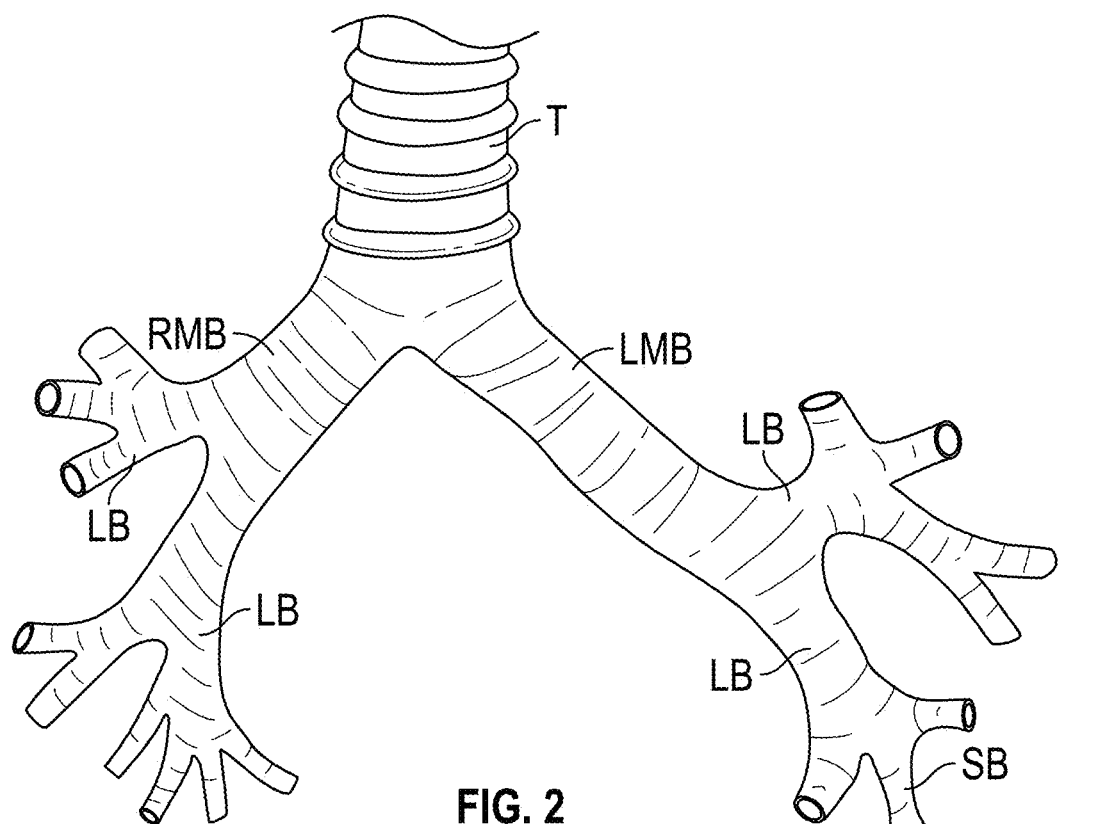
FIG. 2 is a schematic illustration of a bronchial tree of a human subject in isolation.
Figure 3:
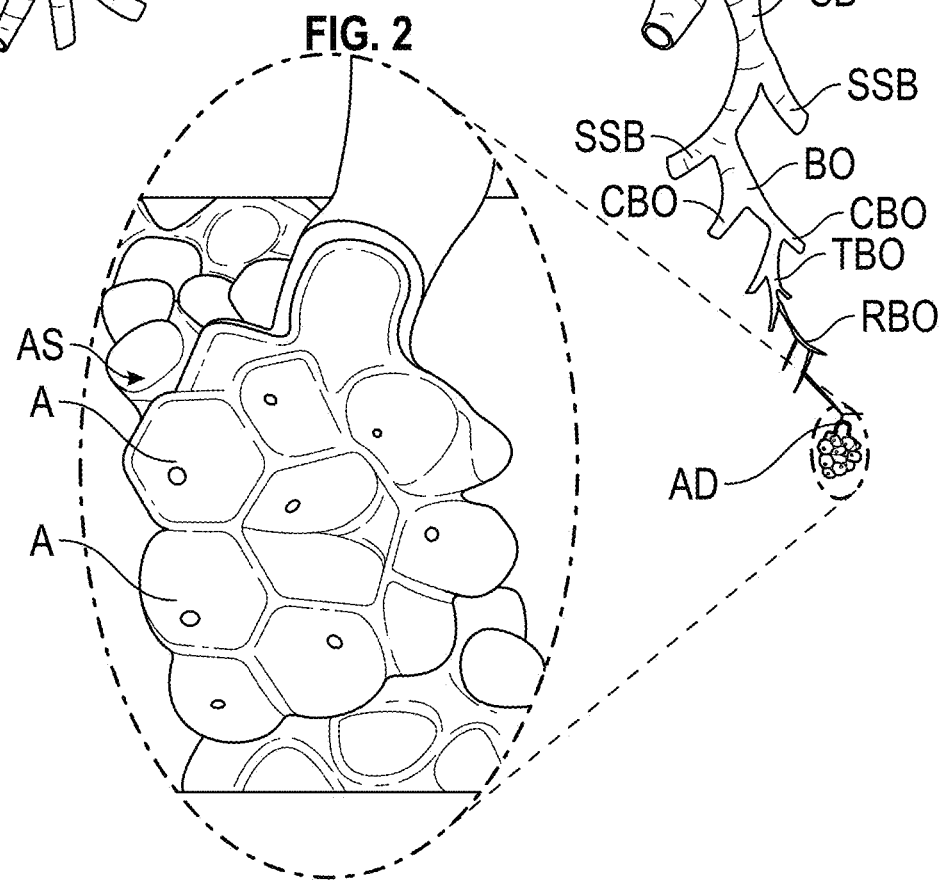
FIG. 3 is an enlarged view of a terminal portion of the bronchial tree shown in FIG. 2.

FIG. 1 is a schematic illustration of a bronchial tree of a human subject within a chest cavity of the subject. As shown in FIG. 1, the bronchial tree includes a trachea T that extends downwardly from the nose and mouth and divides into a left main bronchus LMB and a right main bronchus RMB. The left main bronchus and the right main bronchus each branch to form lobar bronchi LB, segmental bronchi SB, and sub-segmental bronchi SSB, which have successively smaller diameters and shorter lengths as they extend distally. FIG. 2 is a schematic illustration of the bronchial tree in isolation. As shown in FIG. 2, the sub-segmental bronchi continue to branch to form bronchioles BO, conducting bronchioles CBO, and finally terminal bronchioles TBO, which are the smallest airways that do not contain alveoli. The terminal bronchioles branch into respiratory bronchioles RBO, which divide into alveolar ducts AD. FIG. 3 is an enlarged view of a terminal portion of the bronchial tree. As shown in FIG. 3, the alveolar ducts terminate in a blind outpouching including two or more small clusters of alveoli A called alveolar sacs AS. Various singular alveoli can be disposed along the length of a respiratory bronchiole as well.

Bronchi and bronchioles are conducting airways that convey air to and from the alveoli. They do not take part in gas exchange. Rather, gas exchange takes place in the alveoli that are found distal to the conducting airways, starting at the respiratory bronchioles. It is common to refer to the various airways of the bronchial tree as "generations" depending on the extent of branching proximal to the airways. For example, the trachea is referred to as "generation 0" of the bronchial tree, various levels of bronchi, including the left and right main bronchi, are referred to as "generation 1," the lobar bronchi are referred to as "generation 2," and the segmental bronchi are referred to as "generation 3." Further, it is common to refer to any of the airways extending from the trachea to the terminal bronchioles as "conducting airways." FIG. 4 is a table indicating examples of dimensions and generation numbers of different portions of the bronchial tree.

The respiratory bronchioles, alveoli, and alveolar sacs receive air via more proximal portions of the bronchial tree and participate in gas exchange to oxygenate blood routed to the lungs from the heart via the pulmonary artery, branching blood vessels, and capillaries. Thin, semi-permeable membranes separate oxygen-depleted blood in the capillaries from oxygen-rich air in the alveoli. The capillaries wrap around and extend between the alveoli. Oxygen from the air diffuses through the membranes into the blood. Carbon dioxide from the blood diffuses through the membranes to the air in the alveoli. The newly oxygen-enriched blood then flows from the alveolar capillaries through the branching blood vessels of the pulmonary venous system to the heart. The heart pumps the oxygen-rich blood throughout the body. The oxygen-depleted air in the lungs is exhaled when the diaphragm and intercostal muscles relax and the lungs and chest wall elastically return to their normal relaxed states. In this manner, air flows through the branching bronchioles, segmental bronchi, lobar bronchi, main bronchi, and trachea, and is ultimately expelled through the mouth and nose.

Figure 5:
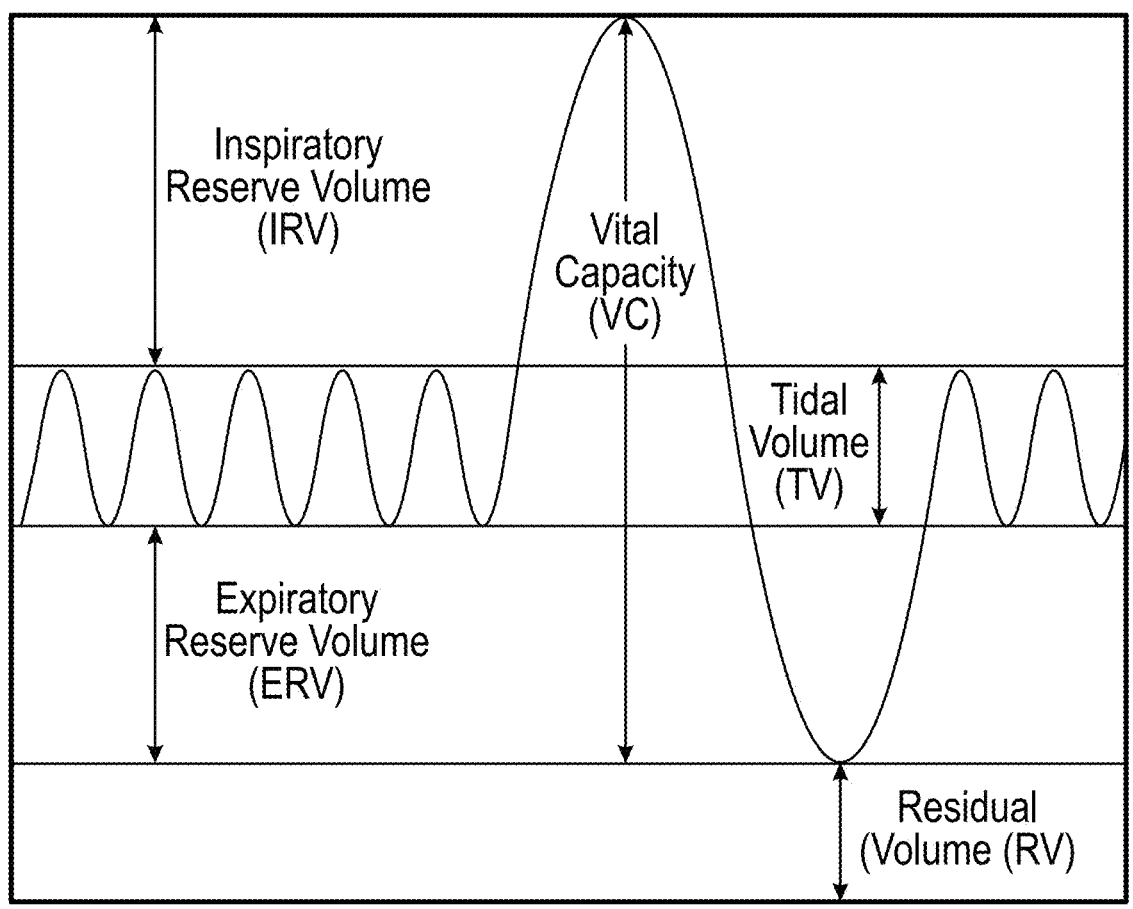
FIG. 5 is a diagram showing lung volumes during normal lung function.

FIG. 5 is a diagram showing lung volumes during normal lung function. Approximately one-tenth of the total lung capacity is used at rest. Greater amounts are used as needed (e.g., with exercise). Tidal Volume (TV) is the volume of air breathed in and out without conscious effort. The additional volume of air that can be exhaled with maximum effort after a normal inspiration is Inspiratory Reserve Volume (IRV). The additional volume of air that can be forcibly exhaled after normal exhalation is Expiratory Reserve Volume (ERV). The total volume of air that can be exhaled after a maximum inhalation is Vital Capacity (VC). VC equals the sum of the TV, IRV, and ERV. Residual Volume (RV) is the volume of air remaining in the lungs after maximum exhalation. The lungs can never be completely emptied. The Total Lung Capacity (TLC) is the sum of the VC and RV. Evaluation of lung function may be used to determine a patient's eligibility for therapy, as well as to evaluate a therapy's effectiveness.

Figure 6:
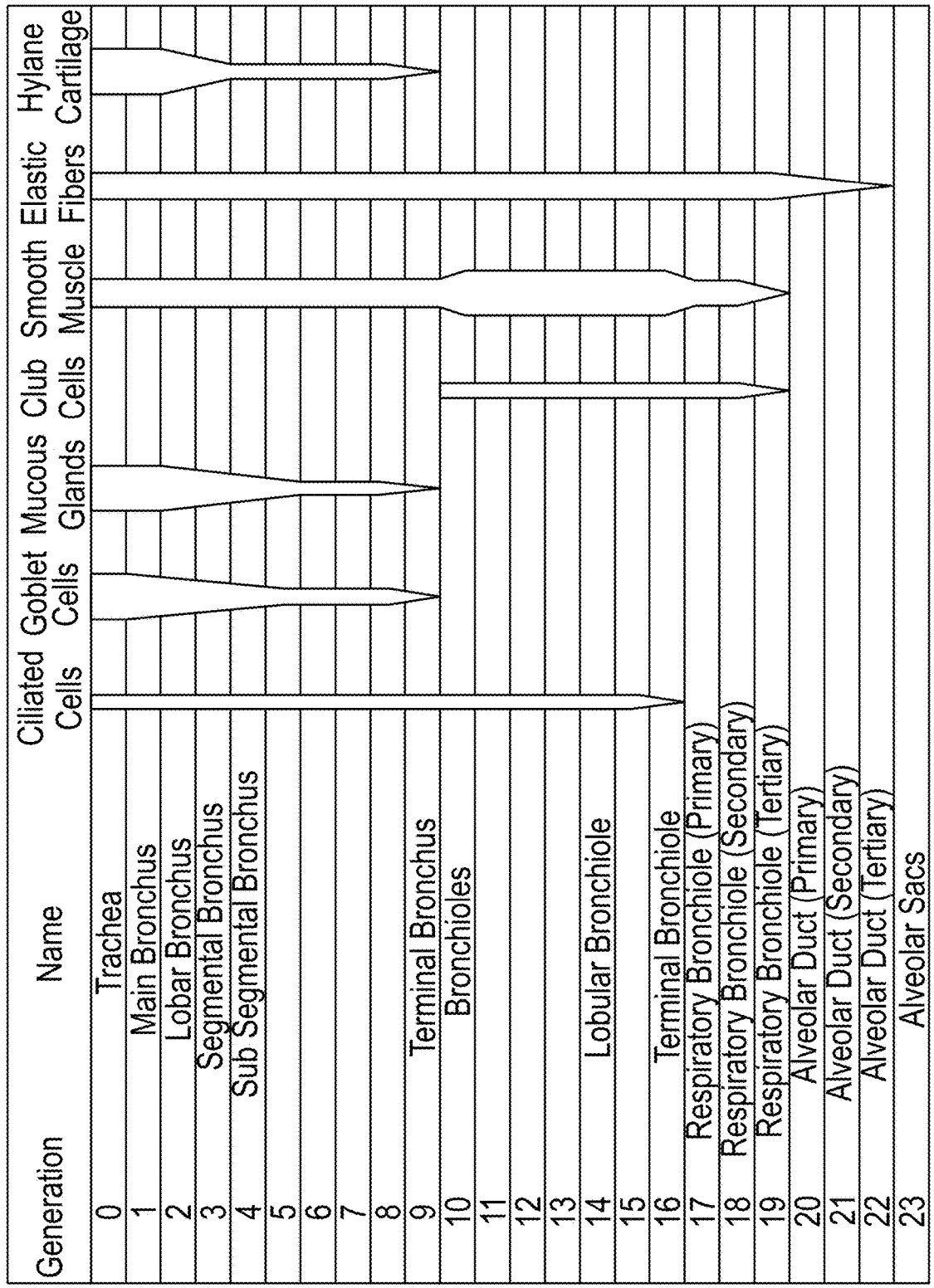
FIG. 6 is a table showing airway wall composition at different portions of a bronchial tree of a human subject.
Figure 7:
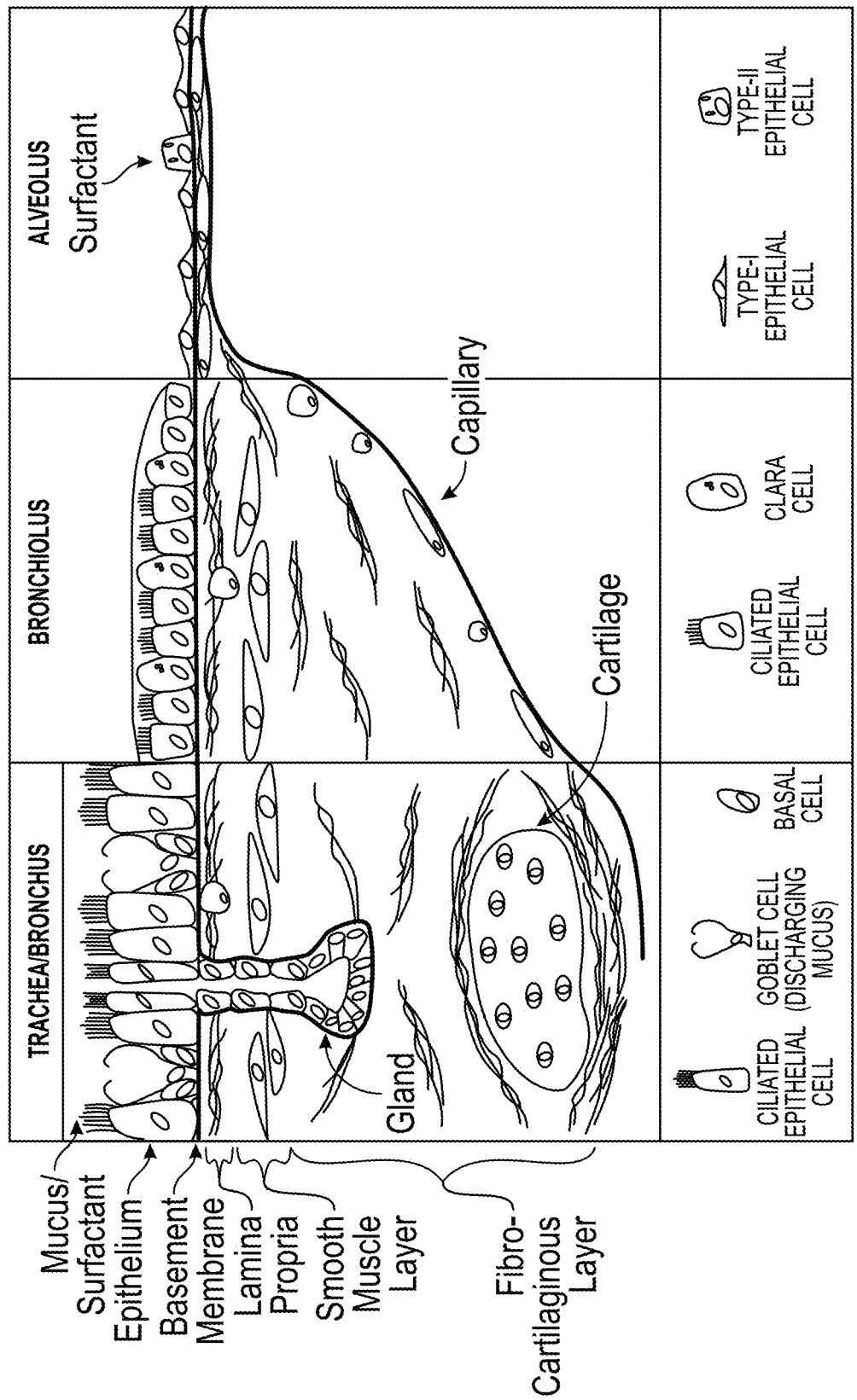
FIG. 7 is an anatomical illustration of airway wall composition at different portions of a bronchial tree of a human subject.

FIG. 6 is a table showing airway wall composition at different portions of a bronchial tree. FIG. 7 is an anatomical illustration of airway wall composition at different portions of a bronchial tree. As shown in FIGS. 6 and 7, the walls of the bronchi, bronchioles, alveolar ducts and alveoli are include epithelium, connective tissue, goblet cells, mucous glands, club cells, smooth muscle elastic fibers, and hyaline cartilage with nerves, blood vessels, and inflammatory cells interspersed throughout. Most of the epithelium (from the nose to the bronchi) is covered in ciliated pseudostratified columnar epithelium, commonly called respiratory epithelium. The cilia located on these epithelium beat in one direction, moving mucous and foreign material such as dust and bacteria from the more distal airways to the more proximal airways and eventually to the throat, where the mucus and/or foreign material are cleared by swallowing or expectoration. Moving down the bronchioles, the cells are more cuboidal in shape but are still ciliated.

The proportions and properties of various components of the airway wall vary depending on the location within the bronchial tree. For example, mucous glands are abundant in the trachea and main bronchi but are absent starting at the bronchioles (e.g., at approximately generation 10). In the trachea, cartilage presents as C-shaped rings of hyaline cartilage, whereas in the bronchi the cartilage takes the form of interspersed plates. As branching continues through the bronchial tree, the amount of hyaline cartilage in the walls decreases until it is absent in the bronchioles. Smooth muscle starts in the trachea, where it joins the C-shaped rings of cartilage. It continues down the bronchi and bronchioles, which it completely encircles. Instead of hard cartilage, the bronchi and bronchioles are composed of elastic tissue. As the cartilage decreases, the amount of smooth muscle increases. The mucous membrane also undergoes a transition from ciliated pseudostratified columnar epithelium to simple cuboidal epithelium to simple squamous epithelium.

Pulmonary Disease

Figure 8:
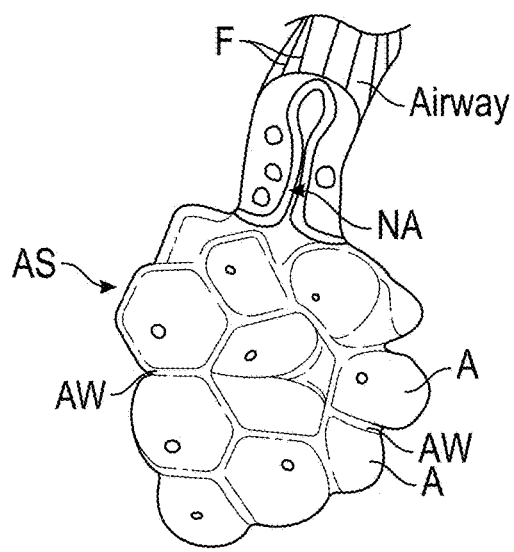
FIG. 8 is an anatomical illustration showing small airway narrowing in emphysematous lung tissue.
Figure 9:
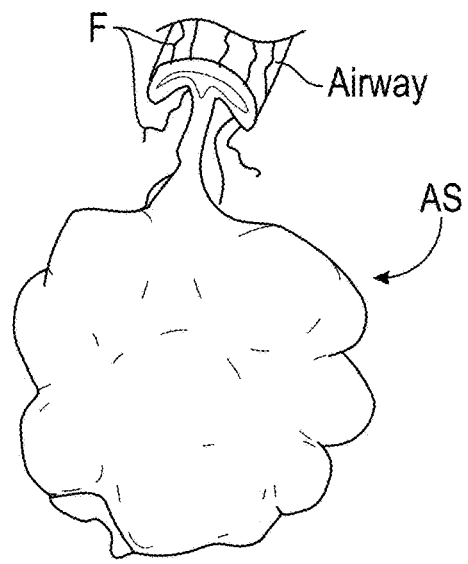
FIG. 9 is an anatomical illustration showing alveolar wall damage in emphysematous lung tissue.
Figure 10:
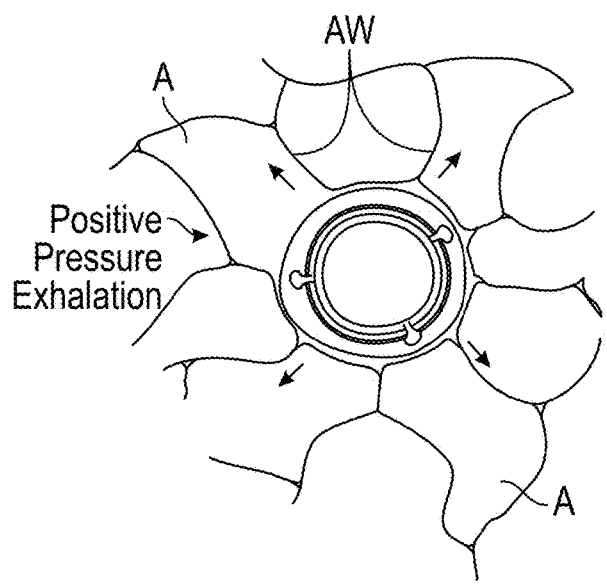
FIG. 10 is an anatomical illustration showing normal airway patency during exhalation in healthy lung tissue.
Figure 11:
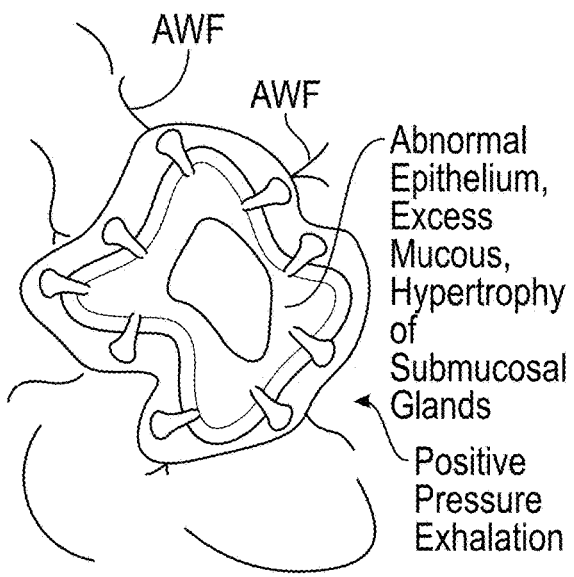
FIG. 11 is an anatomical illustration showing airway collapse during exhalation in emphysematous lung tissue.

FIG. 8 is an anatomical illustration showing small airway narrowing in emphysematous lung tissue. FIG. 9 is an anatomical illustration showing alveolar wall damage in emphysematous lung tissue. FIG. 10 is an anatomical illustration showing normal airway patency during exhalation. FIG. 11 is an anatomical illustration showing airway collapse during exhalation in emphysematous lung tissue.

COPD, and emphysema in particular, is characterized by irreversible destruction of the alveolar walls that contain elastic fibers that maintain radial outward traction on small airways and are useful in inhalation and exhalation. As shown in FIGS. 8-11, when these elastic fibers are damaged, the small airways are no longer under radial outward traction and collapse, particularly during exhalation. Furthermore, emphysema destroys the alveolar walls. As shown in FIG. 9, this results in one larger air space and reduces the surface area available for gas exchange. The lungs are thus unable to perform gas exchange at a satisfactory rate, which causes a reduction in oxygenated blood. Additionally, the large air spaces of diseased lung combined with collapsed airways results in hyperinflation (air trapping) of the lung and an inability to fully exhale. Moreover, the hyperinflated lungs apply continuous pressure on the chest wall, diaphragm, and surrounding structures, which causes shortness of breath and can prevent a patient from walking short distances or performing routine tasks. Both quality of life and life expectancy for patients with late-stage emphysema are extremely low, with fewer than half of patients surviving an additional five years.

Figure 12:
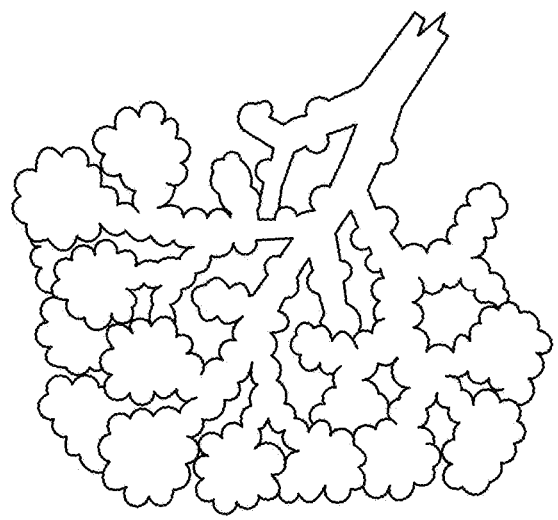
FIG. 12 is an anatomical illustration showing normal acinar.
Figure 13:
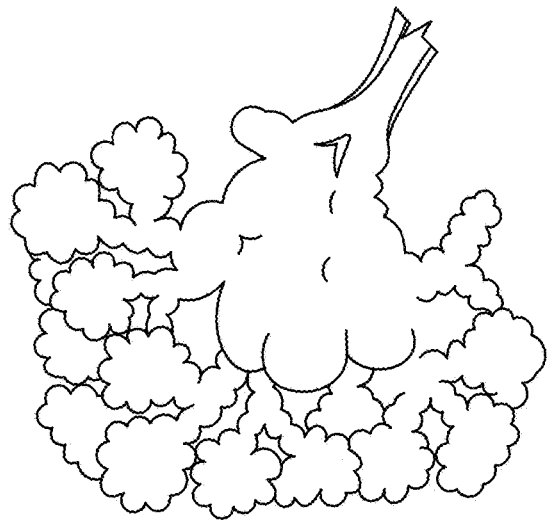
FIG. 13 is an anatomical illustration showing centriacinar emphysema.
Figure 14:
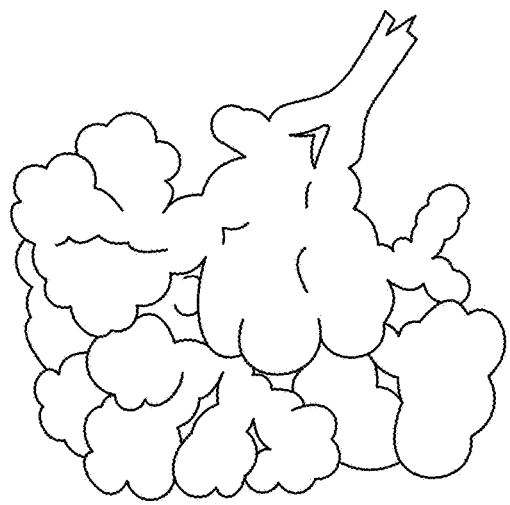
FIG. 14 is an anatomical illustration showing panacinar emphysema.
Figure 15:
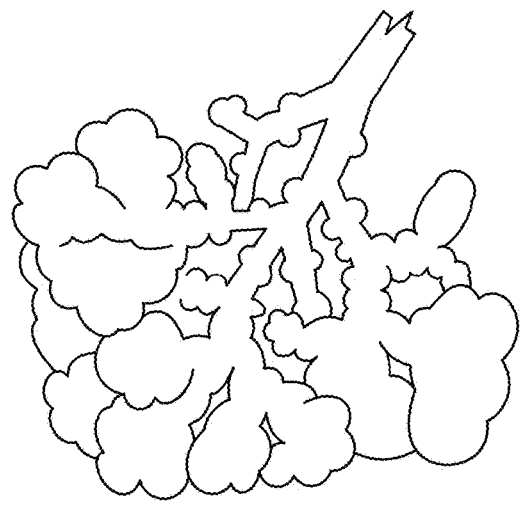
FIG. 15 is an anatomical illustration showing paraseptal emphysema.

There are three types of emphysema: centriacinar, panacinar, and paraseptal. FIG. 12 is an anatomical illustration showing normal acinar. FIG. 13 is an anatomical illustration showing centriacinar emphysema, which involves the alveoli and airways in the central acinus, including destruction of the alveoli in the walls of the respiratory bronchioles and alveolar ducts. FIG. 14 is an anatomical illustration showing panacinar emphysema, which is characterized by destruction of the tissues of the alveoli, alveolar ducts, and respiratory bronchioles. This produces a fairly uniform dilatation of the air space throughout the acini and evenly distributed emphysematous changes across the acini and the secondary lobules. FIG. 15 is an anatomical illustration showing paraseptal emphysema, which is characterized by enlarged airspaces at the periphery of acini resulting predominately from destruction of the alveoli and alveolar ducts. The distribution of the paraseptal emphysema is usually limited in extent and occurs most commonly along the posterior surface of the upper lung. It often coexists with other forms of emphysema.

One further aspect of the progression of emphysema and associated alveolar wall destruction is that the airflow between neighboring alveoli, known as collateral ventilation or collateral air flow, is increased. Collateral ventilation can significantly undermine the clinical utility of endobronchial valves. As discussed above, these valves are designed to allow one-way air passage to cause atelectasis of the diseased lobe. However, collateral ventilation causes inflation of the lobe, thereby preventing atelectasis.

Novel Endobronchial Implants

Described herein are devices, technologies, and methods for treating patients having pulmonary disease, such as severe emphysema. At least some embodiments of the present technology include endobronchial placement of an implant to establish or improve airway patency. The implant can be placed at a treatment location including a previously collapsed airway, such as a previously collapsed distal airway. Deployment of the implant can release air trapped in a hyperinflated portion of the lung and/or reduce or prevent subsequent trapping of air in this portion of the lung. In at least some cases, it is desirable for a treatment location at which an implant is deployed to include an airway of generation 4 or higher/deeper, such as (from distal to proximal) the respiratory bronchioles, terminal bronchioles, conducting bronchioles, bronchioles or sub-segmental bronchi and then run proximally to a more central, larger airway (e.g., 6th generation or more proximal/lower) such as (from distal to proximal) sub-segmental bronchi, segmental bronchi, lobar bronchi and main bronchi. A single implant may create a contiguous path distal to proximal to reliably create passage for the trapped air. In an alternative embodiment, multiple, discrete implants can be used instead of a single, longer implant. The multiple, discrete implants may be placed in bronchial airways that have collapsed or are at risk of collapse. The use of multiple, discrete implants in select locations in the bronchial tree may have the advantage of using less material, thereby reducing contact stresses and foreign body response (discussed supra), and allow for greater flexibility and customization of therapy. For example, whereas a single implant embodiment may run from a higher generation airway distally to a lower generation airway proximally, a system of multiple, discrete implants may allow for placement of implants in multiple airways of the same generation.

The devices, systems and methods described herein may be administered to different bronchopulmonary segments in order to release trapped air from regions of the lung in the safest and most efficient manner possible. For example, treatment of the left lung may involve one or more of the following segments: Upper Lobe (Superior: apical-posterior, anterior; Lingular: superior, inferior); Lower Lobe: superior, antero-medial basal, lateral basal. Treatment of the right lung may involve one or more of the following segments: Upper Lobe: apical, anterior, posterior; Middle Lobe: medial, lateral; Lower Lobe: superior, anterior basal, lateral basal. The treatments described herein may involve placement of a single implant in a single lung (right or left), a single implant in each lung or multiple implants in each lung. Treatment within a particular lung may involve placing an implant in a specific lobe (e.g., upper lobe) and a specific segment within such lobe or it may involve placement of at least one implant in multiple lobes, segments within a lobe or sub-segments within a segment. Determination of which parts of the lung to treat can be made by the clinical operator (e.g., pulmonologist or surgeon) with the assistance of imaging (e.g., CT, ultrasound, radiography, or bronchoscopy) to assess the presence and pathology of disease and impact on pulmonary function and airflow dynamics.

Figure 16:
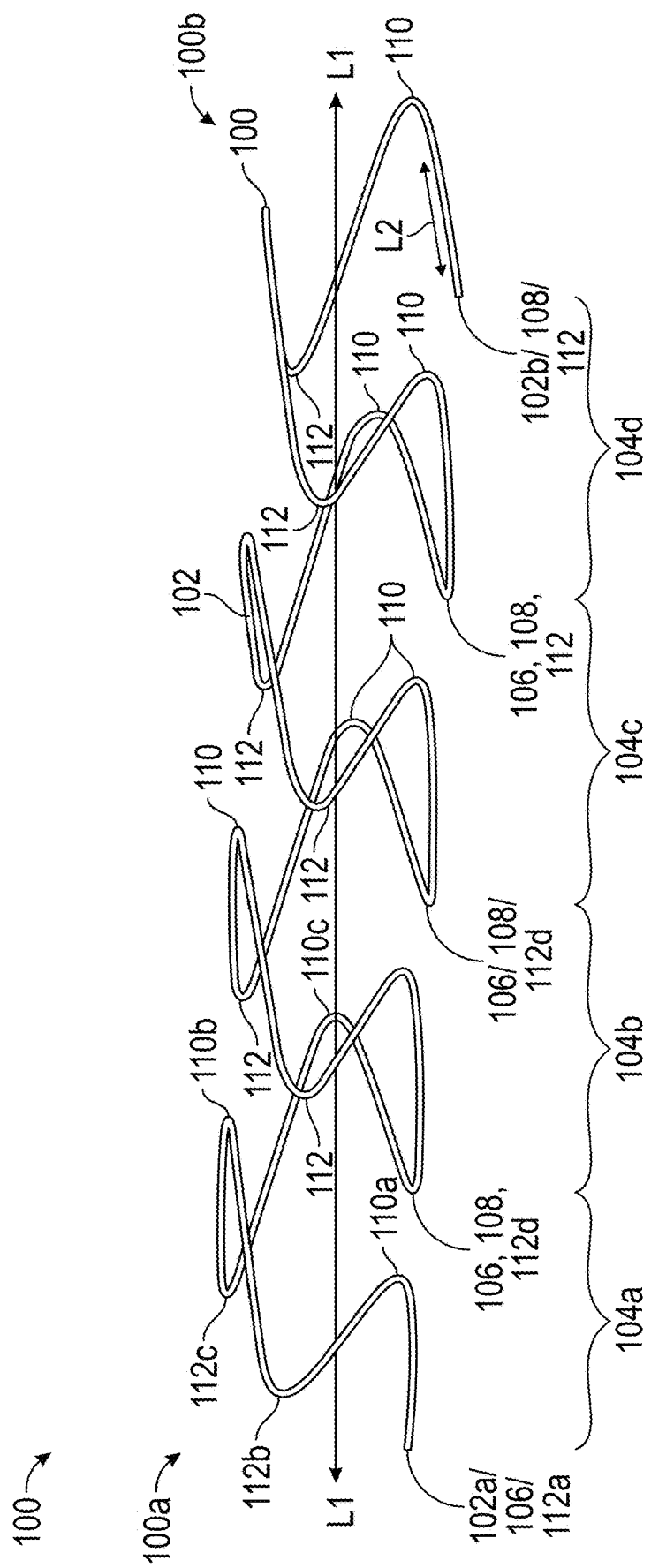
FIG. 16 is a side view of an implant in accordance with at least some embodiments of the present technology.
Figure 17:
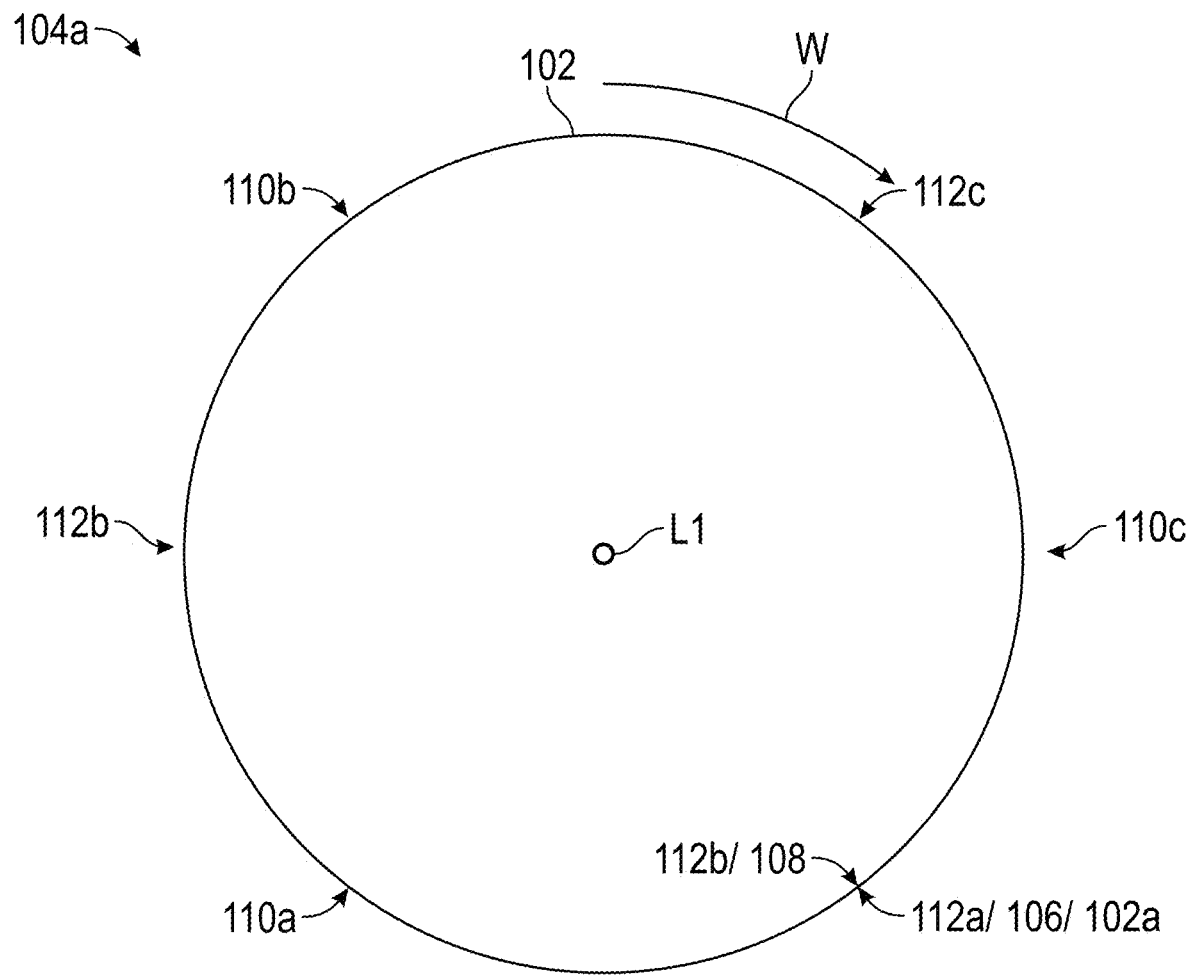
FIG. 17 is a schematic end view of the implant shown in FIG. 16.

FIG. 16 is a side view of an expandable device 100 configured to be positioned in an airway lumen, shown in an expanded, unconstrained state. FIG. 17 is an end view of the device 100. As shown in FIG. 16, the device 100 can comprise a generally tubular structure configured to be positioned within an airway lumen. For example, the device 100 may be configured to be implanted in an airway lumen such that the device 100 maintains a lumen of a minimum desired diameter in the airway. The device 100 has a first end portion 100a, a second end portion 100b opposite the first end portion 100a, and a central longitudinal axis L1 extending between the first and second end portions 100a, 100b. As used herein, the term "longitudinal" can refer to a direction along an axis that extends through the lumen of the device while in a tubular configuration, the term "circumferential" can refer to a direction along an axis that is orthogonal to the longitudinal axis and extends around the circumference of the device when in a tubular configuration, and the term "radial" can refer to a direction along an axis that is orthogonal to the longitudinal axis and extends toward or away from the longitudinal axis.

The device 100 can comprise an elongated member 102 wound about the longitudinal axis L1 of the device 100. In some embodiments, the elongated member 102 is heat set in a novel three-dimensional (3D) configuration such that the elongated member 102 is configured to self-expand to the preset configuration. In some embodiments, the elongated member 102 is not heat set and/or configured to self-expand. For example, the elongated member 102 is balloon-expandable. In some embodiments, the elongated member 102 is balloon-expandable and self-expanding. The elongated member 102 has a first end 102a and a second end 102b opposite the first end 102a along a longitudinal axis L2 of the elongated member 102. The elongated member 102 can comprise a wire, a coil, a tube, a filament, a single interwoven filament, a plurality of braided filaments, a laser-cut sheet, a laser-cut tube, a thin film formed via a deposition process, and other suitable elongated structures and/or methods, such as cold working, bending, EDM, chemical etching, water jet, etc. The elongated member 102 can be formed using materials such as nitinol, stainless steel, cobalt-chromium alloys (e.g., 35N LT®, MP35N (Fort Wayne Metals, Fort Wayne, Indiana)), Elgiloy, magnesium alloys, tungsten, tantalum, platinum, rhodium, palladium, gold, silver, or combinations thereof, or one or more polymers, or combinations of polymers and metals. In some embodiments, the elongated member 102 may include one or more drawn-filled tube ("DFT") wires comprising an inner material surrounded by a different outer material. The inner material, for example, may be radiopaque material, and the outer material may be a superelastic material.

Although the device 100 shown in FIG. 16 comprises a single elongated member 102, the device 100 may comprise any number of elongated members 102. A single elongated member, such as a single wire expandable device, can be easier to remove and/or reposition as the operator can grab the elongated member on one end and pull it through a working channel of a scope. The elongated member will straighten out in either the balloon expandable or self-expanding form.

Referring to FIG. 16, the elongated member 102 may be wound about the longitudinal axis L1 of the device 100 in a series of windings or loops 104, four of which are shown in FIG. 16 and individually labeled 104a-104d. Each of the loops 104 can extend around the longitudinal axis L1 of the device 100 between a first end 106 and a second end 108. In some embodiments, the loops 104 are connected end to end such that, for example, a second end 108 of the first loop 104a is the first end 106 of the second loop 104b. The second end 108 can be disposed approximately 360 degrees from the first end 106 about the longitudinal axis L1 of the device 100. That is, the first and second ends 106, 108 can be disposed at generally equivalent circumferential positions relative to the longitudinal axis L1 of device 100. In some embodiments, the device 100 has a circular cross-sectional shape. In other embodiments, the device 100 may have other suitable cross-sectional shapes (e.g., oval, square, triangular, polygonal, irregular, etc.). The cross-sectional shape of the device 100 may be generally the same or vary along the length of the device 100 and/or from loop to loop.

The expanded cross-sectional dimension of the device 100 may be generally constant or vary along the length of the device 100 and/or from loop to loop. For example, as discussed herein, the device 100 can have varying cross-sectional dimensions along its length to accommodate different portions of the airway. For instance, the device 100 can have a first cross-sectional dimension along a first portion configured to be positioned in a more distal portion of the airway (such as, for example, in a terminal bronchiole and/or emphysematous areas of destroyed and/or collapsed airways), and a second cross-sectional dimension along a second portion configured to be positioned more proximally (such as in a primary bronchus and/or another portion that has not collapsed). The second portion, for example, can be configured to be positioned in a portion of the airway that is less emphysematous than the collapsed distal portion and/or has cartilage in the airway wall (preferably rings of cartilage and not plates), which can occur at the lobar (generation 2) or segmental (generation 3) level.

In some embodiments, the expanded cross-sectional dimension of the device 100 in an unconstrained (i.e., removed from the constraints of a catheter or airway), expanded state is oversized relative to the diameter of the native airway lumen. For example, the expanded, unconstrained cross-sectional dimension of the device 100 can be at least 1.5× the original (non-collapsed) diameter of the airway lumen in which it is intended to be positioned. In some embodiments, the device 100 has an expanded, cross-sectional dimension that is about 1.5× to 6×, 2× to 5×, or 2× to 3× the diameter of the original airway lumen. Without being bound by theory, it is believed that expanding the airway lumen to the greatest diameter possible without tearing the airway wall will provide the greatest improvement in pulmonary function (for example, as measured by outflow, FEV, and others).

As shown in FIG. 16, the elongated member 102 may undulate along its longitudinal axis L2 as it winds around the longitudinal axis L1 of the device 100, forming a plurality of alternating peaks 110 (closer to the second end portion 100b of the device 100) and valleys 112 (closer to the first end portion 100a of the device 100). At least some of the valleys 112 can be at different locations along the longitudinal axis L1 of the device 100 than at least some of the peaks 110. Additionally or alternatively, at least some of the valleys 112 can be at different longitudinal locations than at least some others of the valleys 112 and/or at least some of the peaks 110 can be at different longitudinal locations than at least some others of the peaks 110.

As an example, three peaks 110 and four valleys 112 of the first loop 104a have been individually labeled as peaks 110a-110c and valleys 112a-d. As shown in FIGS. 16 and 17, for the first loop 104a in the direction of the wind W, the elongated member 102 extends from the first end 106 of the elongated member 102, which comprises a first valley 112a of the first loop 104a, to a first peak 110a of the first loop 104a along a first longitudinal direction toward the second end portion 100b of the device 100. The elongated member 102 can then extend from the first peak 110a to a second valley 112b along a second longitudinal direction opposite of the first longitudinal direction, from the second valley 112b to a second peak 110b along the first longitudinal direction, from the second peak 110b to a third valley 112c along the second longitudinal direction, from the third valley 112c to a third peak 110c along the first longitudinal direction, and from the third peak 110c to a fourth valley 112d (which is also the second end 108 of the first loop 104a) along the second longitudinal direction. Thus, when traveling in a direction of the wind W around a given loop 104, the loop 104 does not consistently progress from the first end portion 100a of the device 100 to the second end portion 100b of the device 100 (or vice versa), but rather undulates so that along certain portions of its length, the loop 104 becomes progressively closer to the first end portion 100a of the device 100, and along other portions of its length the loop becomes progressively closer to the second end portion 100b of the device 100.

Although the first and second ends 106, 108 of one of the loops 104 may be generally aligned circumferentially, the first and second ends 106, 108 are longitudinally offset. The first peak 110*a* can be closer to the second end portion 100*b* of the device 100 than the first valley 112*a*. The second valley 112*b* can be closer to the first end portion 100*a* of the device 100 than the first peak 110*a* and/or the first valley 112*a*. The second peak 110*b* can be closer to the second end portion 100*b* of the device 100 than the second valley 112*b*, the first peak 110*a*, and/or the first valley 112*a*. The third valley 112*c* can be closer to the first end portion 100*a* of the device 100 than the second peak 110*b* and/or closer to the second end portion 100*b* of the device 100 than the first valley 112*a* and/or the second valley 112*b*. In some embodiments, the third valley 112*c* can be substantially longitudinally aligned with the first peak 110*a*. The third peak 110*c* can be closer to the second end portion 100*b* of the device 100 than the third valley 112*c*, the second peak 110*b*, the second valley 112*b*, the first peak 110*a*, and/or the first valley 112*a*. The fourth valley 112*d* can be closer to the first end portion 100*a* of the device 100 than the third peak 110*c* and/or closer to the second end portion 100*b* of the device 100 than the third valley 112*c*, the second valley 112*b*, the first peak 110*a*, and/or the first valley 112*a*. In some embodiments, the fourth valley 112*d* can be substantially longitudinally aligned with the second peak 110*b*.

Although FIGS. 16 and 17 show a device 100 comprising four loops 104, each having four peaks 110 and four valleys 112, in some embodiments one or more of the loops 104 has more or fewer peaks 110 and/or more or fewer valleys 112. For example, in some embodiments one or more of the loops 104 has one, two, three, four, five, six, seven, eight, etc. peaks 110 per loop 104 and one, two, three, four, five, six, seven, eight, etc. valleys 112 per loop 104. The loops 104 may have the same or a different number of peaks 110, and the loops 104 may have the same or a different number of valleys 112. A circumferential distance (e.g., an angular separation) between adjacent ones of the peaks 110 and valleys 112 can be uniform or non-uniform in a given loop 104. In some embodiments, adjacent ones of the peaks 110 and valleys 112 can be spaced apart around a circumference of the device 100 by about 90 degrees, about 120 degrees, about 150 degrees, about 180 degrees, about 210 degrees, about 240 degrees, about 270 degrees, about 300 degrees, and/or about 330 degrees. In addition, the amplitude of the peaks 110 may be the same or different along a given loop 104 and/or amongst the loops 104, and the amplitude of the valleys 112 may be the same or different along a given loop 104 and/or amongst the loops 104. Moreover, the peaks 110 and valleys 112 can have the same or different amplitudes.

As shown in FIG. 16, a portion of the elongated member 102 between adjacent peaks 110 and valleys 112 can be linear, curved, or both. Adjacent portions of the elongated member 102 between two sets of adjacent peaks 110 and valleys 112 can form a V-shaped and/or U-shaped structure. At least some of the valleys 112 can be concave toward the second end portion 100*b* of the device 100 and/or at least some of the peaks 110 can be concave toward the first end portion 100*a* of the device 100.

Figure 18:
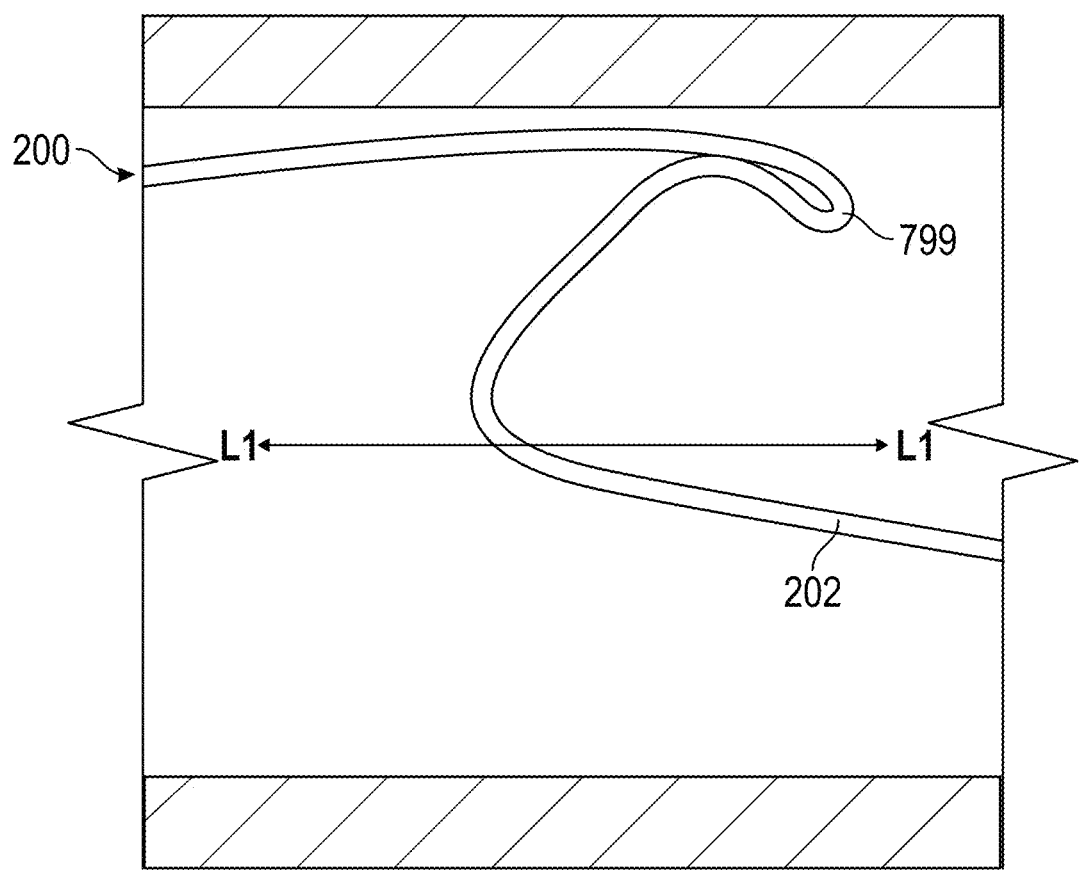
FIG. 18 is a side view of a portion of an implant in accordance with at least some embodiments of the present technology within an airway.

In some embodiments, for example as shown in FIG. 16, the elongated member 102 can extend around a circumference of the device 100 and/or along a longitudinal axis L1 of the device 100, without substantially extending radially away or towards the longitudinal axis L1. Still, in some embodiments, a device 200 can comprise an elongated member 202 that undulates radially with respect to a longitudinal axis L1 of the device 200. As shown in FIG. 18, for example, the elongated member 202 can form peaks 799 and/or valleys 799 that are located closer to the longitudinal axis L1 than intermediate portions of the elongated member 202 between the peaks 799 and valleys 799. The apices of each "V" can be bent radially inward toward the center of the lumen, so that only the longitudinally-extending portions of the elongated member 202 are touching the bronchial wall. Such a configuration can prevent the stent from impeding mucus flow along the wall of the bronchus.

The radial mechanism of expansion allows the expandable device 700 to be easily designed and delivered by both self-expansion and balloon-expansion. The zig-zag pattern of the devices disclosed herein, including the example shown in FIG. 16, is configured to conform to different diameter airways with a single design, whereas conventional coils are a fixed diameter. This is especially advantageous for achieving gradual airway dilation over time. The expandable device stores expansion potential in the stent design which is achieved via beams that bend and elastic potential is established. The expandable device in balloon expandable form also has a unique potential to form a coil by expanding the zig-zags all the way to a straight line when geometrically designed this way.

Figure 19:
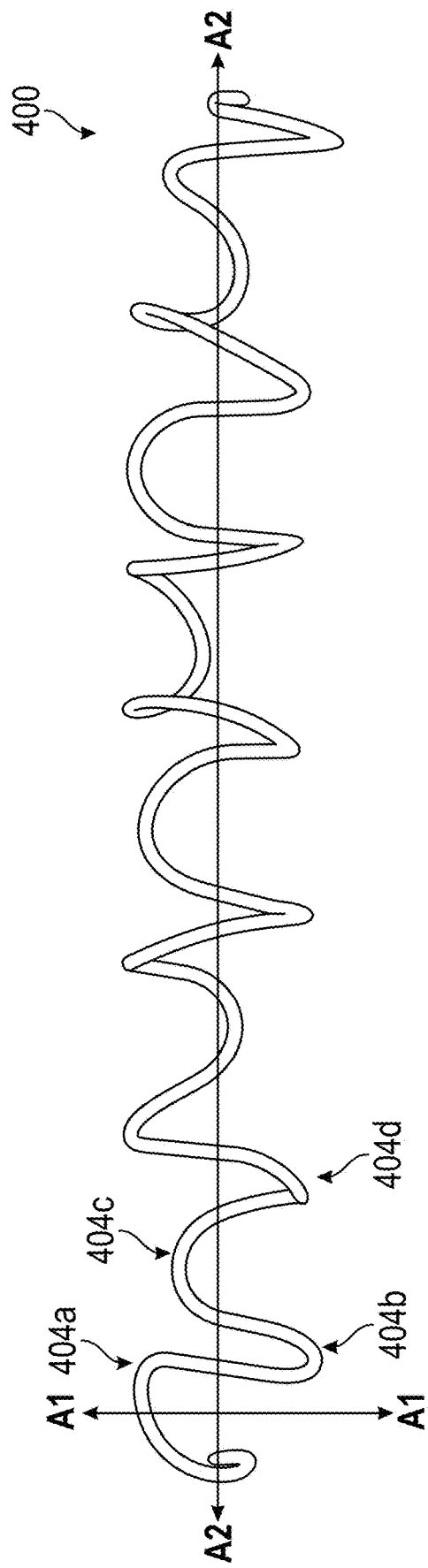
FIG. 19 is a side view of an implant in accordance with at least some embodiments of the present technology.
Figure 20:
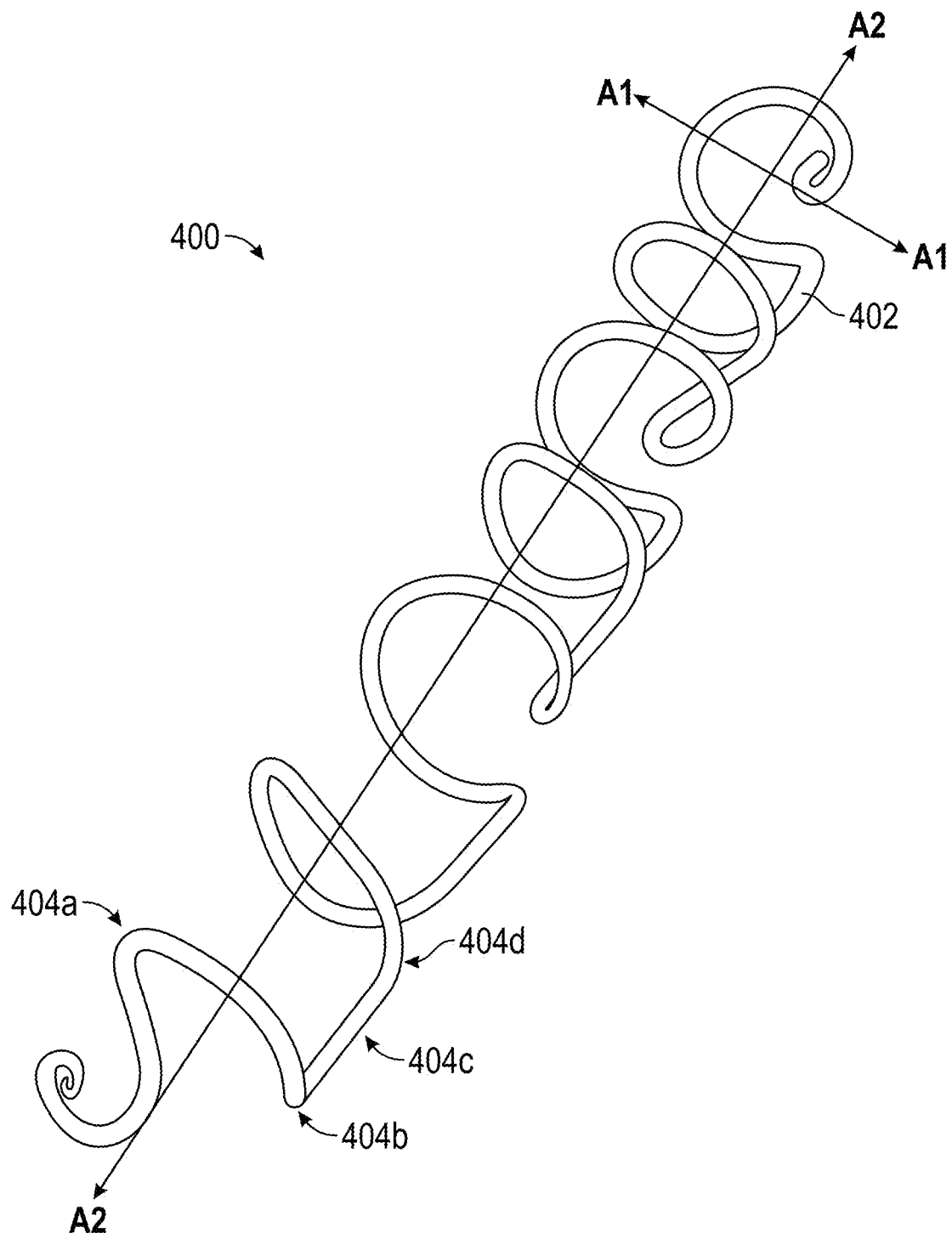
FIG. 20 is a perspective view of the implant shown in FIG. 19.

In some embodiments, for example as shown in FIGS. 19 and 20, a device 400 comprises an elongated member 402 wound about two or more axes that are angled relative to one another. In FIGS. 19 and 20, the elongated member 402 is wound about a first axis A1 to form a first loop 404*a*, wound about a second axis A2 to form a second loop 404*b*, wound about the first axis A1 to form a third loop 404*c*, etc. In some embodiments, the second axis A2 is a central longitudinal axis. Additionally or alternatively, the first axis A1 can be substantially orthogonal to the second axis A2. The elongated member 402 can be partially wound about each axis such that each of the loops 404 comprises an open loop. In some embodiments, the elongated member 402 is wound such that each of the loops 404 is V-shaped or U-shaped.

Figure 21:
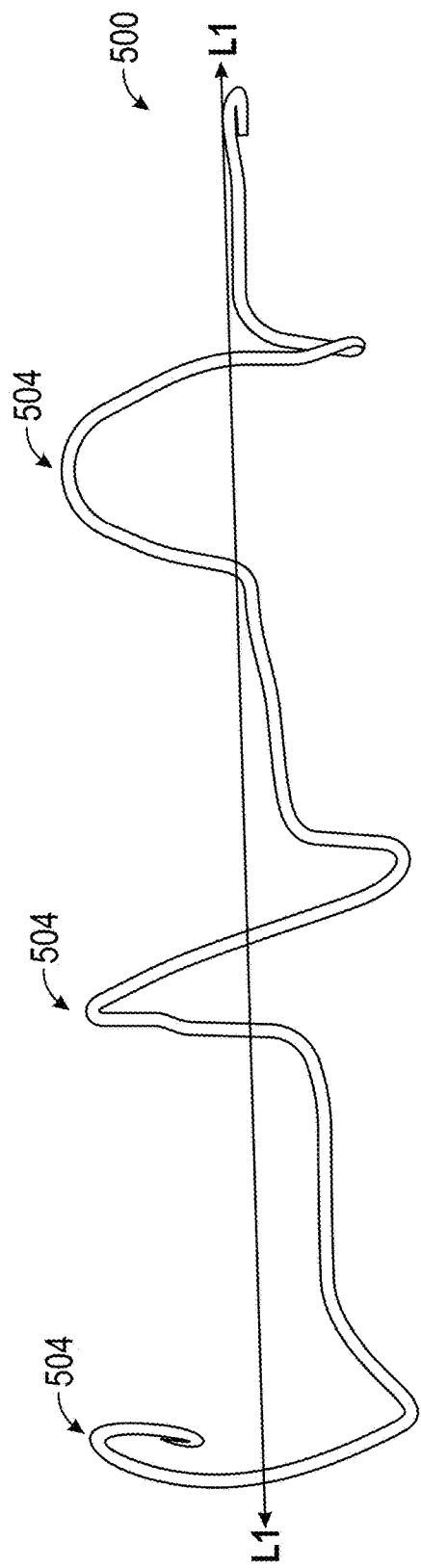
FIGS. 21-23 are side views of respective implants in accordance with at least some embodiments of the present technology.

FIG. 21 depicts an expandable device 500 comprising an elongated member 502 wound about a longitudinal axis L1 of the device 500 such that the elongated member 502 forms one or more loops 504. At least one of the loops 504 can comprise a first end 506 and a second end 508. The second end 508 can be located at a substantially equivalent circumferential position as the first end 506. In some embodiments, for example as shown in FIG. 21, the second end 508 is longitudinally spaced apart from the first end 506. A second end 508 of one of the loops 504 can be connected to a first end 506 of an adjacent one of the loops 504 by a connector portion 510. In some embodiments, the connector portion 510 extends along the longitudinal axis L1 of the device 500 without substantially extending about a circumference of the device 500.

Figure 22:
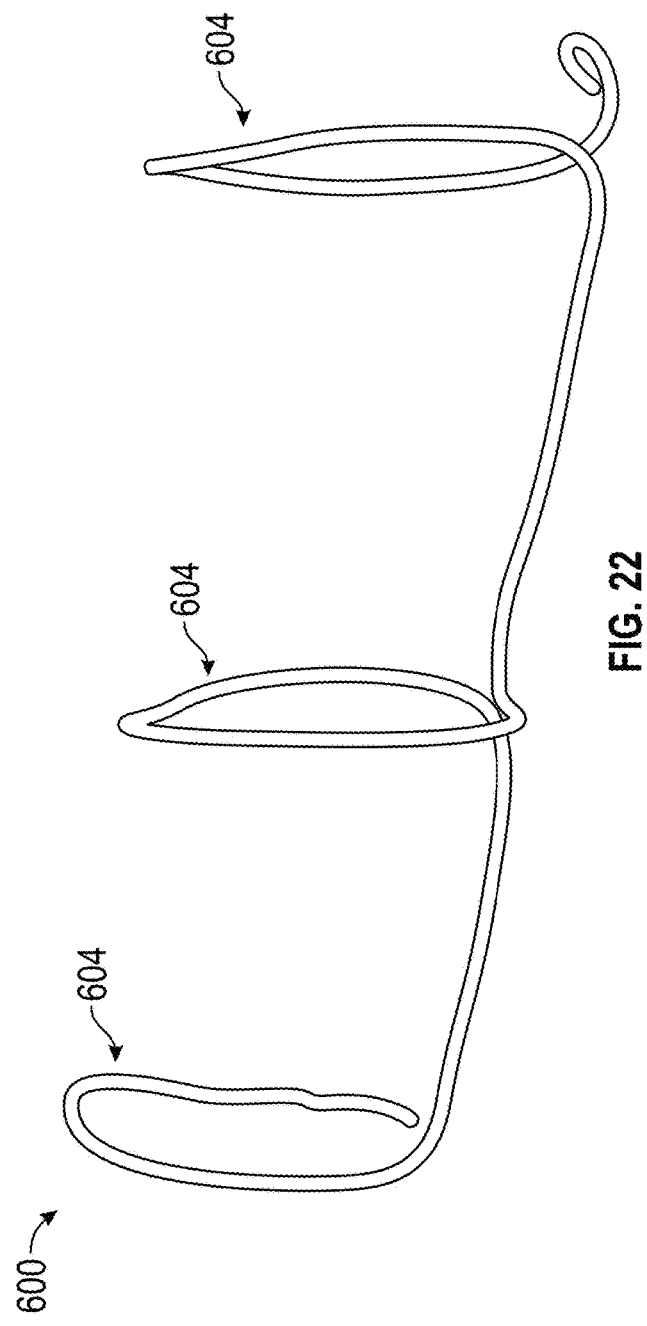

FIG. 22 depicts an expandable device 600 comprising an elongated member 602 wound about a longitudinal axis L1 of the device 600 such that the elongated member 602 forms one or more loops 604. The loops 604 can each comprise a first end 606 and a second end 608. Similar to the loops 504 shown in FIG. 21, the first end 606 and the second end 608 can be substantially circumferentially aligned. However, as shown in FIG. 22 and unlike loops 504, the first end 606 and the second end 608 can be longitudinally aligned such that loops 604 are substantially closed.

Figure 23:
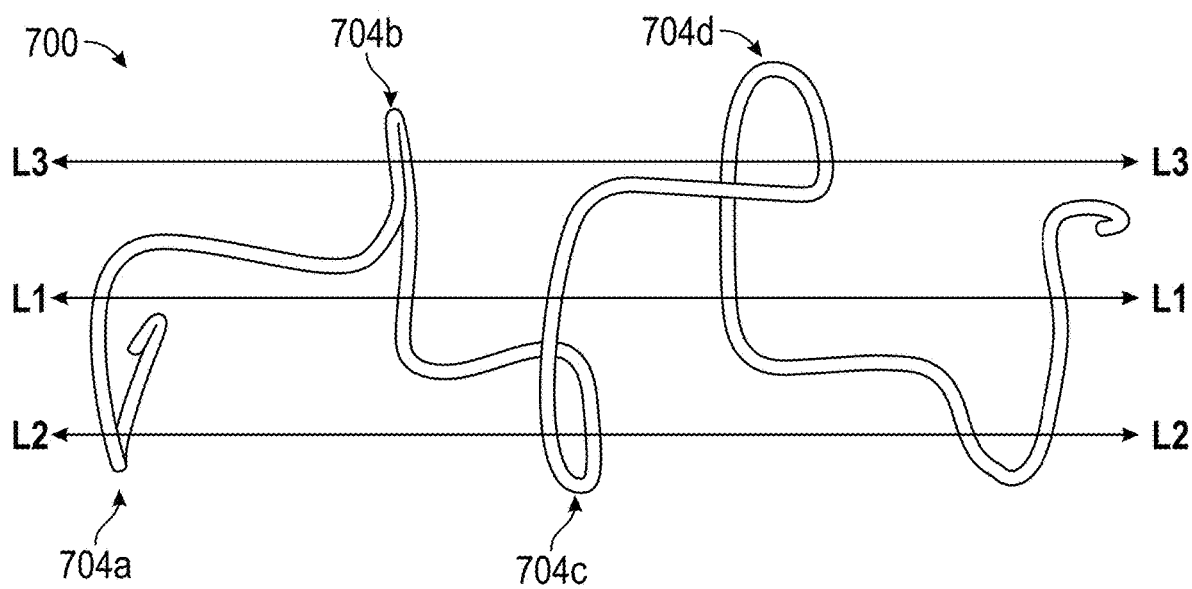
Figure 24:
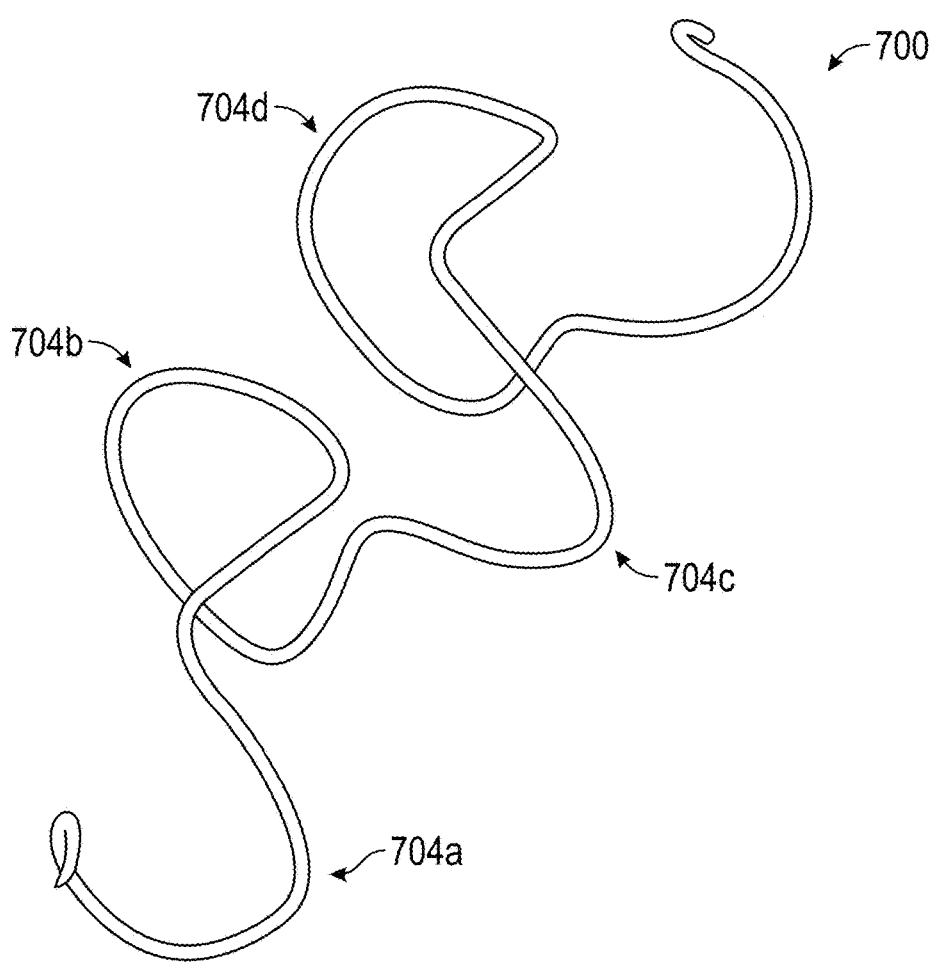
FIG. 24 is a perspective view of the implant shown in FIG. 23.

In some embodiments, for example as shown in FIGS. 21 and 22, a device can have loops that are each wound about the same axis. Additionally or alternatively, at least some of the loops can be wound about different axes. For example, FIGS. 23 and 24 depict a device 700 having a first, central longitudinal axis L1. The device 700 comprises an elongated member 702 forming loops 704. As shown in FIGS. 23 and 24, alternating ones of the loops 704 can be wound about distinct axes. For example, a first loop 704a is wound about a second longitudinal axis L2, a second loop 704b is wound about a third longitudinal axis L3, a third loop 704c is wound about the second longitudinal axis L2, a fourth loop 704d is wound about the third longitudinal axis L3, and a fifth loop 704e is wound about the second longitudinal axis L2. The second longitudinal axis L2 and/or the third longitudinal axis L3 can be substantially parallel to the first longitudinal axis L1.

Figure 25:
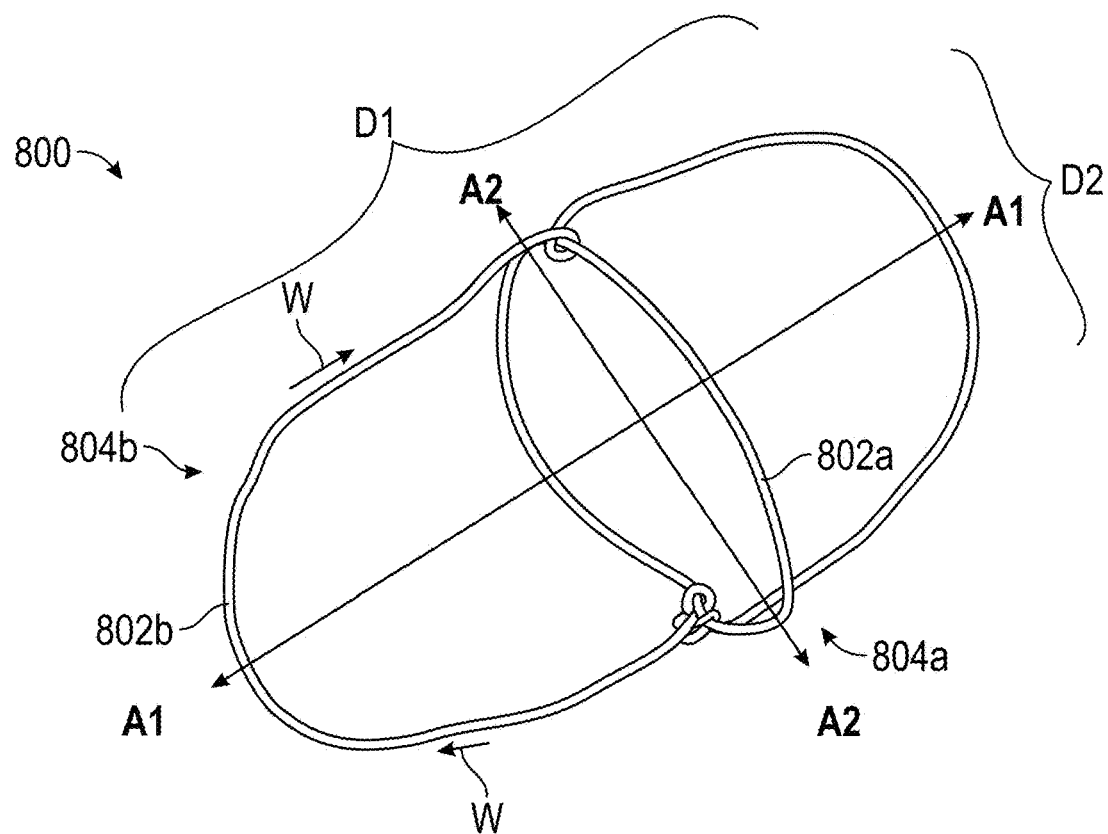
FIGS. 25-31 are perspective views of respective implants in accordance with at least some embodiments of the present technology.

According to various aspects of the present technology, an expandable device can comprise two or more loops wound about non-parallel axes. For example, the expandable device 800 shown in FIG. 25 comprises a first elongated member 802a wound about a first axis A1 to form a first loop 804a. The device 800 can also comprise a second elongated member 802b wound about a second axis A2 to form a second loop 804b. In some embodiments, the second axis A2 is substantially orthogonal to the first axis A1. Additionally or alternatively, the second axis A2 can be disposed at any suitable angle to the first axis A1 such as, but not limited to, between 0° and 90°, between 10° and 80°, between 20° and 70°, between 30° and 60°, between 40° and 50°, about 0°, about 5°, about 10°, about 20°, about 30°, about 40°, about 50°, about 60°, about 70°, about 80°, or about 90°. As shown in FIG. 25, the second loop 804b can be formed by at least partially winding the second elongated member 802b about the second axis A2 along wind direction W, winding the second elongated member 802b about the first elongated member 802a along wind direction W in a complete loop, and winding the second elongated member 802b about the second axis A2 along wind direction W. The device 800 can be configured to be positioned within an airway such that the first and second elongated members 802a, 802b contact the airway wall and maintain a minimum desired diameter of the airway lumen.

Figure 26:
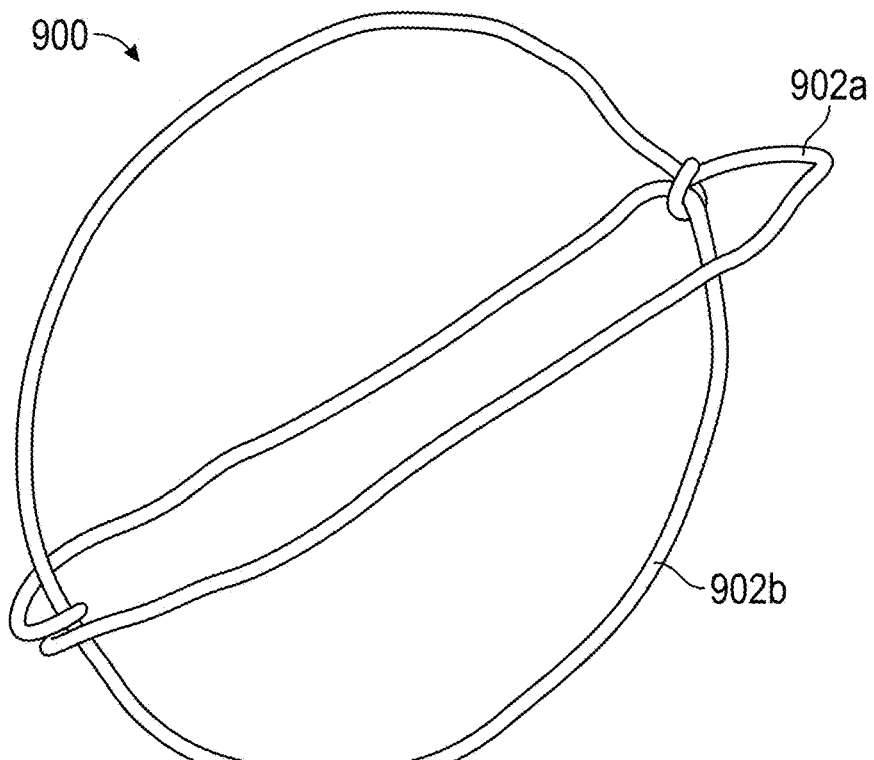
Figure 27:
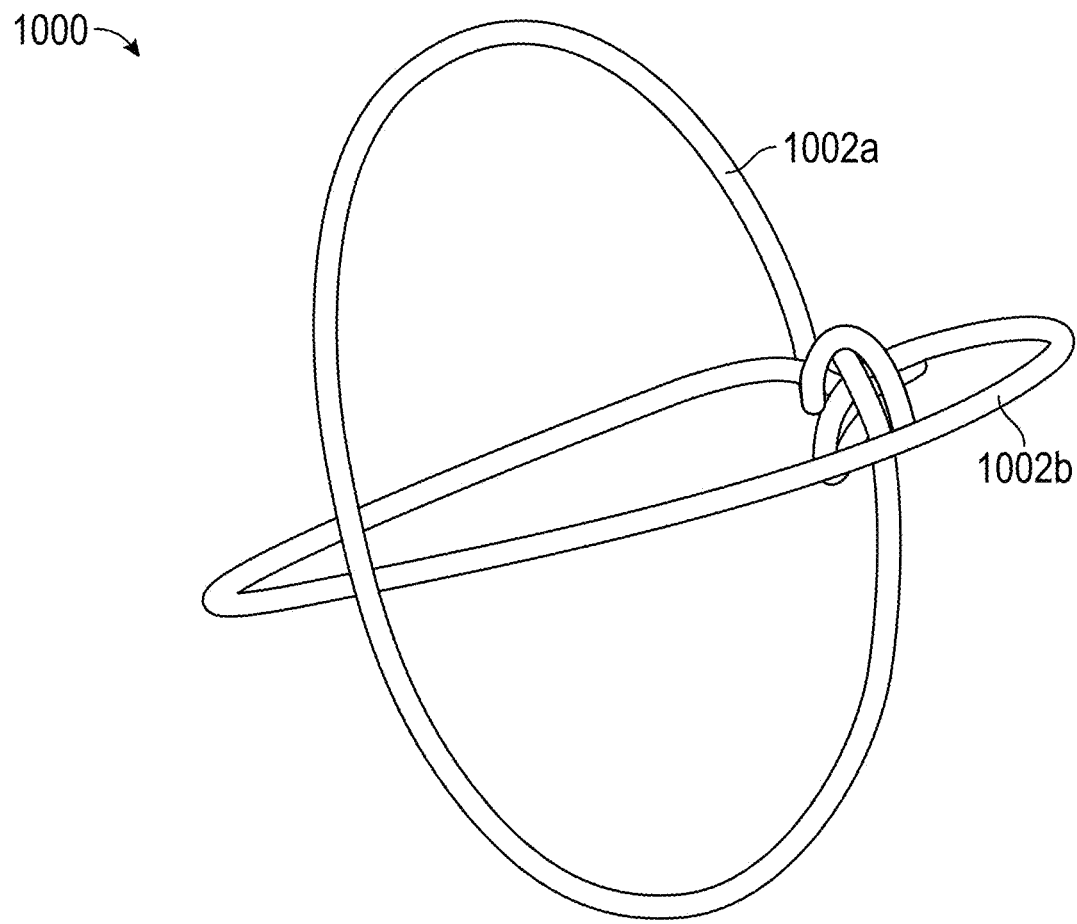

As shown in FIG. 25, in some embodiments, a first dimension D1 of the device 800 along the first axis A1 is greater than a second dimension D2 of the device 800 along the second axis A2. The second loop 804b can have a substantially oblong two-dimensional (2D) shape, whereas the first loop 804a has a substantially round 2D shape. Additionally or alternatively, a device can comprise first and second loops 804a, 804b having substantially similar 2D shapes. For example, the device 900 shown in FIG. 26 comprises first and second loops 902a, 902b both having substantially round 2D shapes and the device 1000 shown in FIG. 27 comprises first and second loops 1002a, 1002b both having substantially oblong 2D shapes.

Figure 28:
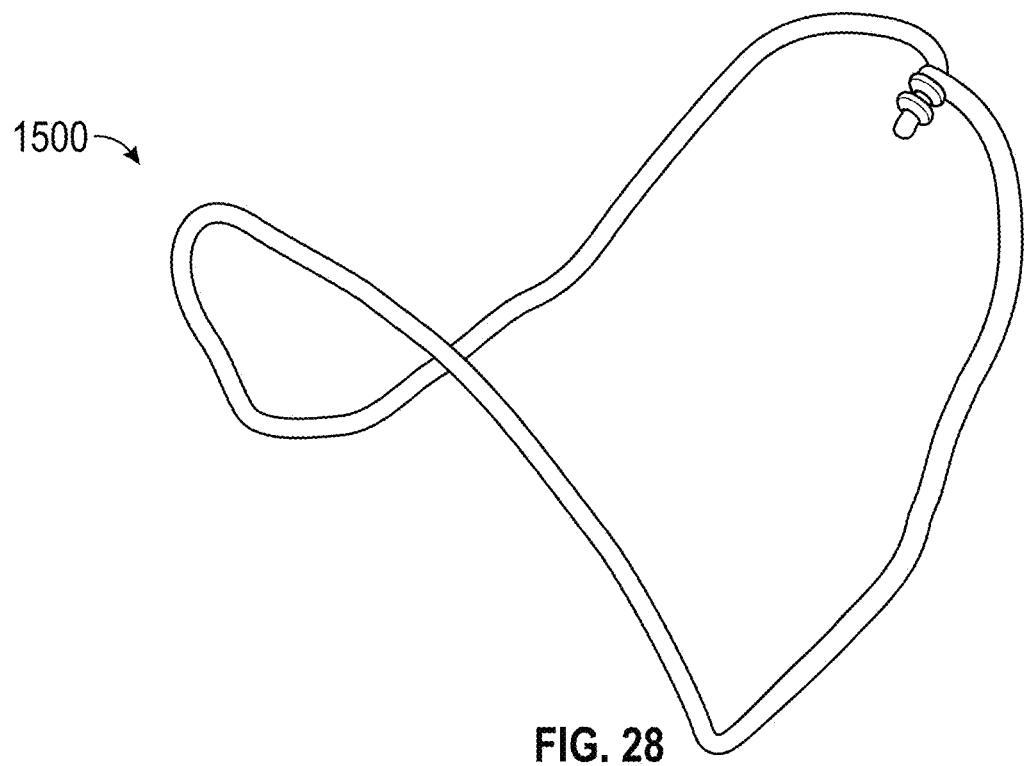
Figure 29:
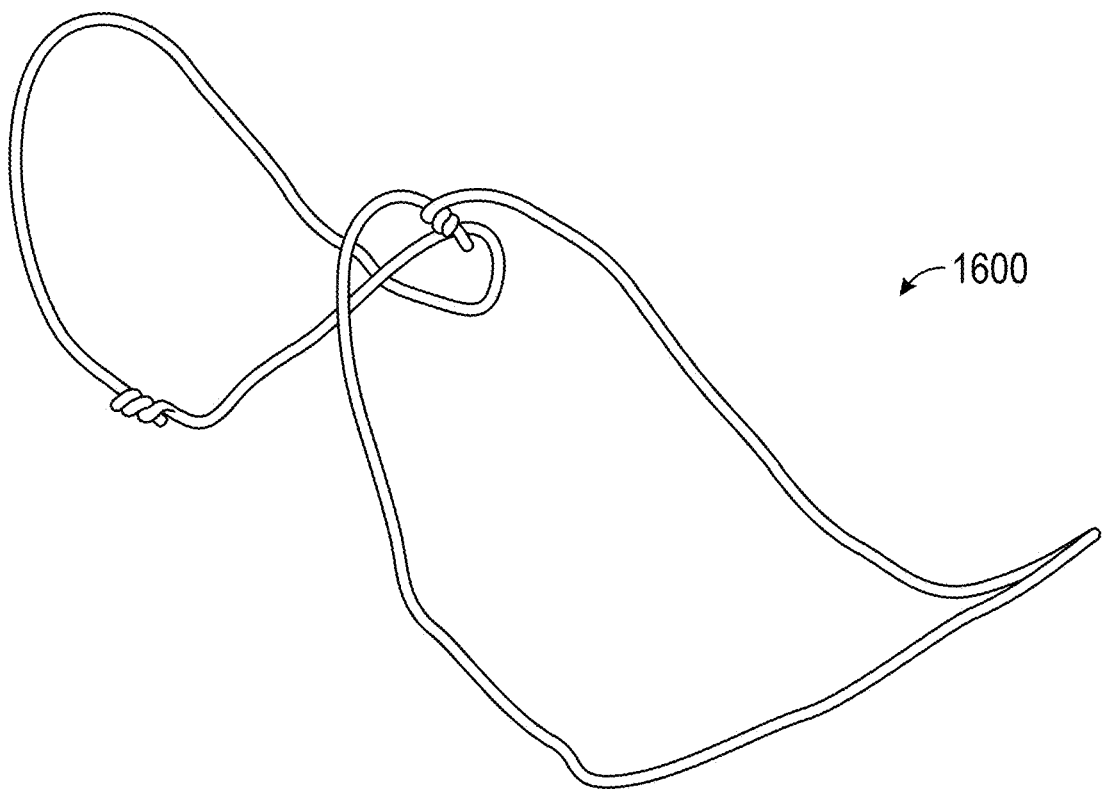
Figure 30:
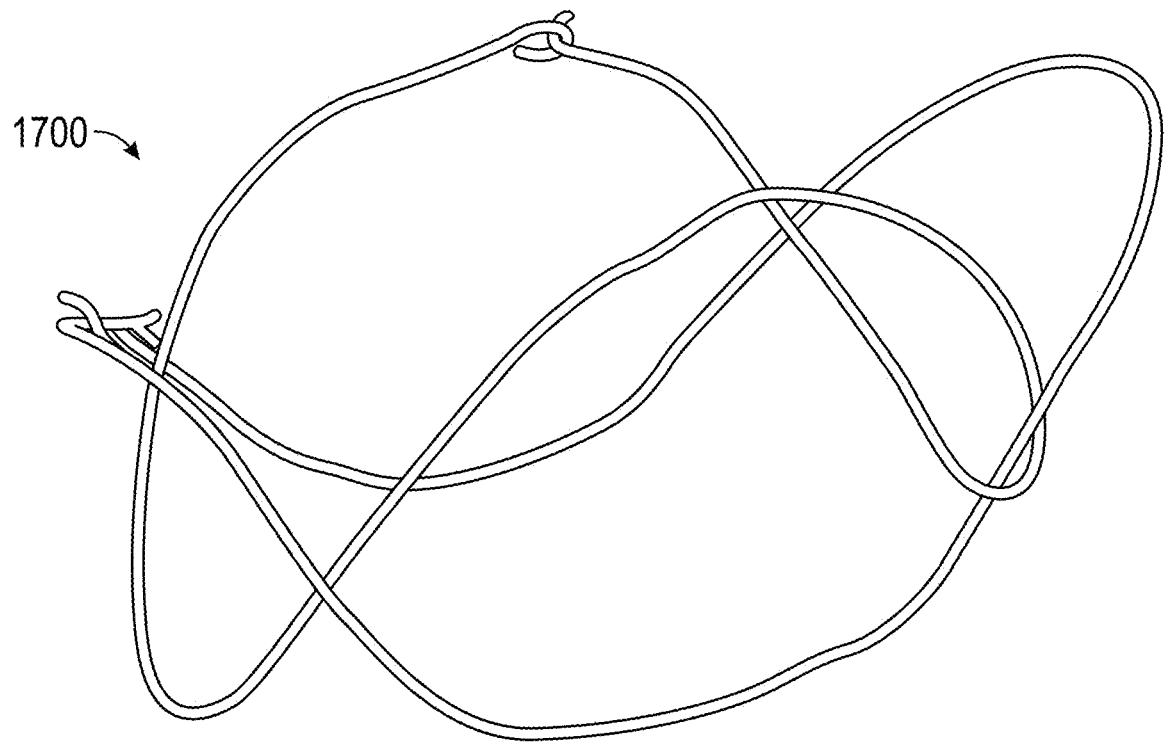

FIGS. 28, 29 and 30 depict expandable devices 1500, 1600 and 1700, respectively, configured in accordance with several embodiments of the present technology. As shown in FIGS. 28-30 an expandable device (e.g., device 1500, device 1600, device 1700, etc.) can comprise one or more loops having a saddle shape. In embodiments in which the device comprises multiple saddle-shaped loops, the loops can be connected end to end (see FIG. 29, for example) and/or can be overlapping (see FIG. 30, for example). The devices shown in FIGS. 28-30 are configured to provide scaffolding with as little structure as possible. The devices are configured to contact the airway wall to help prop it open and support the airway to allow air to pass freely.

Figure 31:
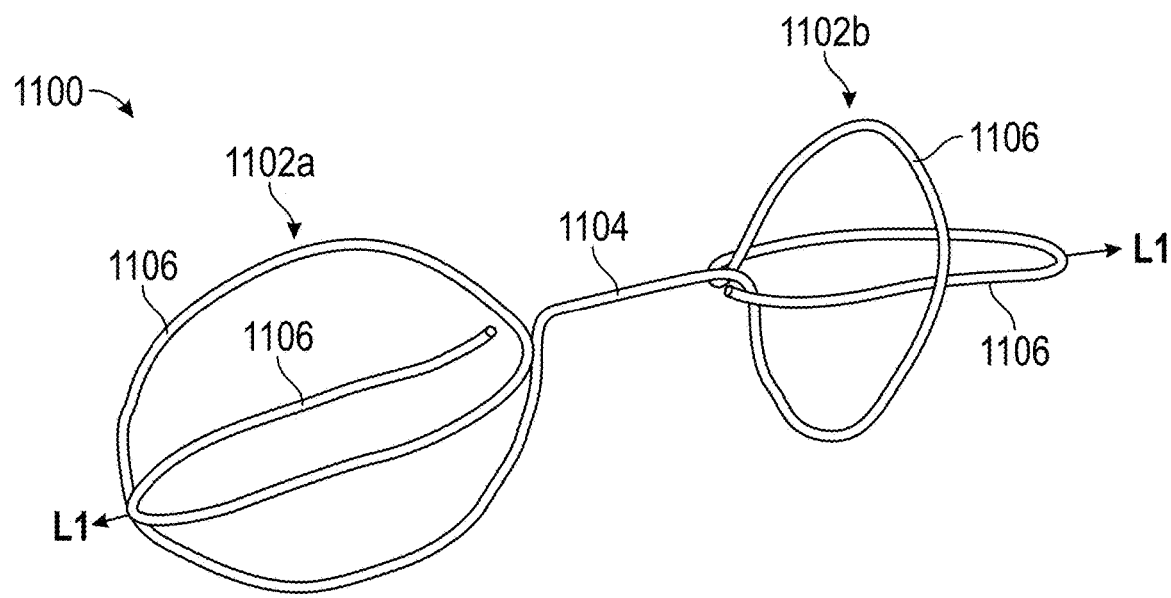
Figure 32:
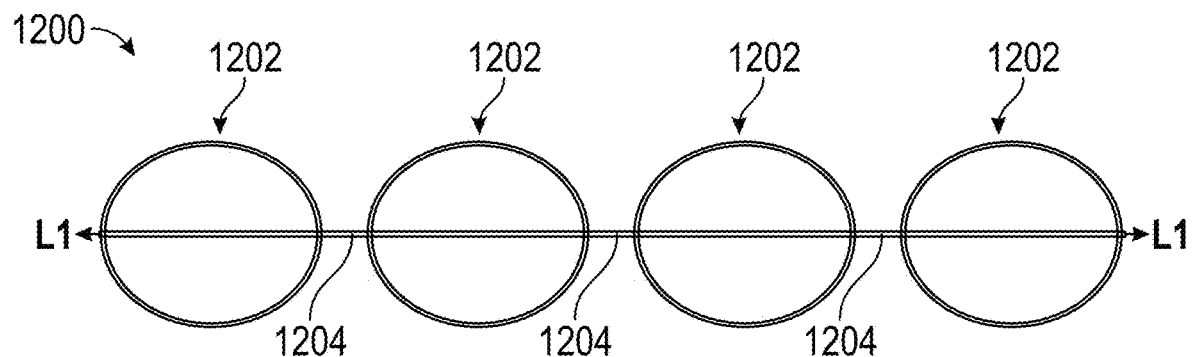
FIGS. 32 and 33 are side views of respective implants in accordance with at least some embodiments of the present technology.

In some embodiments, for example as shown in FIGS. 31 and 32, an expandable device of the present technology can comprise two or more support portions connected by one or more connector portions. FIG. 31 depicts a device 1100 comprising a first support portion 1102a and a second support portion 1102b (collectively "support portions 1102) connected to one another by a connector portion 1104. The first support portion 1102a and/or the second support portion 1102b can be similar to devices 800-1000 shown in FIGS. 25-27. For example, as shown in FIG. 31, each of the support portions 1102 can comprise two loops 1106, each wound about substantially orthogonal axes. In some embodiments, the connector portion 1104 extends along a central longitudinal axis L1 of the device 1100. The support portions 1102 can be configured to contact an airway wall to maintain a minimum desired diameter of the airway lumen, while the connector portion 1104 can be configured to not contact the airway wall to reduce inflammation of the airway wall due to contact between the device 1100 and the airway wall.

As shown in FIG. 31, in some embodiments, the device 1100 comprises two support portions 1102 and one connector portion 1104. However, other numbers of support portions 1102 and connector portions 1104 are possible. For example, FIG. 32 depicts a device 1200 comprising four support portions 1202 disposed along a central longitudinal axis L1 of the device 1200 with adjacent ones of the support portions 1202 connected by connector portions 1204.

An expandable device in accordance with several embodiments of the present technology can be configured to be positioned within a lumen of an airway such that the expandable device increases a diameter of the lumen and thereby facilitates and/or improves transport of gas through the airway. In some embodiments, an expandable device can be positioned within an airway lumen that is collapsed, narrowed, or otherwise reduced in diameter. Expandable devices of the present technology can have a radial resistive force (RRF) that resists compression of the expandable device by the airway wall and/or a chronic outward force (COF) that is applied to the airway wall by the expandable device. The RRF and/or the COF of an expandable device can be of a significant magnitude such that the expandable device is configured to maintain a minimum desired diameter of the airway lumen. An expandable device of the present technology and/or one or more portions thereof can comprise a stent, a braid, a mesh, a weave, a fabric, a coil, a tube, a valve, and/or another suitable device configured to be positioned within an anatomical passageway, airway lumen or vessel to provide support to the passageway and/or another medical device, and/or to modify biological tissue of the passageway.

In certain applications, it may be desirable for an expandable device to be configured to contact a large surface area of a wall of a passageway. For example, coronary stents are often designed such the stent is configured to contact a large surface area of a wall of a patient's coronary artery. Such design may be advantageous for expandable devices configured to be positioned within a blood vessel in order to prevent or limit adverse outcomes (e.g., expandable device thrombosis, neoatherosclerosis, etc.) associated with interactions between the expandable device and the patient's blood. However, because an airway is configured to transport air, not blood, there is no risk of clotting in the airways. Moreover, while clotting is not a risk in the airways, excessive granulation tissue can form in the airways due to contact and/or relative motion between an expandable device and the airway wall. Such excessive granulation tissue can narrow the airway lumen and inhibit gas transport through the airway. Thus, it may be advantageous for an expandable device configured to be positioned within an airway to be configured to contact a smaller surface area of an airway lumen to prevent or limit granulation tissue formation, facilitate mucous clearance from the airway, etc.

Figure 33:
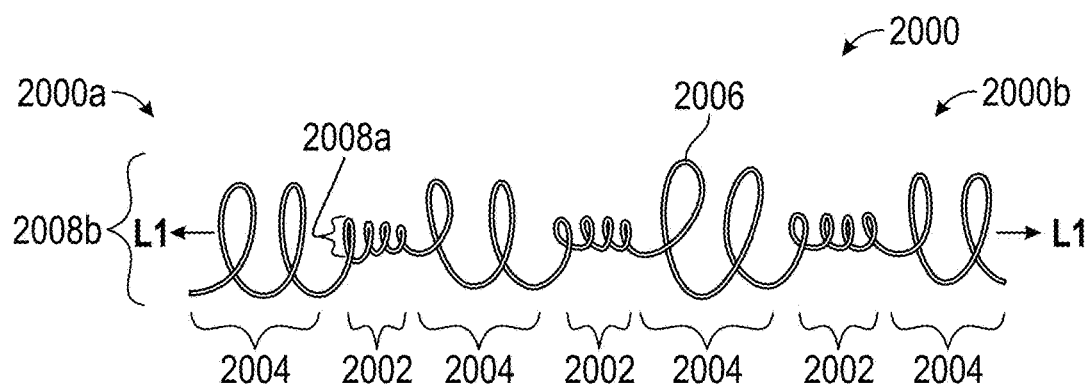

FIG. 33 depicts an expandable device 2000 configured to be positioned within a lumen of an airway such that the expandable device 2000 maintains a minimum desired diameter of the airway lumen. The expandable device 2000 depicted in FIG. 33 can be configured to contact a smaller area of the airway wall when the device 2000 is positioned in the airway lumen relative to a conventional stent. As shown in FIG. 33, the expandable device 2000 can comprise a first end portion 2000a, a second end portion 2000b, and a longitudinal dimension L1 extending between the first and second end portions 2000a, 2000b. The expandable device 2000 can comprise one or more connector portions 2002 and one or more support portions 2004. The support portions 2004 can be connected to the connector portions 2002 and/or monolithic with connector portions 2002. In some embodiments, the expandable device 2000 comprises multiple connector portions 2002 and multiple support portions 2004. Additionally or alternatively, at least some of the connector portions 2002 can be positioned between adjacent support portions 2004. The expandable device 2000 can comprise the same number of connecting portions 2002 and support portions 2004, more connecting portions 2002 than support portions 2004, or more support portions 2004 than connecting portions 2002 (e.g., see FIG. 33). In some embodiments, the expandable device 2000 comprises an elongated member 2006, which can be wound about the longitudinal dimension L1. The elongated member 2006 can comprise a wire, a coil, a braid, a tube, and/or another suitable elongated member. Such flexible construction of the expandable device 2000 can permit longitudinal compression and/or stretching of the expandable device 2000, which may prevent or limit relative motion between the expandable device 2000 and the airway wall as the airways deform longitudinally during respiration, which can in turn prevent or limit granulation tissue formation.

It should be appreciated that the goal of the expandable device is not to eliminate the formation of granulation tissue, as some formation of granulation tissue is expected with any foreign body in the airway, but rather to minimize any clinically meaningful obstruction caused by granulation tissue and/or mucus. It is anticipated that an expandable device with significantly lower contact area will experience a focal foreign body response that will not cause obstruction of the primary airway or distal airways. This focal response might actually be of benefit as partial or full encapsulation of the expandable device may provide stronger mechanical reinforcement of the airway lumen and/or help anchor the expandable device to resist movement due to breathing or coughing.

The expandable device 2000 can have a collapsed, low-profile state in which the expandable device 2000 is configured for delivery through an elongate shaft (e.g., a catheter, etc.) to a treatment location within a patient's airways. Additionally or alternatively, the expandable device 2000 can have an expanded state in which the connector portions 2002 have a first cross-sectional dimension 2008a and the support portions 2004 have a second cross-sectional dimension 2008b. In some embodiments, the second cross-sectional dimension 2008b is greater than the first cross-sectional dimension 2008a.

In these and other embodiments, the expandable device 2000 can be configured to be positioned within the airway lumen such that the support portions 2004 contact the airway wall and the connector portions 2002 do not contact the airway wall. In embodiments in which only the support portions 2004 are configured contact the airway wall, friction applied to the airway wall by the expandable device 2000 due to longitudinal deformation would be limited to the length of the support portions 2004, thereby reducing the risk of granulation tissue formation relative to an expandable device with greater coverage. In some embodiments, the expandable device 2000 can be configured to be positioned within the airway lumen such that both the connector portions 2002 and the support portions 2004 contact the airway wall. When the expandable device 2000 is positioned within the airway lumen, the support portions 2004 can be configured to resist compression by the airway wall and/or apply a radially outward force to the airway wall such that, at least at the support portions 2004, a minimum desired diameter of the airway lumen is maintained. In some embodiments, the second cross-sectional dimension 2008b can substantially correspond to the minimum desired diameter of the airway lumen.

The minimum desired diameter of the airway lumen can be based on a desired capacity for air flow through the airway. In some embodiments, the minimum desired diameter of the airway lumen is based, at least in part, on a nominal diameter of a lumen of a corresponding airway in healthy patients. In some embodiments, the nominal diameter is based on measurements obtained from healthy patients of similar demographics (e.g., sex, age, race, etc.). Additionally or alternatively, the minimum desired diameter of the airway lumen can be based, at least in part, on a diameter of one or more airway lumens in a specific patient. In some embodiments, the minimum desired diameter of the airway is at least as large as a diameter of a lumen of a healthy airway of a corresponding generation. The minimum desired diameter of the airway lumen can be about 0.1 mm, about 0.2 mm, about 0.3 mm, about 0.4 mm, about 0.5 mm, about 0.6 mm, about 0.7 mm, about 0.8 mm, about 0.9 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm. In some embodiments, the minimum desired diameter of the airway is at least 0.1 mm, at least 0.2 mm, at least 0.3 mm, at least 0.4 mm, at least 0.5 mm, at least 0.6 mm, at least 0.7 mm, at least 0.8 mm, at least 0.9 mm, at least 1 mm, at least 2 mm, at least 3 mm, at least 4 mm, at least 5 mm, at least 6 mm, at least 7 mm, at least 8 mm, at least 9 mm, at least 10 mm, at least 11 mm, at least 12 mm, at least 13 mm, at least 14 mm, at least 15 mm, at least 16 mm, at least 17 mm, at least 18 mm, at least 19 mm, at least 20 mm, at least 21 mm, at least 22 mm, at least 23 mm, at least 24 mm, or at least 25 mm.

As airflow resistance through an airway is related to the inverse of the fourth power of the radius of the airway lumen, even small increases in the diameter of the airway lumen can significantly improve an airway's airflow capacity. Moreover, as a patient may have multiple collapsed airways that have extremely high airflow resistance, it may be advantageous for an airway treated with an expandable device of the present technology to have an airflow capacity sufficient to compensate for multiple nonfunctioning airways. Thus, it may be advantageous for the expandable device 2000 to be configured to maintain a diameter of an airway lumen that is greater than a nominal diameter of a lumen of a corresponding healthy airway. Accordingly, the second cross-sectional dimension 2008b can be at least as large as such nominal diameter. For example, the second cross-sectional dimension 2008b can be about 0.1 mm larger than the nominal diameter, about 0.5 mm larger than the nominal diameter, about 1 mm larger than the nominal diameter, about 1.5 mm larger than the nominal diameter, about 2 mm larger than the nominal diameter, about 2.5 mm larger than the nominal diameter, about 3 mm larger than the nominal diameter, or more.

In some embodiments, the minimum desired diameter of the airway can be based, at least in part, on a desired functional measure and/or outcome measure and/or a desired change in a functional or outcome measure. Such functional and outcome measures can include, but are not limited to, forced vital capacity (FVC), forced expiratory volume in one second ($FEV_1$), forced expiratory volume in six seconds ($FEV_6$), functional residual capacity (FRC), total lung capacity (TLC), residual volume (RV), diffusing capacity of the lung for carbon monoxide ($D_{L,CO}$), ($P_{a,O2}$), arterial oxygen saturation ($S_{p,O2}$), health related quality of life (HRQoL), other relevant functional and/or outcome measures, or combinations thereof. For example, it may be acceptable for the minimum desired diameter of the airway lumen to be less than the nominal diameter of a corresponding healthy airway lumen if the minimum desired diameter is associated with desirable and/or sufficient improvements in a functional measure and/or an outcome measure.

In some embodiments, it may be beneficial to perform airflow diagnostic measurements within the airway before, during and/or after administration of the expandable device to confirm improvement in expiratory flow and pulmonary function. Conventional pulmonary function tests like spirometry can be administered separately from the procedure to administer the expandable device or interventional diagnostics can be administered periprocedurally to measure bronchial air flow and pressure (e.g., Chartis® Pulmonary Assessment System). The data obtained from these tests can help inform decisions related to initial treatment, the adequacy of the administered treatment and, if further treatment is required, the extent and location of additional expandable devices.

Implants in accordance with at least some embodiments of the present technology are configured to be placed across multiple airway generations. These implants can have the same or different properties at different axial regions. Expandable devices in accordance with at least some embodiments of the present technology comprise a plurality of treatment zones, each having an expanded cross-sectional dimension, hoop strength, length, and/or flexibility that is tailored to the particular portion of the airway in which it is intended to reside. With reference again to FIG. 33, the expandable device 2000 can be positioned within a patient's airways such that it spans multiple generations and crosses one or more bifurcations in which a proximal airway branches into distal airways. In such embodiments, discrete regions of a first airway branch in each generation spanned by the expandable device 2000 could be supported by the discrete support portions 2004. The connector portions 2002 can be designed to span bifurcations between airway generations. Thus, in some embodiments, the connector portions 2002 can be configured to permit the passage of air, mucous, etc. through the device 2000 and into a second airway branch in each generation that does not contain the device 2000. For device 2000 and any of the devices disclosed herein, the minimalist design (and the low wire gage) is particularly advantageous so as not to block and create occlusion risk for the accessory openings to distal airways.

Figure 34:
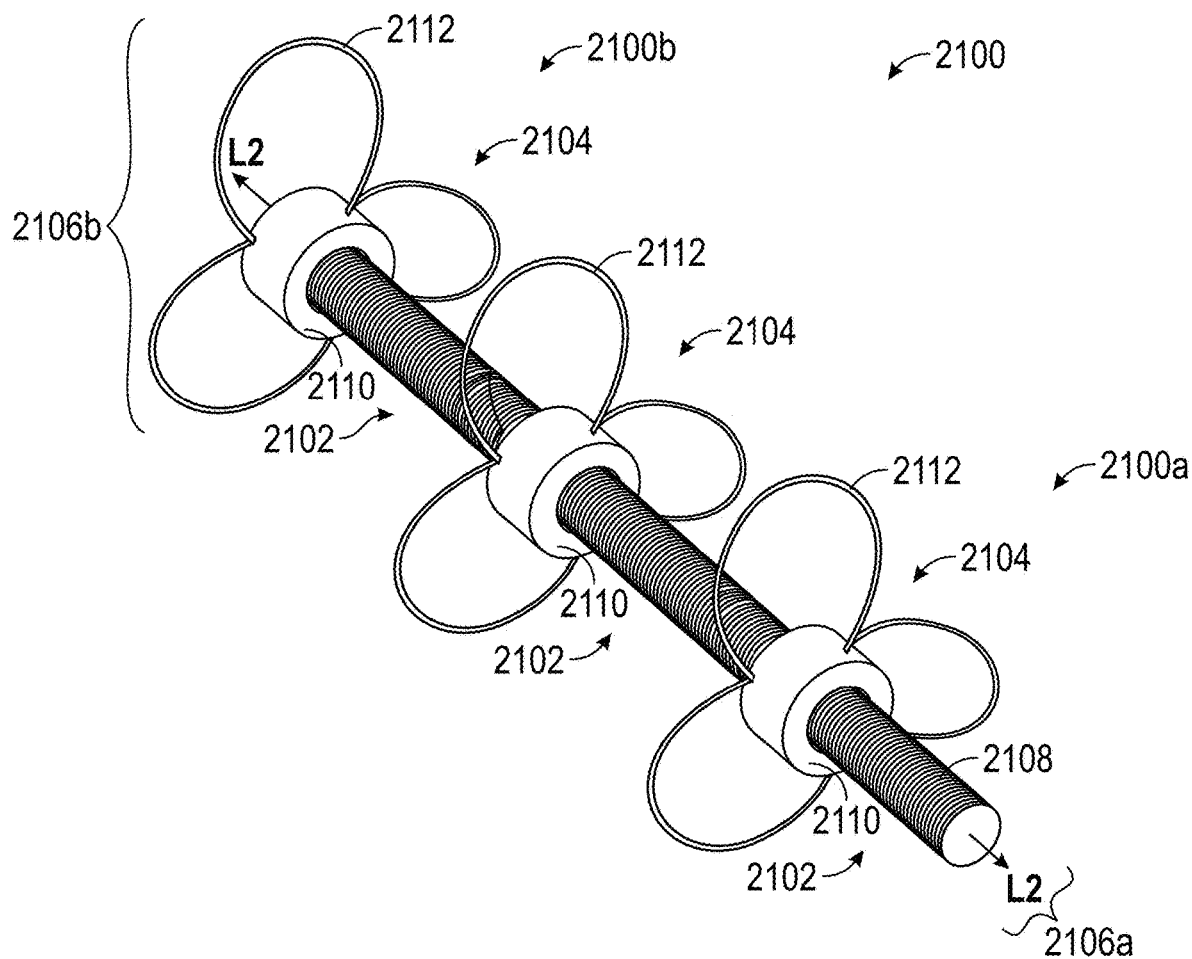
FIG. 34 is a perspective view of an implant in accordance with at least some embodiments of the present technology.

FIG. 34 depicts an expandable device 2100 in accordance with several embodiments of the present technology. The expandable device 2100 can be similar to any of the expandable devices disclosed herein, except as detailed below. The expandable device 2100 can comprise a first end portion 2100a, a second end portion 2100b, and a longitudinal dimension L2 extending between the first and second end portions 2100a, 2100b. The expandable device 2100 can comprise one or more connector portions 2102 and one or more support portions 2104 connected to the connector portions 2102. In some embodiments, the connector portions 2102 can have a first radial dimension 2106a and the support portions 2104 have a second radial dimension 2106b. The second radial dimension 2106b can be larger than the first radial dimension 2106a.

As shown in FIG. 34, the expandable device 2100 can comprise alternating connector portions 2102 and support portions 2104. The expandable device 2100 can comprise the same number of connector portions 2102 and support portions 2104 (see FIG. 34), more connector portions 2102 than support portions 2104, or more support portions 2104 than connector portions 2102. In some embodiments, for example as shown in FIG. 34, the first end portion 2100a of the expandable device 2100 comprises a connector portion 2102 while the second end portion 2100b of the expandable device 2100 comprises a support portion 2104. The first end portion 2100a can comprise a connector portion 2102 or a support portion 2104 and the second end portion 2100b can comprise a connector portion 2102 or a support portion 2104.

The connector portions 2102 of the expandable device 2100 can comprise an elongated member 2108, wherein the elongate member 2108 is configured to exhibit flexibility and facilitate movement of the expandable device 2100 with the airways during respiration to prevent or limit granulation tissue formation. For example, as shown in FIG. 34, the elongated member 2108 can comprise a coil. Additionally or alternatively, the elongated member can comprise a wire, a tube, a braid, a spine, a filament, etc. In some embodiments, one or more of the support portions 2104 can comprise a securing member 2110 and one or more supporting members 2112. The securing member 2110 can be configured to secure the supporting members 2112 to one or more of the connecting portions 2102. For example, the securing member 2110 can have a sidewall defining a lumen (e.g., the securing member 2110 can be tubular, etc.) and the lumen of the securing member 2110 can be configured to receive the elongated member 2108. The securing member 2110 can be welded, crimped, glued, adhered, screwed, melted, or otherwise secured to the elongated member 2108. The supporting members 2112 can be welded, crimped, glued, adhered, screwed, melted, or otherwise secured to the securing member 2110. In some embodiments, the supporting members 2112 are monolithic with the securing member 2110. Additionally or alternatively, the supporting members 2112 can be secured directly to the elongated member 2108. In these and other embodiments, one or more of the support portions 2104 of the expandable device 2100 may not include a securing member 2110.

One or more of the support portions 2104 can comprise one or more supporting members 2112, for example one supporting member 2112, two supporting members 2112, three supporting members 2112 (see FIG. 34), four supporting members 2112, five supporting members 2112, six supporting members 2112, seven supporting members 2112, eight supporting members 2112, nine supporting members 2112, ten supporting members 2112, or more supporting members 2112. The supporting members 2112 of one support portion 2104 can be evenly spaced around a circumference of the expandable device 2100 or the supporting members 2112 of one support portion 2104 can be unevenly spaced around a circumference of the expandable device 2100. Additionally or alternatively, the supporting members 2112 of one of the support portions 2104 can be circumferentially aligned or circumferentially offset relative to the supporting members 2112 of another one of the support portions 2104.

As shown in FIG. 34, the supporting members 2112 can protrude radially outwardly relative to the connector portions 2102 such that, when the expandable device 2100 is positioned within an airway lumen, the supporting members 2112 contact the airway wall and maintain a diameter of the airway lumen. In some embodiments, one or more of the supporting members 2112 has a shape that is substantially arcuate, circular, elliptical, oblong, spherical, rectangular, or another suitable shape. One or more of the supporting members 2112 can comprise a substantially one-dimensional (1D), two-dimensional (2D), or three-dimensional (3D) shape.

The supporting members 2112 can be formed from a wire, a coil, a sheet, a tube, deposited material, and/or another suitable stock material. For example, as shown in FIG. 34, each of the supporting members 2112 can comprise a wire that has been bent into the desired shape. Additionally or alternatively, the supporting members 2112 can be formed via additive manufacturing (e.g., 3D printing, thin film deposition, etc.) and/or subtractive manufacturing (e.g., CNC milling, machining, laser cutting, water etching, etc.).

Figure 35:
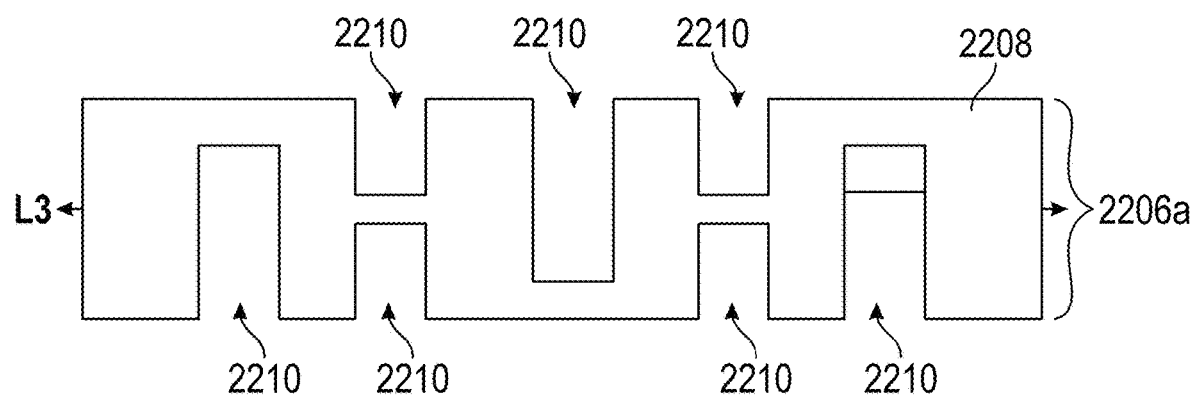
FIG. 35 is a side view of an implant in accordance with at least some embodiments of the present technology.
Figure 36:
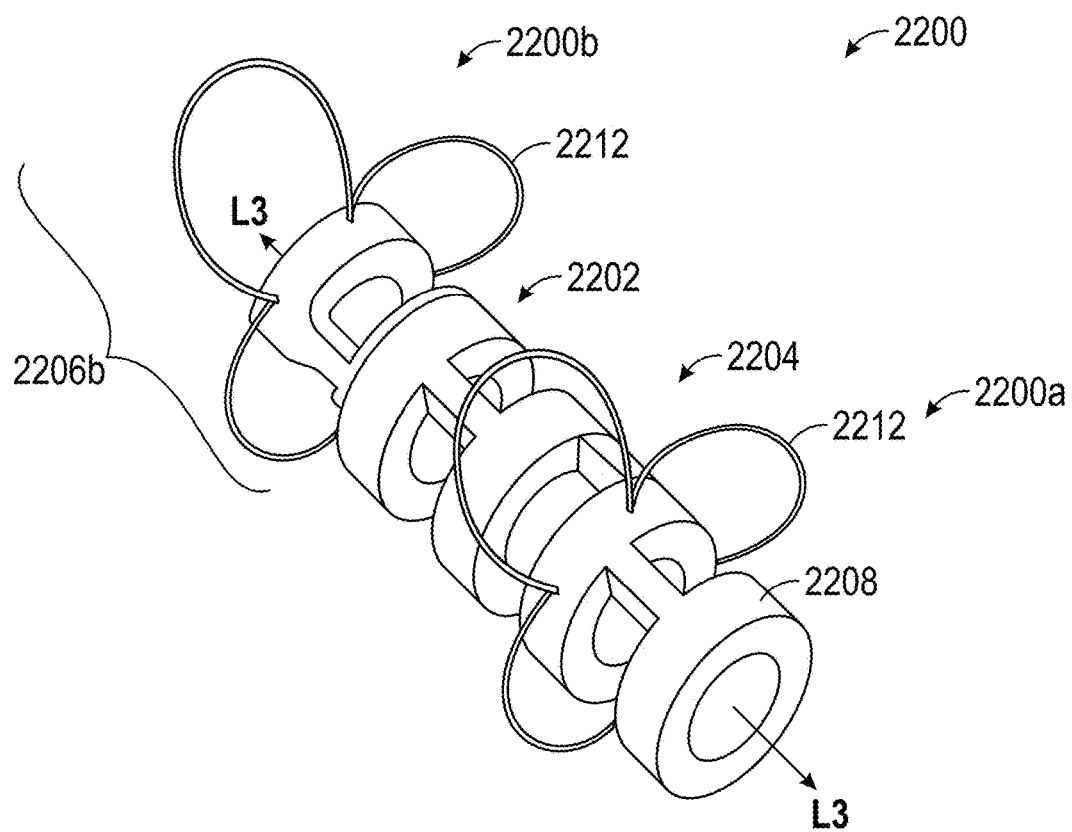
FIG. 36 is a perspective view of an implant in accordance with at least some embodiments of the present technology.

FIGS. 35 and 36 depict an expandable device 2200 according to various embodiments of the present technology. The expandable device 2200 can be similar to any of the expandable devices described herein (e.g., expandable devices 2000, 2100, etc.) except as described below. The expandable device 2200 can comprise a first end portion 2200a, a second end portion 2200b, and a longitudinal dimension L3 extending between the first and second end portions 2200a, 2200b. The expandable device 2200 can comprise a connector portion 2202 and one or more support portions 2204. As shown in FIGS. 35 and 36, the connector portion 2202 can have a first radial dimension 2206a and the support portions 2204 can have a second radial dimension 2206b, which can be smaller than, equivalent to, or larger than the first radial dimension 2206a. The connector portion 2202 can comprise an elongate member 2208, which can comprise a hypotube, a coil, a braid, a mesh, a wire, and/or another suitable structure. For example, as shown in FIGS. 35 and 36, in some embodiments the elongated member 2208 comprises a hypotube defining one or more openings 2210 extending at least partially through a sidewall of the hypotube. The openings 2210 can increase a flexibility of the elongate member 2208, which can facilitate navigation of the expandable device 2200 through tortuous airways. The openings 2210 can be uniformly and/or nonuniformly sized, shaped, spaced along the longitudinal dimension L3 of the device 2200, and/or spaced around a circumference of the elongated member 2208.

The support portions 2204 of the device 2200 can comprise one or more supporting members 2212. In some embodiments, for example as shown in FIG. 35, the supporting members 2212 can be directly secured to the elongated member 2208. The supporting members 2212 can be secured to the sidewall of the elongated member 2208 between the openings 2210. Accordingly, a distribution of the supporting members 2212 about the circumference of the elongated member 2208 and/or the longitudinal dimension L3 of the elongated member 2208 can be based, at least in part, on a corresponding distribution of the openings 2210. In various embodiments, the supporting members 2212 can be welded, crimped, glued, adhered, melted, fastened, screwed, or otherwise secured to the elongate member 2208.

It may be beneficial for one or more parameters of an expandable device of the present technology to be based, at least in part, on a property of the airway the device is configured to be positioned within. For example, it may be desirable for a stiffness of an expandable device to correspond to a stiffness of the airway to prevent or limit granulation tissue formation due to relative motion between the device and the airway. Moreover, in order to facilitate transport of air trapped in hyperinflated parenchymal tissue of a patient out of the patient's body via airways, it may be advantageous for an expandable device of the present technology to be configured to span multiple airway generations when the expandable device is implanted. However, this presents several technical challenges as the mechanical and biological properties of the respiratory system are variable from the proximal, extraparenchymal airways (e.g., the trachea, the primary bronchi, etc.) to the distal, intraparenchymal airways (e.g., the bronchioles, etc.). For example, while the walls of the proximal airways contain cartilage and are internally supported, the amount of hyaline cartilage in the airway walls decreases proximally to distally. As a result, the distal, intraparenchymal airways are highly compliant and expansion and contraction of these airways are controlled by alveolar attachments tethered to the airways. To accomplish the above-noted design objectives and overcome the above-noted challenges, an expandable device configured in accordance with several embodiments of the present technology can have one or more parameters that vary along a length of the expandable device.

An expandable device of the present technology can have at least one region having a stiffness based, at least in part, on mechanical properties of a portion of a patient's airways. For example, because the distal airways are more compliant than the upper airways, a low COF and/or RRF may be sufficient to maintain a desired minimum diameter of a distal airway lumen. Additionally or alternatively, it may be advantageous for a stiffness of a region of an expandable device to be at least partially based on an airway stiffness to prevent or limit granulation tissue forming friction between the device and the airway. For example, because the airways typically decrease in stiffness from the proximal to distal airways, it may be advantageous for an expandable device to also have a decreasing stiffness along its length. In some embodiments, a distal end of an expandable device that is configured to be positioned within intraparenchymal airways can have a lower stiffness than a proximal end of the expandable device that is configured to be positioned within extraparenchymal airways. In some embodiments, a proximal end of an expandable device that is configured to be positioned within intraparenchymal airways can have a lower stiffness than a distal end of the expandable device that is configured to be positioned within extraparenchymal airways.

Figure 37:
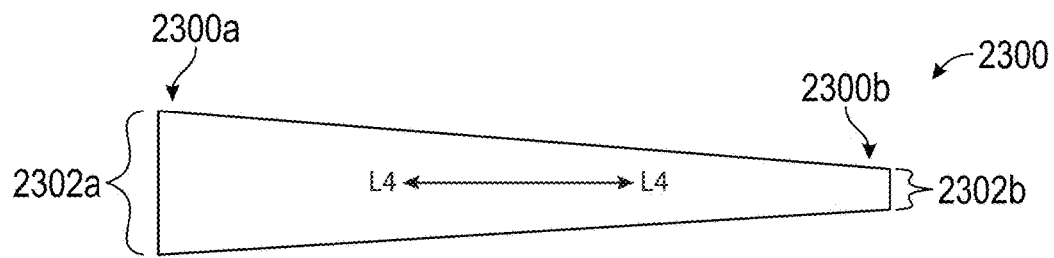
FIG. 37 is a side view of a uniformly tapered wire for use with implants in accordance with at least some embodiments of the present technology.

In some embodiments, an expandable device or one or more portions thereof can comprise a wire (e.g., see FIGS. 33 and 34). In such embodiments, a stiffness of the device can be at least partially based on a thickness of the wire. For example, as shown in FIG. 37, a wire 2300 can have a first end portion 2300a and a second end portion 2300b opposite the first end portion 2300a along a longitudinal dimension L4 of the wire 2300. The first end portion 2300a can be a proximal end portion or a distal end portion. The wire 2300 can have a first thickness 2302a at the first end portion 2300a and a second thickness 2302b at the second end portion 2300b. In some embodiments, the first thickness 2302a can be greater than the second thickness 2302b. Additionally or alternatively, as shown in FIG. 37, the wire 2300 can be tapered along the longitudinal dimension L4.

Figure 38:
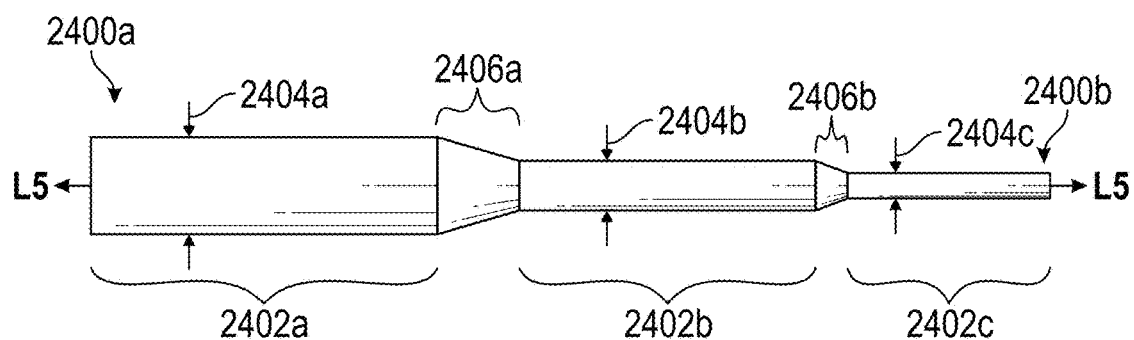
FIG. 38 is a side view of a segmentally tapered wire for use with implants in accordance with at least some embodiments of the present technology.

As shown in FIG. 37, the wire 2300 can be linearly or nonlinearly tapered. Additionally or alternatively, an expandable device can comprise a wire having one or more regions of distinct thickness. For example, FIG. 38 depicts a wire 2400 having a first region 2402a, a second region 2402b, and a third region 2402a (collectively "regions 2402") sequentially arranged along a longitudinal dimension L5 of the wire 2400. Although FIG. 38 depicts three regions 2402, the wire 2400 can have one region 2402, two regions 2402, three regions 2402, four regions 2402, five regions 2402, six regions 2402, seven regions 2402, eight regions 2402, nine regions 2402, ten regions 2402, fifteen regions 2402, twenty regions 2402, or more regions 2402. As shown in FIG. 38, the first region 2402a can have a first thickness 2404a, the second region 2402b can have a second thickness 2404b, and/or third region 2402c can have a third thickness 2404c.

In some embodiments, the first thickness 2404a, the second thickness 2404b, and/or the third thickness 2404c of the wire 2400 shown in FIG. 38 are different. For example, as shown in FIG. 38, the first thickness 2404a can be greater than the second thickness 2402b and/or the third thickness 2404c. In some embodiments, the second thickness 2404b is greater than the third thickness 2404c. Accordingly, the first end portion 2400a can be stiffer than the second end portion 2404b. In embodiments in which the first region 2402a is configured to be positioned in the proximal airways and the third region 2402c is configured to be positioned in the distal airways, an expandable device comprising the wire 2400 can have a stiffness gradient that more closely mimics the stiffness gradient of the airways.

In some embodiments, the wire 2400 comprises one or more transition regions 2406 between the regions 2402 of distinct thickness. For example, as shown in FIG. 38, the wire 2400 can comprise a first transition region 2406a between the first and second regions 2402a, 2402b and a second transition region 2406b between the second and third regions 2402b, 2402c. In some embodiments, a thickness of the wire 2400 can change across a length of at least one of the transition regions 2406 (see FIG. 38). The thickness can change linearly or nonlinearly along the length of the transition region(s) 2406. In some embodiments, one or more of the transition regions 2406 may be omitted such that the thickness of the wire 2400 increases in a stepwise manner.

In some embodiments, an expandable device of the present technology can comprise a tubular elongated member. For example, as previously described with respect to FIGS. 35 and 36, the expandable device 2200 can comprise a connector portion 2202 comprising an elongated member and, in some embodiments, the elongated member may comprise a hypotube. In some embodiments, a stiffness of the expandable device can be based, at least in part, on one or more parameters of the elongated member. As detailed below, such parameters can include a thickness of a sidewall of the elongated member, a diameter of a lumen of the elongated member, a width of a strut of the elongated member, a material property of the elongated member, or another relevant parameter.

Figure 39:
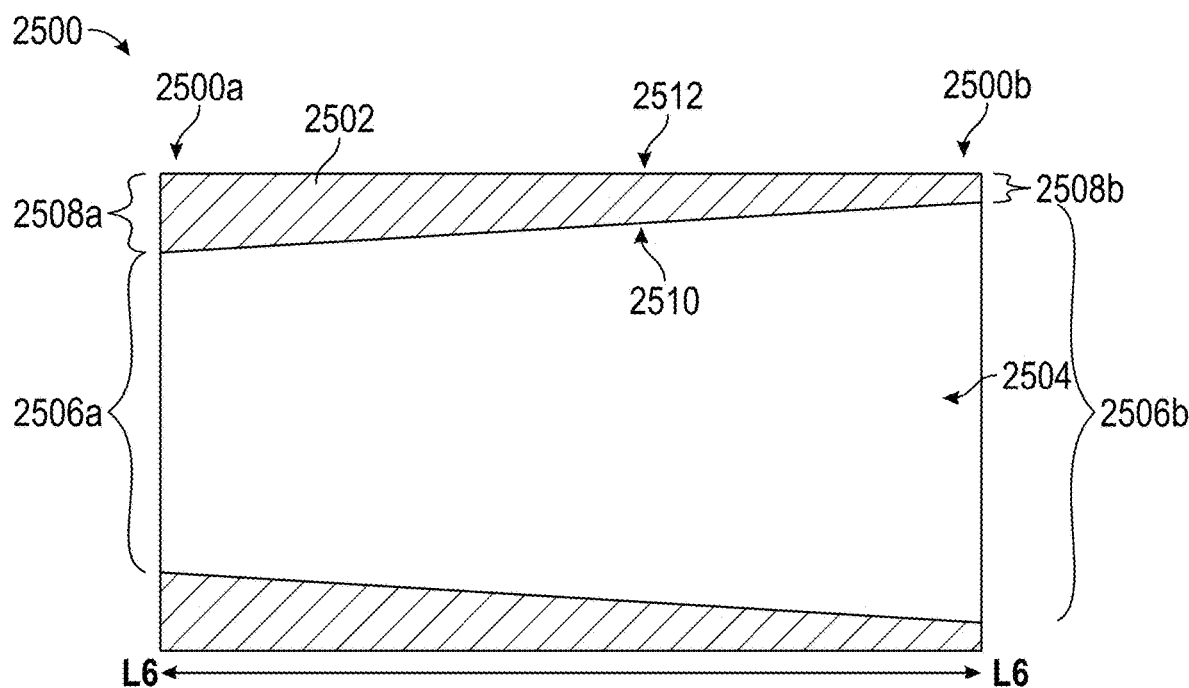
FIG. 39 is a cross-sectional side view of a tapered tube for use with implants in accordance with at least some embodiments of the present technology.

FIG. 39 is a cross-sectional view of an elongated member 2500 that can be used to form an expandable device of the present technology or one or more portions thereof. The elongated member 2500 can comprise a sidewall 2502 defining a lumen 2504 of the elongated member 2500. As shown in FIG. 39, in some embodiments a diameter 2506a of the lumen 2504 at a first end portion 2500a of the elongated member 2500 can be smaller than a diameter 2506b of the lumen 2504 at a second end portion 2500b of the elongated member 2500. As a result, a first thickness 2508a of the sidewall 2502 at the first end portion 2500a can be greater than a second thickness 2508b of the sidewall 2502 at the second end portion 2500b. As shown in FIG. 39, the first and second thicknesses 2508a, 2508b can be defined between a luminal surface 2510 of the elongated member 2500 and an abluminal surface 2512 of the sidewall 2502. In such embodiments, the first end portion 2500a of the elongated member 2500 can be stiffer than the second end portion 2500b. As shown in FIG. 39, a thickness of the sidewall 2502 can decrease (e.g., a diameter of the lumen 2504 can increase) continuously over a longitudinal dimension L6 of the elongated member 2500. Additionally or alternatively, a thickness of the sidewall 2502 can vary along the longitudinal dimension L6 of the elongated member 2500 in discrete steps (e.g., as described with reference to the wire with regions of distinct thicknesses in FIG. 38).

Figure 41:
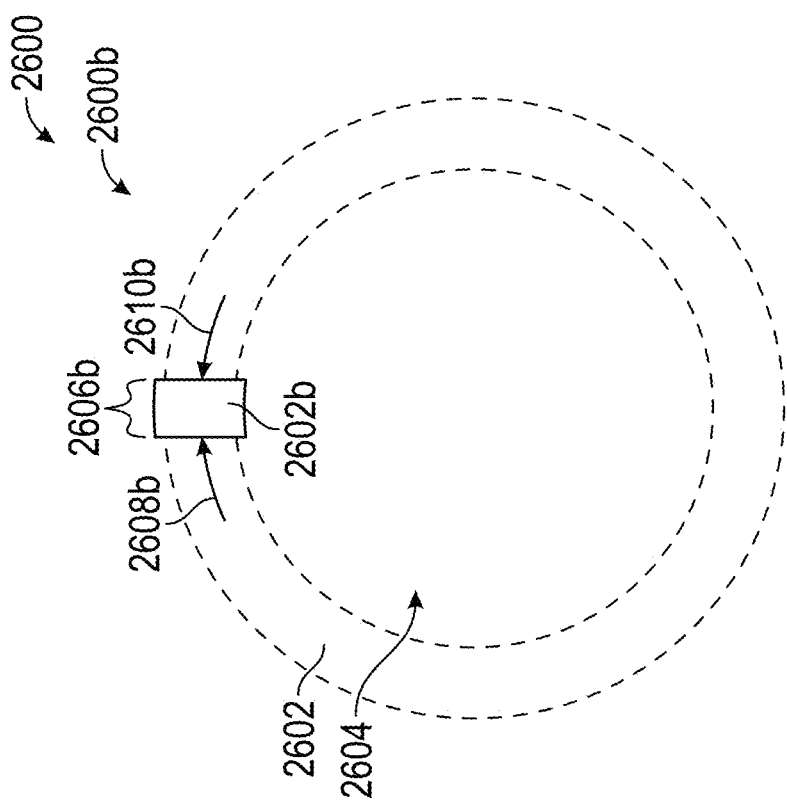
FIG. 41 is an end view of a second end of the elongated member of FIG. 40.
Figure 40:
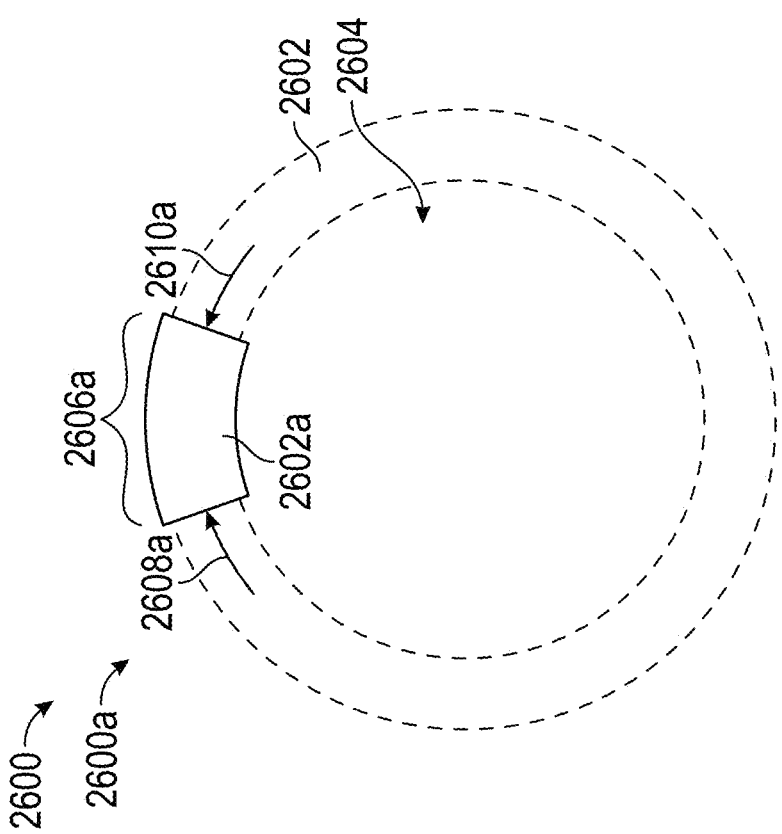
FIG. 40 is an end view of a first end of an elongated member in accordance with at least some embodiments of the present technology.

In some embodiments, an expandable device can comprise an elongated member defining one or more openings extending through a sidewall of the elongated member (see, for example, FIGS. 35 and 36). The elongated member can comprise one or more struts formed comprising the portions of the sidewall located between the openings. According to various embodiments, a stiffness of such expandable devices can be at least partially based on widths of the struts. For example, in some embodiments it may be advantageous for a first end portion of an expandable device to have a larger stiffness, and therefore a larger strut width, than a second end portion of the expandable device. FIGS. 40 and 41 depict an elongated member 2600 having a sidewall 2602 defining a lumen 2604 of the elongated member 2600. Specifically, FIG. 40 is an end view of a first end 2600a of an elongated member 2600 and FIG. 41 is an end view of a second end 2600b of the elongated member 2600. The first end 2600a can be a proximal end and/or a distal end of the elongated member 2600. As shown in FIG. 40, a first strut 2602a of the elongated member 2600 can have a first width 2606a between first and second circumferential surfaces 2608a, 2610a of the first strut 2602a. A second strut 2602b of the elongated member 2600 can have a second width 2606b between first and second circumferential surfaces 2608b, 2610b of the second strut 2602b.

It may be advantageous for a diameter of an expandable device of the present technology to be at least partially based on a diameter of the airways that the expandable device is configured to be positioned within. Sizing a diameter of an expandable device based on a diameter of the airways can facilitate anchorage and retention of the device, limit damage in the airway wall due to excessive strain, limit granulation tissue formation, and/or improve functional and clinical outcomes. Accordingly, in some embodiments an expandable device of the present technology can have a diameter at least partially based on one or more diameters of the airways in which the device is configured to be positioned. However, as with stiffness, the diameter of the airways varies proximally to distally. While the trachea has a nominal diameter between about 10 mm and about 25 mm in adults, the smallest distal airways have diameters less than 1 mm. Thus, in some embodiments a diameter of the expandable device may vary along a length of the expandable device.

Figure 42:
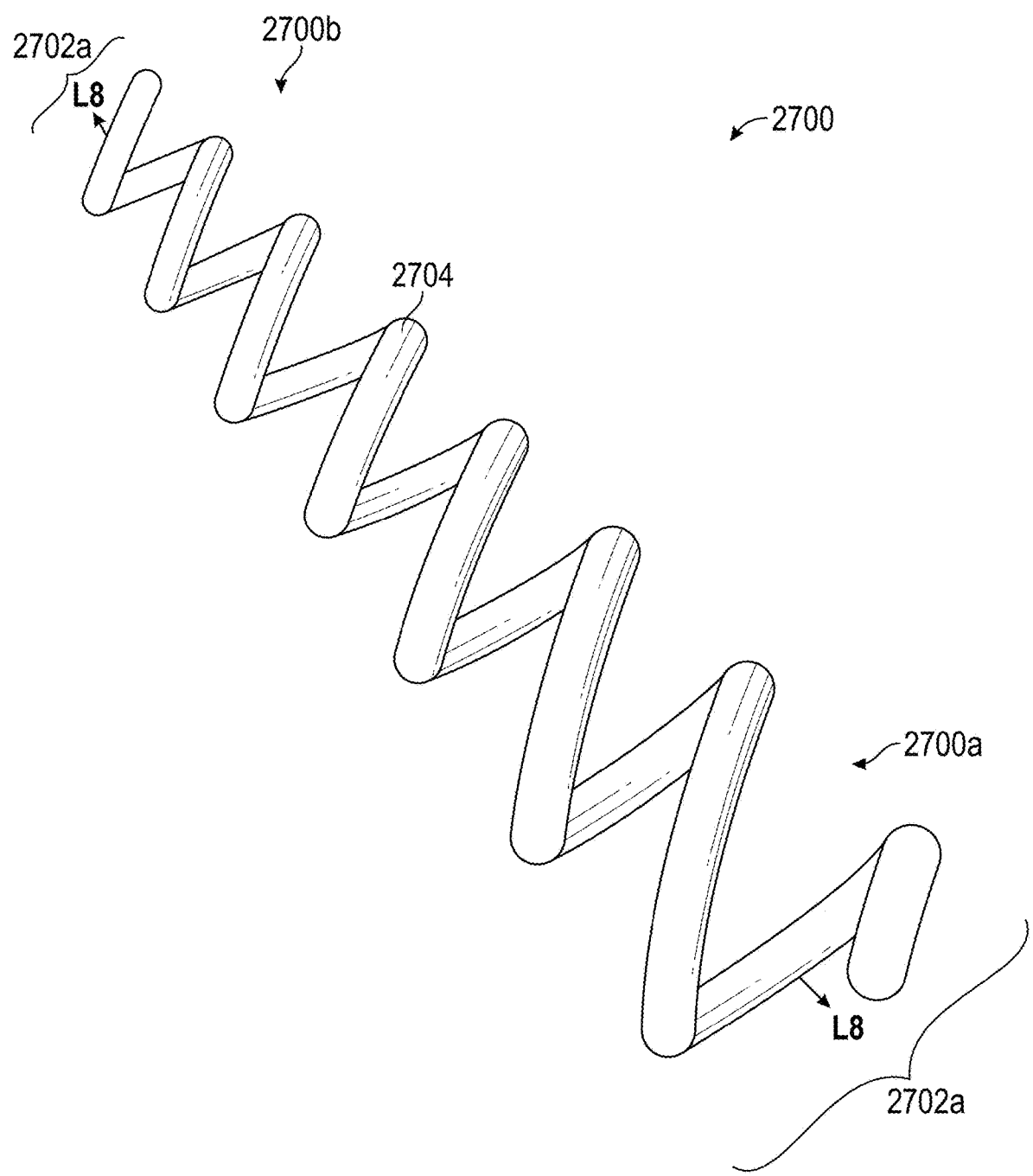

FIG. 42 depicts an expandable device 2700 configured in accordance with several embodiments of the present technology. The expandable device 2700 can have a first end portion 2700a and a second end portion 2700b opposite the first end portion 2700a along a longitudinal dimension L8 of the device 2700. As shown in FIG. 42, in some embodiments a first radial dimension 2702a of the expandable device 2700 at the first end portion 2700a is greater than a second radial dimension 2702b of the expandable device 2700 at the second end portion 2700b. In some embodiments, a radial dimension of the device 2700 can change linearly along the longitudinal dimension L8 (see FIG. 42). Additionally or alternatively, a radial dimension of the device 2700 can change in an exponential manner, a parabolic manner, a step-wise manner, and/or another suitable manner along the longitudinal dimension L8 of the device 2700.

FIG. 43 depicts an expandable device 2800 having a first end portion 2800a and a second end portion 2800b opposite the first end portion 2800a along a longitudinal dimension L9 of the device 2800. The expandable device 2800 can be similar to any of the expandable devices disclosed herein, except as detailed below. As shown in FIG. 43, in some embodiments a radial dimension 2802 of the expandable device 2800 can vary along the longitudinal dimension L9. For example, the radial dimension 2802 can be greater at the first end portion 2800a than at the second end portion 2800b. In some embodiments, the expandable device 2800 comprises an elongated member 2804 wound about the longitudinal dimension L9 to form loops 2806 extending circumferentially about the device 2800. For example, as shown in FIG. 43, the expandable device 2800 can comprise a first loop 2806a, a second loop 2806b, a third loop 2806c, a fourth loop 2806d, and a fifth loop 2806e sequentially arranged along the longitudinal dimension L9.

In some embodiments, the radial dimension 2802 of the device 2800 can vary at one or more of the loops 2806. In FIG. 43, the radial dimension 2802 at the first loop 2806a is greater than the radial dimension 2802 at the second loop 2806b, which is greater than the radial dimension 2802 at the third loop 2806c, which is greater than the radial dimension 2802 at the fourth loop 2806d, which is greater than the radial dimension 2802 at the fifth loop 2806e. Accordingly, the radial dimension 2802 can decrease from the first end portion 2800a of the device 2800 to the second end portion 2800b of the device 2800. Additionally or alternatively, the radial dimension 2802 can increase from the first end portion 2800a of the device 2800 to the second end portion 2800b of the device 2800. In various embodiments, the radial dimension 2802 at any one of the loops 2806 can be greater than the radial dimension 2802 at any other one or more loops 2806.

In some embodiments, at least some of the differences between the radial dimension 2802 at adjacent loops 2806 can be the same (e.g., a difference between the radial dimension 2802 at the first loop 2806a and the radial dimension 2802 at the second loop 2806b is the same as a difference between the radial dimension 2802 at the second loop 2806b and the radial dimension 2802 at the third loop 2806c). Additionally or alternatively, at least some of the differences between the radial dimension 2802 at adjacent loops 2806 can be different.

In some embodiments, for example as shown in FIG. 43, a distance 2808 between each of the loops 2806 along the longitudinal dimension L9 can be substantially the same. However, a length of one airway may be different than a length of other airways that are proximal and/or distal of the airway (e.g., a distal airway may be shorter than a proximal airway, etc.). Thus, it may be beneficial for an expandable device of the present technology to have a design at least partially based on a length of one or more airways. FIG. 44 shows an example of such an expandable device 2900. The expandable device 2900 can be similar to any of the expandable devices disclosed herein, except as detailed below. For example, the expandable device 2900 can comprise a first end portion 2900a and a second end portion 2900b opposite the first end portion 2900a along a longitudinal dimension L10 of the device 2900. The first end portion 2000a can comprise a proximal end portion or a distal end portion. The expandable device 2900 can comprise an elongated member 2902 that is wound about the longitudinal dimension L10 to form loops 2904. For example, as shown in FIG. 44, the device 2900 can comprise a first loop 2904a, a second loop 2904b, a third loop 2904c, a fourth loop 2904d, a fifth loop 2904e, and/or a sixth loop 2904f sequentially arranged along the longitudinal dimension L10.

Adjacent ones of the loops 2904 can be spaced apart according to distances 2906. For example, the first and second loops 2904a, 2904b can be spaced apart according to a first distance 2906a, the second and third loops 2904b, 2904c can be spaced apart according to a second distance 2906b, the third and fourth loops 2904c, 2904d can be spaced apart according to a third distance 2906c, the fourth and fifth loops 2904d, 2904e can be spaced apart according to a fourth distance 2906d, and/or the fifth and sixth loops 2904e, 2904f can be spaced apart according to a fifth distance 2906e. In contrast to the device 2800 depicted in FIG. 43 in which the distances 2808 between loops 2806 have the same magnitude, the device 2900 can comprise at least two of the distances 2906 having different magnitudes (e.g., the first distance 2906a has a different magnitude than the second distance 2906b, the third distance 2906c has a different magnitude than the fifth distance 2906e, etc.). The distances 2906 can decrease from the first end portion 2900a of the device to the second end portion 2900b of the device (see FIG. 44) or vice versa. In some embodiments, the distances 2906 do not change in the same direction along the longitudinal dimension L10 (e.g., the second distance 2906b can be greater than both the first and third distances 2906a, 2906c). The distances 2906 can change linearly or nonlinearly along the longitudinal dimension L10.

Figure 45:
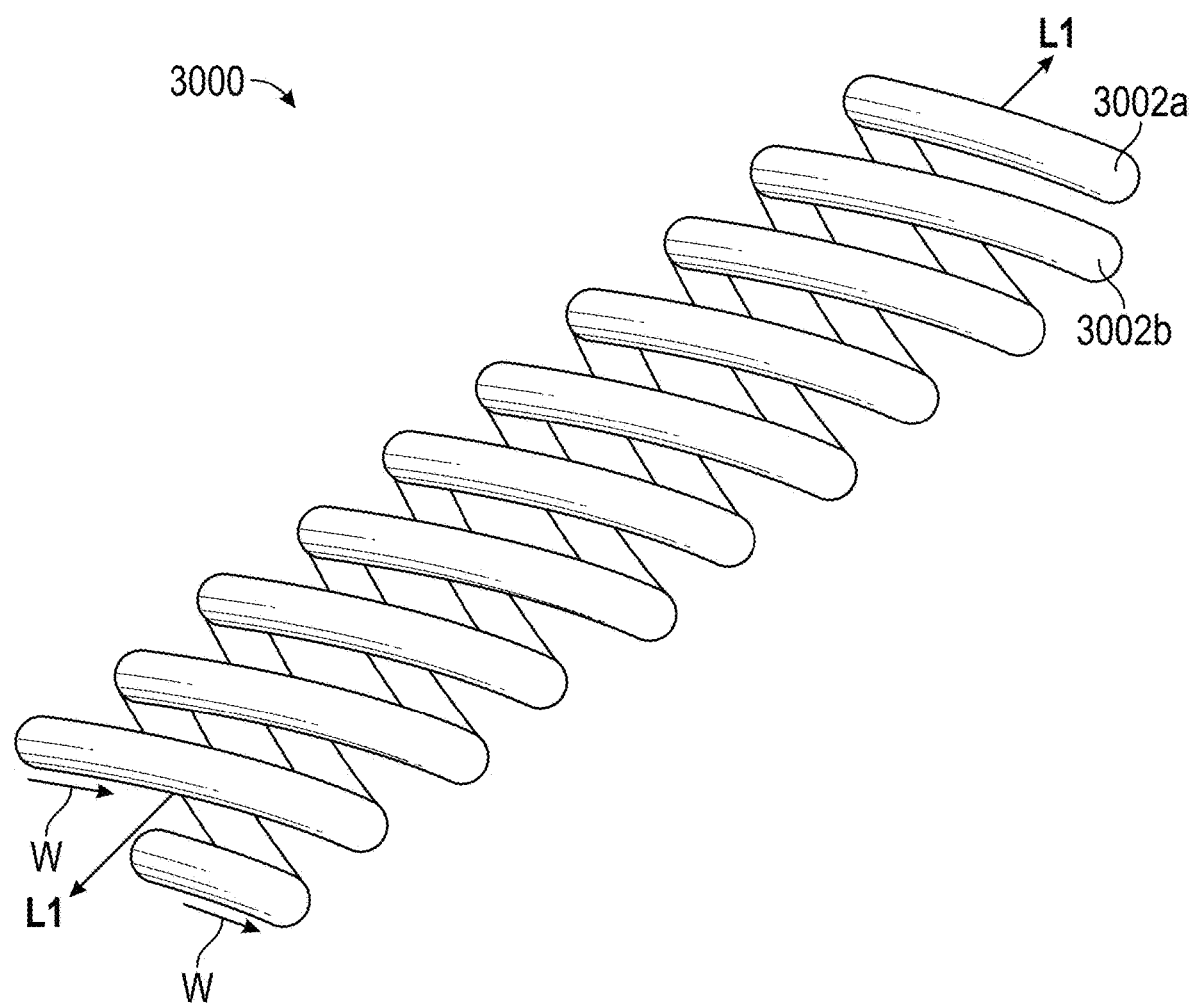

FIG. 45 depicts an expandable device 3000 comprising a first elongated member 3002a and a second elongated member 3002b (collectively "elongated members 3002") that are wound about a longitudinal axis L1 of the device 3000. As shown in FIG. 45, the elongated members 3002 can have the same helical winding direction W. In some embodiments, the first elongated member 3002a can begin at a different circumferential position than the second elongated member 3002b such that, as the elongated members 3002 wind about the longitudinal axis L1, the elongated members 3002 do not overlap.

In any of the above-described embodiments, it may be beneficial to incorporate drug delivery technologies, features and capabilities to counteract an aggressive foreign body response that may, absent such drug delivery, result in occlusion. Broncus Technologies, in development of the Exhale stent for the Airway Bypass procedure, developed a bare metal stent and a paclitaxel-eluting stent. A study in twenty-five dogs demonstrated rapid loss in patency of the bare metal stents and maintenance of patency with the paclitaxel-eluting stents. However, a subsequent human clinical study in over two hundred patients showed that an acute improvement in pulmonary function was not sustained to even thirty days, with stent occlusion suspected as the primary cause of failure. Accordingly, an expandable device possessing a more innovative drug delivery system may be beneficial.

For any of the implants and expandable devices describe herein it may be advantageous to introduce one or more therapeutic agents to address the local healing and/or foreign body responses that may result in full or partial occlusion that undermines the duration of the therapeutic benefit. A utility for controlled, localize drug delivery for a sustained period may preempt or slow the formation of granulation tissue and mucous, thereby mitigating the occlusion risk. This utility may be a formulation of carrier (e.g., polymer, liposome, lipid, etc.) and therapeutic agent that is administered proximate to the treatment site in the airway. This administration of the formulation may occur separately (e.g., needle injection before or after) from the treatment described herein, integrated into the primary procedure (e.g., formulation loaded in the delivery system (e.g., balloon)) or integrated into the implant itself (e.g., expandable device has a polymer-drug coating).

The carrier described herein may adhere to the therapeutic agent to form a matrix. Features may be incorporated into this matrix to achieve a controlled, sustained release of therapeutic agent. One such feature is a releasing agent that is configured to dissolve when contacted by body fluids such that such dissolution will create a porosity of the matrix, thereby allowing for controlled diffusion and release of the therapeutic agent. Suitable releasing agents for use in the present technology include polysorbates, such as Polysorbate 80, Polysorbate 60, Polysorbate 40, and Polysorbate 20; sorbitan fatty acid esters, such as sorbitan monostearate (Span 60), sorbitan tristearate (Span 65), sorbitane trioleate (Span 85), sorbitan monooleate (Span 80), sorbitan monopalmitate, sorbitan monostearate, sorbitan monolaurate, sorbitan monopalmitate, sorbitan trioleate, and sorbitan tribehenate; sucrose esters, such as sucrose monodecanoate, sucrose monolaurate, sucrose distearate, and sucrose stearate; castor oils such as polyethoxylated castor oil, polyoxyl hydrogenated castor oil, polyoxyl 35 castor oil, Polyoxyl 40 Hydrogenated castor oil, Polyoxyl 40 castor oil, Cremophor® RH60, and Cremophor® RH40; polyethylene glycol ester glycerides, such as Labrasol®, Labrifil® 1944; poloxamer; polyoxyethylene polyoxypropylene 1800; polyoxyethylene fatty acid esters, such as Polyoxyl 20 Stearyl Ether, diethylene glycol octadecyl ether, glyceryl monostearate, triglycerol monostearate, Polyoxyl 20 stearate, Polyoxyl 40 stearate, polyoxyethylene sorbitan monoisostearate, polyethylene glycol 40 sorbitan diisostearate; oleic acid; sodium desoxycholate; sodium lauryl sulfate; myristic acid; stearic acid; vitamin E-TPGS (vitamin E d-alpha-tocopherol polyethylene glycol succinate); saturated polyglycolized glycerides, such as Gelucire® 44/14 and Gelucire® 50/13; and polypropoxylated stearyl alcohols such as Acconon® MC-8 and Acconon® CC-6.

Another such feature is the ratio of therapeutic agent to carrier, which can be 1:10, 1:5, 3:10, 2:5, 1:2, 3:5, 7:10, 4:5, 9:10, 1:1, 10:9, 5:4, 10:7, 5:3, 2:1, 5:2, 10:3, 5:1, 10:1. Another such feature is a substantially impermeable coating of the matrix, wherein this coating shall prevent release of therapeutic agent through only portions of matrix that are uncovered (i.e., directional release). Another such feature is the use of multiple layers of coatings or matrices to control and optimize the release profile of one or more therapeutic agents, wherein each layer has either a substantially impermeable coating, a matrix comprising at least one therapeutic agent and polymer or a matrix without a therapeutic agent.

The therapeutic agent may comprise one or more of the following classes of agents: (a) antiproliferative agents, (b) antimucous agents (c) mucolytic material, (d) corticosteroids, (e) antibiotics, (f) anti-inflammatory agents and (g) antimicrobial agents. Examples of antiproliferative agents include sirolimus (rapamycin), everolimus, zotarolimus, paclitaxel, Taxotere (docetaxel), mitomycin-C, gemcitabine, vincristine (leurocristine) and doxorubicin. Examples of antimucous agents include atropine, ipratropium, tiotropium. Examples of mucolytic material include N-acetylcystine and guifensin. Examples of corticosteroids include cortisone, prednisone, prednisolone, methylprednisolone, dexamethasone, betamethasone, hydrocortisone, and others. Examples of anti-inflammatory agents include steroids, prednisone, betamethasone, cortisone, dexamethasone, hydrocortisone and methylprednisolone, non-steroidal anti-inflammatory drugs (NSAIDs), aspirin, Ibuprofen, naproxen sodium, diclofenac, diclofenac-misoprostol, celecoxib, piroxicam, indomethacin, meloxicam, ketoprofen, sulindac, diflunisal, nabumetone, oxaprozin, tolmetin, salsalate, etodolac, fenoprofen, flurbiprofen, ketorolac, meclofenamate, mefenamic acid, COX-2 inhibitors, and others.

In some embodiments the therapeutic agent can be an antibiotic, an antifungal, and/or an antimicrobial, wherein the antibiotic, the antifungal, and/or the antimicrobial is selected from at least one of amoxicillin, amoxicillin/clavulanate, cephalexin, ciprofloxacin, clindamycin, metronidazole, azithromycin, levofloxacin, sulfamethoxazole/trimethoprim, tetracycline(s), minocycline, tigecycline, doxycycline, rifampin, triclosan, chlorhexidine, penicillin(s), aminoglycides, quinolones, fluoroquinolones, vancomycin, gentamycin, cephalosporin(s), carbapenems, imipenem, ertapenem, antimicrobial peptides, cecropin-mellitin, magainin, dermaseptin, cathelicidin, α-defensins, and α-protegrins, ketoconazole, clortrimazole, miconazole, econazole, intraconazole, fluconazole, bifoconazole, terconazole, butaconazole, tioconazole, oxiconazole, sulconazole, saperconazole, voriconazole, terbinafine, amorolfine, naftifine, griseofulvin, haloprogin, butenafine, tolnaftate, nystatin, cyclohexamide, ciclopirox, flucytosine, terbinafine, amphotericin B, and others.

In some embodiments, the expandable device does not include drug-eluting material. This can be useful, for example, to simplify manufacturing and regulatory compliance of the expandable device. Furthermore, as discussed elsewhere in this disclosure, expandable devices in accordance with at least some embodiments of the present technology have one or more other features (e.g., structural and/or performance features) that reduce or eliminate the need for drugs that suppress foreign body response. In these and other cases, the expandable device can include an uncoated wire, such as a bare metal wire.

Modifying Airway Wall

In some of the embodiments described herein, it may be advantageous for the expandable device to modify and/or alter the airway wall. In one example, the expandable device comprises self-expanding capabilities (e.g., nitinol construction), whereby deployment of the expandable device results in the application of a chronic outward force to the airway wall that causes a gradual dilation of the airway wall and expansion of the airway lumen. In this example, the self-expansion of the expandable device would cause the airway wall to expand beyond its native diameter. Additionally, or alternatively, expansion of the expandable device can be facilitated by a balloon configured to be inflated to force expansion of the expandable device. Forced expansion of the expandable device via a balloon (incorporated as part of a delivery system or separate from the delivery system) may be advantageous because the size and pressure of the balloon can be adjusted to control the expansion of the expandable device.

Controlled expansion of the expandable device is desirable in that such controlled expansion will allow for controlled modification of the airway wall. In one example, it may be desirable to cause dilation of the airway wall to increase the cross-sectional area of the airway lumen, but without creating substantial injury to the airway wall. An increase in the cross-sectional area would improve expiratory outflow, thereby yielding a therapeutic benefit in emphysema patients. In other examples, it may be desirable to cause greater dilation of the airway wall so as to create tears, perforations and/or fenestrations in the airway wall. These tears, perforations and/or fenestrations may create openings to other pockets of trapped air within the diseased parenchyma adjacent to the airway, thereby improving expiratory outflow and pulmonary function. Moreover, these tears, perforations and/or fenestrations, if substantial enough in size and number, may prevent the occlusion that resulted in previous attempts to release trapped air. As such, the expandable devices disclosed here can have self-expanding and./or balloon expandable features and capabilities to best achieve the desired modification of the airway wall.

Figures 46, 47:
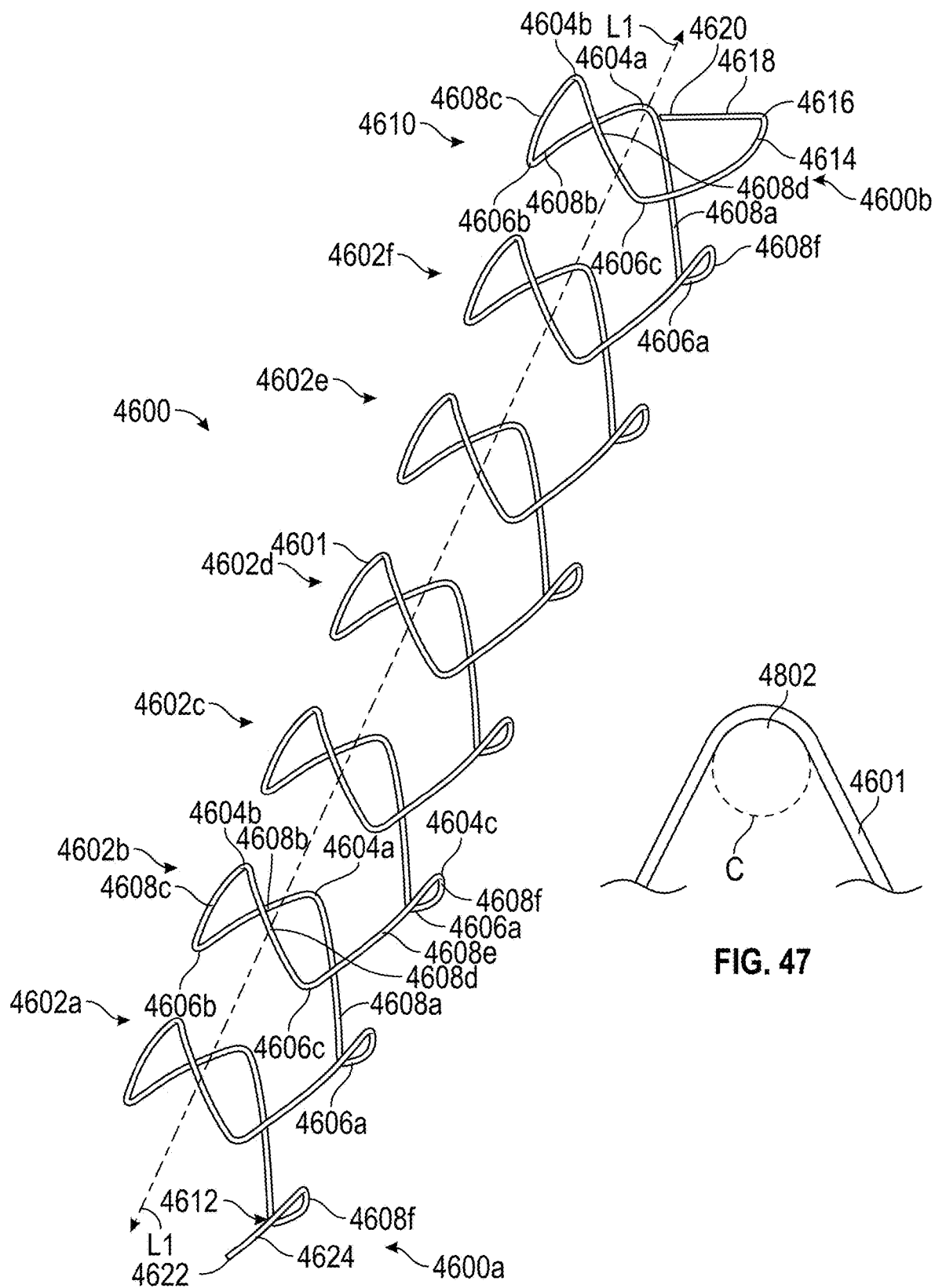

FIG. 46 is a perspective view of an expandable device 4600 configured in accordance with several embodiments of the present technology. In FIG. 46, the device 4600 is shown in an expanded, unconstrained state. The device 4600 has a proximal end portion 4600a, a distal end portion 4600b, and a longitudinal axis L1 extending between the distal and proximal end portions 4600a, 4600b. The device 4600 can comprise a generally tubular structure formed of a wire 4601 wrapped around a longitudinal axis to form a series of bands 4602 (individually labeled as 4602a-4602f), each comprising a 360 degree turn of the wire 4601. The device 4600 further includes a distal structure 4610 distal of the distalmost band 4602f, and a proximal structure 4612 proximal of the proximalmost band 4602a. The wire 4601 undulates between the ends of a given band 4602 such that each band 4602 has a plurality of alternating peaks 4604 (individually labeled as 4604a-4604c) and valleys 4606 (individually labeled as 4606a-4606c) that are connected by struts 4608 (individually labeled as 4608a-46080. The peaks 4604 can comprise the bend apices within a given band 4602 that are closer to and/or point towards the second end portion 4600b of the device 4600, and the valleys 4606 can comprise the bend apices within a given band 4602 that are closer to and/or point towards the first end portion 4600a of the device 4600. The serpentine configuration of each turn of the wire 4601 makes it easier to radially compress the device 4600 onto and/or into a delivery system, and easier to accurately deploy the device 4600, as discussed in greater detail below.

Each band 4602 can have first, second, and third peaks 4604a, 4604b, and 4604c, first, second, and third valleys 4606a, 4606b, and 4606c, and first, second, third, fourth, fifth, and sixth struts 4608a, 4608b, 4608c, 4608d, 4608e, and 4608f The bands 4602 are connected end-to-end such that each band 4602 begins at a first valley 4606a and ends where the sixth strut 4608f meets the first valley 4606a of the next band 4602 (or, in the case of the sixth band 4602f, where the sixth strut 4608f meets the first valley 4606a of the distal structure 4610). Starting at a first valley 4606a and moving distally in a clockwise direction, each band 4602 has a first strut 4608a extending distally from the first valley 4606a to a first peak 4604a, then a second strut 4608b extending proximally from the first peak 4604a to a second valley 4606b, then a third strut 4608c extending distally from the second valley 4606b to a second peak 4604b, then a fourth strut 4608d extending proximally from the second peak 4604b to a third valley 4606c, then a fifth strut 4608e extending distally from the third valley 4606c to a third peak 4604c, then a sixth strut 4608f extending proximally from the third peak 4604 until terminating at the first valley 4606a of the next band 4602. While the device 4600 shown in FIG. 46 comprises three peaks and three valleys per turn, in other embodiments the device 4600 can have any number of peaks and valleys per turn. Moreover, while all of the bands 4602 have the same number of peaks and valleys, in other embodiments some or all of the bands 4602 within the same device can have different numbers of peaks and valleys.

Along the length of the device 4600, and within a given band 4602, the wire 4601 has struts 4608 that extend both proximally and distally in the direction of the wire turn. For example, following the wire 4601 in a clockwise direction around the turn, the device 4601 has struts 4608 that extend distally, then proximally, then distally, then proximally, then distally, thereby forming a plurality of localized, V-shaped braces that when placed within an airway support the airway wall and serve to tent open the airway lumen. This is in contrast to a simple coil in which the wire extends distally continuously as it wraps around each turn. In some embodiments, for example as shown in FIG. 46, the individual first and fifth struts 4608a and 4608e can be longer than the individual second, third, fourth, and sixth struts 4608b, 4608c, 4608d, and 4608f In other embodiments the struts 4608 can have different lengths or configurations. Strut length can be measured along the longitudinal axis of the wire 4601. Likewise, the individual second, third, and fourth struts 4608b, 4608c, and 4608d can be longer than the sixth strut 4608f In some embodiments, the length of the struts 4608 can be determined by the equation 3a−3b=1/pitch, where 'a' is the longer strut and 'b' is the shorter strut 4608.

As previously mentioned, the bands 4602 are connected to one another only by way of the single, continuous wire. Advantageously, all of the peaks 4604 and valleys 4606 are free peaks and valleys, meaning that none of the peaks 4604 and valleys 4606 are connected to a peak, valley, or other portion of a longitudinally adjacent band 4602. This lack of interconnectedness amongst axially adjacent structures provides the device 4600 with enhanced axial flexibility and stretchability as compared to conventional stents that include one or more bridges or other linkages between longitudinally adjacent struts and/or apices. This flexible configuration enables the device 4600 to stretch and bend with the airway in response to different loads (e.g., bending, torsion, tensile) associated with various anatomical conditions (e.g., airway bifurcation, curvature, etc.) and physiological conditions (e.g., respiration, coughing, etc.), thereby allowing the device to move with the airway to minimize relative motion while still maintaining a threshold radial force. In some embodiments, the device 4600 has a ratio of radial force to longitudinal stiffness that is greater than that of conventional stents. This longitudinal and bending flexibility to move with the airway also has the benefit of limiting relative motion between the device 4600 and the airway wall during respiration and other movements like coughing. Relative motion of the device 4600 to the airway wall can cause inflammation and formation of granulation tissue, which over time can partially or completely occlude the newly-opened lumen, thereby obstructing airflow and frustrating the purpose of treatment. Without being bound by theory, the elimination of longitudinal linkages and/or closed cells along the length of the device 4600 may help maintain perfusion of the treated portion of the airway wall, as closed cells can impede blood flow.

As described herein, there are several aspects of the device that contribute to minimizing granulation tissue formation. One aspect is the self-expanding structure and oversizing relative to the airway diameter that produces a chronic outward force against the airway wall that facilitates wall engagement and apposition, thereby minimizing relative motion. A second aspect is the lack of interconnectedness from the free peaks and valleys that allows for considerable flexibility, thereby allowing the device to move with the airway and minimize relative motion. A third aspect is the low material density and high porosity that cause lesser surface area contact with the airway wall, thereby producing less tissue reaction. A fourth aspect is the wire pattern having no closed cells so as to maintain perfusion, thereby minimizing tissue necrosis and local inflammatory reaction.

Another benefit of the lack of interconnectedness associated with the free peaks and valleys of the expandable device is the low tensile force required to disengage the device from the airway wall. A tensile axial load (i.e., pulling) applied to the wire will cause elongation that reduces the diameter of each loop or band, thereby moving each loop or band away from the airway wall. This separation from the airway wall can facilitate retrievability of the device following implantation with minimal trauma or disturbance to the airway wall.

It can be clinically advantageous to place the implant described herein in the distal airway of an emphysematous lung. One historical challenge with conventional, catheter-delivered implants (e.g., stents, braided structures) is the foreshortening that occurs during deployment and implantation. Such foreshortening can make it challenging to accurately deliver the implant to the intended treatment location. Foreshortening is often the result of elongation of the implant during radial compression into a reduced profile for minimally-invasive delivery. Elongation results from the implant's structural design and high material density (i.e., due to the structure and amount of material, the implant cannot stay in the same axial plane when radially compressed). In the device described herein, the lack of longitudinal bridges between axially adjacent structures and relatively low material density (as described below) results in radially compression to a delivery configuration with little to no elongation (e.g., 0%, 5% or less, 10% or less), thereby enabling the device 4600 to be deployed with little to no change in length. Thus, unlike braids and certain stents, the device 4600 does not experience foreshortening when radially expanding. The length of the device 4600 in a compressed, delivery state (for example, see FIG. 49) is substantially the same as the length of the device 4600 in an expanded, unconstrained state. As a result, the device 4600 can be deployed more predictably and with greater landing accuracy.

Figure 51:
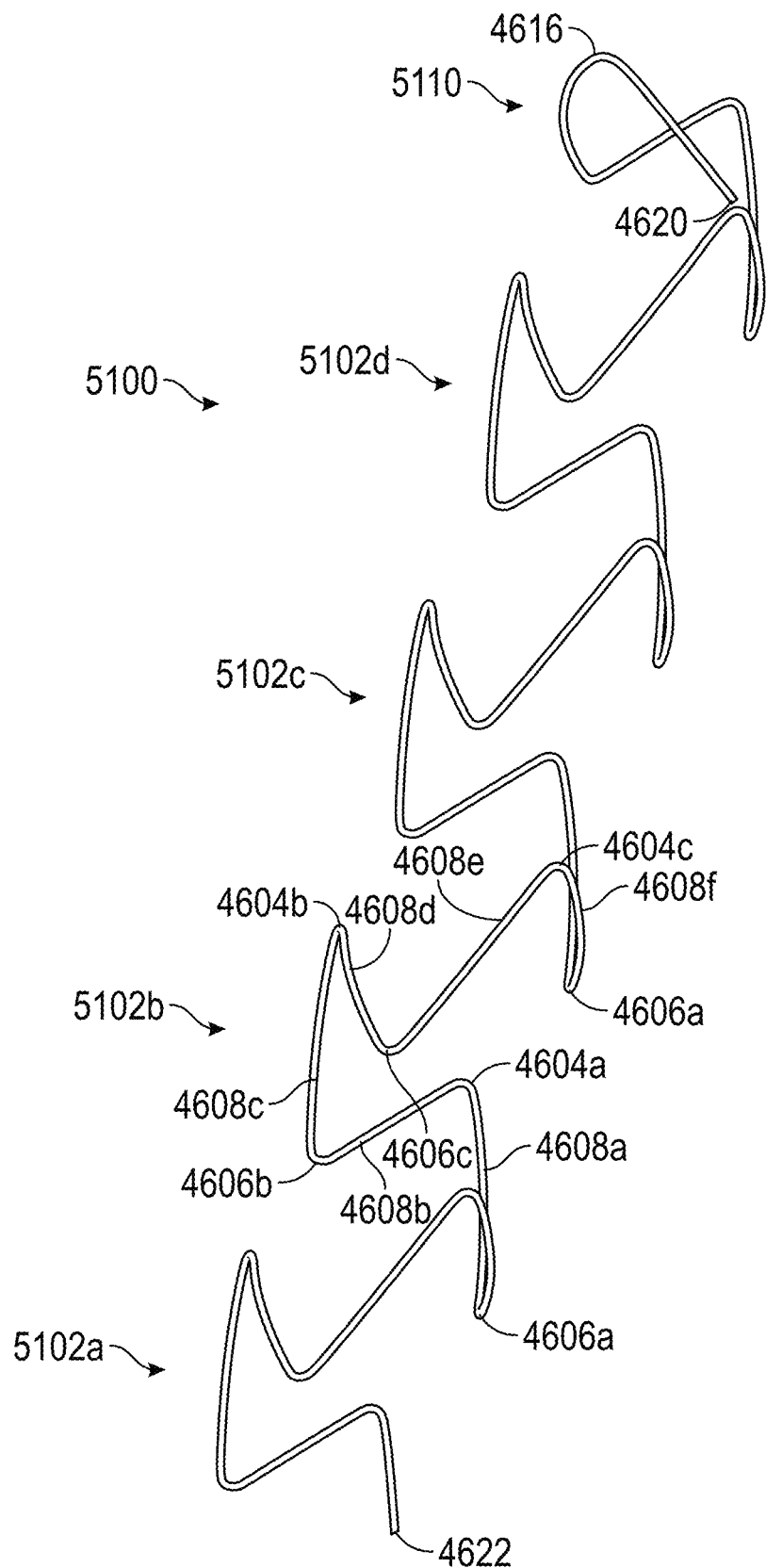
FIG. 51 is a perspective view of an implant in accordance with at least some embodiments of the present technology.

As shown in FIG. 46, the device 4600 can have a turn density that is measured by the number of full (i.e., 360 degree) turns along an inch of the device 4600. It can be advantageous to have a turn density that is low enough (e.g., adjacent turns are longitudinally farther apart) to allow for sufficient spacing between the adjacent turns and/or bands 4602 of the wire 4601 so that the device 4600 can be compressed onto and/or into a delivery system, and low enough that the resulting surface area contact over the length of the device 4600 does not provoke an adverse tissue response. However, it can also be beneficial to have a turn density that is sufficiently high (e.g., adjacent turns are longitudinally closer together) to prevent sagging and/or invagination of the airway wall between adjacent turns (especially during expiratory flow (e.g., exhalation) when the pressure around the outside of the airway are higher than the pressures within the airway), and to ensure sufficient surface area contact for reducing and/or avoiding relative motion and/or migration. As such, the turn density of the present technology can be optimized for delivery system loadability, minimal invagination of the airway wall between turns, minimal relative motion, and minimal local inflammatory response. In some embodiments, the device 4600 has a turn density of about 1 to about 4 turns per inch. In some embodiments, the device 4600 has a turn density of about 1.2 to about 3.5 turns per inch. In particular embodiments, the device 4600 has a turn density of about 1.8 to about 3 turns per inch. In FIG. 46, the device 4600 has a turn density of 3. FIG. 51 shows a device 5100 having a lower turn density of 1.8.

The expanded cross-sectional dimension of the device 4600 may be generally constant or vary along the length of the device 4600 and/or from loop to loop. For example, as discussed herein, the device 4600 can have varying cross-sectional dimensions along its length to accommodate different portions of the airway. For example, in some embodiments the device 4600 can have a diameter that decreases in a distal direction, thereby better approximating the natural distal narrowing of an airway lumen. The diameter may increase in a distal direction gradually over the length of the device 4600, or the device 4600 may have discrete portions with different diameters. For instance, the device 4600 can have a first portion and a second portion along its length. The first portion can have a first cross-sectional dimension that is configured to be positioned in a more distal portion of the airway (such as, for example, in a terminal bronchiole and/or emphysematous areas of destroyed and/or collapsed airways). The second portion can have a second cross-sectional dimension greater than the first cross-sectional dimension and configured to be positioned more proximally (such as in a primary bronchus and/or another portion that has not collapsed). The second portion, for example, can be configured to be positioned in a portion of the airway that is less emphysematous than the collapsed distal portion and/or has cartilage in the airway wall (preferably rings of cartilage and not plates), which can occur at the lobar (generation 2) or segmental (generation 3) level.

In some embodiments, the device 4600 can have a diameter that increases in a distal direction. The diameter may decrease gradually in a proximal direction over the length of the device 4600, or the device 4600 may have discrete portions with different diameters. For instance, the device 4600 can have a generally uniform diameter much of its length, then a larger diameter over the last distal 1-3 turns (which could be bands 4602 and/or a distal structure 4610). In some embodiments, the device 4600 has a first portion and a second portion along its length. The first portion can have a first cross-sectional dimension that is configured to be positioned in a more distal portion of the airway (such as, for example, in a terminal bronchiole and/or emphysematous areas of destroyed and/or collapsed airways). The second portion can have a second cross-sectional dimension less than the first cross-sectional dimension and configured to be positioned more proximally (such as in a primary bronchus and/or another portion that has not collapsed). The second portion, for example, can be configured to be positioned in a portion of the airway that is less emphysematous than the collapsed distal portion and/or has cartilage in the airway wall (preferably rings of cartilage and not plates), which can occur at the lobar (generation 2) or segmental (generation 3) level. Having an enlarged diameter at a distal portion of the device 4600 can be beneficial for exerting more radial force on the distal airways to produce more dilation, or in some cases even create tears in the airway wall. According to some embodiments, it may be beneficial for the device 4600 to be configured to create tears only along certain portions of the airway engaged by the device 4600. Additionally or alternatively, if the lung is particularly diseased, a distal enlargement might better contact the emphysematous lung and help anchor the device.

In some embodiments, the wire 4601 has a circular cross-sectional shape. In other embodiments, the wire 4601 may have other suitable cross-sectional shapes along its length (e.g., oval, rectangle, square, triangular, polygonal, irregular, etc.). In some embodiments, the cross-sectional shape of the wire 4601 varies along its length. Varying the cross-sectional shape of the wire 4601 may be beneficial to varying the mechanical performance of the device 4600 along its length (e.g., transition from lower to higher radial strength proximal to distal or vice versa). Alternatively or additionally, different cross-sectional shapes allows for different distributions of contact force on the airway wall. For example, a wire having an ovular cross-sectional shape will have greater contact area, wider distribution of contact force and, accordingly, lower contact stress at any point on the device 4600 as compared to a circular cross-section. Without being bound by theory, it is believed that is may be beneficial to utilize a cross-sectional shape with rounded edges, as rounded edges may present a less traumatic surface to the airway wall than straight edges. For example, while a wire having a rectangular cross-sectional shape and linear corners can be used with the present technology, in some cases it may be advantageous to utilize a rectangular wire with curved corners.

The wire 4601 can have a generally constant cross-sectional area along its length, or may have a varying cross-sectional area along its length. It may be beneficial to vary the cross-sectional area of the wire 4601, for example, to vary the radial force and/or flexibility of the device 4600 along its length. For instance, the device 4600 will have a lower radial force and/or be more flexible along portions in which the wire 4601 has a smaller cross-sectional area than along portions in which the wire 4601 has a greater cross-sectional area. In some embodiments, the wire 4601 has a diameter of no more than 0.005 inches, no more than 0.006 inches, no more than 0.007 inches, no more than 0.008 inches, no more than 0.009 inches, no more than 0.01 inches, no more than 0.011 inches, no more than 0.012 inches, no more than 0.013 inches, no more than 0.014 inches, and no more than 0.015 inches.

In some embodiments, the expanded cross-sectional dimension of the device 4600 in an unconstrained, expanded state (i.e., removed from the constraints of a delivery shaft, airway and sitting at rest on a table), can be oversized relative to the diameter of the native airway lumen. For example, the expanded, unconstrained cross-sectional dimension of the device 4600 can be at least 1.5× the original (non-collapsed) diameter of the airway lumen in which it is intended to be positioned. In some embodiments, the device 4600 has an expanded, cross-sectional dimension that is about 1.5× to 6×, 2× to 5×, or 2× to 3× the diameter of the original airway lumen. Without being bound by theory, it would be clinically beneficial to expand the airway lumen to the greatest diameter possible. A large airway diameter will allow for more efficient release of trapped air, thereby optimizing improvement in pulmonary function (for example, as measured by outflow, FEV, and others). Additionally, there may be clinical benefit in controlled dilation of the airway wall by the implantable device 4600, with or without the aid of an expandable device (e.g., balloon), to create one or more tears in the airway wall to further facilitate the release of air trapped in the surrounding emphysematous lung.

Given that the cartilaginous support in bronchial airways tends to decline proximal to distal, it may be beneficial to have a device with variable turn density, wherein the turn density in the distalmost portion of the device is greater than the turn density in the proximalmost portion of the device. This device configuration, with greater turn density distally and lower turn density proximally, may optionally include lower radial stiffness distally and greater radial stiffness proximally.

The distal structure 4610 is the first portion of the device 4600 to be deployed in the airway lumen. As a result, the distal structure 4610 can be similar to the bands 4602, but adapted to provide greater circumferential force and a soft, atraumatic landing structure. The final apex 4616 of the wire 4601, for example, can be angled so as to orient the distal terminus 4620 of the wire 4601 proximally, and have a greater radius of curvature in its relaxed, unconstrained state than the other apices so as to provide a rounder, softer bend for first contacting the airway wall. In some embodiments, the distal apex 4616 has approximately the same radius of curvature in the relaxed, unconstrained state as the rest of the apices. Additionally or alternatively, the distal terminus 4620 of the wire 4601 can comprise other atraumatic elements, such as a ball (having a cross-sectional dimension only slightly greater than a cross-sectional dimension of the wire 4601) and/or a looped portion of the wire 4601. To enable a greater anchoring force at the distal end portion 4600*b* of the device 4600, the third valley 4606*c* of the distal structure 4610 can have a greater radius of curvature so as to substantially align the final apex 4616 (which is a peak) with the second-to-last peak 4604*b* of the distal structure 4610.

The proximal end portion 4600*a* of the device 4600 can comprise a single, proximally-extending strut 4624 and a free proximal terminus 4622. Similar to the distal terminus 4620, the proximal terminus 4622 can extend in a proximal direction to limit trauma to the airway wall. The free proximal terminus can also be beneficial for retrieval of the device 4600, if necessary.

The wire 4601 can be any elongated element, such as a wire (e.g., having a circular or ovular cross-sectional shape), a coil, a tube, a filament, a single interwoven elongated element, a plurality of braided and/or twisted elongated elements, a ribbon (have a square or rectangular cross-sectional shape), and/or others. As such, the term "wire," as used herein, refers to the traditional definition of a wire (e.g., metal drawn out into the form of a thin flexible thread or rod), as well as the other elongated elements detailed herein. The wire 4601 can be cut from a sheet of material then wound around a mandrel into the three-dimensional configuration. In some embodiments, the device 4600 is formed by cutting a tube such that the only remaining portions of the tubular sidewall comprise the wire 4601. The sheet and/or tube can be cut via laser cutting, electrical discharge machining (EDM), chemical etching, water jet, air jet, etc. The wire 4601 can also comprise a thin film formed via a deposition process. The elongated member 102 can be formed using materials such as nitinol, stainless steel, cobalt-chromium alloys (e.g., 35N LT®, MP35N (Fort Wayne Metals, Fort Wayne, Indiana)), Elgiloy, magnesium alloys, tungsten, tantalum, platinum, rhodium, palladium, gold, silver, or combinations thereof, or one or more polymers, or combinations of polymers and metals. In some embodiments, the wire 4601 may include one or more drawn-filled tube ("DFT") wires comprising an inner material surrounded by a different outer material. The inner material, for example, may be radiopaque material, and the outer material may be a superelastic material.

The cross-sectional area of the wire 4601 can be selected based on several factors, such as turn density, radial force, and ability to radially compress for delivery. All else equal (such as turn density, length of wire, wire material, etc.), the greater the cross-sectional area of the wire 4601, the greater the radial force exerted on the airway wall. However, the greater the cross-sectional area of the wire 4601 and associated radial force, the more difficult it is to compress the device 4600 into and/or onto a delivery system. As such, the wire 4601 of the present technology has a cross-sectional area that, along with the turn density of the wire 4601, provides the device 4600 with a radial force sufficient to maintain airway patency, resist strain and associated cycle fatigue from anatomical loading during respiration and coughing and reduce and/or eliminate relative motion while still allowing the device 4600 to be compressed down to a diameter of less than 3 mm, and in some cases less than 2 mm.

It can be advantageous to have a radial force high enough to resist migration and, via improved wall apposition, reduce relative motion between the device 4600 and the airway wall, as relative motion can irritate the wall tissue and cause a foreign body response that may contribute to occlusion of the airway. The radial force must also be sufficient to maintain patency of the airway, and in some cases dilate the airway to a diameter that is larger than the native diameter of the airway, for example this could be 2-3 times greater. The radial force exerted by the device 4600 on the airway wall is determined, at least in part, by the turn density of the device 4600 and the cross-sectional area of the wire 4601. For example, the greater the cross-sectional area of the wire 4601, the greater the radial force. The greater the turn density of the device 4600, the greater the radial force. Likewise, the lower the cross-sectional area of the wire 4601, the lower the radial force. The lower the turn density of the device 4600, the lower the radial force. The devices 4600 of the present technology can have a radial force per unit length of no more than 7 g/mm, no more than 6 g/mm, no more than 5 g/mm, no more than 4 g/mm, no more than 3 g/mm, no more than 2 g/mm, or no more than 1 g/mm. In some embodiments, the device 4600 has a radial force per unit length of from about 1 to about 5 g/mm. The radial force required to hold open a collapsed airway and maintain patency during respiration is less than that required by stents used to push or hold back tumor growth or atherosclerosis. Such conventional stents typically have a radial force per unit length of about 10 g/mm or greater.

The device 4600 may be configured to have minimal surface area contact with the airway wall to reduce the amount of foreign body response (such as inflammation and granulation tissue) and risk of airway occlusion. As used in this discussion, "contacting surface area" refers to the surface area of the portion of the device 4600 that contacts the inner surface of the airway wall, which is less than the total surface area of the wire 4601. Minimizing the contacting surface area of the device 4600 can also be beneficial for limiting and/or avoiding occlusion of other distal branch openings, and for enabling more efficient mucociliary clearance. The contacting surface area of the device 4600, however, also impacts the device's ability to resist migration and relative motion. As such, the devices 4600 of the present technology can be configured to have a contacting surface area that is low enough to minimize (or localize) an adverse tissue reaction and allow for sufficient mucociliary clearance, but high enough to provide good contact with the airway and resist motion. The devices 4600 of the present technology can have, for example, a contacting surface area of no more than 20%, no more than 19%, no more than 18%, no more than 17%, no more than 16%, no more than 15%, no more than 14%, no more than 13%, no more than 12%, no more than 11%, no more than 10%, no more than 9%, no more than 8%, no more than 7%, no more than 6%, or no more than 5%. Said another way, the porosity of the device 4600 can be at least 80%, at least 81%, at least 82%, at least 83%, at least 84%, least 85%, at least 86%, at least 87%, at least 88%, at least 89%, at least 90%, at least 91%, at least 92%, at least 93%, at least 94%, or at least 95%.

In some embodiments, regardless of whether the wire 4601 is made of and/or includes a radiopaque material, the device 4600 can include one or more radiopaque markers. The radiopaque markers, for example, can be disposed at one or both ends of the device 4600 to facilitate accurate positioning and placement.

Figure 48:
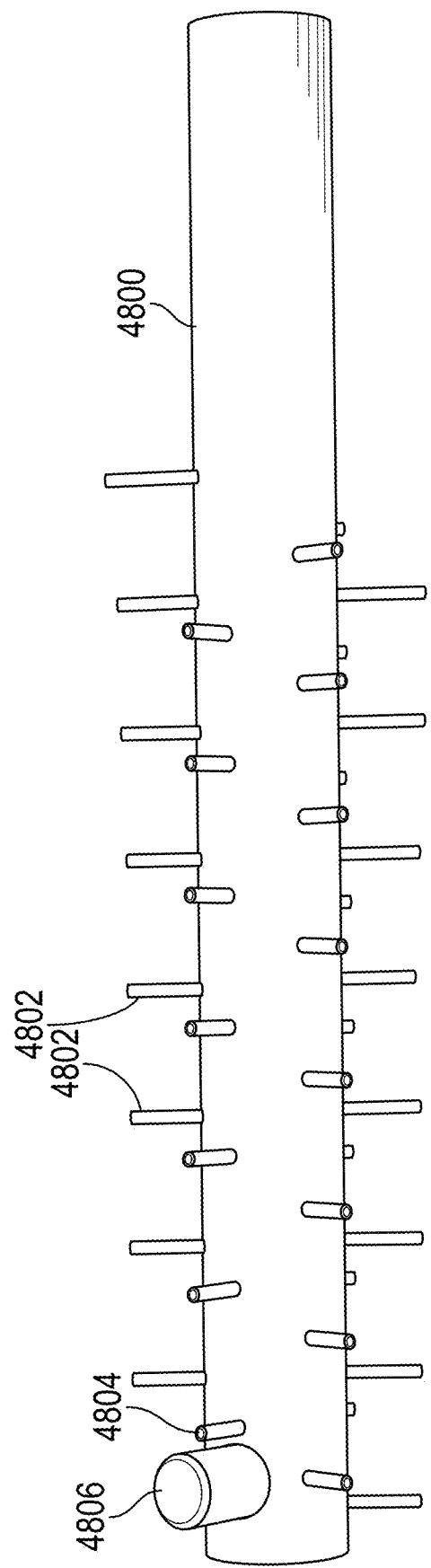
FIG. 48 is a side view of a mandrel configured for use in manufacturing an implant in accordance with at least some embodiments of the present technology.

In some embodiments, the device 4600 is manufactured by wrapping the wire 4601 around a mandrel according to a predetermined wrap pattern, then heat setting the wire 4601 while held in place on the mandrel so that when the wire 4601 is removed from the mandrel, the wire 4601 substantially maintains its on-mandrel shape. FIG. 48 shows a mandrel 4800 configured for use in manufacturing the devices of the present technology. As shown in FIG. 48, the mandrel 4800 can be generally cylindrical and include a plurality of posts 4802 extending radially away from an outer surface of the mandrel 4800. The posts 4802 can be arranged in a pattern that produces a desired wrap geometry. The radius of curvature of the posts 4802, for example, can determine the radius of curvature of the apices. FIG. 47 shows a portion of the wire 4601 wrapped around one of the posts 302. Different apices along the device 4600 can have the same radii of curvature or different radii of curvature.

Figure 49:
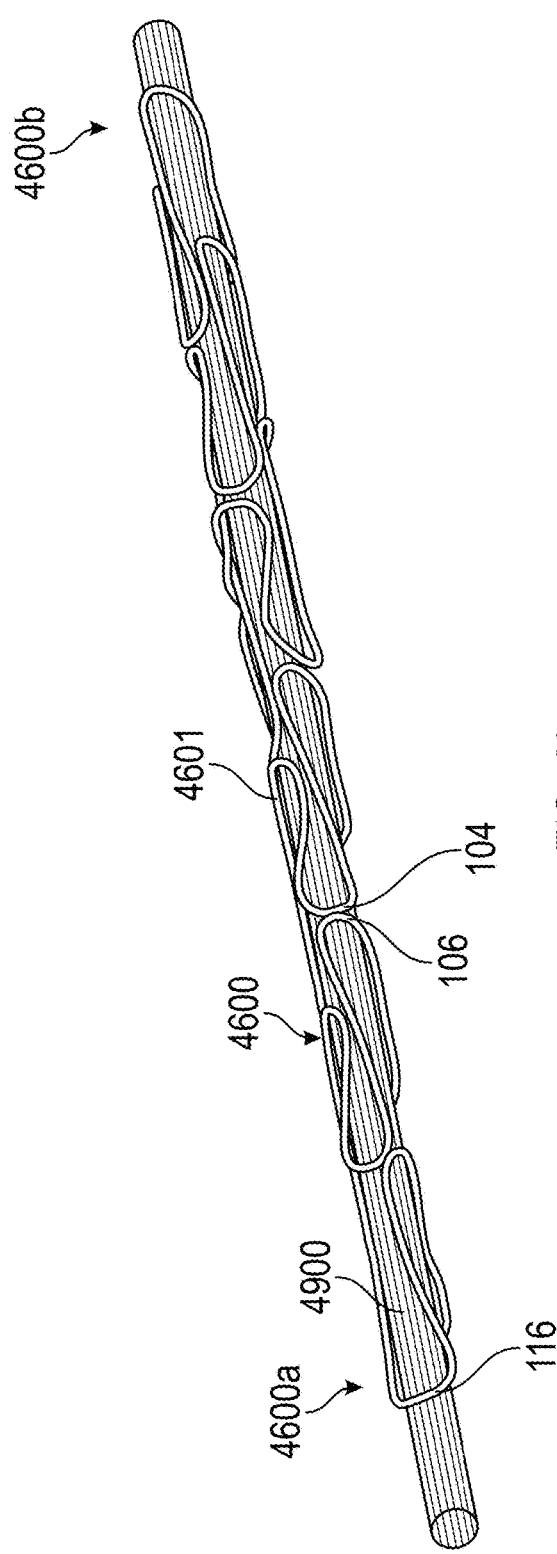
FIG. 49 is a perspective view of the implant shown in FIG. 46 in a radially compressed state around a delivery member.
Figure 50:
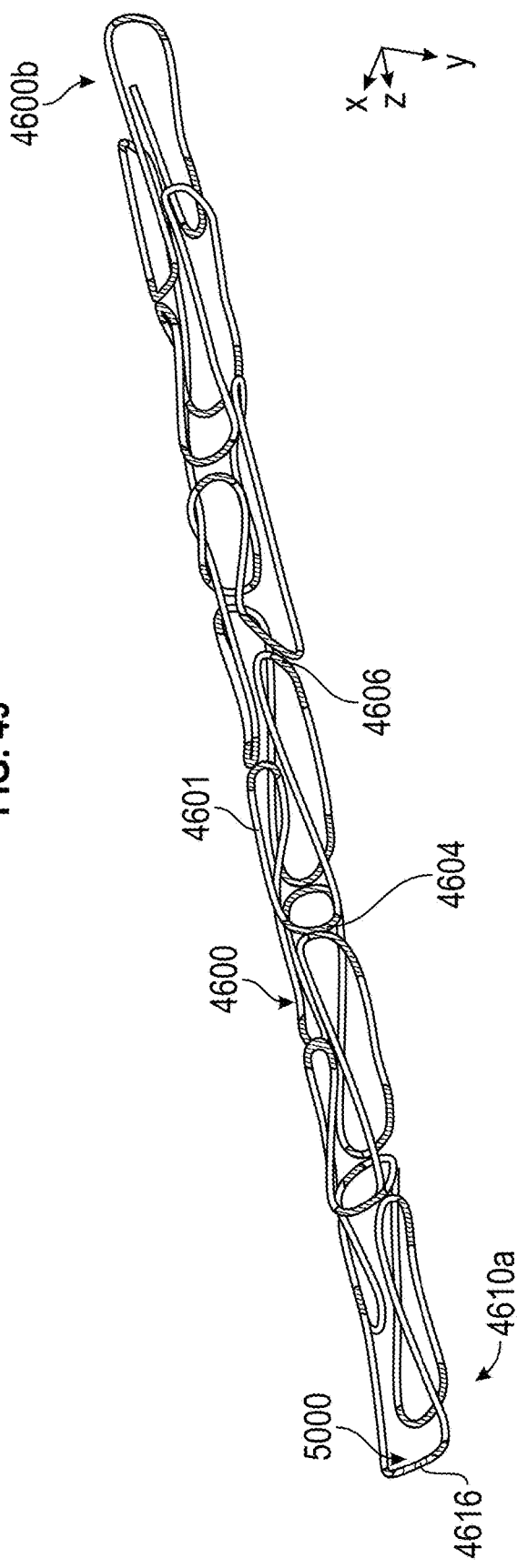
FIG. 50 is a perspective view of the implant shown in FIG. 46 in the radially compressed state shown in FIG. 49 with portions of the implant highlighted for finite element analysis.

In some cases it may be beneficial to use posts having a radius of curvature that closely resembles a shape of the apices when the device 4600 is compressed down onto and/or into a delivery system. FIG. 49 shows the device 4600 in a radially compressed state, positioned over an elongated delivery member 4900. As the device 4600 gets radially compressed, the two struts 4608 adjacent any given peak 4604 or valley 4606 get pinched together, thereby placing a strain on the attached apex. FIG. 50, for example, shows a finite element analysis performed on the device 4600 to calculate cyclic strains, since the device 4600, when implanted, will exhibit cyclic strain in the form of respiration, coughing, and others. As shown in FIG. 50, the strain amplitude peaked at the distal portion where the apex 4616 was heat set to have a radius of curvature that was greater than that of the other apices (such as peak 4604 and valley 4606). The apices that were heat set around smaller diameter posts (having small radii of curvature) were projected to experience less strain and fatigue compared to the distal apex 4616 when forced into a compressed state. Accordingly, it may be desirable for the apices to have an average radius of curvature that is no greater than 2.5 mm (e.g., 2.5 mm or less, 2 mm or less, 1 mm or less, 0.5 mm or less, or within a range from 0.35 mm to 0.60 mm).

Figure 52:
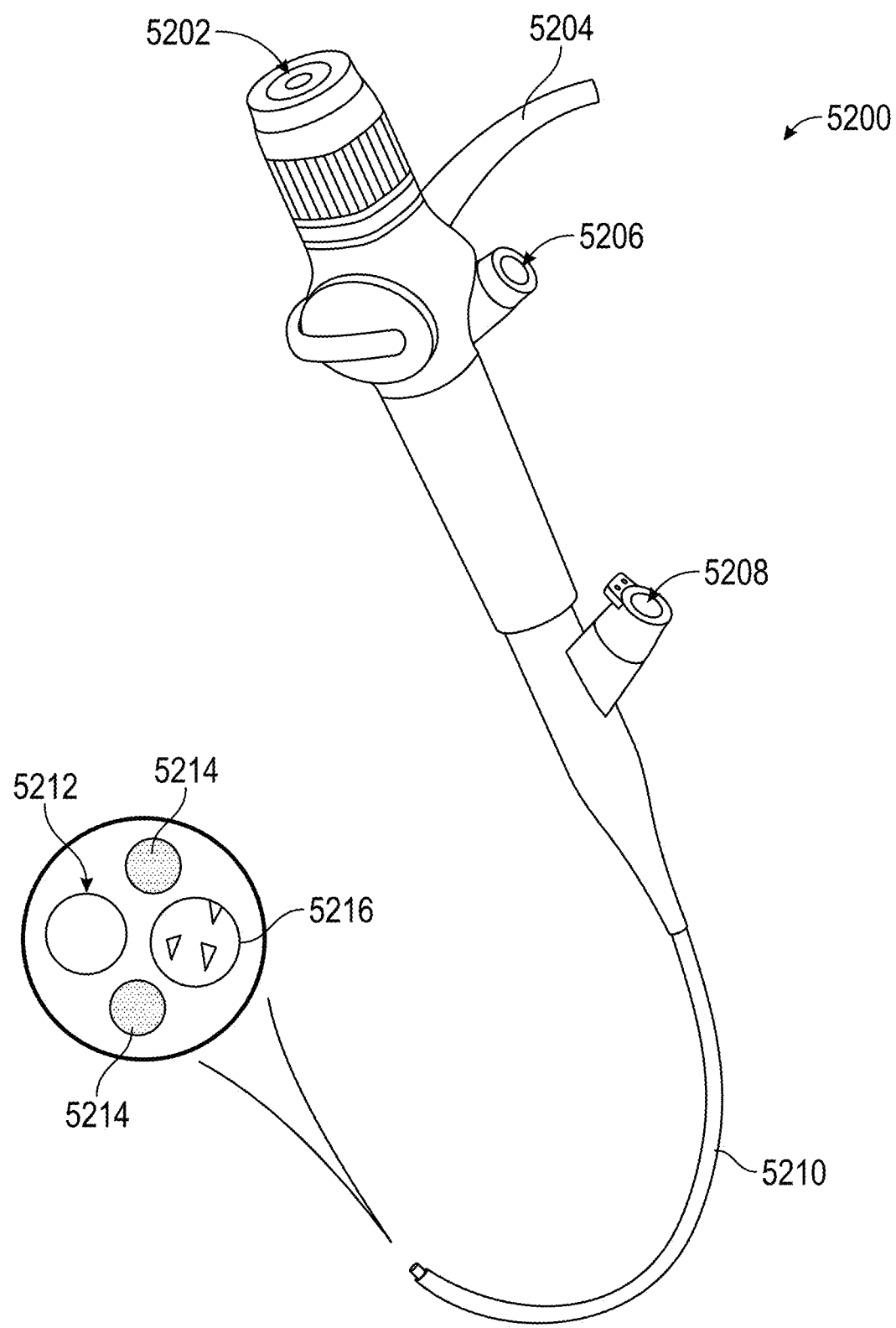
FIG. 52 is a perspective view of a bronchoscope for use with implants in accordance with at least some embodiments of the present technology.

The device 4600 can be configured for delivery through a working channel of a bronchoscope. An example bronchoscope 5200 is shown in FIG. 52. As shown, the bronchoscope 5200 can have a handle with an eyepiece or camera head 5202, a cable 5204 for the light source used for image processing, a suction portion 5206, and a working channel port 5208. The bronchoscope includes an elongated shaft 5210 configured to be advanced through a patient's nose and down through their trachea to the lungs. The shaft 5210 includes several lumens, including a lumen 5216 supporting a camera or fiberoptic cable bundle, lumens 5214 supporting the light source, and the outlet of the working channel 5212. The working channel lumen can have a diameter of about 3 mm or less.

Figure 53:
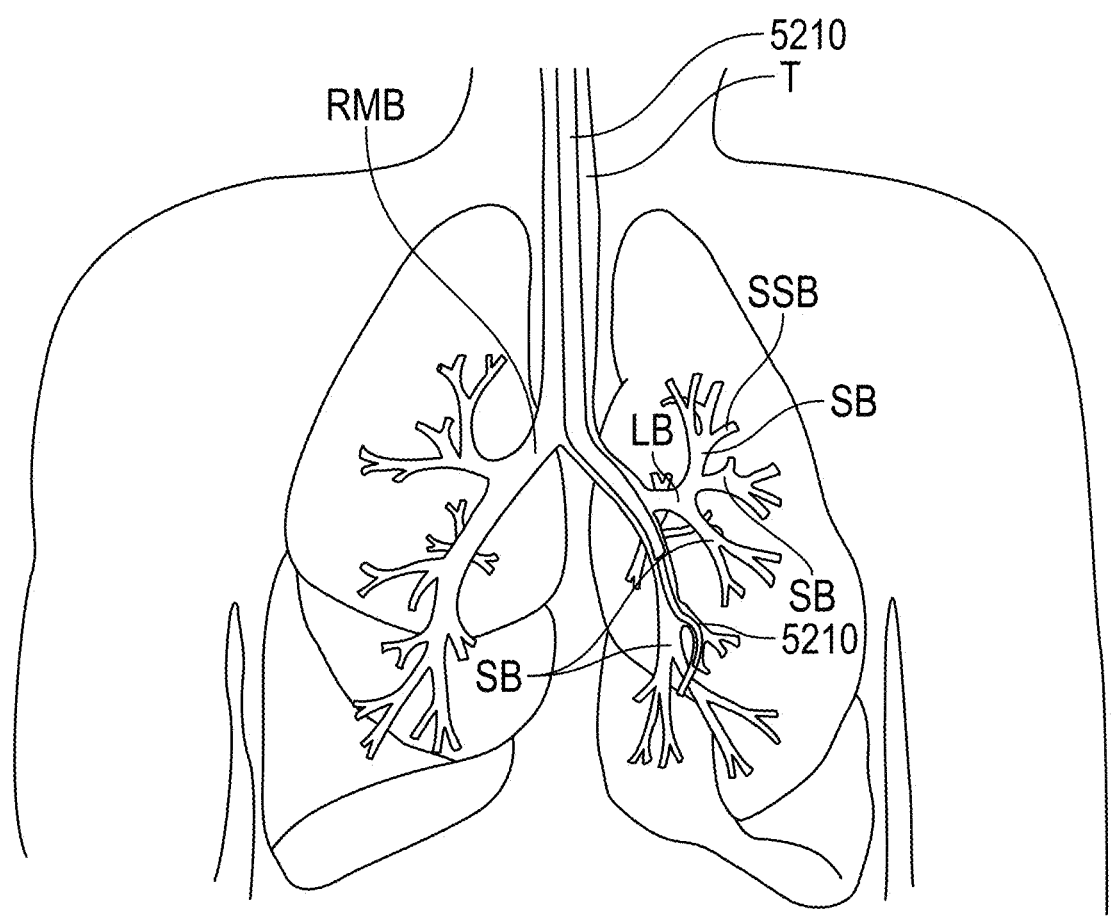
FIGS. 53 and 54 are illustrations showing different respective times during deployment of an implant in accordance with at least some embodiments of the present technology.
Figure 54:
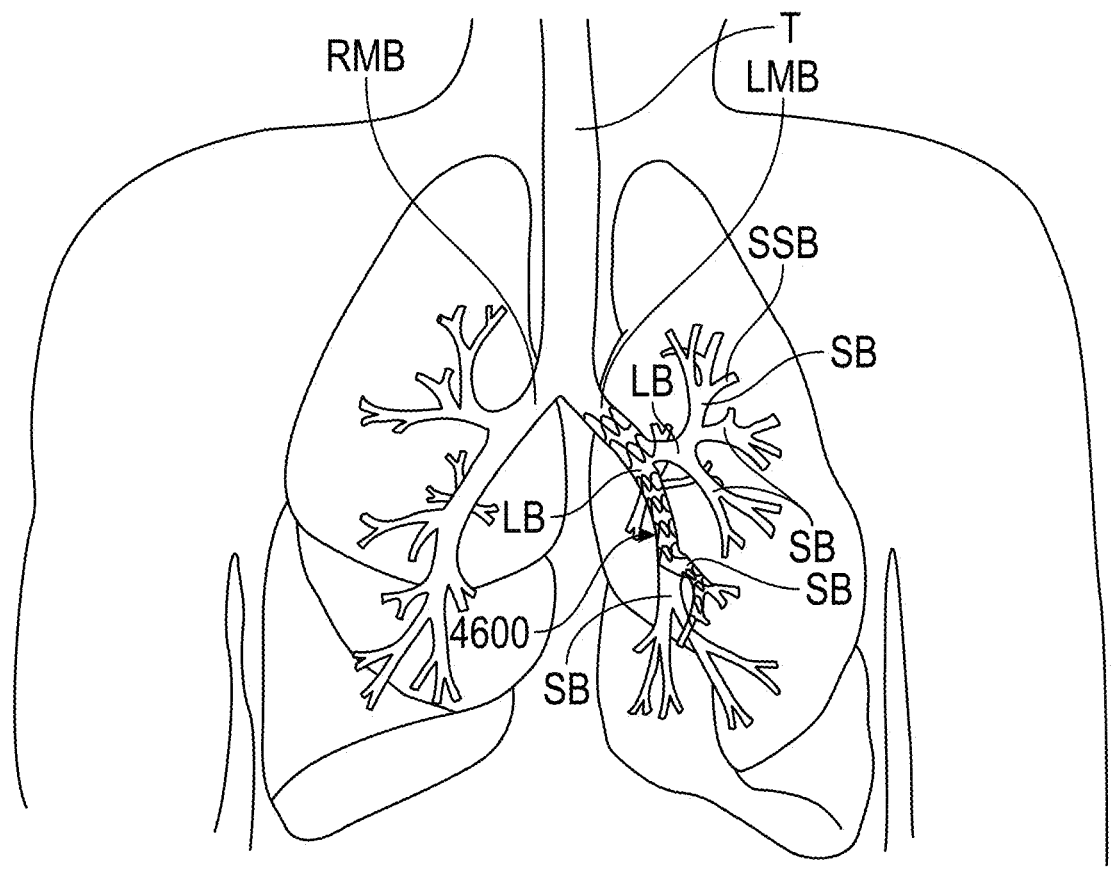

As shown in FIG. 53, the elongated shaft 5210 of the bronchoscope 5200 can be advanced through the trachea and bronchial tree until the diameter of the elongated shaft 5210 approximately matches that of a distended airway and can no longer advance. The position at which the elongated shaft 5210 ceases advancement depends on the bronchoscope being used. For a typical bronchoscope with a 5-6 mm diameter, this would occur in most patients in the $3^{rd}$ to $6^{th}$ generation bronchi. The device 4600 can then be deployed in a distal to proximal direction. FIG. 54 shows the device 4600 after deployment. The distal end portion 4600b of the device 4600 can be placed in a distal airway (e.g., $12^{th}$ to $15^{th}$ generation, having a native diameter of 3 mm or less, including in some cases less than 1 mm) with the proximal end portion 4600a of the device 4600 positioned in a proximal airway (e.g., $2^{nd}$ to $4^{th}$ generation, having a native diameter of about 4-8 mm). In some embodiments, it may be beneficial to position the proximal end portion 4600a of the device 4600 in a portion of the airway with more cartilaginous tissue (e.g., cartilage-reinforced airways) for better anchoring. The device 4600 and/or wire 4601 can be configured to self-expand to a preset configuration and/or diameter. In some embodiments, the wire 4601 is not heat set and/or configured to self-expand. For example, in some embodiments, the device 4600 and/or wire 4601 is balloon-expandable. In some embodiments, the device 4600 and/or wire 4601 is balloon-expandable and self-expanding.

In some embodiments, the device 4600 can be deployed to a discrete length (e.g., 20, 30, 40, 50, 60 cm, etc.) or, given the axial flexibility of the device 4600, the device 4600 and/or delivery system can be designed for variable length deployment (e.g., each device can be designed to be deployed to up to +/−5 cm of its nominal length) to accommodate variability in patient anatomy. According to some embodiments, the present technology includes multiple devices 4600 delivered in series. The devices placed in series may have different lengths to accommodate and fit different treatment lengths. The multiple devices can overlap, touch, or be spaced apart. If spaced apart, the devices may be spaced no more than a predetermined distance apart in the airway (e.g., 5 mm, 1.0 cm, 1.5 cm, 2.0 cm).

FIG. 55A shows the distal portion of a delivery system 5500 configured in accordance with several embodiments of the present technology. The delivery system 5500 can be configured for delivery through a working channel of a bronchoscope. For example, in some embodiments the delivery system 5500 has an outer diameter of no greater than 3 mm. In some embodiments, the delivery system 5500 has an outer diameter of no greater than 2 mm. The system 5500 can include an outer sheath 5502, an inner sheath 5508 configured to be slidably disposed within the outer sheath 5502, and an elongated shaft or other delivery member 5506 disposed within the inner sheath 5508. The outer sheath 5502 can be configured to encase the entire delivery system and engage with the working channel 5212 of the bronchoscope 5200. For example, in some embodiments a proximal end of the outer sheath 5502 is fixed to a handle (not shown) of the delivery system 5500. The inner sheath 5508 is configured to be retracted to expose and deploy the device 4600. In at least some embodiments, the axial position of the delivery member 5506 is fixed relative to the axial position of the outer sheath 5502. For example, a proximal end of the delivery member 5506 can be fixed to the handle of the delivery system 5500. Moreover, the overall delivery system 5500 with the exception of the inner sheath 5508 can be fixed to the bronchoscope 5200. In other embodiments, counterpart delivery systems can have other suitable combinations of movable and fixed components.

In some embodiments, the system 5500 optionally includes a tapered, atraumatic tip 5512 at the distal end of the elongated member 5506. The system 5500 can further include a proximal stop 5504 positioned around the elongated member 5506 and within the inner sheath 5508. The proximal stop 5504 can have a distal-facing surface 5514 configured to abut a proximal end of the device 4600. In some embodiments, the system 5500 optionally includes a pad or other conformable member 5510 radially positioned between the device 4600 and the elongated member 5506. The conformable member 5510 can be more resilient than the elongated member 5506. The conformable member 5510 can have an intimate engagement with the device 4600 when it is radially compressed. For example, as shown in FIG. 55B, the conformable member 5510 can form an indentation 5516 around the device 4600 that helps the device 4600 maintain its axial position. In this or another manner, the device 4600 can be 'tacked' into the conformable member 5510 to hold it in place until the inner sheath 5508 is fully retracted.

In at least some cases, the delivery system 5500 includes features to facilitate fluoroscopic and/or bronchoscopic visualization during delivery and/or deployment of the implant 4600. For example, the delivery system 5500 can include a first radiopaque marker 5518 at a distalmost portion of the tip 5512 to indicate a distalmost feature of the delivery system 5500. The first radiopaque marker 5518, for example, can be a cap or an embedded plug. The delivery system 5500 can further include a second radiopaque marker 5520 at a distalmost portion of the inner sheath 5508 to facilitate estimating a location of a distal end of the device 4600 during delivery and deployment. The second radiopaque marker 5520, for example, can be an annular band. In addition or alternatively, the delivery system 5500 can include pad printed lines or other visual features (not shown) at an outer surface of the inner sheath 5508. These features can facilitate bronchoscopic visualization. For example, one line can be at the proximal end of the device 4600 to indicate where relative to an airway region the proximal end of the device 4600 will be placed after deployment. Furthermore, different indicators can be used to indicate proximal ends of devices of different lengths. For example, one circumferential line can indicate the proximal end of a 70 mm device, two circumferential lines can indicate the proximal end of a 85 mm device, three circumferential line can indicate the proximal end of a 100 mm device, etc.

The elongated shaft 5210 of the bronchoscope 5200 can be advanced through the trachea and bronchial tree until the diameter of the elongated shaft 5210 approximately matches that of a distended airway and can no longer advance. The position at which the elongated shaft 5210 ceases advancement may be different depending on the bronchoscope being used. For a typical bronchoscope with a 5-6 mm diameter, this would occur in most patients in the 3$^{rd}$ to 6$^{th}$ generation bronchi. The delivery system 5500 can then be advanced distally through the distal opening of the working channel 5212 such that the outer sheath 5502 is exposed within the airway lumen. The delivery system 5500 can be advanced distally until the distal end portion of the outer sheath 5502 is positioned within a distal portion of the airway (such as, for example, in a terminal bronchiole and/or emphysematous areas of destroyed and/or collapsed airways). With the outer sheath 5502 and elongated delivery member 5506 held in position, the inner sheath 5508 can be retracted to expose and deploy the device 4600 at a desired location.

It will be appreciated that other delivery systems are within the scope of the present technology. Moreover, the bronchoscope 5200 and delivery system 5500 can be used with any of the expandable devices disclosed herein.

Additional examples of expandable devices, systems, and methods for treating COPD and/or devices, systems, and methods for modifying an airway wall can be found, for example, in U.S. Pat. No. 9,592,138, filed Sep. 13, 2015, titled PULMONARY AIRFLOW, which is incorporated by reference herein in its entirety.

Additional Example

Figure 56A:
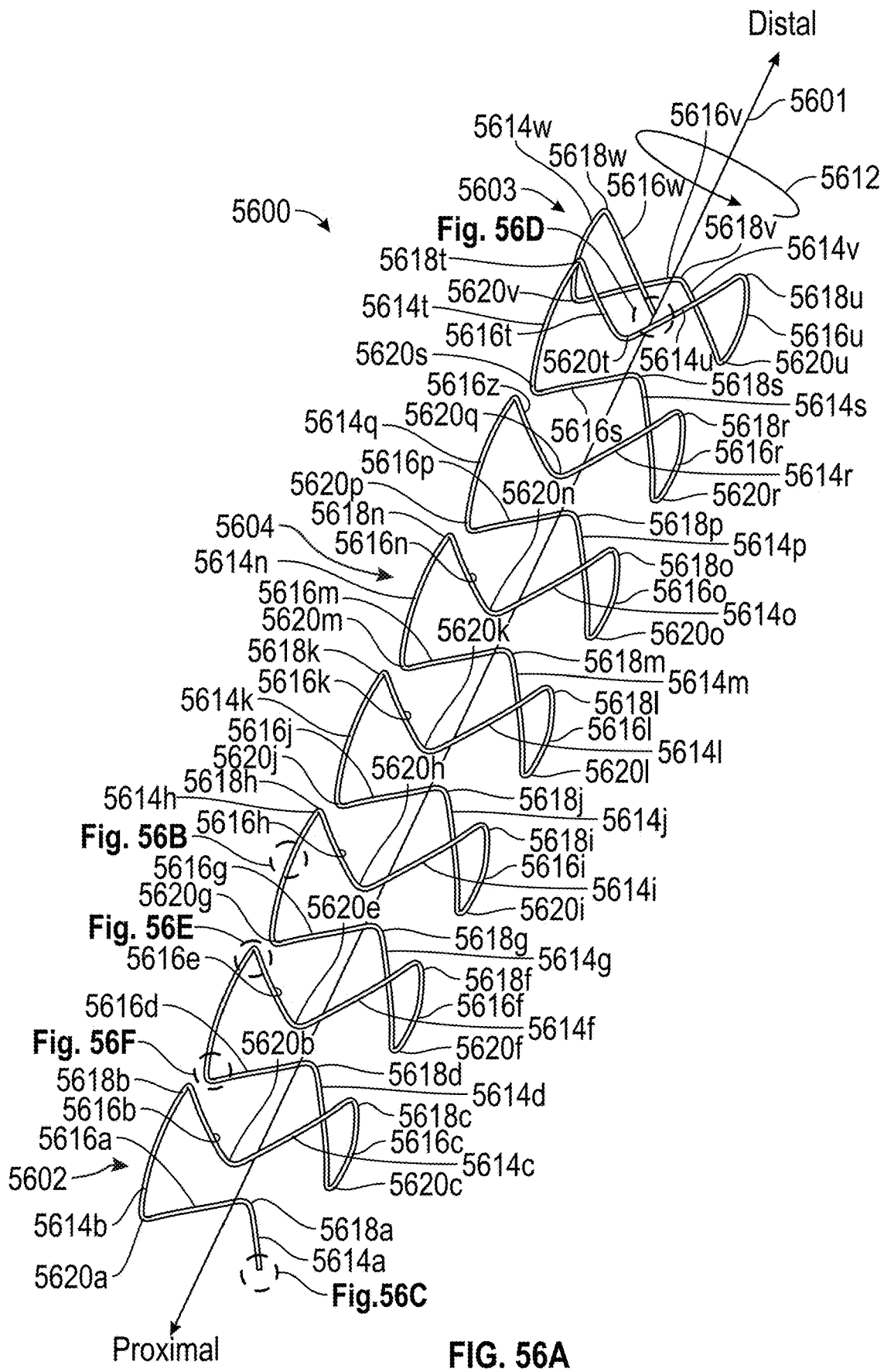
FIG. 56A is a perspective view of an implant in accordance with at least some embodiments of the present technology in an unconstrained state.
Figure 58:
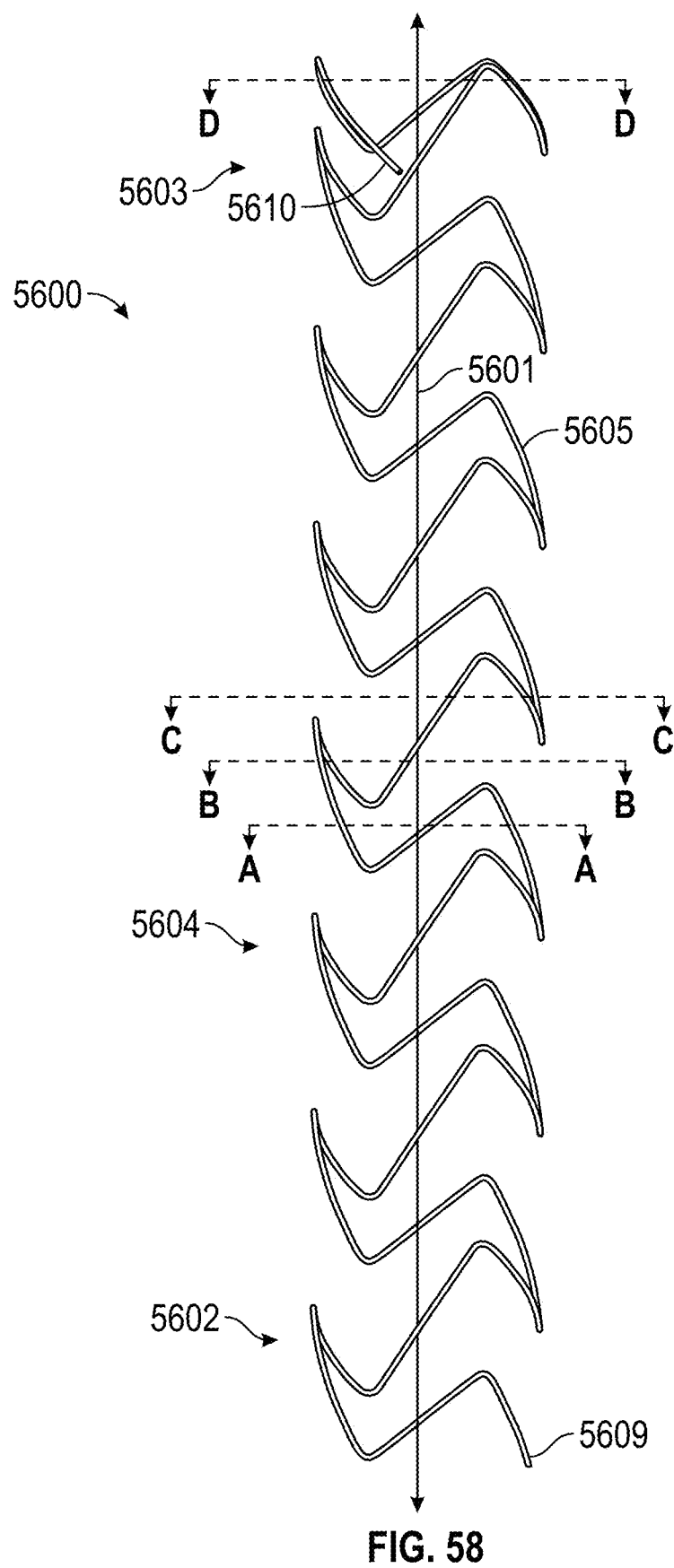
FIG. 58 is a profile view of the implant shown in FIG. 56A in the unconstrained state.
Figure 59:
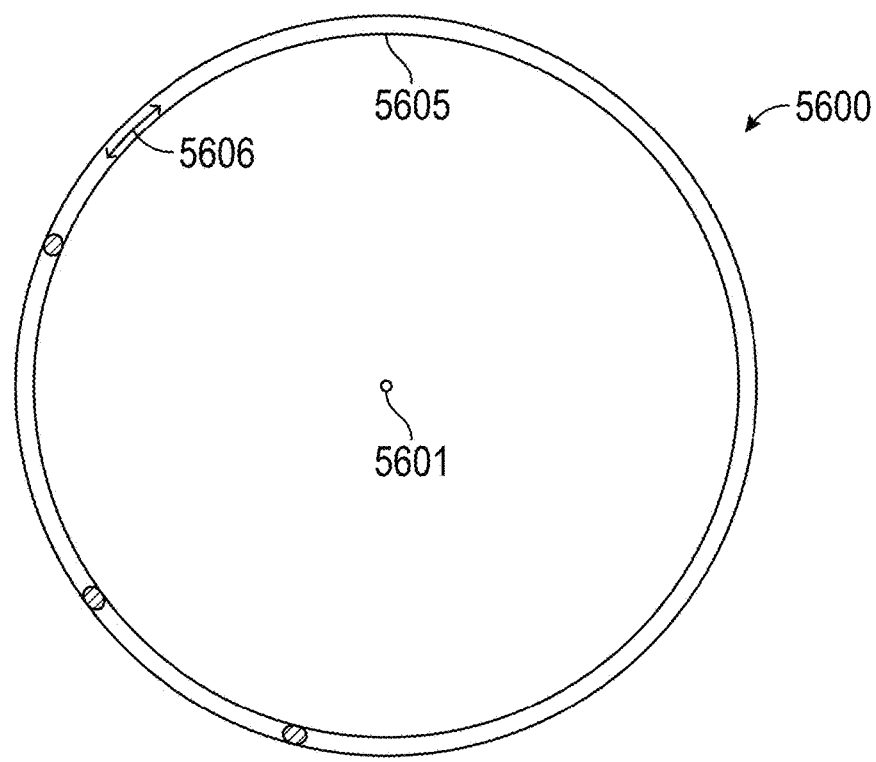
FIG. 59 is a cross-sectional view of the implant shown in FIG. 56A in the unconstrained state taken along the line A-A in FIG. 58.
Figure 60:
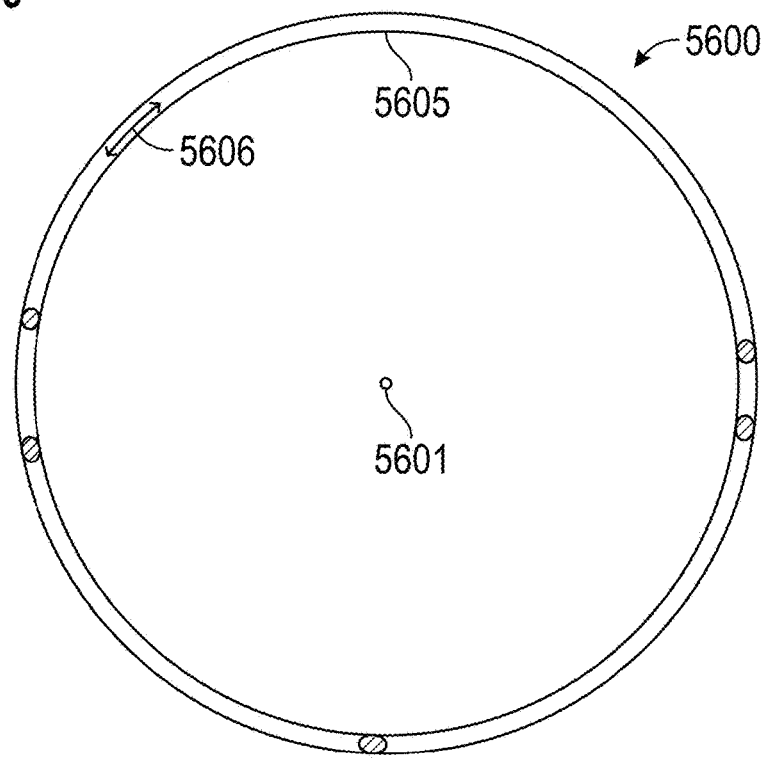
FIG. 60 is a cross-sectional view of the implant shown in FIG. 56A in the unconstrained state taken along the line B-B in FIG. 58.
Figure 61:
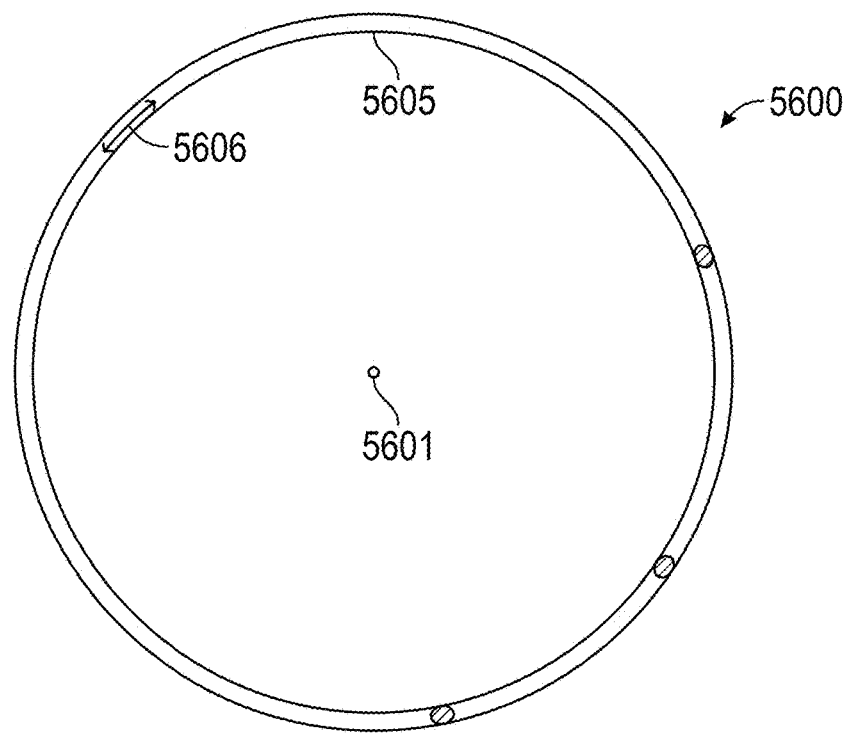
FIG. 61 is a cross-sectional view of the implant shown in FIG. 56A in the unconstrained state taken along the line C-C in FIG. 58.
Figure 62:
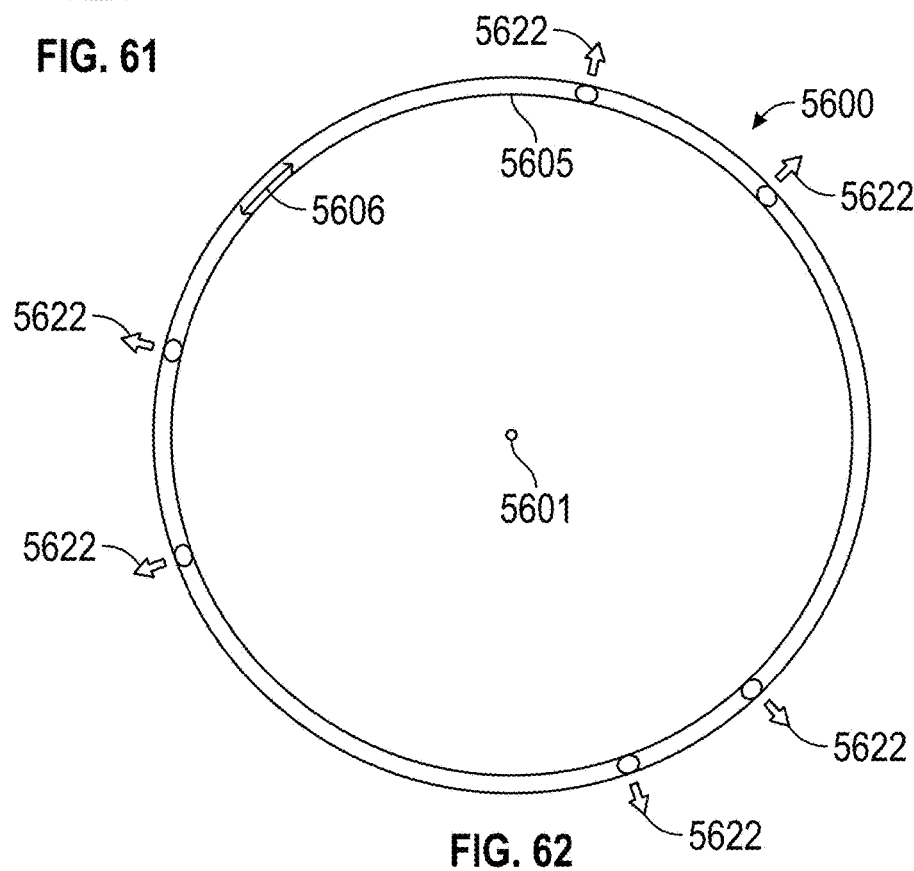
FIG. 62 is a cross-sectional view of the implant shown in FIG. 56A in the unconstrained state taken along the line D-D in FIG. 58.

FIGS. 56A, 57A and 58 are a perspective view, an end view, and a profile view, respectively of the implant 5600 in accordance with at least some embodiments of the present technology. FIGS. 56B-56F are callouts corresponding to FIG. 56A. FIG. 57B is a callout corresponding to FIG. 57A. In FIGS. 56A-58, the implant 5600 is in an unconstrained state. This can be a state the implant 5600 assumes in the absence of external sources of constraint, such as a sheath during delivery of the implant 5600 or a wall of a bronchial tree after deployment of the implant 5600. Features of the implant 5600 are described herein with respect to the implant 5600 in this unconstrained state unless otherwise specified. With reference to FIGS. 56A-58 together, the implant 5600 can be elongate with a longitudinal axis 5601. The implant 5600 can include a proximal end portion 5602 and a distal end portion 5603 spaced apart from one another along the longitudinal axis 5601. Between the proximal end portion 5602 and the distal end portion 5603 along the longitudinal axis 5601, the implant 5600 can include an intermediate portion 5604. The overall implant 5600 can be configured to be deployed at a treatment location within a bronchial tree of a human subject. Aspects of examples of this deployment are described in detail below. In at least some cases, the proximal end portion 5602 and the distal end portion 5603 are configured to be deployed at different respective airways. For example, the proximal end portion 5602 can be configured to be deployed at a first airway and the distal end portion 5603 can be configured to be deployed at a second airway of a generation greater than a generation of the first airway. The respective generations of the first and second airways can be different by 1, 2, 3, 4, 5, 6, or an even greater number depending on features such as the length and diameter of the implant 5600. The first airway can be of a generation 2 or greater, such as 2, 3, 4, 5 or 6.

The implant 5600 can further include a wire 5605 extending along a wire path 5606. The wire path 5606 can extend between a first end 5607 at the proximal end portion 5602 and an opposite second end 5608 at the distal end portion 5603. The wire path 5606 can be continuous between the first end 5607 and the second end 5608. Furthermore, the wire 5605 can include a first terminus 5609 at the first end 5607 and a second terminus 5610 at the second end 5608. The wire path 5606 can extend in a circumferential direction 5612 about the longitudinal axis 5601. Some, most, or all of the wire 5605 and the wire path 5606 can be within a tubular region 5611 coaxially aligned with the longitudinal axis 5601. In the illustrated embodiment, the tubular region 5611 has a circular cross-sectional shape perpendicular to the longitudinal axis 5601. In other embodiments, a counterpart of the tubular region 5611 can be ovoid, triangular with rounded corners, square with rounded corners, otherwise polygonal with rounded corners, or have another suitable shape perpendicular to a counterpart of the longitudinal axis 5601. Furthermore, although the longitudinal axis 5601 and the tubular region 5611 are straight in the illustrated embodiment, in other embodiments, the longitudinal axis 5601 and the tubular region 5611 can be curved. For example, a counterpart of the implant 5600 can be curved, angled, serpentine, or have another suitable nonlinear shape. Such a nonlinear shape, for example, can be selected to correspond to a shape of an airway region in which the counterpart of the implant 5600 is to be deployed.

With reference again to FIGS. 56A-58, in the illustrated embodiment the overall wire path 5606 between the first end 5607 and the second end 5608 includes seven complete turns about the longitudinal axis 5601. In other embodiments, a counterpart of the wire path 5606 can include another suitable number of turns, such as another suitable number of turns corresponding to a desired pitch and overall length of a counterpart of the implant 5600. In at least some embodiments, the wire path 5606 at the intermediate portion 5604 includes three or more complete turns, such as four turns, five turns, six turns, or more. In these and other embodiments, the wire path 5606 at the proximal end portion 5602 can include one complete turn closest to the first end 5607. Similarly, the wire path 5606 at the distal end portion 5603 can include one complete turn closest to the second end 5608. Delineation between the proximal end portion 5602, the distal end portion 5603, and the intermediate portion 5604 can be based on turns and/or based on segments of the longitudinal axis 5601. For example, the proximal end portion 5602 can be coextensive with a proximalmost 10% of the longitudinal axis 5601, the distal end portion 5603 can be coextensive with a distalmost 10% of the longitudinal axis 5601, and the intermediate portion can be coextensive with an intermediate 80% of the longitudinal axis 5601. Alternatively, the proximal end portion 5602 can be coextensive with a proximalmost 15% of the longitudinal axis 5601, the distal end portion 5603 can be coextensive with a distalmost 15% of the longitudinal axis 5601, and the intermediate portion can be coextensive with an intermediate 70% of the longitudinal axis 5601. Other suitable delineations are also possible.

The wire 5605 can include first legs 5614 (individually identified as first legs 5614a-5614w) and second legs 5616 (individually identified as second legs 5616a-5616w) alternatingly disposed along the wire path 5606. The first legs 5614a-5614w can extend distally in the circumferential direction 5612 while the second legs 5616a-5616w extend proximally in the circumferential direction 5612. In the illustrated embodiment, all of the first legs 5614a-5614w and all of the second legs 5616a-5616w have these specified orientations. In other embodiments, a counterpart of the wire 5605 can include only some (e.g., most, all but one, all but two, etc.) counterparts of the first legs 5614a-5614w and/or counterparts of the second legs 5616a-5616w having the specified orientations. For example a counterpart of the wire 5605 can include counterparts of the first legs 5614a-5614w and counterparts of the second legs 5616a-5616w having the specified orientations only at a counterpart of the intermediate portion 5604, but not at a counterpart of the proximal end portion 5602 and/or not at a counterpart of the distal end portion 5603. Furthermore, in the illustrated embodiment and in at least some other embodiments, the first legs 5614a-5614w and the second legs 5616a-5616w and counterparts thereof can have any suitable features of corresponding portions of other devices described herein.

With reference again to FIGS. 56A-58, the wire 5605 can include first apex portions 5618 (individually identified as first apex portions 5618a-5618w) disposed at respective first apex points 5619 along the wire path 5606. The wire 5605 can also include second apex portions 5620 (individually identified as second apex portions 5620a-5620v) disposed at respective second apex points 5621 along the wire path 5606. In at least some cases, the first legs 5614a-5614w and the second legs 5616a-5616w are alternatingly disposed along the wire path 5606. Furthermore, the first legs 5614a-5614w and the second legs 5616a-5616w can be interspersed among the first apex portions 5618a-5618w and the second apex portions 5620a-5620v along the wire path 5606. As shown in FIG. 56A, the first apex portions 5618a-5618w can point distally (i.e., more toward the distal end portion 5603 than toward the proximal end portion 5602 along the longitudinal axis 5601). Correspondingly, portions of the wire 5605 nearest to the first apex portions 5618a-5618w can extend away from the first apex portions 5618a-5618w proximally. Similarly, the second apex portions 5620a-5620v can point proximally (i.e., more toward the proximal end portion 5602 than toward the distal end portion 5603 along the longitudinal axis 5601). Correspondingly, portions of the wire 5605 nearest to the second apex portions 5620a-5620v can extend away from the second apex portions 5620a-5620v distally. In the illustrated embodiment and in at least some other embodiments, the first apex portions 5618a-5618w and the second apex portions 5620a-5620v and counterparts thereof can have any suitable features of corresponding portions of other devices described herein.

The overall implant 5600, the proximal end portion 5602, the distal end portion 5603, and/or the intermediate portion 5604 can consist essentially of the wire 5605. Furthermore, the wire 5605 throughout the implant 5600, at the proximal end portion 5602, at the distal end portion 5603, and/or at the intermediate portion 5604 can consist essentially of various combinations of the first legs 5614a-5614w, the second legs 5616a-5616w, the first apex portions 5618a-5618w, and the second apex portions 5620a-5620v. In the illustrated embodiment, the proximal end portion 5602 includes the four of the first legs 5614 (first legs 5614a-5614d), three of the second legs 5616 (second legs 5616a-5616c), three of the first apex portions 5618 (the first apex portions 5618a-5618c), and three of the second apex portions 5620 (the second apex portions 5620a-5620c). These components correspond to a portion of the wire 5605 extending along a single complete turn of the wire path 5606 closest to the first end 5607 but with the first leg 5614d extending slightly beyond this turn along the wire path 5606 toward the second end 5608. In the illustrated embodiment, the distal end portion 5603 includes three of the first legs 5614 (first legs 5614u-5614w), three of the second legs 5616 (second legs 5616u-5616w), three of the first apex portions 5618 (the first apex portions 5618u-5618w), and two of the second apex portions 5620 (the second apex portions 5620u-5620v). These components correspond to a portion of the wire 5605 extending along a single complete turn of the wire path 5606 closest to the second end 5608 but with the second leg 5616u extending slightly beyond this turn along the wire path 5606 toward the first end 5607. Finally, in the illustrated embodiment, the intermediate portion 5604 includes 16 of the first legs 5614 (the first legs 5614e-5614t), 17 of the second legs 5616 (the second legs 5616d-5616t), 17 of the first apex portions 5618 (the first apex portions 5618d-5618t), and 17 of the second apex portions (the second apex portions 5620d-5620t). These components correspond to a portion of the wire 5605 extending along five complete turns of the wire path 5606. In other embodiments, as discussed above, counterparts of the proximal end portion 5602, the distal end portion 5603, and the intermediate portion 5604 can have other suitable delineations. Furthermore, these counterparts can include other suitable quantities and/or types of components.

In at least some cases, the wire 5605 is unbranched throughout the wire path 5606. For example, the wire 5605 can lack bifurcations, trifurcations, or other types of junctions at which the wire 5605 divides. In addition or alternatively, the wire 5605 can be untethered throughout the wire path 5606. For example, the wire 5605 can lack bridges or other structural connections between different portions of the wire 5605 spaced apart from one another along the wire path 5606 and/or between the wire 5605 and other implant components. By way of nonbinding theory, these features alone or in combination with other features described herein may be useful to reduce a foreign body response associated with the implant 5600, to increase longitudinal flexibility of the implant 5600, and/or for one or more other reasons. In other embodiments, a counterpart of the wire 5605 can be branched, tethered, and/or present with other implant components.

With reference again to FIGS. 56A-58, the first terminus 5609 and/or the second terminus 5610 can be untethered. In contrast, wire ends in conventional implants are typically tethered in some manner, such as by being tied or otherwise bonded to other wire portions. This tethering is intuitive because untethered wire ends are conventionally assumed to have greater potential than tethered wire ends to cause trauma, to migrate, and/or to exhibit other undesirable behaviors after implant deployment. With reference again to FIGS. 56A-57B, the inventors recognized that making the first terminus 5609 and/or the second terminus 5610 untethered had potential benefits and that associated problems could be mitigated or even eliminated with other implant features. Among the benefits is supporting mucociliary clearance. The inventors recognized that a lack of branching and/or tethering at other portions of the wire 5605 and/or the lack of structures of the implant 5600 other than the wire 5605, as discussed above, can also support this objective. Moreover, without wishing to be bound to this theory, the inventors identified mucociliary clearance as useful for supporting long-term use of the implant 5600 without loss of airway patency due to mucus impaction or the accumulation of granulation tissue. Accordingly, the implant 5600 can be configured to allow mucociliary clearance from a location immediately distal to the implant 5600 to a location immediately proximal to the implant 5600 while the implant 5600 is deployed at a treatment location within a bronchial tree.

As best shown in FIG. 58, the first terminus 5609 can be at a proximalmost end of the implant 5600. Correspondingly, the implant 5600 can include a given one of the first legs 5614 at the first end 5607 of the wire path 5606. Furthermore, a pitch of the wire path 5606 at the proximal end portion 5602 can be about the same as (e.g., within 10% of) a pitch of the wire path 5606 at the intermediate portion 5604. These features and a lack of tethering at the first terminus alone or in combination can facilitate retrievability of the implant 5600. For example, although the implant 5600 is expected to be suitable for indefinite use, in some cases it may be useful to remove the implant 5600 from a treatment location after deployment. This may be the case, for example, when a clinician deploys the implant 5600 improperly or when unexpected and unusual biological processes cause an airway region in which the implant 5600 is deployed to eventually lose patency. Retrieving the implant 5600 can include gripping the wire 5605 at or near the first terminus 5609 and pulling the wire 5605 proximally. The described features of the first terminus 5609 can facilitate gripping access and can help guide the wire 5605 away from airway walls in response to pulling force. For example, the implant 5600 generally and the proximal end portion 5602 particularly can be configured to unwind and elongate rather than maintain the same shape perpendicular to the longitudinal axis 5601 during retrieval. Accordingly, rather than dragging across the airway walls proximally, the implant 5600 can tend to disengage inwardly and then move proximally during retrieval. This can reduce or eliminate excess trauma.

FIGS. 59, 60, 61 and 62 are cross-sectional views of the implant 5600 taken along lines A-A, B-B, C-C, and D-D in FIG. 58, respectively. As shown in FIGS. 59-62, planes perpendicular to the longitudinal axis 5601 at different portions of the implant 5600 can intersect more than one circumferentially spaced apart portion of the implant 5600. This contrasts with a simple coil. The inventors have discovered that contacting more than one circumferentially spaced apart portions of a wall of an airway region can be useful for establishing and maintaining airway patency. Portions of the implant 5600 that a plane perpendicular to the longitudinal axis 5601 intersects can correspond to portions of the implant 5600 that contact a wall of an airway region when the implant 5600 is deployed. Accordingly, as shown in FIGS. 58-62, the implant 5600 can contact three circumferentially spaced apart portions of a wall of an airway region at a plane perpendicular to the longitudinal axis 5601 at the line A-A, five such portions at the line B-B, three such portions at the line C-C, and six such portions at the line D-D. Lines A-A, B-B, and C-C are at the intermediate portion 5604 whereas line D-D is at the distal end portion 5603. In at least some cases, any given plane perpendicular to the longitudinal axis 5601 at the intermediate portion 5604 and/or a middle 50% of a length of the implant 5600 along the longitudinal axis 5601 intersects at least three (e.g., from three to five) circumferentially spaced apart points along the wire path 5606.

As FIGS. 59-62 suggest, the implant 5600 can be configured to contact more circumferentially spaced apart portions of a wall of an airway region at planes perpendicular to the longitudinal axis 5601 at the distal end portion 5603 than at planes perpendicular to the longitudinal axis 5601 at the intermediate portion 5604. For example, the implant 5600 can be configured to intersect at least a first number of circumferentially spaced apart points along the wire path 5606 at any given plane perpendicular to a middle 50% of a length of the implant 5600 along the longitudinal axis 5601 and to intersect at least a greater second number of circumferentially spaced apart points along the wire path 5606 at any given plane perpendicular to distalmost 5% of the length of the implant 5600 along the longitudinal axis 5601. In at least some cases, the second number of circumferentially spaced apart points is at least five. Furthermore, among the circumferentially spaced apart points along the wire path 5606 at which any given plane perpendicular to distalmost 5% of the length of the implant 5600 along the longitudinal axis 5601 intersects the implant, a maximum circumferential spacing between any circumferentially neighboring pair of the points can be no more than 180 degrees, such as no more than 120 degrees. Conversely, for at least one neighboring pair of circumferentially spaced apart points, there may be a minimum circumferential spacing of at least 60 degrees, such a at least 90 degrees, 120 degrees, or 150 degrees.

The inventors recognized a relatively large number of and/or relatively circumferentially balanced positioning of points of contact between the distal end portion 5603 and an airway region as potentially useful to facilitate deployment of the implant 5600. For example, in at least some cases, the implant 5600 is deployed by causing relative movement between a sheath and the implant 5600 such that the implant 5600 is gradually uncovered and allowed to expand radially. In these and other cases, the distal end portion 5603 can expand before other portions of the implant 5600. When this expansion begins, the distal end portion 5603 may have no established connection to the airway region. If a counterpart of the distal end portion 5603 initiated and/or propagated connection with an airway region at a single point, the force exerted against the airway region at that point would potentially cause asymmetrical expansion of the airway region. This, in turn, would potentially cause the counterpart of the distal end portion 5603 to move unpredictable during deployment, leading to potential trauma and/or suboptimal control over positioning. In contrast, with reference again to FIG. 62, the distal end portion 5603 can be configured to exert force (corresponding to arrows 5622) at a sufficient number of circumferentially spaced apart portions of the airway region to cause the airway region to expand relatively uniformly, thereby reducing potential trauma and/or enhancing control over positioning. After its deployment, the distal end portion 5603 can anchor the implant 5600 such that further radial expansion of the implant 5600 does not cause trauma or unduly compromise control over positioning of the implant 5600 even if such further expansion propagates along a relatively small number of points and/or points that are relatively circumferentially unbalanced.

Implant Geometry and Contact Density

Figure 63:
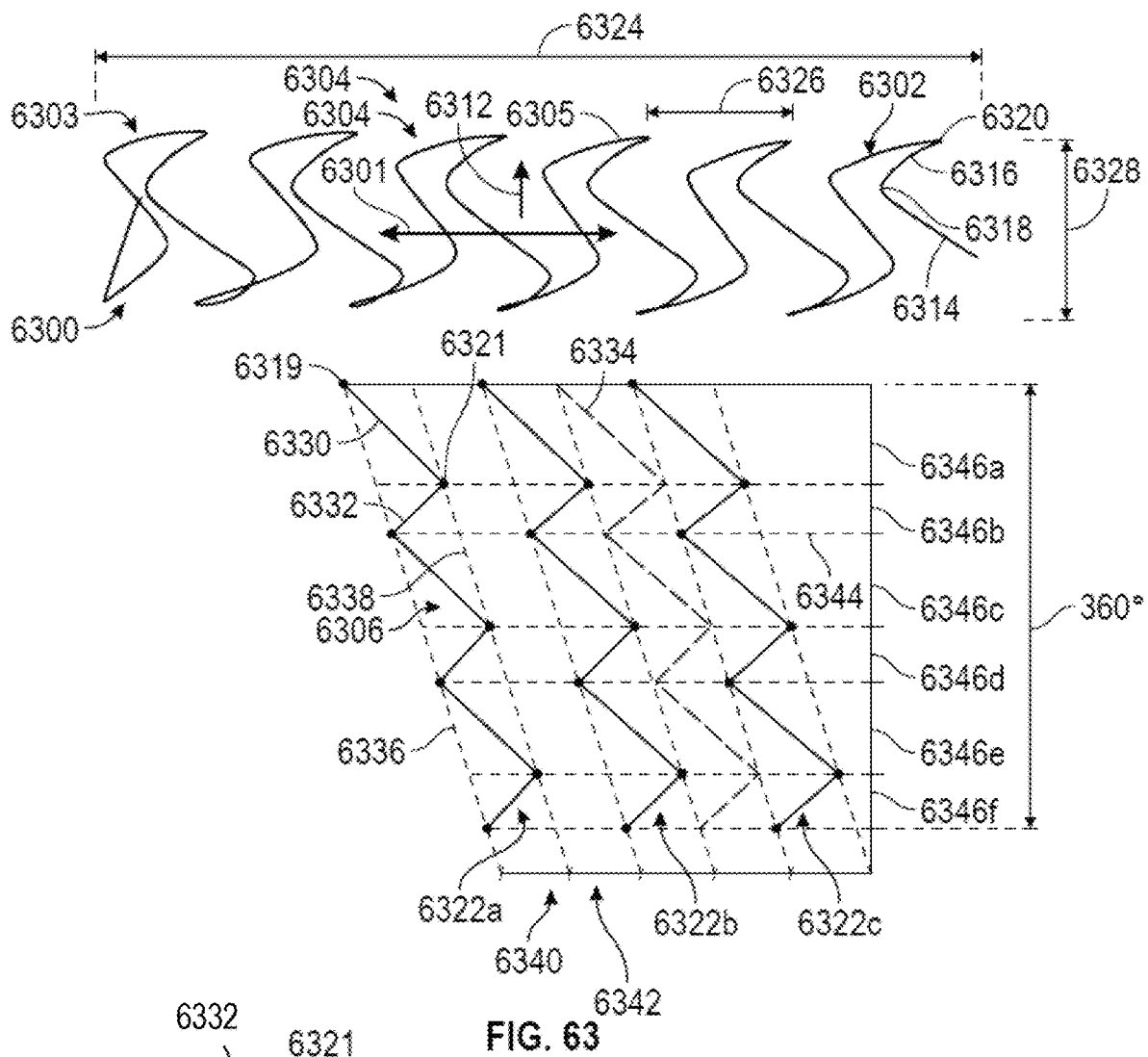
FIG. 63 is a profile view of an implant in accordance with at least some embodiments of the present technology in an unconstrained state juxtaposed with a schematic diagram of portions of a wire path at an intermediate portion of the implant.

FIG. 63 is a profile view of an implant 6300 in accordance with at least some embodiments of the present technology in an unconstrained state juxtaposed with a schematic diagram illustrating certain geometrical aspects of the implant 6300. The implant 6300 is generally similar to the implant 5600 described above except that the implant 6300 has fewer turns and different wire termination features. With reference to FIGS. 56A-56F and 63 together, the implant 6300 can include or define a longitudinal axis 6301, a proximal end portion 6302, a distal end portion 6303, a intermediate portion 6304, a wire 6305, a wire path 6306, a circumferential direction 6312 (as indicated and curving into the page), first legs 6314, second legs 6316, first apex portions 6318, first apex points 6319, second apex portions 6320, and second apex points 6321 at least generally corresponding to the longitudinal axis 5601, the proximal end portion 5602, the distal end portion 5603, the intermediate portion 5604, the wire 5605, the wire path 5606, the circumferential direction 5612, the first legs 5614, the second legs 5616, the first apex portions 5618, the first apex points 5619, the second apex portions 5620, and the second apex points 5621, respectively, of the implant 5600.

With reference now to FIG. 63, the wire path 6306 is shown in a two-dimensional unwound representation with portions of the wire path 6306 corresponding to three successive turns 6322 (individually identified at turns 6322a-6322c) of the wire path 6306 at the intermediate portion 6304. The vertical axis in the schematic diagram corresponds to circumferential position and spacing in the circumferential direction 6312 about the longitudinal axis 6301. The horizontal axis in the schematic diagram corresponds to longitudinal position and spacing along the longitudinal axis 6301. The implant 6300 can define a length 6324 along the longitudinal axis 6301, a pitch 6326 along the longitudinal axis 6301, and a diameter 6328 perpendicular to the longitudinal axis 6301. In the schematic diagram, first segments 6330 of the wire path 6306 correspond to lengths of the first legs 6314. Similarly, second segments 6332 of the wire path 6306 correspond to lengths of the second legs 6316. For the sake of simplicity, the first and second segments 6330, 6332 are represented as straight lines between neighboring first and second apex points.

In the illustrated embodiment, the length 6324 is about 50 mm, the average pitch 6326 at the intermediate portion 6304 is about 8.1 mm, and the average diameter 6328 is about 10 mm. In other embodiments, these dimensions can be different. For example, a counterpart of the length 6324 can be within a range from 50 mm to 200 mm, such as from 70 mm to 200 mm or from 70 mm to 120 mm. Alternatively, a counterpart of the length 6324 can be less than 50 mm or greater than 200 mm. A counterpart of the average pitch 6326 at the intermediate portion 6304 can be within a range from 4 mm to 12 mm, such as from 6 mm to 12 mm, or from 6 mm to 10 mm. Alternatively, a counterpart of the average pitch 6326 can be less than 4 mm or greater than 12 mm. A counterpart of the average diameter 6328 can be within a range from 2 mm to 20 mm, such as from 4 mm to 20 mm, or from 5 mm to 15 mm. Alternatively, a counterpart of the average diameter 6328 can be less than 2 mm or greater than 20 mm. In other embodiments, counterparts of the implant 6300 can have still other suitable dimensions.

With reference again to the illustrated embodiment, the average pitch 6326 at the distal end portion 6303 can be smaller than the average pitch 6326 at the intermediate portion 6304 and smaller (e.g., from 10% to 50% smaller) than the average pitch 6326 at the proximal end portion 6302. This pitch difference can correspond to a greater number of circumferentially spaced apart portions of the wire 6305 along which contact between the implant 6300 and an airway wall simultaneously propagates during deployment of the distal end portion 6303 relative to deployment of the intermediate portion 6304. In addition or alternatively, this pitch difference can correspond to a greater degree of circumferential balance among portions of the wire 6305 along which contact between the implant 6300 and an airway wall simultaneously propagates during deployment of the distal end portion 6303 relative to deployment of the intermediate portion 6304. As discussed above, the number of contact portions and/or the circumferential balance of these contact portions can be useful to reduce potential trauma and/or enhance control over positioning during implant deployment.

The pitch 6326 can also be relevant to performance characteristics of the implant 6300, such as enhancing mucociliary clearance. In at least some cases, the implant 6300 is configured to define an unobstructed mucociliary clearance region extending along a continuous mucociliary clearance path 6334 from the location immediately distal to the implant 6300 to the location immediately proximal to the implant 6300 while the implant 6300 is deployed at a treatment location within a bronchial tree of a human subject. As shown in FIG. 63, the mucociliary clearance path 6334 can extend between successive turns of the wire path 6306. An average width of the mucociliary clearance region parallel to the longitudinal axis 6301 can be significantly greater than an average cross-sectional diameter of the wire 6305 perpendicular to the wire path 6306. This can correspond to a synergistic combination of relatively small contact area between the implant 6300 and an airway wall thereby a foreign body response and relatively large area available for mucociliary clearance. These features alone or together can increase the time (potentially indefinitely) during which an airway region in which the implant 6300 is deployed remains patent. In at least some cases, the average width of the mucociliary clearance region parallel to the longitudinal axis 6301 is at least 10 times (e.g., within a range from 10 times to 20 times) the average cross-sectional diameter of the wire 6305 perpendicular to the wire path 6306. In addition or alternatively, the average pitch 6326 can be within a range from 50% to 110% (e.g., from 70% to 90%) of the average diameter 6328. This can be the case, for example, at the intermediate portion 6304 and/or throughout the implant 6300.

The implant 6300 can be configured to resiliently transition from a low-profile delivery state to an expanded deployed state. The average diameter 6328 can be significantly different between these states. By way of nonbinding theory, the inventors have found that this feature has great potential to facilitate establishing and maintaining airway patency. Expansion of an airway well beyond its native diameter creates a relatively large free-passage area that is less likely or at least slower to become occluded due to mucus impaction or the accumulation of granulation tissue. In some embodiments, the average diameter 6328 when the implant 6300 is in the deployed state is at least 3 times (e.g., at least 3.5 times, at least 4 times, at least 4.5 times, or at least 5 times) the average diameter 6328 when the implant 6300 is in the delivery state. In these and other embodiments, the average diameter 6328 when the implant 6300 is in the illustrated unconstrained state is at least 4 times (e.g., at least 4.5 times, at least 5 times, at least 5.5 times, or at least 6 times) the average diameter 6328 when the implant 6300 is in the delivery state. Furthermore, a ratio of the average diameter 6328 to the length 6324 can be within a range from 1:5 to 1:30, such as from 1:10 to 1:30.

In the illustrated embodiment, the diameter 6328 is consistent throughout the length 6324. In at least some cases, the diameter 6328 varies no more than 5% or no more than 10% throughout the length 6324. Relatedly an average of the diameter 6328 at the proximal end portion 6302 can be no more than 5% different or no more than 10% different than an average of the diameter 6328 at the distal end portion 6303. This may be counterintuitive because the distal end portion 6303 is configured to be deployed at a more distal portion of a bronchial tree than the portion at which the proximal end portion 6302 is deployed. More distal airway regions of a bronchial tree are typically narrower than more proximal portions. Having the diameter 6328 be relatively consistent throughout the length 6324 can be beneficial, however, for establishing and/or maintaining airway patency. For example, it may be beneficial for a degree of relative hyper-expansion of a wall of an airway region to be greater distally than proximally. This is expected to follow from deployment of a consistent diameter implant in a distally narrowing airway region. Other advantages are also possible. Furthermore, in other embodiments, a counterpart of the diameter 6328 may be inconsistent along a counterpart of the length 6324. For example, a counterpart of the diameter 6328 may increase or decrease along the counterpart of the length 6324. In these cases, an average counterpart diameter 6328 of a counterpart proximal end portion 6302 can be smaller or larger than an average counterpart diameter 6328 of a counterpart distal end portion 6303.

With reference again to FIG. 63, the first apex portions 6318 at the intermediate portion 6304 can define a first helix 6336. Similarly, the second apex portions 6321 at the intermediate portion 6304 can define a second helix 6338. In at least some cases, the longitudinal axis 6301 is an axis of symmetry about which the first and second helixes 6336, 6338 are wound. The implant 6300 can define a first helical band 6340 between the first helix 6336 and the second helix 6338. In the illustrated embodiment, successive turns of the first helical band 6340 are spaced apart from one another along the longitudinal axis 6301 such that the implant 6300 defines a second helical band 6342 intertwined with the first helical band 6340. In at least some cases, an average width of the first helical band 6340 is within a range from 30% to 75% of the average pitch 6326 at the intermediate portion 5604 when the implant 6300 is in the deployed state. As the implant 6300 transitions from the delivery state toward the deployed state or the unconstrained state, the average width of the first helical band 6340 parallel to the longitudinal axis 6301 can decrease and an average width of the second helical band 6342 parallel to the longitudinal axis 6301 can increase. Conversely, as the implant 6300 transitions from the deployed state or the unconstrained state toward the delivery state, the average width of the first helical band 6340 parallel to the longitudinal axis 6301 can increase and the average width of the second helical band 6342 parallel to the longitudinal axis 6301 can decrease.

In some cases, it is useful for the second helical band 6342 to still be present when the implant 6300 is in the delivery state. Stated differently, in these cases, it can be useful for successive turns of the first helical band 6340 to be spaced apart from one another along the longitudinal axis 6301 when the implant 6300 is in the delivery state. This can be useful, for example, to reduce or eliminate overlapping of the wire path 6306 when the implant 6300 is in the delivery state. Overlapping of the wire path 6306 can cause the implant 6300 to be less compact in the delivery state than would otherwise be the case. This can be disadvantageous as it may reduce an ability of the implant 6300 to be delivered intraluminally to more distal airways. In other cases, a counterpart of the second helical band 6342 may be eliminated when a counterpart of the implant 6300 is in a delivery state. Stated differently, in these other cases, successive turns of a counterpart of the first helical band 6340 may be overlapping when the counterpart of the implant 6300 is in the delivery state. The circumferential alignment of features within a counterpart of the first helical band 6340 between successive turns thereof can affect whether a counterpart of the wire path 6306 does or does not overlap in these cases. When the circumferential alignment of these features is such that a counterpart of the wire path 6306 does not overlap, then overlapping a counterpart of the first helical band 6340 when a counterpart of the implant 6300 is in a delivery state may be advantageous. For example, via nesting or interdigitation, this overlapping may allow more longitudinally expansive structures to be present in the same longitudinal space. As discussed below, however, circumferential alignment of features within the first helical band 6340 has other implications which may outweigh, conflict with, or be complementary with this potential advantage.

As shown in FIG. 63, a given three of the first apex points 6319 and the corresponding first apex portions 6320 at respective neighboring turns 6322 of the wire path 6306 at the intermediate portion 6304 can be circumferentially aligned with one another. For example, the given three of the first apex points 6319 and the corresponding first apex portions 6320 can be within 5 degrees or within 10 degrees of circumferential alignment with one another. Furthermore, this circumferential alignment can be present for one, some, or all of the first apex points 6319 and the corresponding first apex portions 6320 at the neighboring turns 6322. The lines 6344 in FIG. 63 indicate this circumferential alignment. In at least some cases, the circumferential alignment in the stated ranges persists as the implant 6300 transitions between the delivery state and the deployed state or between the delivery state and the unconstrained state. Accordingly, the given three of the first apex points 6319 and the corresponding first apex portions 6320 at the respective neighboring turns 6322 of the wire path 6306 at the intermediate portion 6304 can be circumferentially aligned with one another when the implant 6300 is in the delivery state, the deployed state, and the unconstrained state. By way of nonbinding theory, this persistence of circumferential alignment may have certain advantages, such as reducing or eliminating a tendency of the implant 6300 to shift after deployment at a treatment location. Such shifting may increase a foreign body response, increase airway erosion, and/or have other undesirable effects.

In FIG. 63, line segments 6346 represent circumferential spacing between successive apex points among the first and second apex points 6319, 6321 along the wire path 6306 at the intermediate portion 6304. In at least some embodiments, an average of this circumferential spacing is within a range from 35 degrees to 95 degrees, such as from 55 degrees to 65 degrees. As with the circumferential alignment, the average circumferential spacing can persist as the implant 6300 transitions between the delivery state and the deployed state or between the delivery state and the unconstrained state. In at least some cases, the average circumferential spacing between successive apex points among the first and second apex points 6319, 6321 along the wire path 6306 at the intermediate portion 6304 when the implant 6300 is in the delivery state is no more than 5% or no more than 10% different than when the implant 6300 is in the deployed state. Similarly, this average circumferential spacing when the implant 6300 is in the delivery state can be no more than 5% or no more than 10% different than when the implant 6300 is in the unconstrained state. By way of nonbinding theory, this persistence of circumferential spacing may have certain advantages similar to the advantages discussed above with regard to the persistence of circumferential alignment.

Figure 64A:
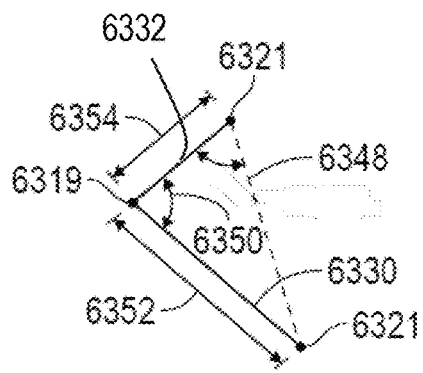
FIGS. 64A-65B are diagrams showing different respective subtended angles relevant to the implant shown in FIG. 63.
Figure 64B:
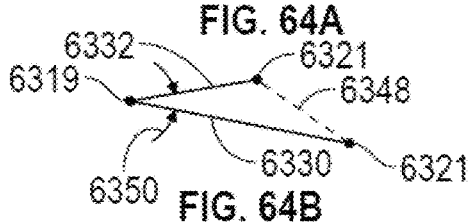
Figure 65A:
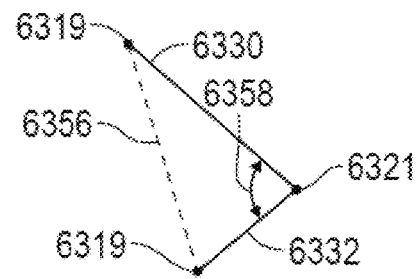
Figure 65B:
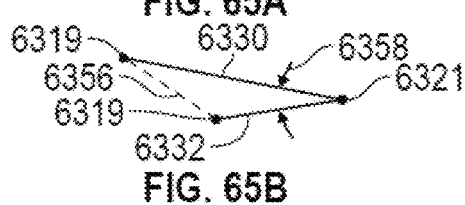

FIGS. 64A-65B are diagrams showing different respective subtended angles relevant to the implant 6300. In particular, FIGS. 64A and 64B illustrate a portion of the wire path 6306 corresponding to a given one of the first segments 6330 (corresponding to a given one of the first legs 6314) and a given one of the second segments 6332 (corresponding to a given one of the second legs 6316) at opposite sides of a given one of the first apex points 6319 when the implant 6300 is in the unconstrained state and the delivery state, respectively. Similarly, FIGS. 65A and 65B illustrate a portion of the wire path 6306 corresponding to a given one of the first segments 6330 and a given one of the second segments 6332 at opposite sides of a given one of the second apex points 6321 when the implant 6300 is in the unconstrained state and the delivery state, respectively. As shown in FIG. 64A, a first line 6348 between a pair of the second apex points 6321 neighboring one another along the wire path 6306 subtends a first angle 6350 from an intervening one of the first apex points 6319 along the wire path 6306. FIG. 64A also illustrates a length 6352 of the given first segment 6330 and a length 6354 of the given second segment 6332 at opposite sides of the given first apex point 6319. As shown in FIG. 65A, a second line 6356 between a pair of the first apex points 6319 neighboring one another along the wire path 6306 subtends a second angle 6358 from an intervening one of the second apex points 6321 along the wire path 6306. In at least some cases, one or both of the first and second angles 6350, 6358 are within a range from −20 degrees to 20 degrees (e.g., from −20 degrees to 10 degrees) when the implant 6300 is in the delivery state and within a range from 20 degrees to 90 degrees (e.g., from 40 degrees to 90 degrees) when the implant 6300 is in the deployed state. This angle can be negative when segments of the wire path 6306 at opposite sides of an apex point converge and then diverge as they extend away from the apex point.

An average length 6352 of the first legs 6314 at the intermediate portion 6304 can be different than an average length 6354 of the second legs 6316 at the intermediate portion 6304. For example, the average length 6352 of the first legs 6314 at the intermediate portion 6304 can be greater than (e.g., from 20% to 50% greater than) an average length 6354 of the second legs 6316 at the intermediate portion 6304. Furthermore, a ratio of the average length 6352 of the first legs 6314 at the intermediate portion 6304 to the average length of the second legs 6316 at the intermediate portion 6304 can be greater than a threshold value of n/(n−1) with n being an average number of the first legs 6314 per complete turn 6322 of the wire path about the longitudinal axis at the intermediate portion. For example, the ratio of the average length 6352 of the first legs 6314 at the intermediate portion 6304 to the average length of the second legs 6316 at the intermediate portion 6304 can be within a range from 80% to 99% of the threshold value. This may facilitate avoiding overlap of the wire path 6306 when the implant 6300 is in the delivery state without unduly compromising a degree to which the implant supports an airway region and inhibits invagination of a wall of the airway region.

The implant 6300 can have a surprisingly small airway contact density. In general the amount of force needed to expand an airway region wall is relatively independent of the amount of contact between an implant and the airway region wall. Accordingly, smaller airway contact density corresponds to a need for greater force density. The inventors discovered that airways in a human bronchial tree are capable of withstanding surprisingly high force densities. Accordingly, airway contact density can be reduced without unduly compromising performance. Furthermore, low contact density is expected to have beneficial impacts on maintaining airway patency. For example, low contact density is expected to reduce foreign body response and facilitate mucociliary clearance. Moreover, high force density may actually be beneficial by increasing stability as further discussed below. Airway-to-implant contact density is expected to correspond to the following Equation 1 (Eq. 1):

$$\frac{A_{iw}}{A_i} = \frac{n \cdot (l_s + l_l) \cdot d_w}{2 \cdot d_a \cdot l_p} \quad \text{(Eq. 1)}$$

$A_i$ = area supported by a single turn $A_{iw}$ = area of a single turn $d_w$ = diameter of implant -continued $d_a$ = diameter of airway $n$ = number of implant bends per turn In at least some embodiments, the implant 6300 is configured to occupy from 5% to 30%, such as from 5% to 15%, of a total area of the first helical band 6340 when the implant 6300 is in the deployed state.

Implant Stability

Figure 65:
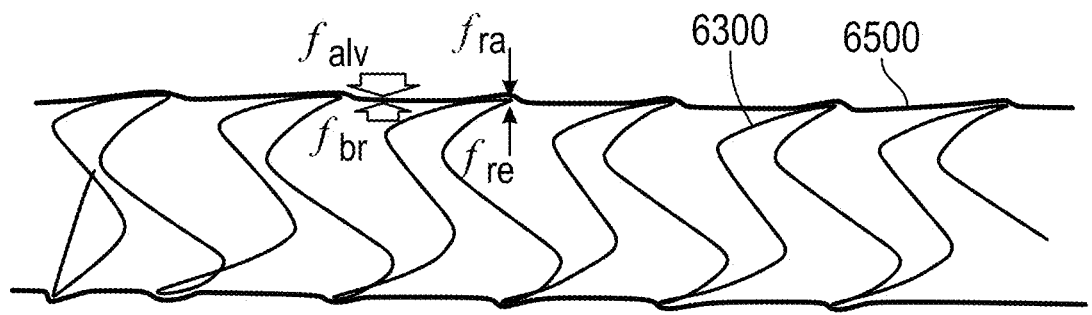

FIG. 65 is a profile view of the implant 6300 in a deployed state within an airway region 6500. In this state, radial forces on the implant 6300 and on the airway region 6500 are expected to be in balance in accordance with the following Equation 2 (Eq. 2):

$$f_{ra} + f_{alv} = f_{re} + f_{br} \quad \text{(Eq. 2)}$$

$f_{re}$ = force of radial expansion of a single wire $f_{ra}$ = force of reaction of airway of a single wire $f_{alv}$ = force applied by alveolar pressure to a single wire turn $f_{br}$ = force applied by bronchial pressure to a single wire turn The diameter 6328 and the radial spring constant of the implant 6300 can be selected in view of the following Equation 3 (Eq. 3):

$$f_{re} = k_{ir}(d_{in} - d_a) = k_{ar}(d_{an} - d_a) + \pi \cdot d_a \cdot l_p \cdot (P_{alv} - P_{br}) \quad \text{(Eq. 3)}$$

$f_{re}$ = force of radial expansion of a single wire $k_{ir}$ = spring constant of implant in radial direction $k_{ar}$ = spring constant of airway in radial direction $d_{in}$ = nominal diameter of implant $d_a$ = diameter of airway $d_{an}$ = nominal diameter of airway $l_p$ = implant pitch length $P_{lv}$ = pressure in the alveoli $P_{br}$ = pressure in the bronchi As discussed above, the inventors discovered that airways in a human bronchial tree are capable of withstanding surprisingly high force densities and that high force densities may be beneficial to enhance implant stability and/or for other reasons. Accordingly, the diameter to which the implant 6300 is configured to expand an airway can be many times greater (e.g., at least 2 times, 2.5 time, 3 times, 3.5 times, or 4 times greater) than a nominal diameter of the airway.

Stable contact between an implant and an airway wall can be challenging to achieve for at least two reasons. First, relevant airway regions are typically tortuous, branched, and/or of widely varying diameter. Second, these airway regions typically move significantly and nonuniformly during respiration, coughing, sneezing, etc. Relative movement between an airway region and an implant can cause or contribute to irritation, erosion, foreign body response, and/or other factors that tend to decrease long-term patency. Together with or instead of high force density, the inventors recognized that relatively low resistance to longitudinal deformation together with relatively high resistance to radial deformation can enhance implant stability.

Figure 66:
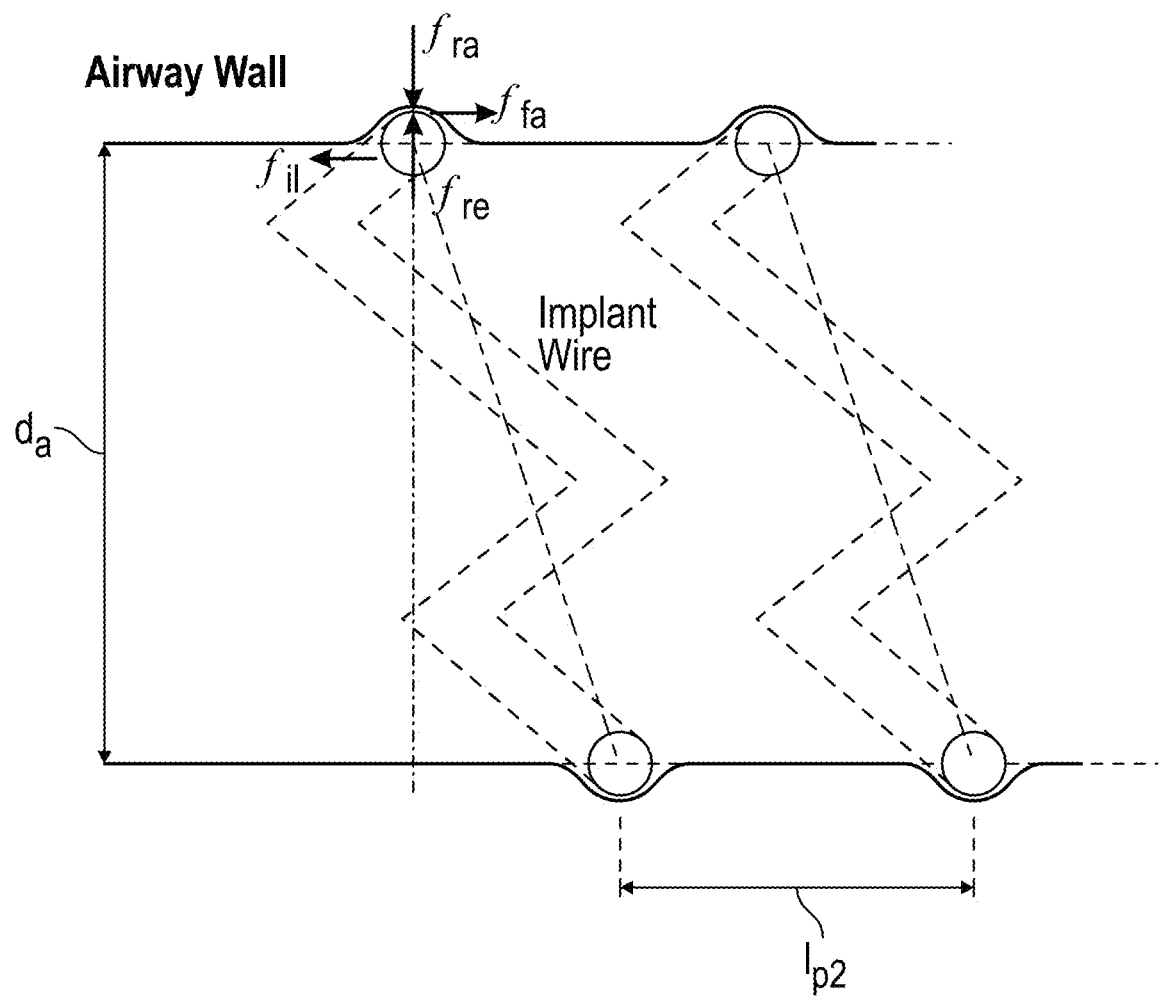
FIG. 66 is a schematic diagram illustrating certain forces and dimensions relevant to implants in accordance with at least some embodiments of the present technology.

FIG. 66 is a schematic diagram illustrating certain forces and dimensions relevant to implants in accordance with at least some embodiments of the present technology. In FIG. 66, two neighboring turns of an implant 6600 are shown in a deployed state in an airway region 6602. Both radial and longitudinal forces are identified. In at least some cases, when the force of the implant 6600 reacting to elongation/shortening is less than the force of friction on the implant 6600, the implant 6600 tends to remain stable during breathing. The radial and longitudinal spring constants of the implant 6600 can be selected in accordance with the following Equation 4 (Eq. 4):

$$\frac{k_{il}}{k_{ir}} \leq \mu_{a-i} \frac{(d_{in} - d_a)}{(l_{pn} - l_{p2})} \quad \text{(Eq. 4)}$$

$k_{ir}$ = spring constant of implant in radial direction $k_{il}$ = spring constant of implant in longitudinal direction $\mu_{a-i}$ = coefficient of friction between airway and spring $d_a$ = diameter of airway $d_{in}$ = nominal diameter of implant $l_{pn}$ = nominal implant pitch $l_{p2}$ = distance between adjacent turns with lung motion Implants in accordance with at least some embodiments of the present technology have a ratio of radial spring constant to longitudinal spring constant within a range from 10:1 to 80:1, such as from 15:1 to 80:1 or from 20:1 to 80:1.

Figure 67:
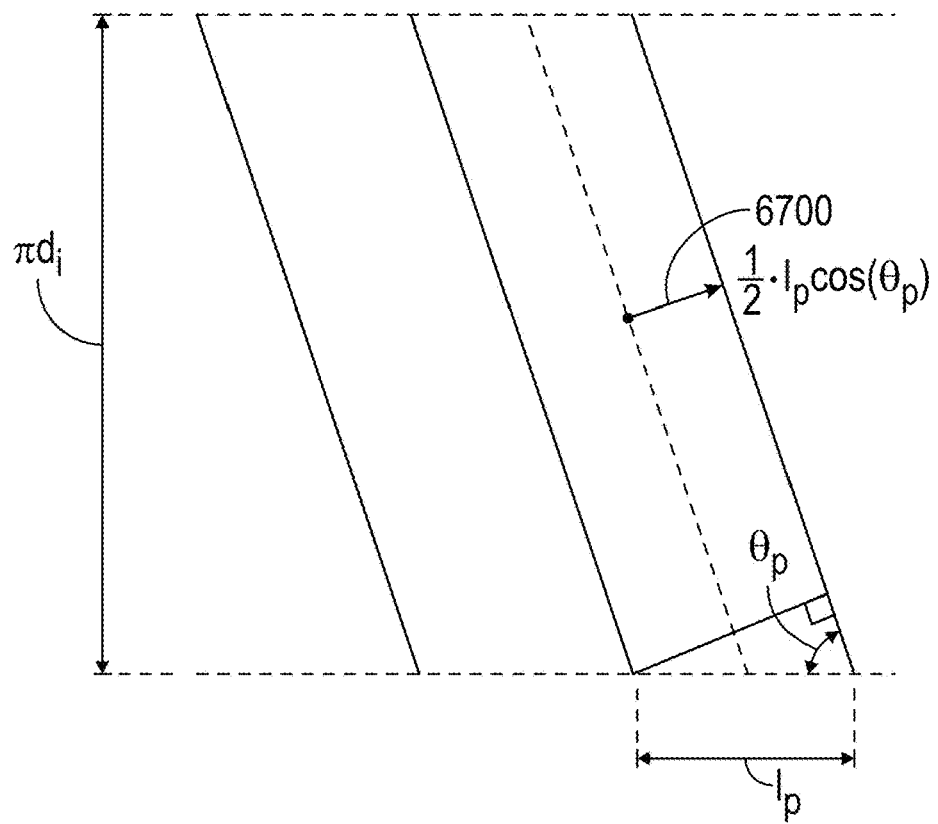
FIG. 67 is a schematic diagram illustrating a maximum distance between a point on an airway wall and a wire path of a simple coil.
Figure 68:
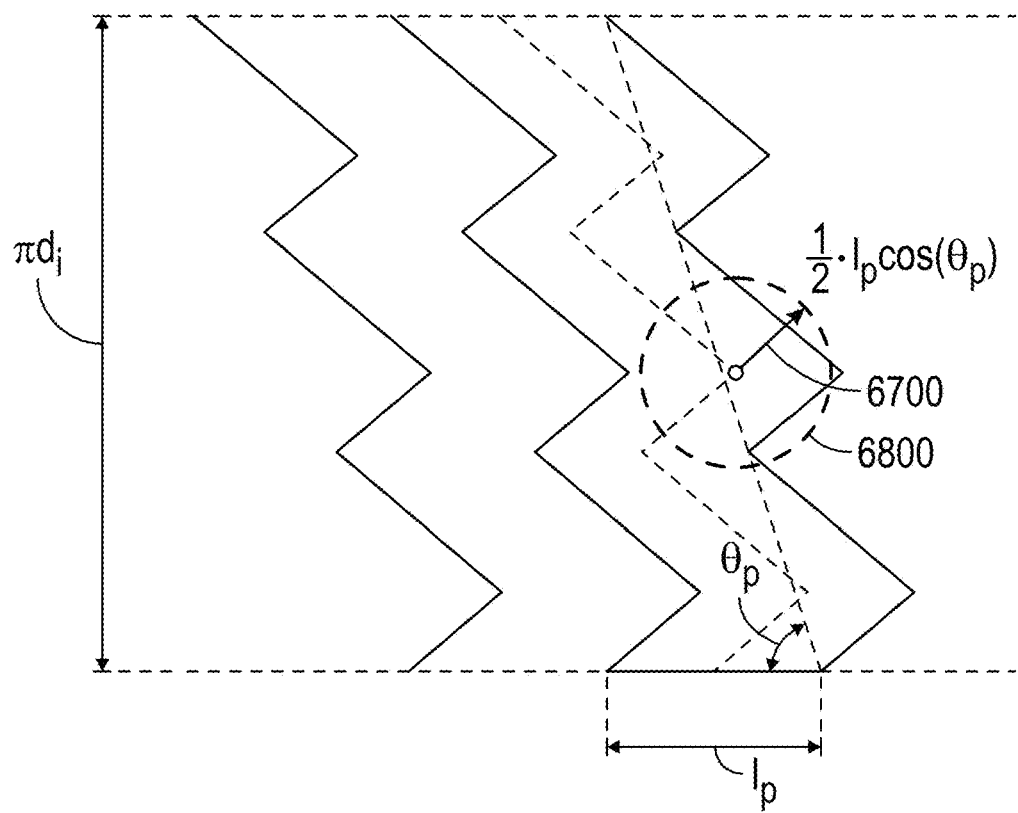
FIG. 68 is a schematic diagram illustrating a maximum distance between a point on an airway wall and a wire path of an implant in accordance with at least some embodiments of the present technology.

A wire including alternating first and second legs can support an airway to a greater extent than a wire shaped as a simple coil even if both wires have the same pitch. FIG. 67 is a schematic diagram illustrating a maximum distance between a point on an airway wall and a wire path of a simple coil. FIG. 68 is a schematic diagram illustrating a maximum distance between a point on an airway wall and a wire path of an implant in accordance with at least some embodiments of the present technology. The maximum distance in FIG. 67 is represented by line 6700 and can be calculated using the following Equation 5 (Eq. 5):

$$\text{maximum distance} = \frac{1}{2} \cdot l_p \cos \theta_p \quad \text{(Eq. 5)}$$

$l_p$ = implant pitch length $\theta_p$ = implant pitch angle

In FIG. 68, a circle 6702 having a radius equal to the length of the line 6700 is centered on a point along a line midway between neighboring turns of the wire path. The circle overlaps the wire path indicating that a portion of an airway at the point is closer to the wire and thus better supported with the wire path of FIG. 68 and with the wire path of FIG. 67.

Another implant feature the inventors recognized as potentially relevant to maintaining stable contact between an implant and an airway wall during respiration is resistance to flattening from a tubular form toward a more planar form. Some tubular structures have longitudinally distributed substructures (e.g., helical turns) that easily domino or otherwise collapse on one another in response to shear stress parallel to the structures' longitudinal axes. This is problematic because this type of shear stress may occur in airways during respiration. In contrast to blood vessels that expand and contract to a limited extent and primarily radially rather than longitudinally during pulsatile blood flow, airways during respiration expand and contract far more significantly and do so both radially and longitudinally. Accordingly, achieving an adequate resistance to flattening can be far more challenging in the context of pulmonary implants than in the context of vascular implants. Due to the structural features discussed below and/or for other reasons, implants in accordance with at least some embodiments of the present technology are well suited to resisting flattening. For example, implants in accordance with at least some embodiments of the present technology have a ratio of radial spring constant to longitudinal shear modulus suitable for resisting flattening. This ratio, for example, can be within a range from 0.005 to 0.100. In addition or alternatively, implants in accordance with at least some embodiments of the present technology have a ratio of longitudinal spring constant to longitudinal shear modulus suitable for resisting flattening. This ratio, for example, can be within a range from 0.5 to 5.0.

The above and/or other properties that promote stable wall contact during respiration can be related to certain structural features of implants in accordance with at least some embodiments of the present technology. One such feature is the complete or relative absence of stiff bridges between successive helical turns or other longitudinally distributed implant substructures. This feature can promote relatively low resistance to longitudinal deformation together with relatively high resistance to radial deformation, which, as discussed above, tends to promote stable contact between an implant and an airway wall during respiration. This feature can also increase the tendency of an implant to flatten from a tubular form toward a more planar form, which, as also discussed above, can have the opposite effect. The inventors discovered, however, that the latter effect can be at least partially mitigated by increasing the average spacing (e.g., pitch) between successive helical turns or other longitudinally distributed implant substructures. Furthermore, both the complete or relative absence of stiff bridges between successive helical turns or other longitudinally distributed implant substructures and the increased spacing between these substructures synergistically help to maintain improved airway patency. Both of these features tend to facilitate mucociliary clearance and/or to reduce foreign body response. Implants in accordance with at least some embodiments of the present technology include longitudinally distributed substructures (e.g., helical turns) within a first helical band extending around a longitudinal axis and define an unobstructed second helical band between windings of the first helical band. In at least some cases, this feature is present together with a ratio of pitch to diameter within a range from 0.3:1 to 1.5:1, such as from 0.5:1 to 1.2:1.

Implant Deployment

Figure 69:
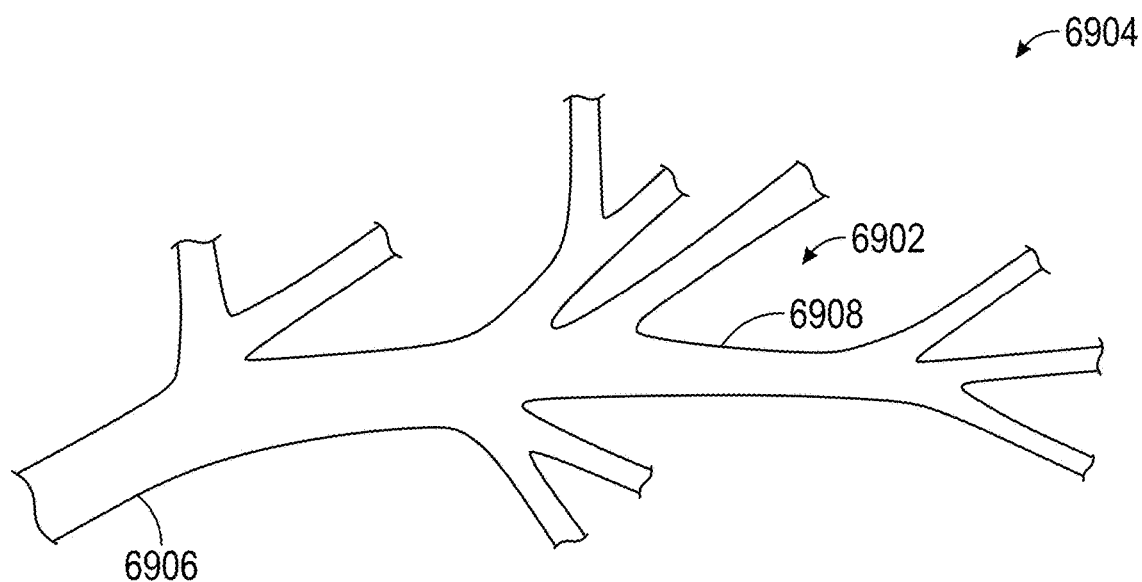
FIG. 69 is an anatomical illustration of an airway region at which an implant in accordance with at least some embodiments of the present technology can be deployed.

FIG. 69 is an anatomical illustration of an airway region 6902 within a bronchial tree 6904 of a human subject. FIGS. 70-75 are partially schematic illustrations of different respective times during deployment of an implant at the airway region 6902. This deployment will now be described primarily with respect to the implant 6300 (FIG. 63) and the delivery system 5500 (FIG. 55A). It should be understood, however, that the deployment can be practiced with any suitable implant or delivery system described herein. Furthermore, the implant 6300 and other implants described herein can be compatible with other suitable types of deployment. With reference to FIGS. 55A, 63 and 69-75 together, the implant 6300 can be moved intraluminally within the bronchial tree 6904 toward a treatment location at the airway region 6902. The treatment location can include a first airway 6906 and a second airway 6908 distal to the first airway 6906. A generation of the second airway 6908 can be greater than a generation of the first airway 6906. For example, the generation of the second airway 6908 can be at least 1, 2, 3, 4, 5 or 6 greater than a generation of the first airway 6906. Furthermore, a generation of the first airway 6906 can be at least 3, 4, 5, 6 or an even higher number.

Figure 70:
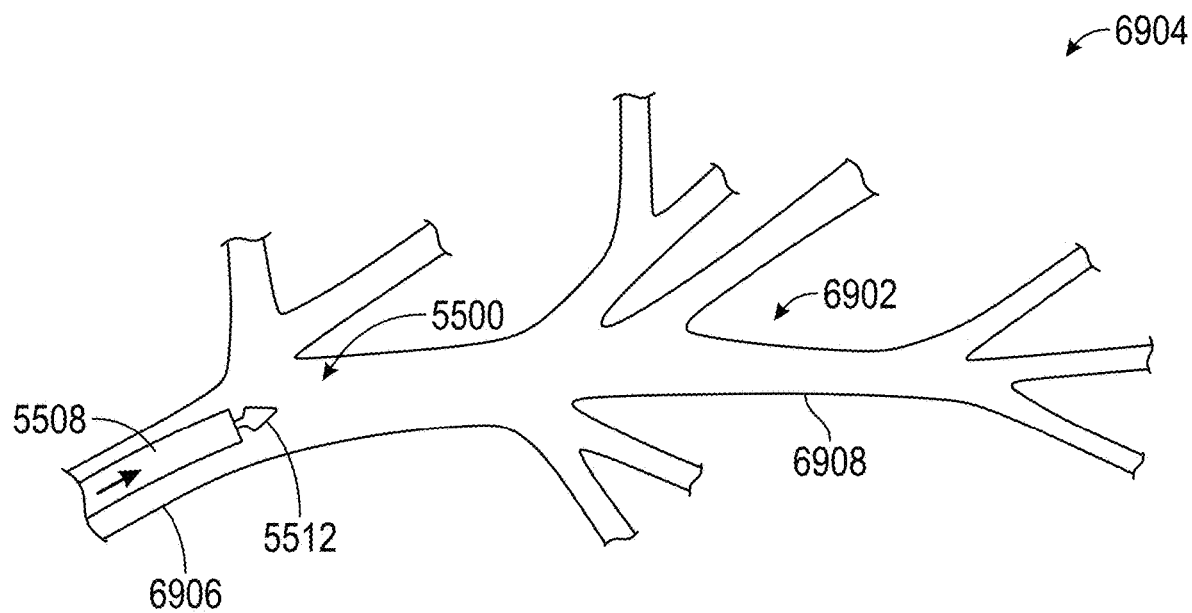
FIGS. 70-75 are partially schematic illustrations of different respective times during deployment of an implant in accordance with at least some embodiments of the present technology at the airway region shown in FIG. 69.
Figure 71:
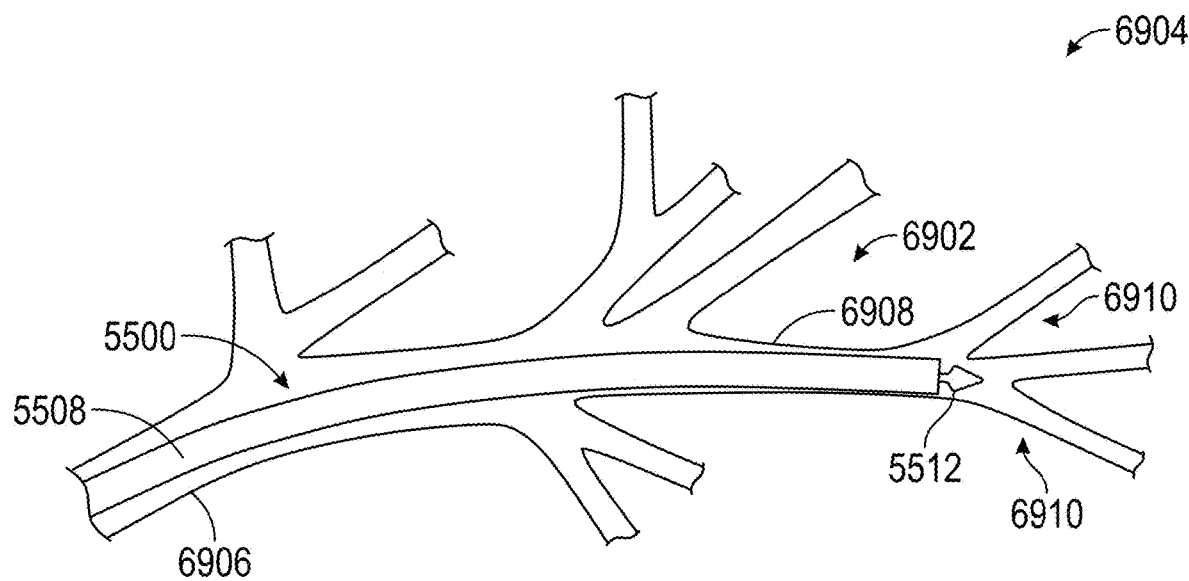

Movement of the implant 6300 toward the treatment location can occur while the implant 6300 is in the low-profile delivery state. For example, the inner sheath 5508 can extend around the implant 6300 and constrain radial expansion of the implant 6300 during this intraluminal movement. As shown in FIGS. 69 and 70, the delivery system 5500 can be moved distally until the tip 5512 reaches a restriction 6910 (e.g., a bifurcation or trifurcation) of the bronchial tree 6904 too narrow to admit farther distal movement of the delivery system 5500. In some cases, the tip 5512 expands portions of the airway region 6902 at the restriction 6910. In other cases, the delivery system 5500 is not moved distally far enough to cause this to occur. Interaction between the tip 5512 and the restriction 6910 can be discerned via tactilely (e.g., a clinician may feel resistance when the tip 5512 reaches the restriction 6910), fluoroscopically (e.g., via fluoroscopic imaging of a radiopaque marker (not shown) at the tip 5512), visually (e.g., via an endoscopic camera (not shown) incorporated into the delivery system 5500), and/or in another suitable manner. In other cases, as described above in the context of FIG. 55A, the delivery system 5500 can be deployed via a working channel of a bronchoscope. In these cases, a distal end of the bronchoscope (rather than the tip 5512) may interact with the restriction 6910 to limit a degree to which the implant 6300 can be advanced distally within the bronchial tree 6904. In these cases, a camera of the bronchoscope can be used to guide positioning of the implant 6300.

Figure 72:
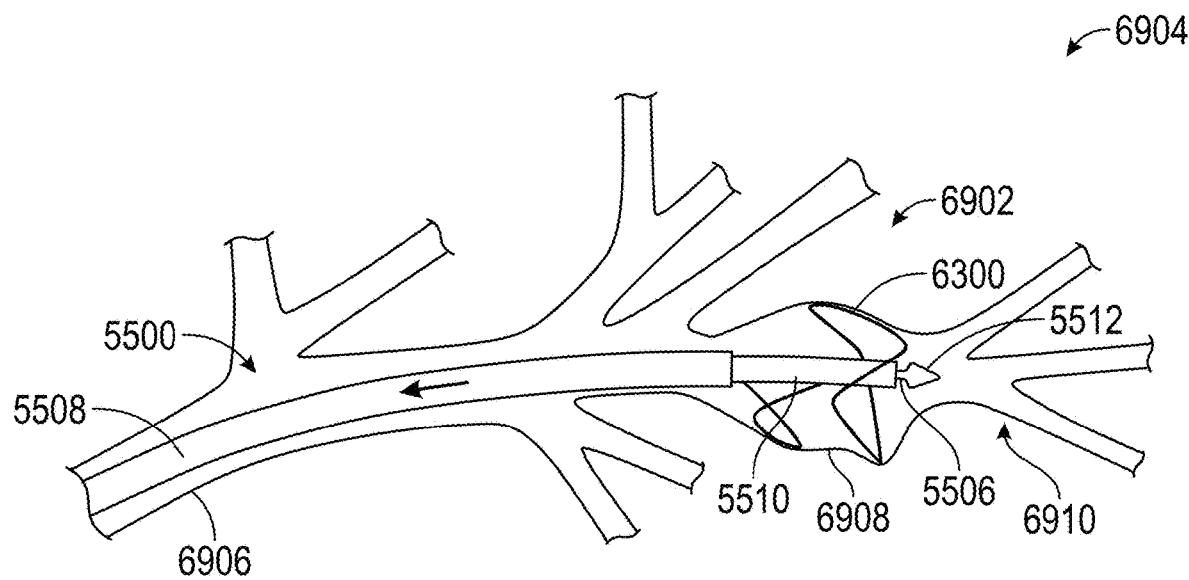

Once suitably located, the implant 6300 can be transitioned from the delivery state to the expanded deployed state at the treatment location. As shown in FIG. 72, this can include causing relative movement between the implant 6300 and the inner sheath 5508. For example, the inner sheath 5508 can be retracted to expose the implant 6300 progressively beginning with a distalmost portion of the implant 6300 and moving proximally. Exposing the implant 6300 can allow the implant to self expand. For example, exposing the implant 6300 can release at least some resilient bias of the implant 6300 until the implant 6300 assumes an equilibrium state at which outward radial force from the implant 6300 equals inward radial force from the airway region 6902. In at least some cases, the implant 6300 is more resiliently biased at the first and second apex portions 6318, 6320 than at the first and second legs 6314, 6316. Accordingly, the implant 6300 can be considered to include springs at the first and second apex portions 6318, 6320 and connectors at the first and second legs 6314, 6316. In other embodiments, the springs and connectors can have other suitable forms. Furthermore, the springs may be replaced with non-resilient expandable structures configured to expand via a mechanism (e.g., a balloon or other secondary structure within the implant 6300) other than resilience.

During relative movement between the implant 6300 and the inner sheath 5508, the proximal stop 5504 can inhibit proximal movement of the overall implant 6300 and the conformable member 5510 can inhibit proximal movement of individual turns of the implant 6300. Thus, the implant 6300 can be deployed in a controlled manner to at least generally retain its longitudinal positioning and configuration as it expands radially. In at least some cases, the length 6324 of the implant 6300 is about the same (e.g., no more than 5% or 10% different) immediately after transitioning the implant 6300 relative to while the implant 6300 is still within the inner sheath 5508. Transitioning the implant 6300 can begin with expanding the distal end portion 6303 at the second airway 6908. This can include contacting a wall of the second airway 6908 and an untethered terminus of the wire 6305 at a portion of the wall of the second airway 6908 proximal to a distalmost end of the implant 6300. Expanding the distal end portion 6303 at the second airway 6908 can also include contacting the wall of the second airway 6908 and a given one of the second legs 6316 at an end of the wire path 6306. Transitioning the implant 6300 can proceed with expanding the intermediate portion 6304 and then expanding the proximal end portion 6302 at the first airway 6906. Expanding the proximal end portion 6302 at the first airway 6906 can include contacting a wall of the first airway 6906 and an untethered terminus of the wire 6305 at a portion of the wall of the first airway 6906 at a proximalmost end of the implant 6300. Expanding the proximal end portion 6302 at the first airway 6906 can also include contacting the wall of the first airway 6906 and a given one of the first legs 6314 at an end of the wire path 6306.

In at least some cases, contact between a wall of the airway region 6902 and the implant 6300 simultaneously propagates along different numbers of circumferentially spaced apart portions of the wall during expansion of different portions of the implant 6300. For example, contact between the wall and the implant 6300 can simultaneously propagate along a greater number of circumferentially spaced apart portions of the wall during deployment of the distal end portion 6303 than during deployment of the intermediate portion 6304 or during deployment of the proximal end portion 6302. In particular examples contact between the wall and the implant 6300 simultaneously propagates along five or more circumferentially spaced apart portions of the wall during deployment of the distal end portion 6303 and simultaneously propagates along three or more circumferentially spaced apart portions of the wall during deployment of the intermediate portion 6304 and during deployment of the proximal end portion 6302.

In at least some cases, during some (e.g., at least 50% or 75% by change in the diameter 6328) or all of expansion of the implant 6300 at the treatment location, an average degree of curvature of the wire path 6306 at the first and second apex portions 6318, 6320 increases, a width of the first helical band 6340 parallel to the longitudinal axis 6301 decreases, a helical length of the first helical band 6340 increases, a width of the second helical band 6342 parallel to the longitudinal axis 6301 increases, a given three of the first apex portions 6318 at respective neighboring turns 6322 of the wire path 6306 remain within 5 degrees of circumferential alignment with one another, a given three of the second apex portions 6320 at respective neighboring turns 6322 of the wire path 6306 remain within 5 degrees of circumferential alignment with one another, an average circumferential spacing between successive apex points among the first and second apex points 6319, 6321 collectively along the wire path 6306 remains within a range from 35 degrees to 95 degrees, the average circumferential spacing between the successive apex points remains within a range from 55 degrees to 65 degrees, and/or the average circumferential spacing in degrees between the successive apex points changes by no more than 5%.

Figure 73:
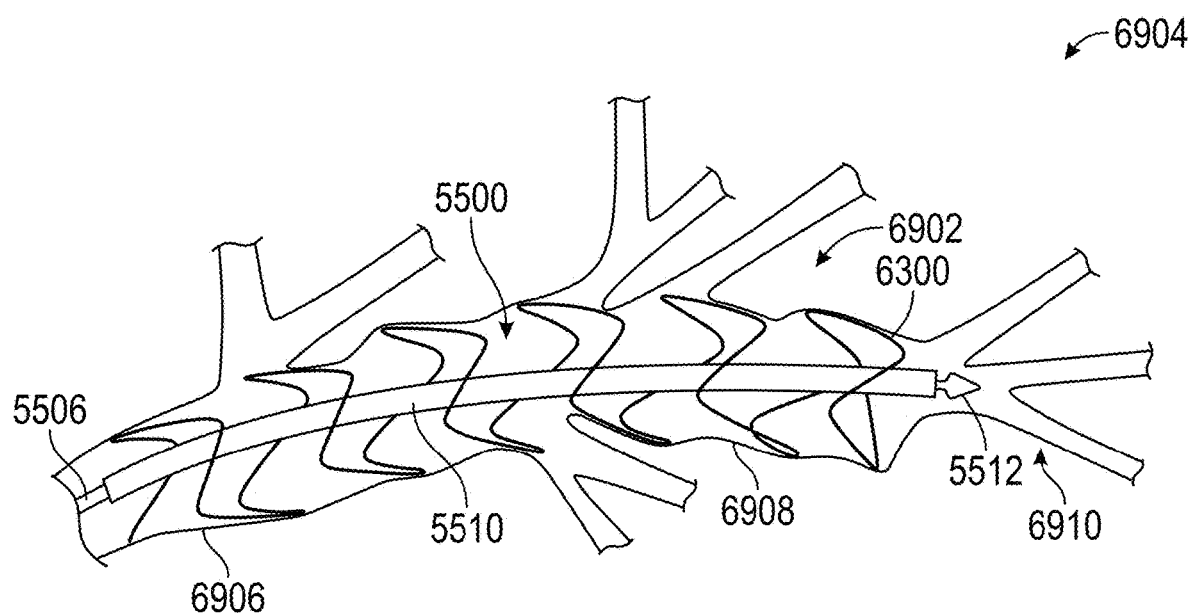
Figure 74:
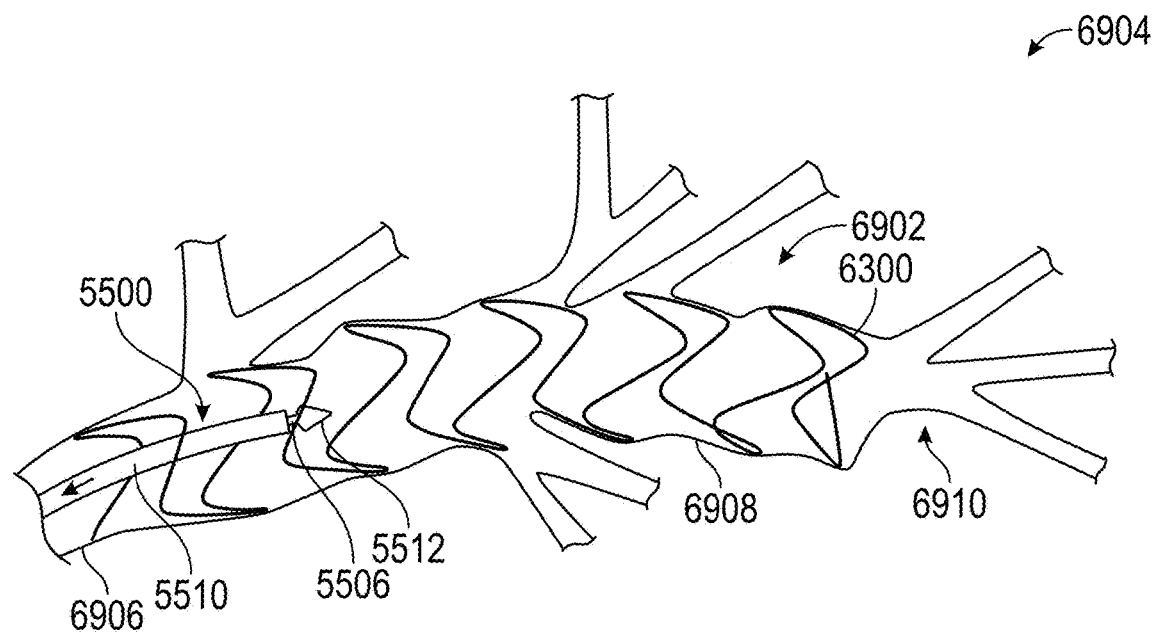
Figure 75:
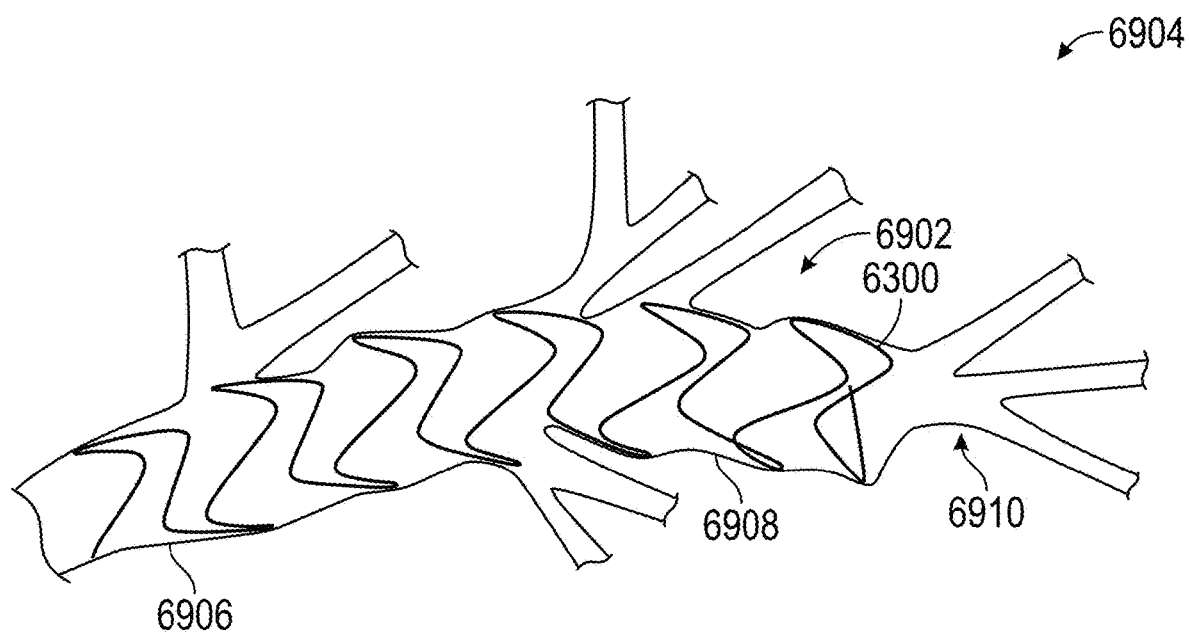

As shown in FIGS. 73-75, transitioning the implant 6300 can free the implant from the conformable member 5510. The conformable member 5510 can then be withdrawn proximally along with other portions of the delivery system 5500, thereby leaving the implant 6300 in the deployed state at the treatment location. Immediately after transitioning the implant 6300, the implant 6300 can exert a force against a wall of the bronchial tree of, for example, at least 0.05 megapascals. The airway region 6902 may be extremely flexible such that transitioning the implant 6300 expands a wall portion of the bronchial tree 6904 coextensive with the length 6324 of the implant 6300 well beyond a native diameter of this wall portion. Furthermore, the average diameter 6328 of the implant 6300 in the deployed state can be the same as or similar to (e.g., from 70% to 100% or from 80% to 100%) the average diameter 6328 of the implant 6300 in the unconstrained state. In addition or alternatively, a ratio of an average of the diameter 6328 of the implant 6300 immediately after transitioning the implant 6300 and the length 6324 of the implant 6300 immediately after transitioning the implant 6300 can be within a range from 1:5 to 1:15.

Figure 76:
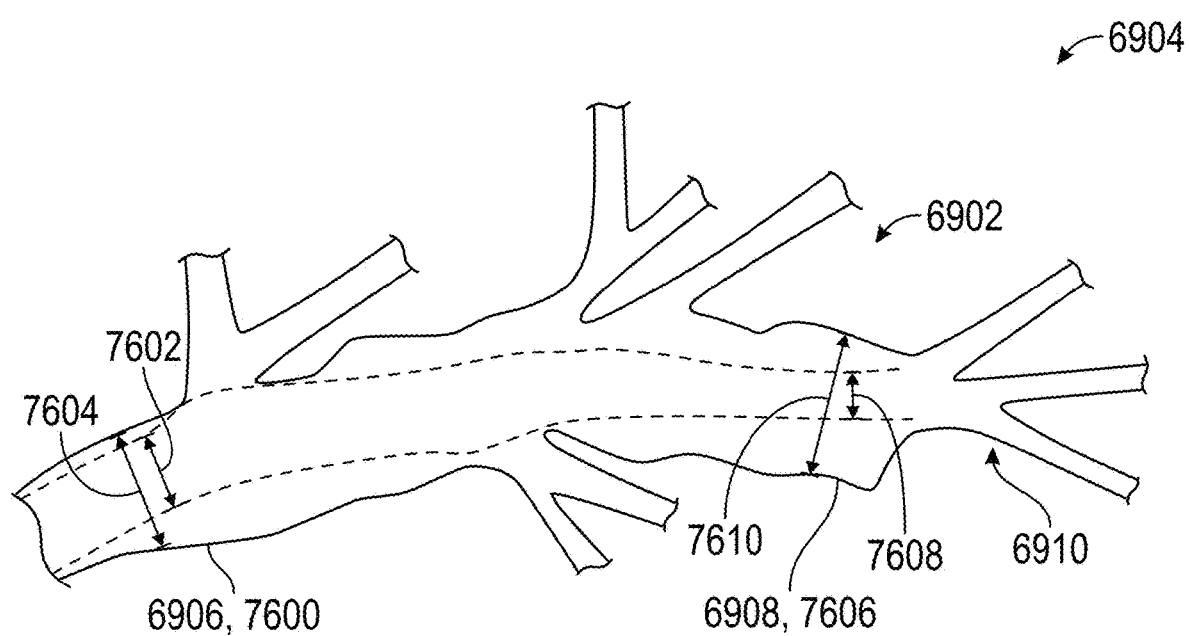
FIG. 76 is an anatomical illustration of the airway region shown in FIG. 69 with certain native and expanded dimensions indicated.

FIG. 76 is an anatomical illustration of the airway region 6902 with certain native and expanded dimensions indicated. With reference to FIGS. 55A, 63 and 69-76 together, this can include expanding a first wall portion 7600 coextensive with a distalmost 10% of the length 6324 of the implant 6300 along the longitudinal axis 6301 from a first average native diameter 7602 to a first average expanded diameter 7604 and expanding a second wall portion 7606 coextensive with a proximalmost 10% of the length 6324 of the implant 6300 along the longitudinal axis 6301 from a second average native diameter 7608 to a second average expanded diameter 7610. In at least some cases, an average expanded diameter at the airway region 6902 throughout the length 6324 is at least 2, 2.5, 3, or 4 times larger than an average native diameter at this portion of the airway region 6902. In addition or alternatively, a ratio of the first average expanded diameter 7604 to the first average native diameter 7608 can be greater (e.g., at least 4, 6, 8 or 10 times greater) than a ratio of the second average expanded diameter 7610 to the second average native diameter 7608. Furthermore, the first average expanded diameter 7604 can differ from the second average expanded diameter 7610 relatively little, such as between 0% and 20%.

Improving Pulmonary Function

Figure 77:
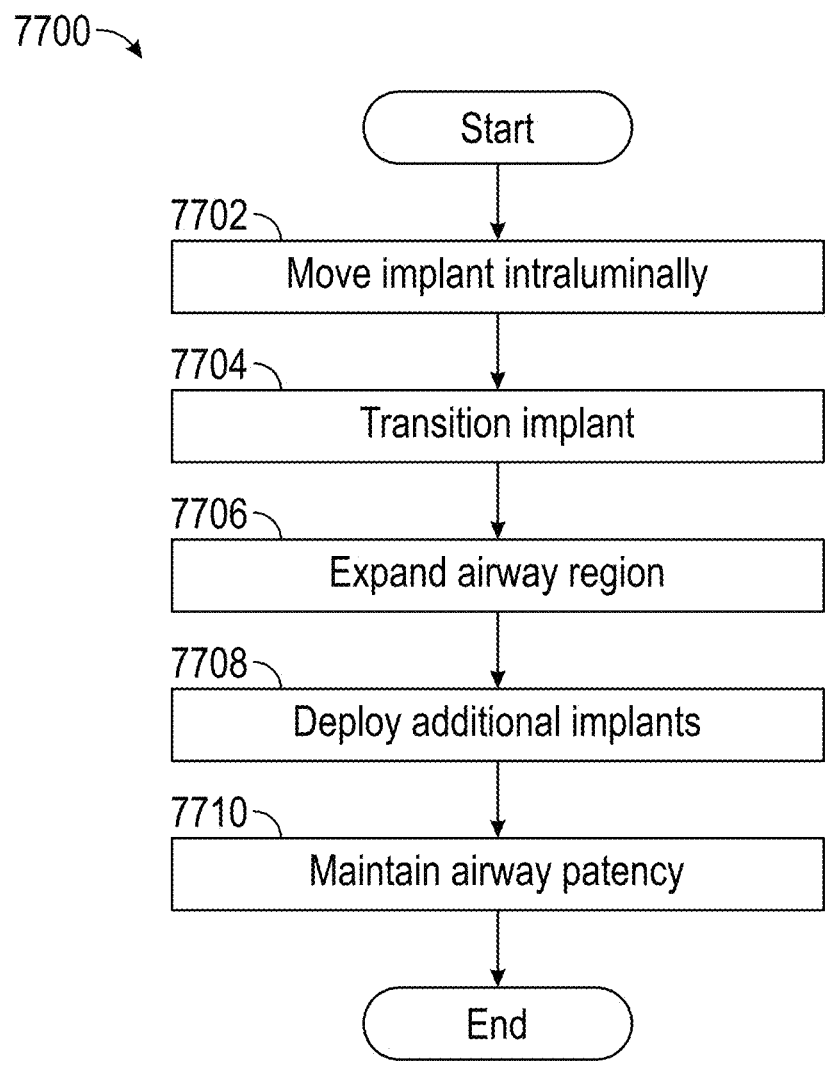
FIG. 77 is a block diagram showing a method for improving pulmonary function in a human subject in accordance with at least some embodiments of the present technology.

FIG. 77 is a block diagram showing a method 7700 for improving pulmonary function in a human subject in accordance with at least some embodiments of the present technology. In at least some cases, the subject is diagnosed with chronic obstructive pulmonary disorder. As shown in FIG. 77, the method 7700 can include moving an implant intraluminally within a bronchial tree of the subject toward a treatment location within the bronchial tree while the implant is in a low-profile delivery state (block 7700), transitioning the implant from the delivery state to an expanded deployed state at the treatment location (block 7700) and expanding an airway region at the treatment location (block 7700). These portions of the method 7700 are discussed in detail above in connection with implant deployment. The method 7700 can further include deploying additional implants (block 7700). For example, the deployment process described above with reference to FIGS. 69-75 can be repeated with additional implants at different respective airway regions. These airway regions, for example, can be associated with different pulmonary bullae. Deployment of the initial and subsequent implants can release trapped air and reduce or prevent further trapping of air at these pulmonary bullae.

Although not shown in FIG. 77, the method 7700 in some cases can include further modifying the airway region at which a given implant is deployed after deployment of the implant. When a treatment includes deploying multiple implants, this further modification can occur at one, some, or all of the treatment locations. As discussed above with reference to FIGS. 69-75, deploying the implant can expand a wall of an airway region to a first average expanded diameter. Further modification can include subsequently further expanding the wall to a second average expanded diameter larger than the first average expanded diameter. The balloon can be advanced intraluminally to the treatment location with the implant or after the implant is deployed and the delivery system removed. At the treatment location, the balloon can be expanded to cause both the wall and the implant to expand to the larger second average expanded diameter. In at least some cases, the second average expanded diameter is greater than an average unconstrained diameter of the implant. Thus, the balloon can be used to hyper-expand the implant. This can be useful, for example, to create and/or enlarge broncho fenestrations in the wall. As discussed elsewhere in this disclosure, broncho fenestrations may be therapeutically beneficial to release trapped air, to improve airway patency, and/or for one or more other reasons.

In at least some cases, deployment of a first implant can release a first volume of trapped air, placement of a second implant can release a second volume of trapped air, placement of a third implant can release a third volume of trapped air, etc. Implants can be deployed until a sufficient amount of trapped air is released and a sufficient degree of lung volume reduction is achieved for effective treatment of COPD. In some cases, deploying one implant may be sufficient. In other cases, 2, 3, 4, 5, 6, or even greater numbers of implants may be deployed. Furthermore, one, two or another suitable first quantity of implants may be deployed at one time and one, two or another suitable second quantity of implants may be deployed at a second time hours, days, months or even longer after the first time. In a particular example, a first quantity of implants is deployed, followed by gathering monitoring, testing, and/or patient-reported information during a test period, and then a second quantity of implants is deployed based on a degree to which the first quantity of implants was effective in treating COPD symptoms according to the information. In yet another example, additional implants may be deployed occasionally as COPD progresses and new pulmonary bullae develop over many months or years.

Deploying an implant at a treatment location can cause the treatment location to go from being low patency or nonpatent to having therapeutically effective patency. In at least some cases, a portion of the bronchial tree distal to the treatment location is emphysematous and has collateral ventilation. In these and other cases, deploying one or more implants can increase one-second forced expiratory volume by at least 5% (e.g., at least 10%). The method 7700 can further include maintaining airway patency (block 7700). With reference to FIGS. 69-77 together, the method 7700 can include maintaining a therapeutically effective increase in patency at the treatment location throughout a continuous maintenance period while the implant 6300 is in the deployed state at the treatment location. The maintenance period can be at least 3 months, 6 months, 9 months, or another suitable period. During the maintenance period, a first area of a wall portion of the bronchial tree 6904 coextensive with the length 6324 of the implant 6300 along the longitudinal axis 6301 can be in direct contact with the implant 6300 and a second area of the wall portion can be out of direct contact with the implant 6300. The second area can be at least 5, 8, 10, 12, 14 or more times larger than the first area. In addition or alternatively, the wire 6305 can occupy from 5% to 30% (e.g., from 5% to 15%) of a total area of the first helical band 6340 during the maintenance period. Furthermore, a maximum invagination of the wall portion at the second area can be no more than 50% of the average expanded diameter of the implant 6300 during the maintenance period. Maintaining airway patency can also include maintaining a mucociliary clearance region at the treatment location substantially free of granulation tissue and mucoid impaction throughout the maintenance period. In addition or alternatively, maintaining airway patency includes maintaining the mucociliary clearance region substantially free of one some or all of inflammation, inflammatory cells, granulation tissue, fibrosis, fibrotic cells, tissue hyperplasia, tissue necrosis, granulation tissue, and mucoid impaction. The mucociliary clearance region can extend along a continuous mucociliary clearance path from a location immediately distal to the implant 6300 to a location immediately proximal to the implant 6300. In at least some cases, the mucociliary clearance region is maintained at an average width parallel to the longitudinal axis 6301 at least 10, 12, 14, 16 or more times greater than an average cross-sectional diameter of the wire 6305 perpendicular to the wire path 6306.

Part of maintaining airway patency can be reducing or eliminating excessive shifting of the implant 6300 during respiration. Relatedly, maintaining patency can include resisting elongation of the implant 6300 along the longitudinal axis during a full respiration cycle by the subject with a resisting force less than a force of friction between the implant 6300 and a wall of the bronchial tree at the treatment location. This feature alone or together with other features can reduce or prevent airway irritation and associated formation of granulation tissue and/or other response that may reduce airway patency during the maintenance period. In at least some cases, the implant maintains airway patency and/or other desirable therapeutic performance levels described herein during the maintenance period without the presence of a drug-eluting material between expandable structures of the implant and a wall of the bronchial tree at the treatment location.

Experimental Example 1: Pressure Testing Different Implant Types

Figure 78:
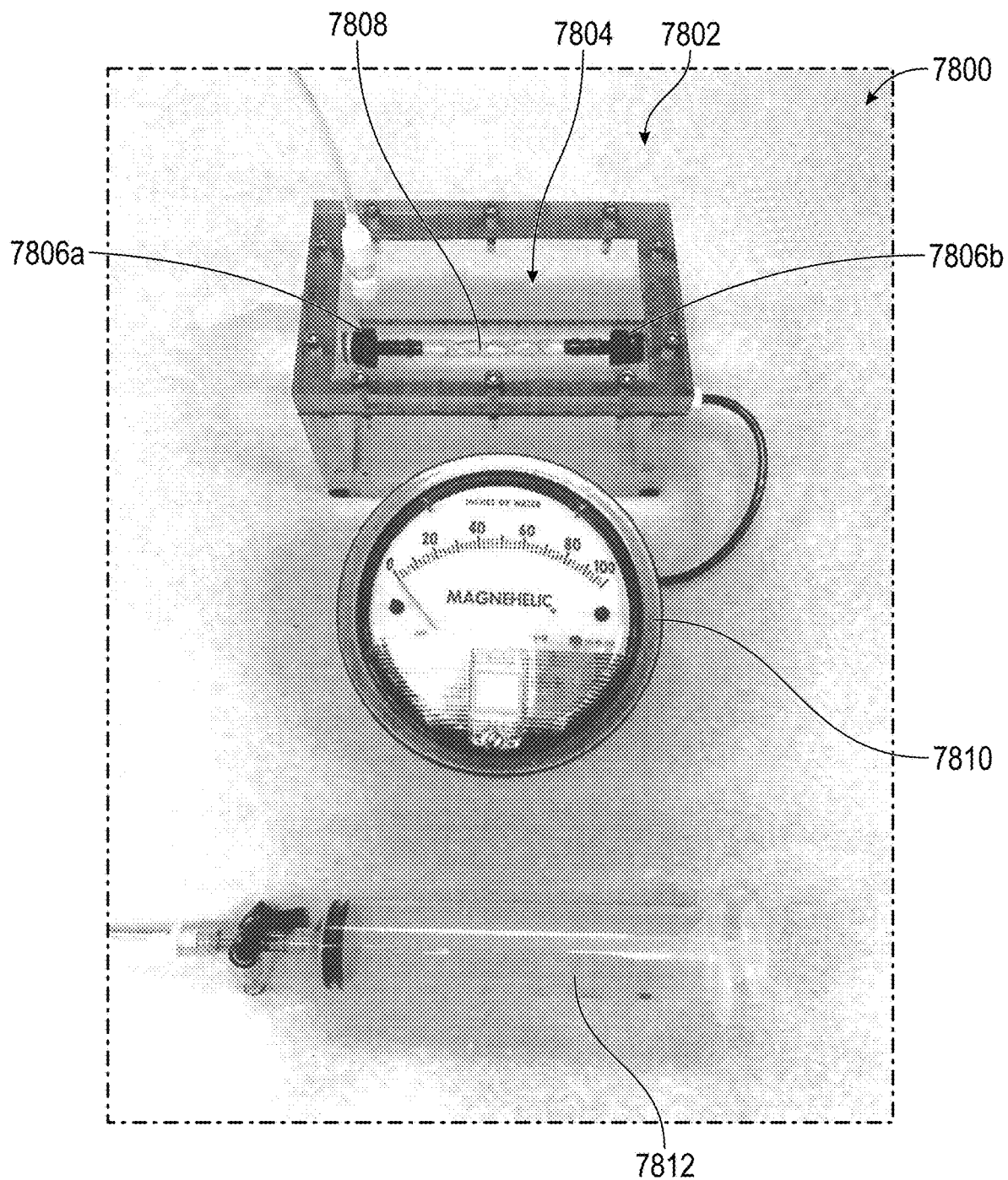
FIG. 78 is an image of an experimental apparatus used to test implants in accordance with at least some embodiments of the present technology.

In an experiment, two different implant types were deployed in an airway analog and constricted to observe their behavior in response to airway constriction during a cough. FIG. 78 is an image of an apparatus 7500 used in this experiment. As shown in FIG. 78, the apparatus 7500 includes a testing chamber 7502 defining a sealed interior volume 7504. The testing chamber 7502 further includes opposing sidewall ports 7506 (individually identified as sidewall ports 7506a, 7506b) and a silicone tube 7508 extending through the interior volume 7504 between the sidewall ports 7506a, 7506b. The tube 7508 has an inner diameter of 6 mm. The apparatus 7500 further comprises a pressure gauge 7510 configured to display a pressure within the interior volume 7504 around the tube 7508 and a syringe 7512 configured to control this pressure. During testing, the tube 7508 was used as an airway analog subject to different external pressures within the interior volume 7504 to mimic pressures an airway in a human bronchial tree would experience during coughing. The sidewall ports 7506 were left open to the atmosphere. Similar to the flexibility of an anatomical airway, the tube 7508 was experimentally observed to collapse at an external pressure of less than 2 inches of water.

Figure 79:
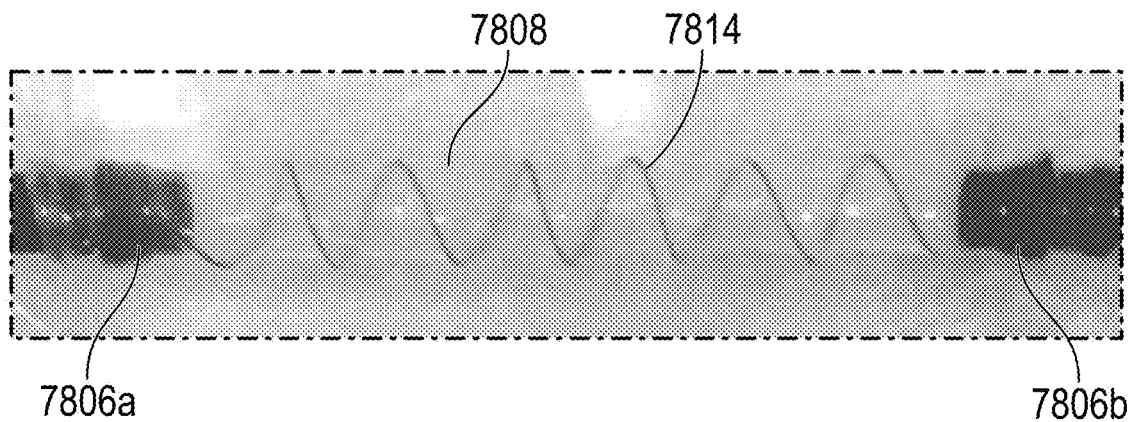
FIG. 79 is an image of a first simple coil having a relatively large turn density in the apparatus shown in FIG. 78 set to atmospheric pressure.
Figure 80:
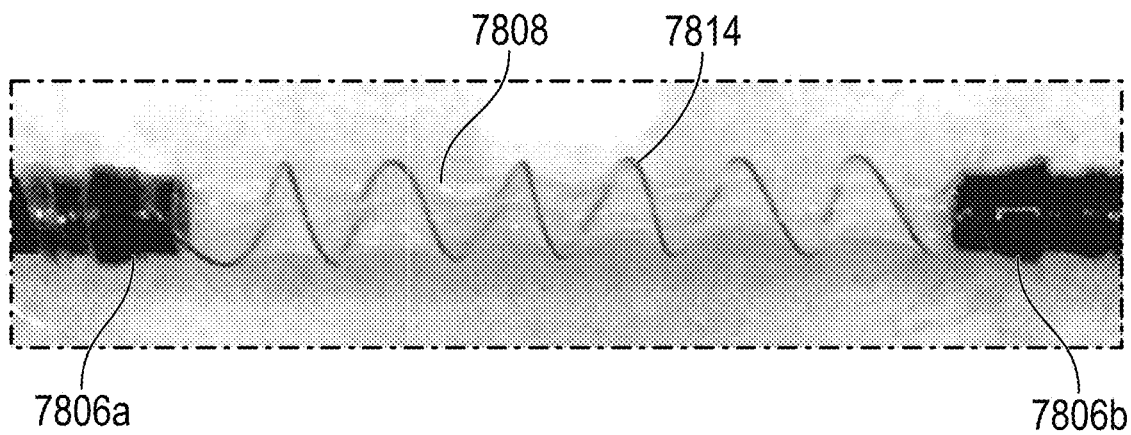
FIG. 80 is an image of the first simple coil shown in FIG. 79 in the apparatus shown in FIG. 78 set to a pressure of 80 inches of water.

FIGS. 79 and 80 are images of a first simple coil 7514 having a relatively large turn density in the apparatus 7500 set to atmospheric pressure and set to a pressure of 80 inches of water, respectively. A pressure of 80 inches of water is theorized to be representative of the pressure an anatomical airway may experience during a cough. As shown in FIG. 80, the first simple coil 7514 was observed to exhibit minimal radial contraction at the cough pressure. Significant invagination between turns of the first simple coil 7514 was also observed.

Figure 81:
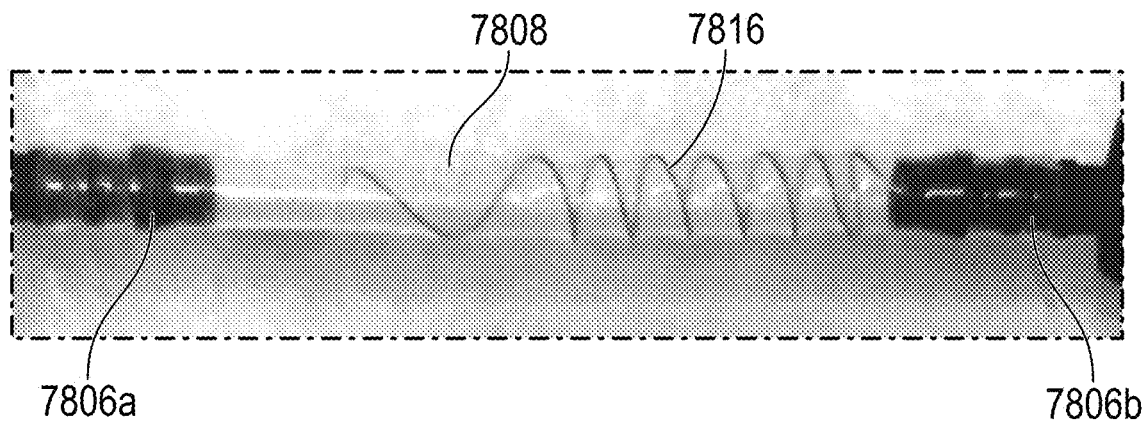
FIG. 81 is an image of a second simple coil having a relatively small turn density in the apparatus shown in FIG. 78 set to atmospheric pressure.
Figure 82:
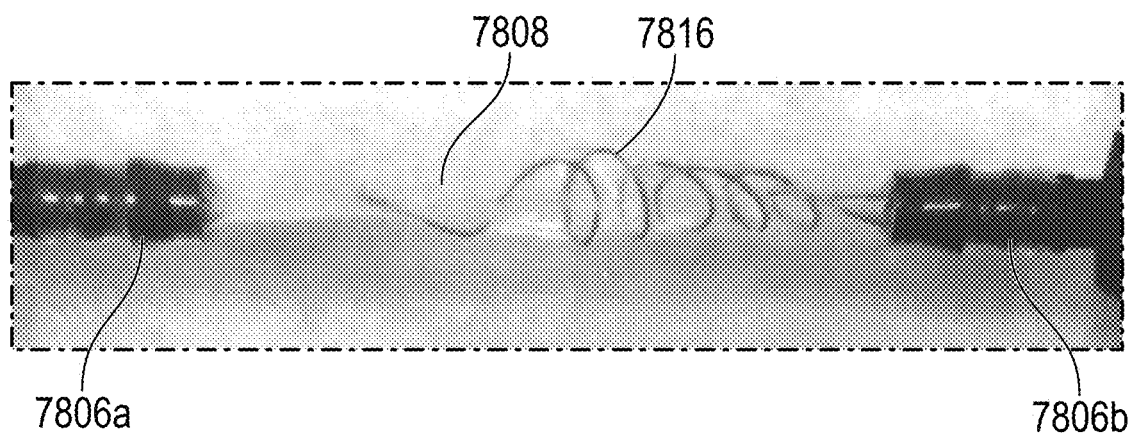
FIG. 82 is an image of the second simple coil shown in FIG. 81 in the apparatus shown in FIG. 78 set to a pressure of 80 inches of water.

FIGS. 81 and 82 are images of a second simple coil 7516 having a relatively small turn density in the apparatus 7500 set to atmospheric pressure and set to a pressure of 80 inches of water, respectively. As shown in FIG. 82, the second simple coil 7516 was observed to collapse at the cough pressure. In particular, the turns of the second simple coil 7516 collapsed on one another in a pancaking or domino manner and the tube 7508 flattened. In a clinical application, this behavior is expected to correspond to a failure to maintain patency.

Figure 83:
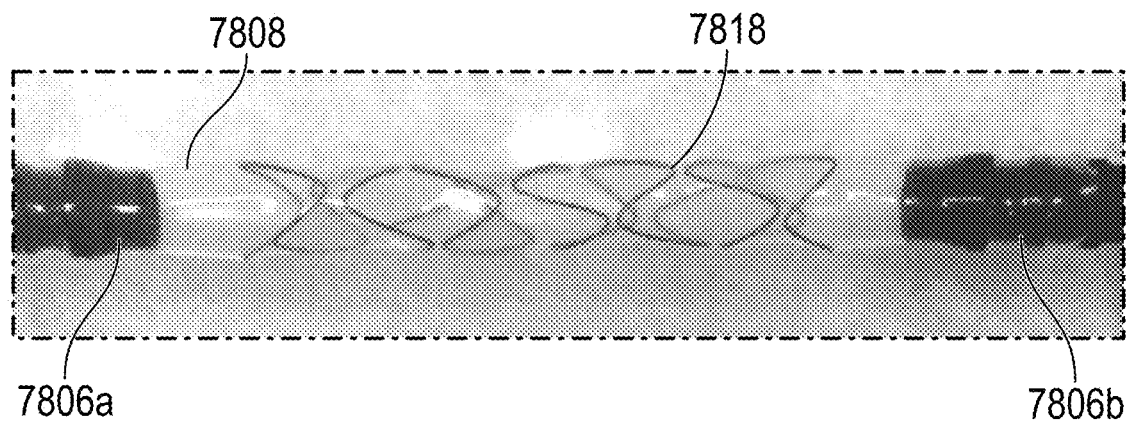
FIG. 83 is an image of an implant in accordance with at least some embodiments of the present technology in the apparatus shown in FIG. 78 set to atmospheric pressure.
Figure 84:
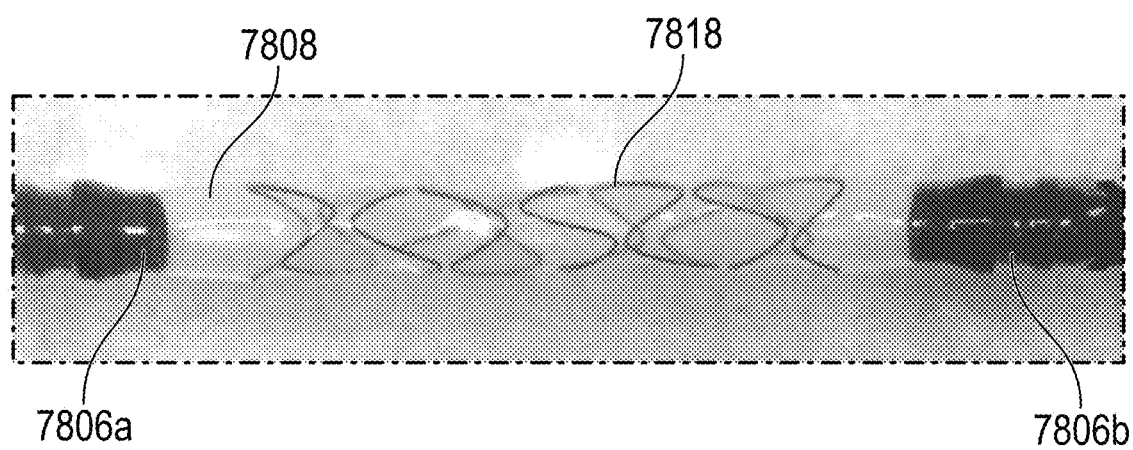
FIG. 84 is an image of the implant shown in FIG. 83 in the apparatus shown in FIG. 78 set to a pressure of 80 inches of water.

FIGS. 83 and 84 are images of an implant 7518 in accordance with at least some embodiments of the present technology in the apparatus 7500 set to atmospheric pressure and set to a pressure of 80 inches of water, respectively. The implant 7518 was tested at approximately the same turn density as the turn density at which the first simple coil 7514 was tested. As shown in FIG. 84, at the cough pressure, the implant 7518 contracted radially, limited invagination relative to the first simple coil 7514, and did not collapse like the second simple coil 7516. These behaviors are expected to result in a greater ability of the implant 7518 to maintain patency relative to the first simple coil 7514 or the second simple coil 7516.

Although this experiment was primarily directed to observing collapse behavior, deployment behavior was also observed. In particular, it was noted that the first simple coil 7514 required manual manipulation from outside the tube 7508 to achieve the desired turn density for the experiment. In contrast, the implant 7518 deployed without requiring this manipulation. By way of nonbinding theory, this advantageous deployment behavior may be related to simultaneously propagating contact between the tube 7508 and the implant 7518 at multiple circumferentially spaced apart locations.

Experimental Example 2: Human Emphysematous Lung Experiments

A first experiment involved measurement of pulmonary function by forced expiratory maneuver (FEM) in ex vivo human emphysematous lungs at baseline and after treatment in accordance with at least some embodiments of the present technology ("test treatment"). The test treatment included implantation and expansion of devices in accordance with at least some embodiments of the present technology ("test implants"), with up to three test implants used per lung. For each forced expiratory maneuver, the peak expiratory flow was measured under full implant dilation conditions. The expiratory flow rates were then integrated electronically to produce expiratory volume for each of the first 12-15 seconds. From these curves, the FEV1 (i.e., forced expiratory volume or the amount of air that can be forced out from a lung in one second) were estimated. FEV1 is the most common metric used to assess pulmonary function. In patients with severe emphysema, FEV1 is significantly reduced.

Figure 85:
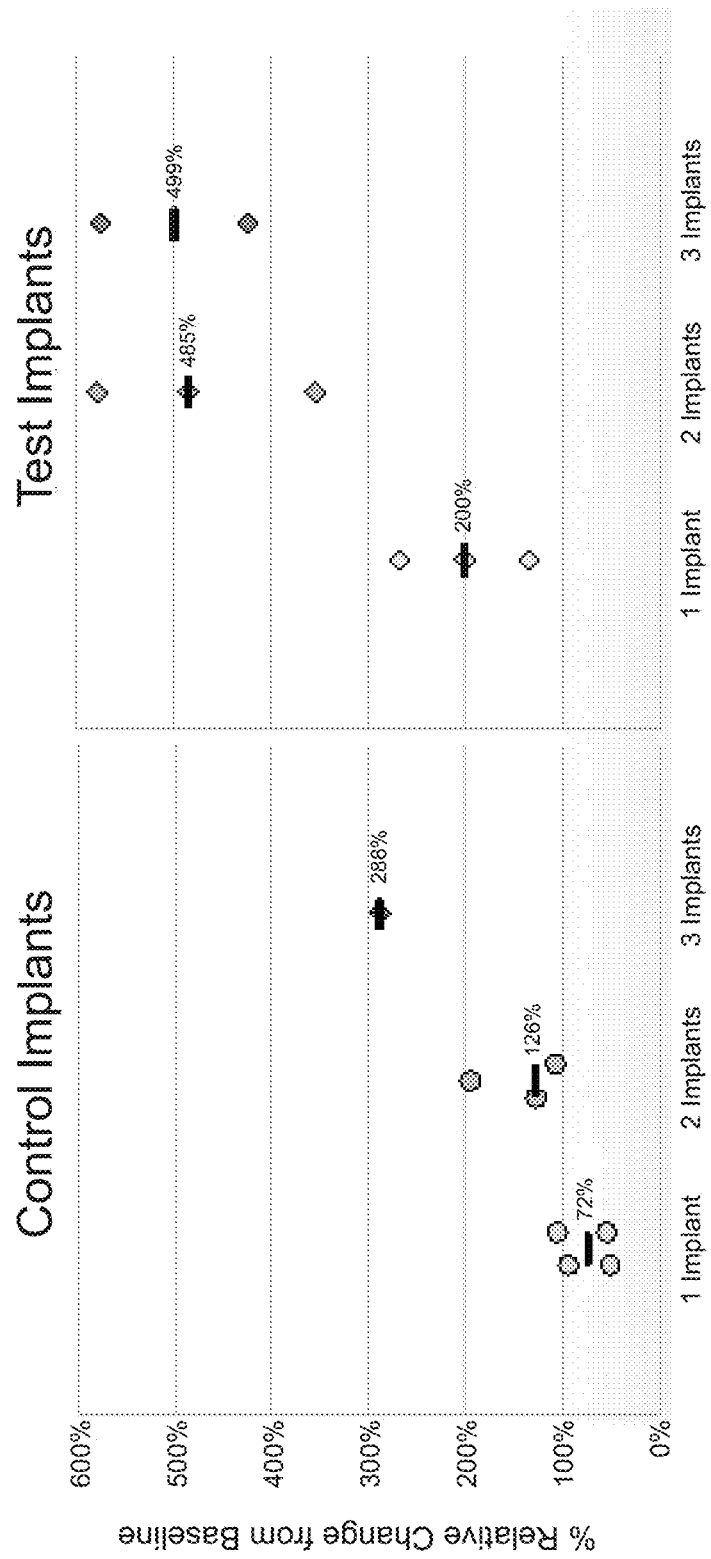
FIG. 85 is a chart showing results from an ex vivo human emphysematous lung study in which implants in accordance with at least some embodiments of the present technology were tested against control implants for their capacity to improve pulmonary function.

FIG. 85 is a chart summarizing the experimental results. It was hypothesized that the placement of test implants would improve pulmonary function in human emphysematous lungs. The results supported this hypothesis. When off the shelf implants ("control implants") were used, the FEV1 value increased, but not as much as it did with the test implants. The results further indicated that increasing the number of test implants used increased the effect on FEV1. As shown in FIG. 1, the placement of one test implant increased the FEV1 of emphysematous lungs by ~200% whereas the placement of three test implants increased the FEV1 of emphysematous lungs by almost 500%.

In another experiment within the first study, FEV1 was measured after test implants were implanted and allowed to expand normally (i.e., constrained by the limitations of the airway anatomy) and then measured again after the test implants were further dilated using a balloon. The results indicated that dilation of the test implants (either by balloon dilation, resilient self expansion, or both) may have created tears (alternatively referred to as "broncho-fenestrations") in the airway walls. Furthermore, the broncho-fenestrations may have increased the efficacy of the test implants. Table 2-1 below shows the results of this experiment.

TABLE 2-1

| Timepoint | FEV1 (L) Mean | % Δ from BL |
|---|---|---|
| Baseline (BL) | 0.17 | — |
| Post-implant of test implant | 0.29 | 70.6 |
| Post-dilation of test implant | 0.34 | 100.0 |

In another experiment, different designs of test implants were compared to better understand how turn density and wire thickness affect the ability of the test implants to prevent invagination of airway tissue and to maintain airway patency. A compression maneuver used in this experiment included changing the pressure of a lung ventilating chamber from −12 cm $H_2O$ to +28 cm $H_2O$ to test lungs with different types of test implants. The airway patency was assessed qualitatively using a small diameter bronchoscope during the compression maneuvers. It was found that a wire thickness of 0.012 made the test implants too stiff to load under the particular conditions of this experiment. Further, a turn density of 1.2 turns/in resulted in airway tissue invagination and loss of airway patency regardless of wire thickness. Overall, it was determined that a wire thickness in the range of 0.009 in-0.011 in and turn density in the range of 1.8-3 turns/in were the most promising design parameters for preventing airway tissue invagination and maintaining airway patency in human emphysematous lungs. Tables 2-2 and 2-3 below show the results of this experiment. In these tables, "Y" represents patent airways and "N" represents collapsed airways. Patency was a binary (Yes/No) assessment of the presence of any visible air passage extending from the proximal to distal end of the test implant. In Table 2-3, percent narrowing was the estimated relative change in airway caliber between −12 cmH2O and 28 cmH2O assessed roughly at the mid-point along the length of the test implant. The following grading system was applied to percent narrowing: 0: 0%, 1: 1-25%, 2: 26-50%, 3: 51-75%, and 4: 76-100%. Implant length was affected by implantation in the airway as well as subsequent dilation of the implant, which resulted in the effective turn density of the implants differing from the nominal turn densities.

TABLE 2-2

| Turn Density | 0.010" | 0.011" | 0.012" |
|---|---|---|---|
| 1.2 turns/in | N | N | Too stiff to load |
| 1.8 turns/in | Y | Y | Too stiff to load |
| 3.0 turns/in | Y | Y | Too stiff to load |
| 4.0 turns/in | Y | Too stiff to load | Too stiff to load |

TABLE 2-3

| Wire Diameter (inches) | Turn Density (turns/inch) Nominal | Effective | Patent Pre-Dilation | Post-Dilation | Percent Narrowing Pre-Dilation | Post-Dilation |
|---|---|---|---|---|---|---|
| 0.009 | 3.0 | 2.8 | Y | Y | 1 | 3 |
|  |  | 3.5 | Y | Y | 1 | 3 |
|  |  | 4.3 | Y | Y | 0 | 3 |
| 0.010 | 1.8 | 2.4 | Y | N | 2 | 4 |
|  |  | 2.4 | Y | Y | 3 | 3 |
|  |  | 2.4 | Y | Y | 1 | 3 |

Experimental Example 3: Rabbit Study

Severe foreign body reaction to implanted devices is characterized by increased inflammation, excessive fibrosis, mucous hypersecretion, and tissue necrosis. These reactions tend to originate at or near the point of contact or interface between the implant and airway tissue, and ultimately result in stent occlusion and reduced device patency. It is hypothesized that the severity of such foreign body reaction can be controlled by reducing the contact density (i.e., surface area of implant-tissue interface/total surface area of airway tissue spanning the length of the implant) of the implant. A secondary hypothesis is that occurrence of foreign body reaction (FBR) is localized or limited to the points of contact between the implant and airway tissue.

The objectives of this study were to: (1) assess if implants in accordance with at least some embodiments of the present technology with lower contact density ("test implants") produce significantly less severe foreign body reaction than those with a higher contact density ("control implants") and (2) assess if the occurrence of FBR is limited to the point of contacts between the implant and airway tissue. Study endpoints are presented in Table 3-1.

TABLE 3-1

| Assessment Method | Performed by | Description (example) | Success Criteria |
|---|---|---|---|
| Bronchoscopic Tissue Assessment | Study Surgeon(s) | Assessed test article sites for stenosis via bronchoscopy | No success criteria were defined for this endpoint. Results were summarized |

TABLE 3-1-continued

| Assessment Method | Performed by | Description (example) | Success Criteria |
|---|---|---|---|
| Gross Pathology | Trained Prosector | Assessed test article treated tissues for abnormalities | No clinically significant findings that were deemed related to the test article |

This study utilized a chronic lagomorph model with 20 animals [n=10 control implant and n=10 test implant]. The control implants were made of Elgiloy material (a non-magnetic Cobalt-Chromium-Nickel-Molybdenum alloy) while test implants were made of Nitinol. Rabbits were chosen as the animal model for this investigation because of the striking similarity between rabbits and humans in terms of airway anatomy. In fact, the rabbit model has been extensively used to study lung pathophysiology including the effects of inflammatory response to lung injury caused by physical force. In our study, each rabbit was implanted with one tracheobronchial implant under bronchoscopic guidance and survived for 90±3 days with bronchoscopic inspection repeated at 30±3 days, and 60±3 days.

At the end of the study, post-mortem, bronchoscopic inspection of the airways of the animals was performed and stenosis of the trachea and the bronchi was assessed. For 12 animals, the implants were placed in the trachea, and for 8 animals the implants were placed in the bronchus. The number of implants in each group (i.e., trachea or bronchus) was decided based on the size of the implants that were available for testing. Table 3-2 shows the overall study design and treatment groupings.

TABLE 3-2

| Group ID | Study Article | Implant Location | # of Animals | Procedure Type(s) | Timing |
|---|---|---|---|---|---|
| 01 | Test Implant 1 | Trachea | 6 | Implant | Day 0 |
| | | | | Follow-up | Day 28 ± 3 |
| | | | | | Day 60 ± 4 |
| | | | | Termination | Day 90 ± 3 |
| 02 | Control Implant 1 | Trachea | 6 | Implant | Day 0 |
| | | | | Follow-up | Day 28 ± 3 |
| | | | | | Day 60 ± 4 |
| | | | | Termination | Day 90 ± 3 |
| 03 | Test Implant 2 | Left main bronchus | 4 | Implant | Day 0 |
| | | | | Follow-up | Day 28 ± 3 |
| | | | | | Day 60 ± 4 |
| | | | | Termination | Day 90 ± 3 |
| 04 | Control Implant 2 | Left main bronchus | 4 | Implant | Day 0 |
| | | | | Follow-up | Day 28 ± 3 |
| | | | | | Day 60 ± 4 |
| | | | | Termination | Day 90 ± 3 |

As shown in Table 3-2, one test or control article was implanted in either the trachea or the left main bronchus. Follow-up evaluations 28 and 60 days after implantation consisted of bronchoscopic evaluation of implant patency and fluoroscopic imaging. An additional post-mortem bronchoscopic evaluation was performed at Day 90.

The schedule of assessments and data recordings is shown in Table 3-3. Day 0 was defined as the date of implantation. In Table 3-3, "X*" indicates that fluoroscopic imaging was optional at Days 28 and 60.

TABLE 3-3

| | Day 0 | Day 28 ± 3 | Day 60 ± 4 | Day 90 ± 3 |
|---|---|---|---|---|
| Implant Implantation | X | | | |
| Bronchoscopic Evaluation | X | X | X | X |
| Fluoroscopic Imaging | X | X* | X* | |
| Euthanasia | | | | X |
| Gross Pathology | | | | X |

The anesthetized rabbits were positioned in sternal recumbency with neck hyperextension. Tracheal access was gained by passing a rigid bronchoscope through the mouth, oropharynx and ultimately the larynx and advancing the tip of the bronchoscope into the trachea. A slim telescope was passed through the rigid bronchoscope for visual inspection and documentation. Each animal had one test or control article (implant) placed in the trachea or left main bronchus.

The implant delivery system was inserted directly through the rigid bronchoscope and the implants deployed under fluoroscopic guidance. Implants placed in the trachea were positioned approximately 1 cm proximal to the main carina. Implants placed in the main bronchus had their most proximal extent located 2-3 mm caudal to the tracheal carina. Once placed, the delivery system was removed, and the animal was transferred to post-operative recovery.

On Day 28 and Day 60, the animals underwent a bronchoscopic procedure to visually assess the implanted airways. The animals were anesthetized, positioned in sternal recumbency on a table with neck hyperextension, and tracheal access was gained by passing a rigid bronchoscope through the mouth, oropharynx and ultimately the larynx and advancing the tip of the bronchoscope into the upper trachea. Intubation was not performed due to the risk of interference with the test article placement. A slim telescope was passed through the rigid bronchoscope for visual assessment of the implant site. A visual score from the bronchoscopic inspection of the airways of the animals was performed for five sections in each trachea/bronchi containing an implant: (1) tissue immediately cranial to the proximal end of the implant, (2) proximal end of the implant, (3) central part of the implant, (4) distal end of the implant, (5) tissue immediately caudal to the distal end of the implant. Each of the five sections was scored as to the degree of stenosis according to the following scale: 0: 0%; 1: 1-10%; 2: 10-25%; 3: 25-50%; 4: 50-75%; 5: 75-100%. Stenosis was defined as narrowing of the airway lumen for any reason, including encroachment by the implant itself, mucous, granulation tissue, or fibrosis. Observations regarding implant placement, stenosis length (mm), presence of granulomatous tissue, amount of mucous, or any abnormalities were also noted.

On Day 28 and Day 60, fluoroscopic imaging was performed in the anesthetized animal immediately after the bronchoscopic procedure described above. Anteroposterior fluoroscopic images of the region of the thorax containing the implant were recorded. The animal was recovered from anesthesia and returned to housing. The animals were observed and clinical observations documented SID (once a day) until their termination day, and all medical treatments incurred throughout the life of the animals were recorded. Euthanasia was performed on Day 90±3 via lethal injection of euthanasia solution. Death was verified by auscultation or pulse monitoring. A post-mortem bronchoscopy was performed immediately after euthanasia. The bronchoscopy procedure and assessment performed were as described for bronchoscopy performed during the Day 28 and Day 60 follow-up evaluations.

A gross examination of the entire tracheobronchial tree (with the implant(s) in situ) was performed to the level of the second-generation bronchi, beyond the distal extent of all implants, for any abnormalities that could be attributed to the test article. The lungs were also examined for any abnormalities. All gross findings, normal and abnormal, were documented. The tracheobronchial tree was collected with a minimum of 1 cm of trachea/bronchi proximal and distal to the implants, anatomy permitting. The lung was inflated with 10% neutral buffered formalin (NBF) and then immersion fixed in 10% NBF for potential future analysis.

The stenosis scores recorded during the bronchoscopy procedure for each of the 5 levels were summarized at Days 28, 60, and 90 for each implant type using descriptive statistics (mean, standard deviation, minimum, maximum). A total stenosis score, calculated as the sum of the stenosis scores at the 5 levels, was also summarized for each implant type. General trends related to other findings noted during the bronchoscopies were described. Abnormal findings documented at the time of necropsy were tabulated by frequency of occurrence for each study group. The stenosis scores assessed by the study surgeon at the time of necropsy were summarized for each study group using descriptive statistics (mean, standard deviation, minimum, maximum). Implant length, width at the cranial end of the implant, and width at the caudal end of the implant were obtained from the fluoroscopic image recordings. A fiducial marker of known length in the fluoroscope's field of view was used to calibrate the measurement. Changes in implant length and width between Day 0, 30, and 60 were summarized for each study group using descriptive statistics (mean, standard deviation, minimum, maximum).

A limited necropsy was performed at the scheduled termination. The entire tracheal/main bronchi tree was collected, with a minimum of 1 cm of trachea/bronchi proximal and distal to the implants, anatomy permitting. The lung tissue was left attached to the tracheal tree. Lungs attached to the tracheal tree were expanded via the airways with 10% NBF. All collected tissues were immersion fixed in 10% NBF for histopathological analysis. Lung tissues with tracheobronchial tree for 20 animals were received for histology processing and histopathology fixed in 10% NBF. All animals had a section taken approximately ½ cm cranial to the proximal end of the implant and a section taken approximately ½ cm caudal to the distal end of the implant. Each animal also had three sections taken in the area of the implant: proximal implant (no more than ½ cm from the proximal end of the implant), mid implant (approximately in the center of the implant), and distal implant (no more than ½ cm from the distal end of the implant).

Additionally for bronchial animals, three sections were taken from the right bronchus (untreated), a cranial section, a mid-bronchus section, and a caudal section. These sections serve as the untreated normal tissue to compare to the treated left bronchus. In order to have untreated tracheal sections to compare to the sections taken from the tracheal implants, 2 animals with bronchial implants also had a tracheal section taken. the site numbers were as follows: site #1: ½ cm cranial to proximal end of implant section, site #2: proximal implant section, site #3: mid implant section, site #4: distal implant section, site #5: ½ cm caudal to distal end of implant section, site #6: right bronchus cranial section (bronchial implants only), site #7: right bronchus mid-section (bronchial implants only), and site #8: right bronchus caudal section (bronchial implants only).

The study pathologist removed the implants from 4 tracheal animals (2 control animals: E5FA8E and E5FF70 and 2 test: E84FF1 and 0E8209) and 2 bronchial animals (1 control animal: E5F859 and 1 test animal: E60648) for paraffin processing of all sections. The remainder of the 14 animals had Site #1 and Site #5 sections taken, as well as any untreated tissue sections taken (Site #6-8 and tracheal control sections), and then were prepped for shipment. This included inking the left side of the tracheobronchial tree, inking the cranial edge of the tissue sample with implant, and to ensure orientation, placing a suture on the cranial edge and opening the dorsal aspect of the airway. Tissues were then shipped for histology processing.

All tissues trimmed were placed in tissue processing cassettes and routinely processed, embedded in paraffin and sectioned on a microtome at approximately 4-6 μm before staining with Hematoxylin and Eosin (H&E). Orientation of trimmed sections was maintained throughout trimming. Upon receipt for plastic processing, the tissues were trimmed following directions provided by the study pathologist and submitted for processing and embedding in Spurr plastic (SP) resin. The resulting plastic block was sectioned to sample up to three (3) levels through the implanted implant region, with two (2) slides captured at each level. One slide was stained with H&E, while the other was left unstained for possible future staining. Stained slides were shipped for histopathological analysis by the study pathologist.

All histology slides were examined using light microscopy by the study pathologist. Tissue sections from the implant-airway tissue interface were analyzed using H&E staining to assess the foreign body reaction to test and control implants and compared to untreated control airway tissue architecture. Inflammation, the primary aspect of the foreign body reaction to implants, was quantified using four different metrics. These included two semi-quantitative grading scales utilized to assign scores to each tissue section by a study pathologist, namely i.) inflammation severity and ii.) percentage of airway circumference affected by inflammation. The grading scale for inflammation severity was: not present: 0, minimal: 1, mild: 2, moderate: 3, marked: 4, and severe: 5. The grading scale for percentage of airway circumference affected by inflammation was: <5%: 0, 5-20%: 1, 21-50%: 2, 51-75%: 3, and 76-100%: 4. In addition, the thickness of the subepithelial tissue layer and the mucosal membrane were quantitatively measured to assess secondary effects of inflammation at the implant-tissue interface. A common secondary effect of severe inflammation is the hyperplasia of the surrounding airway tissue, evidenced by thickening of the subepithelial and mucosal tissues in the airway surrounding the implants.

The bronchoscopic evaluation of the trachea and bronchus performed at Days 28, 60 and 90 indicated that the implanted test implants and control implants remained in the correct position for the study duration. On Days 28, 60 and 90 bronchoscopic assessment of the left main bronchi implanted with the test implant had a less tortuous and less tapered lumen from the proximal to distal end of the implant and airways implanted with the control implant also had a less tapered lumen. Further, in contrast to Day 0 it was now possible to advance a 3.5 mm scope all the way to the distal end of the implant for both the test implant and control implant.

At Day 28, the proximal and distal ends of the test implant wire were frequently observed to be away from the airway wall, sitting free in the airway lumen. Epithelialization was noted at several places along the wire for three of six test implants implanted in the trachea. Mucous was observed in most implant locations, typically as build up on the ends of the implant and/or small amounts occasionally along the length of the implant wire. White nodules, unclear whether mucous or granulation tissue, were noted sporadically along the wire, and were most frequently observed in the tracheal implants. At Day 60, test implants implanted in both the trachea and the left main bronchus were frequently noted to have areas of poor contact with the airway wall, typically at the proximal and distal ends. Mucous and secretions within the region of the implant were typically described as minimal. Whitish nodules along the length of the wire were observed in all animals and were worse in areas of poor contact between the wire and the airway wall. Whether the nodules represented dried mucous or granulomas was unclear. Epithelialization of regions of the implant wire was noted for two test implants implanted in the trachea. At Day 90, mucous impaction was frequently observed where the wire was lifted off the airway wall, typically at the proximal and distal ends of the implant. Otherwise, the amount of mucous was minimal. Occasional areas of white nodularity were observed along the length of the implant wire. These nodules could usually be dislodged with the tip of the bronchoscope suggesting that the nodules were primarily mucous as opposed to granulation tissue. Areas where the implant wire was embedded in the airway wall or epithelialized were frequently observed.

At Day 28, thin mucous was observed throughout the body of most of the implanted control implants, which occasionally contributed to the narrowing of the lumen. Whitish nodules were noted for all control implants implanted in the trachea, commonly occurring throughout the body of the implant as well as at the distal and proximal ends. In one case (E5FF70) two large nodules at the distal end of the implant led to significant stenosis. At Day 60, nearly all control implants implanted in the trachea and main bronchus were associated with copious secretions and thick mucous. Whitish nodules were typically observed throughout the length of the implants, with some nodules clearly identified as granulomas. At Day 90, moderate to extensive mucous along the implant was most commonly observed. Of the four bronchi implanted with the control implant, all exhibited significant stenosis with mucous as a contributing factor in three cases. Three of the six implants in the trachea were noted to have portions embedded in the airway and/or epithelialized. White nodules were most frequently observed along implants in the trachea.

During the bronchoscopic evaluation of the implanted main bronchi, the number of visibly patent airways branching off from the mainstem bronchus was noted. For the bronchi implanted with the test implant, multiple patent side branches were observed in all animals at all timepoints. Bronchi implanted with the control implant tended to have fewer patent side branches visible, and in some cases, no side branches were visible. A summary of the number of patent side branch airways observed in the bronchi implanted with the test and control articles is shown in Table 3-4.

TABLE 3-4

| Device | N | # of visibly patent side branch airways mean ± SD (min-max) | | |
|---|---|---|---|---|
| | | Day 28 | Day 60 | Day 90 |
| test implant | 4 | 4.5 ± 1.0 (4-6) | 5.3 ± 1.0 (4-6) | 5.3 ± 1.7 (3-7) |
| control implant | 4 | 1.8 ± 1.0 (1-3) | 2.0 ± 1.4 (0-3) | 1.3 ± 1.5 (0-3) |

In general, airways implanted with both the test implant and control implant demonstrated variable amounts of stenosis, mucus, and tissue changes possibly suggestive of granuloma formation. The tissue reaction in airways implanted with the test implant tended to be milder compared to airways implanted with the control implant. For the test implant, the regions where tissue reaction and/or mucous were observed were discrete, limited to where the wire was pulled off the wall or where the wire was in contact with the wall. The most pronounced reaction was seen in areas where the implant had poor contact with the tissue. Tissue reaction to the control implant tended to be more pronounced and distributed more diffusely throughout the airway. Unlike airways implanted with the test implant, copious secretions and thick mucous were frequently observed in airways implanted with the control implant.

Scoring of luminal stenosis severity at the proximal, central, and distal regions of the implant as well as immediately cranial to the proximal end of the implant and caudal to the distal end of the implant is shown in Table 3-5 for the Day 28, 60, and 90 time points.

TABLE 3-5

| Device | Location (N) | Day Post-implant | Stenosis Score (mean ± SD) | | | | |
|---|---|---|---|---|---|---|---|
| | | | Cranial | Proximal | Central | Distal | Caudal |
| test implant | Trachea (N = 6) | 28 | 0.0 ± 0.0 | 1.3 ± 0.5 | 0.3 ± 0.5 | 1.0 ± 0.6 | 0.0 ± 0.0 |
| | | 60 | 0.0 ± 0.0 | 1.8 ± 0.8 | 0.7 ± 0.5 | 1.2 ± 0.8 | 0.0 ± 0.0 |
| | | 90 | 0.2 ± 0.4 | 1.3 ± 0.8 | 1.0 ± 0.0 | 1.7 ± 1.0 | 0.0 ± 0.0 |
| control implant | Trachea (N = 6) | 28 | 0.0 ± 0.0 | 1.3 ± 0.5 | 1.0 ± 0.0 | 1.0 ± 0.6 | 0.3 ± 0.8 |
| | | 60 | 0.7 ± 1.0 | 1.3 ± 0.8 | 0.8 ± 0.4 | 1.2 ± 0.8 | 0.0 ± 0.0 |
| | | 90 | 0.3 ± 0.8 | 1.8 ± 0.4 | 1.5 ± 0.5 | 1.5 ± 0.5 | 0.3 ± 0.5 |
| test implant | Left Bronchus (N = 4) | 28 | 0.3 ± 0.5 | 1.0 ± 0.0 | 0.0 ± 0.0 | 0.5 ± 0.6 | 0.0 ± 0.0 |
| | | 60 | 0.0 ± 0.0 | 1.8 ± 0.5 | 0.5 ± 0.6 | 0.8 ± 0.5 | 0.0 ± 0.0 |
| | | 90 | 0.0 ± 0.0 | 1.0 ± 0.0 | 0.3 ± 0.5 | 1.0 ± 0.8 | 0.0 ± 0.0 |
| control implant | Left Bronchus (N = 4) | 28 | 0.0 ± 0.0 | 0.3 ± 0.5 | 0.3 ± 0.5 | 0.5 ± 0.6 | 0.0 ± 0.0 |
| | | 60 | 0.0 ± 0.0 | 1.3 ± 0.5 | 2.5 ± 1.3 | 2.0 ± 0.0 | 1.0 ± 1.0 |
| | | 90 | 0.0 ± 0.0 | 1.3 ± 0.5 | 1.5 ± 0.6 | 2.5 ± 1.3 | 2.8 ± 2.2 |

For the test implant, average stenosis scores at any given location did not exceed 2 (10-25% occlusion) and the proximal implant region tended to have the highest score relative to other locations along the implant. The ends of the test implant wire were manufactured with loops. These loops did not always lay flat against the airway wall when implanted, instead extending part way into the airway lumen. This was a significant contributor to the overall stenosis score for test implants. Minimal stenosis extending caudally or cranially beyond the implant was observed. The pattern of stenosis observed in the trachea and left main bronchus were generally similar.

The pattern and magnitude of stenosis for the control implanted in the trachea was similar to that of the test implant. When implanted in the main bronchus however, the control implant was generally associated with higher stenosis scores at the 60 and 90 day follow up time point, approaching an average score of 3 (25-50% occlusion). The stenoses observed in the airways implanted with the control implants tended to present as eccentric or concentric narrowing due to mucous, white nodular material, or possibly fibrotic tissue. Significant stenosis was also observed extending caudally beyond the implant in the main bronchus.

The total occlusion score (sum of the occlusion scores for each of the 5 regions assessed) for each implant type and implant location is shown at Days 28, 60, and 90 in Table 3-6. Maximum total score was 25.

TABLE 3-6

| Device | Location | N | Total Occlusion Score[1] mean ± SD (min-max) | | |
|---|---|---|---|---|---|
| | | | Day 28 | Day 60 | Day 90 |
| test implant | Trachea | 6 | 2.7 ± 1.5 (1-5) | 3.7 ± 1.4 (2-6) | 4.2 ± 1.6 (3-7) |
| control implant | Trachea | 6 | 3.7 ± 0.8 (3-5) | 4.0 ± 2.2 (0-6) | 5.5 ± 1.6 (3-7) |
| test implant | Left bronchus | 4 | 1.8 ± 0.5 (1-2) | 3.0 ± 1.4 (1-4) | 2.3 ± 1.0 (1-3) |
| control implant | Left bronchus | 4 | 1.3 ± 1.5 (0-3) | 7.3 ± 1.7 (5-9) | 8.0 ± 2.9 (4-11) |

In general, total stenosis score increased with time, with exception of the test implants implanted in the left bronchus, where average total occlusion score decreased from 3.0 at 60 days to 2.3 at 90 days. At all follow-up timepoints, the airways implanted with the test implant had a lower total occlusion score than with the control implant. A limited necropsy was performed on the tracheobronchial tree with implant in situ for all twenty study animals. No gross abnormalities were noted. Fluoroscopic imaging was performed for all animals immediately after implant. At Days 28 and 60, images were obtained in 8 of 20 animals and 19 of 20 animals respectively. The fluoroscopic images confirmed that the correct anatomic location of the implants at these time points.

Implant length, measured from the fluoroscopic images obtained at the time of implant and at Day 28 and Day 60 is summarized in Table 3-7.

TABLE 3-7

| Implant Type | Implant Location | Length (mm) Mean ± SD (min-max; N) | | |
|---|---|---|---|---|
| | | At Implant | Day 28 | Day 60 |
| test implant 9 × 60 mm | Trachea | 62.5 ± 3.7 (56.6-68.1; 6) | 73.9 ± 7.6 (64.7-83.2; 4) | 74.3 ± 5.9 (65.4-81.3; 6) |
| control implant 8 × 40 mm | Trachea | 58.1 ± 2.5 (54.6-62.1; 6) | 52.7 ± 2.1 (50.0-54.9; 4) | 57.1 ± 2.1 (53.6-59.0; 6) |
| test implant 7 × 23 mm | Left main bronchus | 25.5 ± 1.1 (24.0-26.5; 4) | — | 21.3 ± 2.4 (19.1-23.9; 3) |
| control implant 6 × 20 mm | Left main bronchus | 31.5 ± 0.6 (30.8-32.1; 4) | — | 25.2 ± 0.5 (24.5-25.7; 4) |

The length of the test implant at the time of implant was similar to its unconstrained length. For test implants implanted in the trachea, the implants tended to elongate with time and were on average 18.9% longer at Day 60 than at the time of implant, whereas the test implants implanted in the bronchus tended to shorten to a similar degree (16.5%). Upon implantation of the control implant, significant elongation of the implant by approximately 50% of its unconstrained length was observed. Between the time of implant and Day 60, the control implanted in the bronchus tended to shorten by 20.0% whereas the length of implants implanted in the trachea initially decreased on average by 9.2% between Day 0 and Day 28 and then returned to a length similar to Day 0 by Day 60.

Implant width, taken at the cranial and caudal ends, as measured from the fluoroscopic images obtained at the time of implant and at Day 28 and Day 60 are shown in Table 3-8.

TABLE 3-8

| Implant Type | Implant Location | Width (mm) mean ± SD (min-max; N) | | | | | |
|---|---|---|---|---|---|---|---|
| | | At Implant | | Day 28 | | Day 60 | |
| | | Cranial | Caudal | Cranial | Caudal | Cranial | Caudal |
| test implant 9 × 60 mm | Trachea | 7.4 ± 0.5 (6.7-7.9; 5) | 7.2 ± 0.9 (6.4-8.2; 5) | 8.4 ± 1.0 (7.2-9.6; 4) | 8.0 ± 0.8 (7.2-9.0; 4) | 8.1 ± 0.7 (7.4-9.4; 6) | 8.8 ± 0.5 (7.8-9.0; 6) |
| control implant 8 × 40 mm | Trachea | 7.5 ± 0.2 (7.2-7.7; 5) | 6.9 ± 0.3 (6.4-7.3; 5) | 7.9 ± 0.3 (7.6-8.2; 4) | 7.9 ± 0.5 (7.5-8.7; 4) | 8.4 ± 0.4 (8.0-8.9; 6) | 8.4 ± 0.2 (8.1-8.6; 6) |
| test implant 7 × 23 mm | Left main bronchus | 5.8 ± 0.6 (5.0-6.2; 4) | 5.2 ± 1.0 (4.1-6.1; 4) | — | — | 6.2 ± 1.1 (5.3-7.4; 3) | 6.0 ± 0.9 (5.2-7.0; 4) |
| control implant 6 × 20 mm | Left main bronchus | 5.0 ± 0.4 (4.4-5.4; 4) | 2.8 ± 0.4 (2.4-3.4; 4) | — | — | 6.5 ± 0.3 (6.2-6.9; 4) | 6.5 ± 0.3 (6.1-6.8; 4) |

On the day of implant, both test implant and control implants were narrower at the caudal end relative to the cranial end, with this difference being most pronounced for the implants in the left main bronchus. The width of the test implant tended to increase modestly over time, being on average 22.2% and 15.3% wider (at the caudal end) at Day 60 compared to Day 0 for implants in the trachea and bronchus respectively. Similarly, the width of the control implants also increased with time, with the most pronounced change occurring at the caudal end of the implant, increasing 132% at Day 60 compared to Day 0.

All 20 study animals recovered from the implantation procedure, and all survived to the Day 90 endpoint; no early deaths or euthanasia occurred during this study. The implants were generally well tolerated. The respiratory-related clinical signs for which a veterinary evaluation occurred ("fish-mouth breathing" and coughing/sneezing when stressed) were mild in nature and resolved without treatment. All 20 implants remained in correct position for the study duration. Fluoroscopic imaging at the follow-up intervals did indicate that modest changes in the geometry of the implant did occur with time. These included variable changes in implant length and implant diameter. None of these geometric changes led to any adverse clinical signs assessed during life or adverse effects as assessed by evaluation of gross pathology at the time of necropsy.

Airways implanted with the test implant and control implant each demonstrated variable amounts of bronchoscopically visible airway tissue responses consisting of mucous, fibrosis, and probable granuloma formation. These responses led to variable degrees of airway occlusion, referred to here-in as stenosis. The following observations were made contrasting the typical airway responses to the test implant and the control implant. First, airway tissue response to the test implant was milder than response to the control implant as demonstrated by lower stenosis scores at all timepoints. Second, stenosis was observed in airways with both implants by Day 30. For the test implant stenosis was stable thereafter, but for the control implant stenosis progressively worsened throughout the study. Third, tissue response to the test implant was limited to locations adjacent to the implant wire. Tissue response in airways implanted with the control implant was evident across the whole area of the device. Fourth, mucous was minimal in airways with the test implant and when present was localized adjacent to the implant's wire. Mucous was copious in airways with the control implant and observed across the whole area of the implant. Fifth, visible, patent airway branches in left lung bronchi implanted with the test implant were more numerous than for bronchi implanted with the control implant. This implies less side branch occlusion with the test implant than the control implant. Sixth, both the test implant and control implant progressively dilated the distal left lung bronchi from Day 0 and Day 30 such that it was possible to pass a 3.5 mm OD scope tip to the end of both implants on Day 30 when this was not possible post-implant on Day 0.

In conclusion, this study demonstrated that the test implant produced less tissue reaction than the control implant with less observed mucous and less overall stenosis. This observation tends to support the hypothesis that lesser tissue contact density implants produce less reaction than greater tissue contact density implants. Alternatively, relative contact force, in combination with contact density, may play a role in eliciting the observed tissue response.

With respect to the tracheal implants, the localization of the tissue reaction to discrete regions along the test implant wire, in contrast to the diffuse reaction to the control implant, suggests that controlling the density and geometry of device-tissue contact can control the overall intensity of tissue response. Providing specific pathways within the implant with no device-tissue contact could potentially improve overall implant patency.

Inflammation associated with the test implants in the area of implantation in the trachea ranged from no inflammation to marked, with an average score of 2.06, which is consistent with mild severity. Inflammation was most often directly associated with the implant profiles. The inflammation was primarily discrete granulomas immediately surrounding the implants within the submucosa, and those implants within the lumen/mucosa which had secondary ulceration and papillary mucosal hyperplasia. The two animals with the most prominent inflammatory reaction (E6065A and E84FF1) had a greater reaction to luminal/mucosal implant profiles, which may have been in response to ongoing irritation of the mucosa secondary to the implant. In addition, animal E6065A had translocation of the distal aspect of the implant into the connective tissue immediately adjacent to the trachea, with secondarily implanted mucosal epithelium. Animal E60168 contained some deep submucosal implant profiles at the mid to distal implantation site causing expansion of the submucosa, and mild distortion of the wall of the trachea. At the level of the distal implant, there was a small necrotic fragment of cartilage associated with deep submucosal implant profiles. The circumference of the trachea affected by inflammation in the area of implantation ranged from <5% to >76%, with an average score of 2.11, which is equivalent to 21-50%.

Inflammation associated with the control implants in the area of implantation in the trachea ranged from mild to marked, with an average score of 2.28, which is consistent with mild severity. Inflammation was most often directly associated with the implant profiles. The inflammation was primarily discrete granulomas immediately surrounding the implants within the submucosa, and those implants within the lumen/mucosa which had secondary ulceration and papillary mucosal hyperplasia. The degree of mucosal hyperplasia extending into the lumen was often increased in severity associated with the control implants (up to moderate) compared to the test implants (up to mild). Some of the deep submucosal implant profiles were associated with minimal to mild loss of superficial tracheal cartilage with mild fibroplasia. The circumference of the trachea affected by inflammation in the area of implantation ranged from 21-50% to >76%, with an average score of 3.27, which is equivalent to 51-75%.

Taken together, in animals with tracheal implants, both test implants and control implants induced a "mild" response. In contrast, test implants showed a trend affecting a lower percentage of the airway circumference when compared to control implants. These study findings supported the hypothesis that reducing the contact density of airway implants reduces the severity of the foreign body reaction to these implants.

The inflammatory reaction in all animals is consistent with a foreign body reaction to the implant and was localized to the site of contact with the wall of the trachea. Those areas of greater reaction were typically luminal/mucosal implant profiles, those very deep in the submucosa (particularly abutting and secondarily affecting the tracheal cartilage), and the rare instance of translocation of the implant into adjacent connective tissue (animal E60168). The test implants were of greater size compared with the control implants (both in length and diameter), and as such, the width diameter used may have been greater than required in some of the animals, leading to secondary translocation of the implant through the wall, and deeply located submucosal implants. Where ulceration and squamous metaplasia of the mucosal epithelium was identified, this was associated with luminal/mucosal implant profiles, and limited to the immediate site of the implants, with no evidence of extension beyond the area of contact with the tracheal wall. In all animals the inflammatory reaction was largely within normal limits at ½ cm cranial and caudal to the site of implantation.

With respect to the bronchial implants, inflammation associated with the test implants in the left bronchus ranged from minimal to moderate, with an average score of 2.08, which is consistent with mild severity. Inflammation was most often directly associated with the implant profiles. The inflammation was primarily discrete granulomas immediately surrounding the implants within the submucosa, and those implants within the lumen/mucosa which had secondary ulceration and papillary mucosal hyperplasia. Three animals exhibited translocation of a portion of the implant into adjacent connective tissue, or alveolar parenchyma (E5F90B, E606F8, and E60648), with discrete granuloma formation in these areas. Animal E606F8 exhibited greater inflammation associated with the implant, extending into adjacent bronchi and bronchioles, which was more than that identified in the untreated (right) bronchus. However, this animal also had a significant granulomatous bronchopneumonia, affecting the left cranial, right middle, and right caudal lung lobes, which was likely pre-existing, and may have contributed to an increased reaction in this animal to the implant. The circumference of the treated bronchus affected by inflammation in the area of implantation ranged from 5-20% to 51-75%, with an average score of 2.08, which is equivalent to 21-50%.

Inflammation associated with the control implants in the area of implantation in the left bronchi ranged from mild to marked, with an average score of 2.67, which is consistent with mild to moderate severity. Inflammation was most often directly associated with the implant profiles. The inflammation was primarily discrete granulomas immediately surrounding the implants within the submucosa, and those implants within the lumen/mucosa which had secondary ulceration and papillary mucosal hyperplasia. One animal (E5F9BE) exhibited significant translocation of part of the distal implant into the alveolar parenchyma (3405 microns from the mucosa of the treated bronchus). There are 13 implant profiles present in the parenchyma in this area. Two medium sized arteries in this area also exhibited acute luminal thrombi. Two other animals exhibited variable distortion of bronchial cartilage, most prominent in animal E5FD24, where there was significant thickening and distortion of the distal bronchus, with pushing of the bronchial cartilage peripherally. The circumference of the trachea affected by inflammation in the area of implantation ranged from 51-75% to >76%, with an average score of 3.58, which is equivalent to >51%.

In animals with bronchial implants, inflammation observed around test implants was significantly reduced when compared to control implants. In animals with control implants, 51-76% or higher percentage of the bronchial circumference was affected by inflammation. In contrast, only 21-50% of the bronchial circumference was affected by inflammation in animals with test implants. Overall, the difference in the foreign body reaction observed between test implants and control implants was more apparent in the bronchus as opposed to the trachea. This may be because of inherent differences in tissue properties, with the overall inflammation observed in the trachea being milder compared to the bronchus. These study findings further support the hypothesis that reducing the contact density of airway implants reduces the severity of the foreign body reaction to these implants.

The inflammatory reaction in all animals was consistent with a foreign body reaction to the implant, and was localized to the site of contact with the wall of the bronchus. Those areas of greater reaction were typically luminal/mucosal implant profiles, those very deep in the submucosa (particularly abutting and secondarily affecting the bronchial cartilage), and translocation of the implant into adjacent connective tissue or alveolar parenchyma (animals E5F90B, E606F8, E60648, and E5F9BE). Both types of implants had some animals with variable distortion of the bronchial cartilage or translocation of part of the implant into adjacent tissue, which suggests the size of the implants may be too large for the size of the bronchi in these animals. Although of note, the degree of distortion of the airways was typically greater with increased "in-contact tissue" with the implant, with these changes in the control implant being more severe than with the test implant. Where ulceration and squamous metaplasia of the mucosal epithelium were identified, this was associated with luminal/mucosal implant profiles, and limited to the immediate site of the implants, with no evidence of extension beyond the area of contact with the bronchial wall.

Table 3-9 is a summary of inflammation severity scores and circumference scores with average scores for bronchial test and bronchial control animals.

TABLE 3-9

| Implant Type | Animal ID | Inflammation Severity Score | | | Inflammation Circumference Score | | |
|---|---|---|---|---|---|---|---|
| | | Area of Implant | Entire Bronchus | Untreated Bronchus (Right) | Area of Implant | Entire Bronchus | Untreated Bronchus (Right) |
| Bronchial Test | E5F90B | 2.33 | 1.80 | 1.67 | 2.00 | 1.40 | 1.33 |
| | E5F7AA | 1.00 | 1.00 | 1.00 | 1.00 | 1.20 | 1.67 |
| | E606F8 | 2.67 | 2.20 | 1.00 | 3.00 | 2.60 | 0.33 |
| | E60648 | 2.33 | 2.00 | 2.00 | 2.33 | 2.40 | 3.33 |
| Average Score | | 2.08 | 1.75 | 1.42 | 2.08 | 1.90 | 1.67 |
| Bronchial control | E6042F | 3.67 | 2.80 | 0.67 | 4.00 | 3.20 | 0.33 |
| | E5F9BE | 2.33 | 2.00 | 0.67 | 3.33 | 2.80 | 0.67 |
| | E5FD24 | 2.00 | 1.60 | 0.33 | 3.00 | 2.20 | 0.33 |
| | E5F859 | 2.67 | 2.40 | 1.33 | 4.00 | 3.40 | 2.33 |
| Average Score | | 2.67 | 2.20 | 0.75 | 3.58 | 2.90 | 0.92 |

Table 3-10 is a summary of inflammation severity scores and inflammation circumference scores with average scores for tracheal test and tracheal control animals. In Table 3-10, circumference score for inflammation is not able to be accurately provided due to implant removal.

TABLE 3-10

| Implant Type | Animal ID | Inflammation Severity Score | | Inflammation Circumference Score | |
|---|---|---|---|---|---|
| | | Area of Implant | Entire Trachea | Area of Implant | Entire Trachea |
| Tracheal Test | E606FF | 1.00 | 1.00 | 0.67 | 0.40 |
| | E60168 | 2.00 | 1.60 | 1.67 | 1.00 |
| | E5F663 | 2.00 | 1.40 | 0.67 | 0.40 |
| | E6065A | 2.67 | 2.00 | 3.67 | 3.20 |
| | E84FF1 | 3.00 | 2.80 | 4.00 | 3.40 |
| | 0E8209 | 1.67 | 1.40 | 2.00 | 1.60 |
| Average Score | | 2.06 | 1.70 | 2.11 | 1.67 |
| Tracheal Control | E60880 | 3.00 | 2.20 | 3.67 | 3.20 |
| | E60188 | 2.00 | 1.60 | 2.67 | 1.60 |
| | E5F70D | 2.00 | 1.60 | 3.33 | 2.00 |
| | E84315 | 2.33 | 1.80 | 2.67 | 1.80 |
| | E5FF70 | 2.00 | 1.60 | NA* | NA* |
| | E5FA8E | 2.33 | 1.80 | 4.00 | 2.60 |
| Average Score | | 2.28 | 1.77 | 3.27 | 2.24 |

Table 3-11 is a summary of inflammation severity scores and inflammation circumference scores with average scores for untreated trachea sections from 2 bronchial animals.

TABLE 3-11

| Implant Type | Animal ID | Inflammation Severity Score | Inflammation Circumference Score |
|---|---|---|---|
| Untreated Trachea (Bronchial Implant Animals) | E5F7AA | 1.00 | 1.00 |
| | E5F90B | 1.00 | 2.00 |
| Average Score | | 1.00 | 1.50 |

Table 3-12 is a summary of animals e5f7aa and e5f90b histopathology results for normal trachea. For Animal ID E5F7AA comments were marked congestion of submucosa and minimal lymphoplasmacytic submucosal infiltrates. For Animal ID E5F90B comments were minimal multifocal submucosal lymphoplasmacytic and polymorphonuclear infiltrates and moderate submucosal edema.

Experimental Example 4: Canine Study

Enlarging and reinforcing with an implant at least one of the anatomic tracheal-bronchial pathways between confluent emphysematous lung parenchyma to large central airways is expected to facilitate expiration and help alleviate some of the adverse consequences of air trapping and dynamic hyperinflation. Implantation and dilation of stent-like structures in the intraparenchymal airways may lead to airway fenestration and bleeding, mucous impaction and potentially vigorous airway tissue reactions over time that may be characterized by the formation of significant foreign body reactions, granulation tissue, fibrosis and low-grade infection. These reactions tend to originate at or near the point of contact between the stent and airway tissue. It was hypothesized that the implantation/dilation in the intraparenchymal airways could be done safely and the amount of mucous accumulation and foreign body reaction could be controlled by minimizing the density of contact between the stent-like structure and airway, and the location controlled by adjusting the geometry of the contact points.

The objectives of this study were to: (1) assess safety of bronchial fenestration via over-dilation of airways, (2) assess if stents with smaller tissue contact density produce overall less total tissue reaction than those with a high tissue contact density, and (3) assess if controlling the geometry of contact can control the location of foreign body response. The bronchoscopic tissue assessment endpoints are presented in Table 4-1. The local tissue response to the test article study endpoints are presented in Table 4-2.

TABLE 4-1

| Assessment Method | Performed by | Description (example) | Success Criteria |
|---|---|---|---|
| Visual inspection of the airways | Study Surgeon(s) | Implant sites may be assessed for stenosis and/or mucous scores via bronchoscopic assessment and fluoroscopic imaging. | No Success Criteria is defined for this Endpoint |

TABLE 4-2

| Assessment Method | Performed by | Description (example) | Success Criteria |
|---|---|---|---|
| Bronchoscopic Tissue Assessment | Study Surgeon | Assess test article sites for stenosis and mucous scoring via bronchoscopy. | No Success Criteria is defined for this Endpoint. Results will be summarized. |

TABLE 3-12

| | Untreated Trachea (Bronchial Implant Animals) | | | Treated Airway | | | | | | | |
|---|---|---|---|---|---|---|---|---|---|---|---|
| Animal ID | Location | Slide ID | Site ID | Mucosa Intact (%) | Submucosal Thickness (microns) | Mucosal Thickness (microns) | Mucosal Squamous Metaplasia (absent/present) | Inflammation severity | Inflammation Type | Inflammation Circumference Affected | Granulation Tissue | Granuloma Formation (absent/present) |
| E5F7AA | Trachea | 6 | Normal (Untreated tissue) | 0 | 850 | 43 | A | 1 | LP | 1 | 0 | A |
| E5F90B | Trachea | 6 | Normal (Untreated tissue) | 0 | 650 | 39 | A | 1 | LP Po | 2 | 0 | A |

TABLE 4-2-continued

| Assessment Method | Performed by | Description (example) | Success Criteria |
|---|---|---|---|
| Gross Pathology | Trained Prosector | Assess test article treated tissues for abnormalities. | No clinically significant findings that are deemed related to the Test Article. |
| Histopathology via Light Microscopy (If requested to be performed) | Study Pathologist | Local tissue response to the test article will be assessed by the Study Pathologist | No Success Criteria is defined for this Endpoint. |

The test articles were three implants: (1) Epic stent, a self-expanding, uncovered wire mesh stent, (2) Express stent, a balloon expandable, uncovered wire mesh stent, and (3) test implant, an uncovered, low density, single-wire implant in accordance with at least some embodiments of the present technology. All test articles were ethylene oxide sterilized at the Test Facility prior to use. The test article usage is described in Table 4-3.

TABLE 4-3

| Test Article Name | Dimensions, mm (d × l) | # Implanted | Implant Dates | Animal IDs |
|---|---|---|---|---|
| Epic stent | 8 × 40 | 2 | 29 Sep. 2021 10 Nov. 2021 | 21C0264, 21C0248 |
| | 8 × 60 | 3 | 29 Sep. 2021 | 21C0245, 21C0264 21C0261 |
| | 10 × 40 | 3 | 10 Nov. 2021 | 21C0394, 21C0392 21C0268 |
| | 10 × 60 | 2 | 29 Sep. 2021 | 21C0248 |
| | DNR | 1 | 10 Nov. 2021 | 21C0284 |
| Express stent | 6 × 57 | 1 | 29 Sep. 2021 | 21C0261 |
| | 8 × 57 | 1 | 29 Sep. 2021 | 21C0245 |
| | 10 × 57 | 2 | 29 Sep. 2021 | 21C0245, 21C0261 |
| Test Implant (1.8) | | 6 | 10 Nov. 2021 | 21C0268, 21C0284 21C0392, 21C0394 |
| Test Implant (3.0) | | 6 | 10 Nov. 2021 | 21C0268, 21C0284 21C0392, 21C0394 |

A healthy canine model, mongrel breed, was selected for evaluation in this study. Seven (7) female and two (2) intact male canines were enrolled into this study. Canine airway anatomy closely resembles that of the human and is an established model for evaluation of the suitability of devices intended for human airway use. The overall study design and treatment groupings are shown in Table 4-4. The implant procedure dates of Group 01 and 02 were staggered by approximately 6 weeks to allow for feedback and learning from Group 01 to be applied to Group 02. The matrix of implants is provided in Table 4-5. The schedule of assessments and data recordings is shown in Table 4-6. Day 0 was defined as the date of initial implantation.

TABLE 4-4

| Group ID | Duration | Study Articles | # of Animals | # of Stents per Animal | Procedure Type(s) | Timing |
|---|---|---|---|---|---|---|
| 01 | 90 days | Test/Control Articles | 4 | 4 | Implant Follow-Up | Day 0 Day 30 ± 3 days Day 60 ± 7 days |
| | | | | | Termination | Day 90 ± 7 days |
| 02 | 90 days | Test/Control Articles | 4 | 4 | Implant Follow-Up | Day 0 Day 30 ± 3 days Day 60 ± 7 days |
| | | | | | Termination | Day 90 ± 7 days |

TABLE 4-5

| Animal | Implant 1 | Implant 2 | Implant 3 | Implant 4 |
|---|---|---|---|---|
| 01 | Express | Express + Dilation | Epic | Wall |
| 02 | Wall | Express | Express + Dilation | Epic + Dilation |
| 03 | Epic | Epic + Dilation | Express | Wall + Dilation |
| 04 | Epic + Dilation | Epic | Wall + Dilation | Express + Dilation |
| 05 | Epic | test implant+ (turn density: 3.0) | test implant+ (turn density: 1.8) | test implant+ (turn density: 3.0) |
| 06 | test implant+ (turn density: 1.8) | Epic | test implant+ (turn density: 3.0) | test implant+ (turn density: 1.8) |
| 07 | test implant+ (turn density: 3.0) | test implant+ (turn density: 1.8) | Epic | test implant+ (turn density: 3.0) |
| 08 | test implant+ (turn density: 1.8) | test implant+ (turn density: 3.0) | test implant+ (turn density: 1.8) | Epic |

TABLE 4-6

|  | Day 0 | Day 30 ± 3 | Day 60 ± 7 | Day 90 ± 7 |
|---|---|---|---|---|
| Implant Implantation | X | | | |
| Bronchoscopic Evaluation | X | X | X | X |
| Fluoroscopic Imaging | X | X | X | |
| CT imaging | X | X (opt) | X (opt) | X (opt) |
| Clinical Pathology (hematology, serum chemistry) | X | X | X | X |
| Euthanasia | | | | X |
| Gross Pathology | | | | X |
| Histopathology | | | | X <if done> |

The anesthetized canines were positioned in sternal recumbency. Isoflurane was used to maintain anesthesia during the entire procedure. Tracheal access was gained by passing an endotracheal tube through the mouth, oropharynx and ultimately the larynx and advancing the tip into the distal trachea. A flexible bronchoscope was passed through the endotracheal tube for visual inspection and documentation. The implant delivery system was inserted either directly through the bronchoscope or over a guidewire, and the implants deployed under direct bronchoscopic and/or fluoroscopic guidance. For self-expanding stents, a balloon was optionally passed (either through the scope or over the wire) to dilate the stent.

Each animal had four implantations performed at various locations throughout the tracheobronchial tree. Implantations consisted of the 4 implants placed in series along the bronchial tree extending from the lobar bronchus proximally to a bronchi ~1 cm from the visceral pleural surface. In stents with balloon inflation, the inflation was maintained for a minimum of 2 minutes. Following implantation, the delivery system was removed. Bronchoscopy was used to assess acute tissue reaction and bleeding. Fluoroscopy was performed to document implant position, length, and deployed diameter. Post-implantation CT scan was optionally performed to document implantation site and assess for intraparenchymal hemorrhage, pneumomediastinum and pneumothorax, following which the animals were transferred to post-operative recovery.

For bronchoscopic assessment, the anesthetized animal was positioned in sternal recumbency and tracheal access was gained via endotracheal tube inserted through the mouth. A flexible bronchoscope was passed through the endotracheal tube for visual assessment of the implant sites. A visual score from the bronchoscopic inspection of the airways of the animals was performed for five sections in each airway containing an implant: (1) tissue immediately cranial to the proximal end of the implant (cranial), (2) proximal end of the implant (proximal), (3) central part of the implant (central), (4) distal end of the implant (distal), and (5) tissue immediately caudal to the distal end of the implant (caudal).

Each of the five sections was scored as to the degree of stenosis (narrowing of the airway lumen for any reason, including encroachment by the implant itself, mucous, granulation tissue, or fibrosis) and mucous according to the following scales: Stenosis: 0: 0%; 1: 1-10%; 2: 10-25%; 3: 25-50%; 4: 50-75%; 5: 75-100%, and Mucous: 0: none, 1: minimal, 2: mild, 3: moderate, 4: severe, 5: copious.

Fluoroscopic imaging was performed in the anesthetized animal immediately after the bronchoscopic procedure described above. Anteroposterior fluoroscopic images of the region of the thorax containing the implant were recorded. CT imaging was performed in the anesthetized animal immediately after the fluoroscopic imaging. After completion of the follow procedures at Day 30 and 60, the animal was recovered and returned to housing. Blood collected at baseline, Day 30, Day 60, and Day 90 was analyzed for standard hematology (CBC) and serum chemistry. Animals were observed and clinical observations documented SID (once a day) until their termination day, and all medical treatments incurred throughout the life of the animals were recorded. Euthanasia was performed Day 90±7 immediately after the follow up procedures (bronchoscopy, fluoroscopy, CT imaging). Heparin was administered IV, followed by a lethal injection of euthanasia solution and potassium chloride. Death was verified by auscultation or pulse monitoring.

Trained staff performed a limited necropsy. A visual score from the inspection of the airways of the animals was performed for five sections in each airway containing an implant. The tracheobronchial tree was collected with a minimum of 1 cm of trachea/bronchi proximal and distal to the implants, anatomy permitting. The lung was inflated with 10% neutral buffered formalin (NBF) and then immersion fixed in 10% NBF for potential future analysis. The stenosis scores recorded during the bronchoscopy procedure for each of the 5 levels were summarized at Days 28, 60, and 90 for each implant type using descriptive statistics (mean, standard deviation, minimum, maximum). A total stenosis score, calculated as the sum of the stenosis scores at the 5 levels, was also summarized for each implant type. General trends related to other findings noted during the bronchoscopies were described. Abnormal findings documented at the time of necropsy were tabulated by frequency of occurrence for each study group. The stenosis scores assessed by the Study Surgeon at the time of necropsy were summarized for each study group using descriptive statistics (mean, standard deviation, minimum, maximum). Implant length, width at the cranial end of the implant, and width at the caudal end of the implant were obtained from the fluoroscopic image recordings. A fiducial marker of known length in the fluoroscope's field of view was used to calibrate the measurement. Changes in implant length and width between Day 0, 30, and 60 were summarized for each study group using descriptive statistics (mean, standard deviation, minimum, maximum).

All four study animals in Group 02 recovered from the implantation procedure and all survived to the Day 90 endpoint; no early deaths or euthanasia occurred during this study. Recovery from the implantation procedure and subsequent follow-up procedures requiring anesthesia were uneventful with clinical findings the day following the procedure (day 1) were consistent with post-op status (mild tachycardia n=2, mild inappetence n=2). Over the duration of the study, the implants were well tolerated. The mean (±SD) percentage change in body weight at 1, 2, and 3 months after the implantation procedure were −4.1±6.0%, 5.6±3.7%, and 8.6±5.8% respectively. No adverse respiratory-related clinical findings were noted. Only one observation was reported which prompted veterinary examination (focal dermatitis on the ventral sternum of animal 21C0394, treated with broad spectrum antibiotics and topical antibiotic/antifungal) which was not considered related to the test articles.

Scoring of luminal stenosis severity at the proximal, central, and distal regions of the implant as well as immediately cranial to the proximal end of the implant and caudal to the distal end of the implant is shown in Table 4-7 for the Day 30, 60, and 90 time points.

TABLE 4-7

| Device | N | Day Post-implant | Cranial | Proximal | Central | Distal | Caudal | Avg - in stent | Avg - all |
|---|---|---|---|---|---|---|---|---|---|
| Epic | 4 | 30 | 0.0 ± 0.0 | 0.8 ± 0.5 | 0.3 ± 0.5 | 0.3 ± 0.5 | 0.3 ± 0.5 | 0.4 ± 0.4 | 0.3 ± 0.3 |
|  |  | 60 | 0.0 ± 0.0 | 1.5 ± 0.6 | 1.0 ± 0.8 | 1.0 ± 0.8 | 1.3 ± 2.5 | 1.2 ± 0.6 | 1.0 ± 0.4 |
|  |  | 90 | 0.0 ± 0.0 | 2.0 ± 0.8 | 0.8 ± 0.5 | 0.5 ± 0.6 | 0.0 ± 0.0 | 1.1 ± 0.6 | 0.7 ± 0.3 |
| Test Implant (1.8 turn density) | 6 | 30 | 0.0 ± 0.0 | 1.2 ± 0.8 | 0.2 ± 0.4 | 0.0 ± 0.0 | 0.0 ± 0.0 | 0.4 ± 0.2 | 0.3 ± 0.1 |
|  |  | 60 | 0.0 ± 0.0 | 1.2 ± 0.8 | 0.0 ± 0.0 | 0.0 ± 0.0 | 0.0 ± 0.0 | 0.4 ± 0.3 | 0.2 ± 0.2 |
|  |  | 90 | 0.0 ± 0.0 | 1.2 ± 1.0 | 0.0 ± 0.0 | 0.0 ± 0.0 | 0.0 ± 0.0 | 0.4 ± 0.3 | 0.2 ± 0.2 |
| Test Implant (3.0 turn density) | 6 | 30 | 0.0 ± 0.0 | 1.0 ± 0.6 | 0.2 ± 0.4 | 0.0 ± 0.0 | 0.0 ± 0.0 | 0.4 ± 0.3 | 0.2 ± 0.2 |
|  |  | 60 | 0.0 ± 0.0 | 1.7 ± 1.2 | 0.3 ± 0.5 | 0.0 ± 0.0 | 0.0 ± 0.0 | 0.7 ± 0.4 | 0.4 ± 0.2 |
|  |  | 90 | 0.0 ± 0.0 | 1.3 ± 0.5 | 0.2 ± 0.4 | 0.0 ± 0.0 | 0.0 ± 0.0 | 0.5 ± 0.2 | 0.3 ± 0.1 |

Scoring of mucous severity at the proximal, central, and distal regions of the implant as well as immediately cranial to the proximal end of the implant and caudal to the distal end of the implant is shown in Table 4-8 for the Day 30, 60, and 90 time points.

TABLE 4-8

| Device | N | Day Post-implant | Cranial | Proximal | Central | Distal | Caudal | Avg - in stent | Avg - all |
|---|---|---|---|---|---|---|---|---|---|
| Epic | 4 | 30 | 0.5 ± 1.0 | 1.3 ± 1.0 | 1.0 ± 0.8 | 1.0 ± 0.8 | 0.5 ± 1.0 | 1.1 ± 0.8 | 0.9 ± 0.8 |
|  |  | 60 | 0.0 ± 0.0 | 1.8 ± 1.0 | 1.8 ± 1.0 | 1.8 ± 1.0 | 1.0 ± 2.0 | 1.8 ± 1.0 | 1.3 ± 0.5 |
|  |  | 90 | 0.0 ± 0.0 | 1.3 ± 0.5 | 1.3 ± 0.5 | 1.3 ± 1.0 | 0.0 ± 0.0 | 1.3 ± 0.6 | 0.8 ± 0.3 |
| Test Implant (1.8 turn density) | 6 | 30 | 0.0 ± 0.0 | 0.0 ± 0.0 | 0.0 ± 0.0 | 0.0 ± 0.0 | 0.0 ± 0.0 | 0.0 ± 0.0 | 0.0 ± 0.0 |
|  |  | 60 | 0.0 ± 0.0 | 0.5 ± 0.5 | 0.2 ± 0.4 | 0.0 ± 0.0 | 0.0 ± 0.0 | 0.2 ± 0.3 | 0.1 ± 0.2 |
|  |  | 90 | 0.0 ± 0.0 | 0.5 ± 0.5 | 0.2 ± 0.4 | 0.0 ± 0.0 | 0.0 ± 0.0 | 0.2 ± 0.3 | 0.1 ± 0.2 |
| Test Implant (3.0 turn density) | 6 | 30 | 0.0 ± 0.0 | 0.5 ± 0.5 | 0.0 ± 0.0 | 0.0 ± 0.0 | 0.0 ± 0.0 | 0.2 ± 0.2 | 0.1 ± 0.1 |
|  |  | 60 | 0.0 ± 0.0 | 0.7 ± 1.2 | 0.2 ± 0.4 | 0.0 ± 0.0 | 0.0 ± 0.0 | 0.3 ± 0.4 | 0.2 ± 0.3 |
|  |  | 90 | 0.0 ± 0.0 | 0.7 ± 0.8 | 0.0 ± 0.0 | 0.0 ± 0.0 | 0.0 ± 0.0 | 0.2 ± 0.3 | 0.1 ± 0.2 |

Experimental Example 5: Radial and Axial Strength of Different Implant Types

In this experiment axial tensile and compressive spring rates and radial compression were compared for an off-the-shelf EPIC™ stent by Boston Scientific ("control implant") and an implant in accordance with at least some embodiments of the present technology ("test implant"). The control implant is a self-expanding nitinol hypotube heat treated to a final outer diameter of 10 mm and is intended for biliary or peripheral vascular use. The particular control implant used in the experiment had a nominal length of 60 mm and a measured length of 62 mm. The test implant was a self-expanding nitinol wire form heat treated to a final outer diameter of 10 mm. The test implant was similar to the implant 5600 shown in FIG. 56A. It had a nominal length of 60 mm and a measured length of 61 mm.

A first test performed on the test implant and the control implant was a 3-point bend test. The proximal ends of each implant were supported to suspend the implant horizontally while weight was applied to a center of the implant until the center of deflected downward 0.25 inches. In this test, the control implant reached the limit at 115 grams whereas the test implant reached the limit at 3 grams. This result indicates that the test implant is significantly less resistant to bending than the control implant. In a second test, each implant was compressed perpendicular to its length between two blocks until the diameter of the implant reduced by 0.25". In this test, the control implant reached the limit at 929 grams or 143,520 dyne/cm whereas the test implant reached the limit at 722 grams or 111,540 dyne/cm. This result indicates that the test implant and the control implant have similar resistance to radial compression. In a third test, each implant was compressed axially (i.e., parallel to its length) until the length of the implant reduced by 0.25". In this test, the control implant reached the limit at 67 grams or 10,351 dyne/cm whereas the test implant reached the limit at 2 grams or 309 dyne/cm. This result indicates that the test implant is significantly less resistant to axial compression than the control implant. The control implant axial compression spring rate based on this result was more than 30 times higher than that of the test implant. In a fourth test, each implant was stretched axially (i.e., parallel to its length) until the length of the implant increased by 0.25". In this test, the control implant reached the limit at 64 grams or 9,887 dyne/cm whereas the test implant reached the limit at 2 grams or 309 dyne/cm. This result indicates that the test implant is significantly less resistant to axial stretching than the control implant. The control implant axial tensile spring rate based on this result was more than 30 times higher than that of the test implant.

The data gathered in this experiment showed that the test implant and the control implant had similar radial strength whereas the test implant was far more flexible in axial compression, tensile stretching, and bending than the control implant. The control implant in this study is the same control implant used in the canine study discussed above. In that study, the control implant was found to cause significantly more granulation tissue growth than the test implant. The observed similarity in radial strength and difference in axial compression, tensile stretching, and bending supports the hypothesis that the ability of the test implant to move with lung tissue rather than resist this movement reduces the formation of granulation tissue and contributes to the ability of the test implant to maintain airway patency long term.

CONCLUSION

This disclosure is not intended to be exhaustive or to limit the present technology to the precise forms disclosed herein. Although specific embodiments are disclosed herein for illustrative purposes, various modifications are possible without deviating from the present technology, as those of ordinary skill in the relevant art will recognize. In some cases, well-known structures and functions have not been shown or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may be disclosed herein in the context of those embodiments, other embodiments may also exhibit such advantages, and not all embodiments need necessarily exhibit such advantages or other advantages disclosed herein to fall within the scope of the present technology. This disclosure and the associated technology can encompass other embodiments not expressly shown or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising," "including," and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various structures. It should be understood that such terms do not denote absolute orientation. The word "diameter" as used herein does not require that the corresponding structure be circular. When used in the context of one or more structures arranged in a noncircular configuration, the word "diameter" means a maximum distance the structure or structures define in a given plane perpendicular to a longitudinal dimension. Similarly, the word "helix" as used herein does not require that the corresponding structure be a geometrically precise helix, but rather than the structure resembles a helix or that a person of ordinary skill in the art would otherwise recognize the structure to have helical characteristics. The word "wire" encompasses any suitable wire-like elongate structure, including structures made by shaping processes (e.g., drawing, casting, and extruding), additive processes (e.g., 3D printing), and subtractive processes (e.g., cutting from a workpiece). Furthermore, these structures can be of any suitable cross-sectional shape (not just round).

Reference herein to "one embodiment," "an embodiment," or similar phrases means that a particular feature, structure, operation, or characteristic described in connection with such phrases can be included in at least one embodiment of the present technology. Thus, such phrases as used herein are not necessarily all referring to the same embodiment. As used herein, the terms "generally," "substantially," "about," and similar terms are terms of approximation and not terms of degree. These terms are intended to account for the inherent variations in measured or calculated values that would be recognized by those of ordinary skill in the art. The word "inventors" as used herein refers to at least one inventor. Unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Finally, it should be noted that various particular features, structures, operations, and characteristics of the embodiments described herein may be combined in any suitable manner in additional embodiments in accordance with the present technology.

We claim:

1. An implant configured to be deployed at a treatment location in a bronchial airway of a human subject, the implant comprising:
    a proximal portion and a distal portion spaced apart from the proximal portion along a longitudinal axis of the implant, wherein the proximal portion is configured to be positioned in a proximal region of the bronchial airway and the distal portion is configured to be positioned in a distal region of the bronchial airway, the distal region comprising a greater generation than the proximal region; and
    a single wire extending along a continuous helical wire path and having an untethered proximal terminus at an end of the proximal portion and an untethered distal terminus at an end of the distal portion,
    wherein the wire path comprises a series of contiguous turns, each turn comprising first and second legs alternatingly disposed along the wire path with the first legs extending distally and the second legs pointing proximally, wherein at least one first leg and at least one second leg meet at an apex portion that points in a longitudinal direction along the longitudinal axis,
    wherein the implant comprises a continuous opening extending between the turns of the wire path from the end of the proximal portion to the end of the distal portion, and
    wherein the implant is configured to resiliently transition from a low-profile delivery state to an expanded unconstrained state, wherein the implant has a first average diameter in the low-profile delivery state and a second average diameter in the expanded unconstrained state, the second average diameter being at least three times larger than the first average diameter.

2. The implant of claim 1, wherein the wire is untethered along the wire path.

3. The implant of claim 1, wherein an average length of the first legs is different than an average length of the second legs.

4. The implant of claim 1, wherein the second average diameter is at least four times larger than the first average diameter.

5. The implant of claim 1, wherein the implant has a substantially constant diameter between the distal and proximal portions when in the expanded unconstrained state.

6. The implant of claim 1, wherein the distal portion has a third average diameter in the expanded unconstrained state and the proximal portion has a fourth average diameter in the expanded unconstrained state, wherein the implant is configured such that a ratio of the third average diameter to an average native diameter of the distal region of the bronchial airway is greater than a ratio of the fourth average diameter to an average native diameter of the proximal region of the bronchial airway.

7. The implant of claim 1, wherein the distal portion has a third average diameter in the expanded unconstrained state and the proximal portion has a fourth average diameter in the expanded unconstrained state, wherein the third average diameter is no more than about 5% different than the fourth average diameter.

8. The implant of claim 1, wherein each of the proximal and distal terminuses comprises an atraumatic element.

9. The implant of claim 1, wherein the wire path comprises a turn density of at least three turns per inch along the longitudinal axis of the implant.

10. The implant of claim 1, wherein the wire comprises first and second apex portions alternatingly disposed along the wire path, the first and second apex portions comprising the apex portion that points in the longitudinal direction, wherein the first apex portions point distally and the second apex portions point proximally.

11. The implant of claim 10, wherein the wire path comprises at least three turns, and wherein both when the implant is in the low-profile delivery state and the expanded unconstrained state, the first apex portions of the at least three turns are within 5 degrees of circumferential alignment with one another and the second apex portions of the at least three turns are within 5 degrees of circumferential alignment with one another.

12. The implant of claim 10, wherein:
the first apex portions define a first helix;
the second apex portions define a second helix; and
the implant comprises a helical band defined between the first and second helixes, wherein successive turns of the helical band are spaced apart along the longitudinal axis of the implant when the implant is in the expanded unconstrained state.

13. The implant of claim 12, wherein the wire occupies between about 5% and about 30% of a total area of the helical band when the implant is in the expanded unconstrained state.

14. The implant of claim 10, wherein the first and second apex portions comprise a structural coupling and wherein the structural coupling consists of the single wire.

15. The implant of claim 1, wherein the continuous opening forms a mucociliary clearance region having an average width at least 10 times greater than an average cross-sectional diameter of the wire, wherein the average width is measured parallel to the longitudinal axis of the implant.

16. The implant of claim 1, wherein an average pitch of the wire path when the implant is in the expanded unconstrained state is between about 50% and about 110% of an average diameter of the implant when the implant is in the expanded unconstrained state.

17. The implant of claim 1, wherein a ratio of a radial spring constant of the implant to a longitudinal spring constant is between about 10:1 to about 80:1.

18. The implant of claim 1, wherein a ratio of a radial spring constant of the implant in Newton-meters to a longitudinal shear modulus of the implant in Pascals is between about 0.005 and about 0.100.

19. The implant of claim 1, wherein a ratio of a longitudinal spring constant of the implant in Newton-meters to a longitudinal shear modulus of the implant in Pascals is between about 0.5 and about 5.0.

20. An implant configured to be deployed at a treatment location in a bronchial airway of a human subject, the implant comprising:
a proximal portion and a distal portion spaced apart from the proximal portion along a longitudinal axis of the implant, wherein the proximal portion is configured to be positioned in a proximal region of the bronchial airway and the distal portion is configured to be positioned in a distal region of the bronchial airway, the distal region comprising a greater generation than the proximal region; and
a single wire extending along a continuous helical wire path and having an untethered proximal terminus at an end of the proximal portion and an untethered distal terminus at an end of the distal portion,
wherein the wire path comprises a series of contiguous turns, each turn comprising first and second legs alternatingly disposed along the wire path with the first legs extending distally and the second legs pointing proximally, wherein at least one first leg and at least one second leg meet at an apex portion that points in a longitudinal direction along the longitudinal axis,
wherein the implant is configured to resiliently transition from a low-profile delivery state to an expanded unconstrained state, wherein the implant has a first average diameter in the low-profile delivery state and a second average diameter in the expanded unconstrained state, the second average diameter being at least three times larger than the first average diameter, and
wherein a ratio of the second average diameter to a length of the implant between the proximal terminus and the distal terminus is between about 1:5 and about 1:30.

21. The implant of claim 20, wherein an average length of the first legs is different than an average length of the second legs.

22. The implant of claim 20, wherein the implant has a substantially constant diameter between the distal and proximal portions when in the expanded unconstrained state.

23. The implant of claim 20, wherein the distal portion has a third average diameter in the expanded unconstrained state and the proximal portion has a fourth average diameter in the expanded unconstrained state, wherein the implant is configured such that a ratio of the third average diameter to an average native diameter of the distal region of the bronchial airway is greater than a ratio of the fourth average diameter to an average native diameter of the proximal region of the bronchial airway.

24. The implant of claim 20, wherein the wire comprises first and second apex portions alternatingly disposed along the wire path, wherein the first apex portions point distally and the second apex portions point proximally, and wherein:
the first apex portions define a first helix;
the second apex portions define a second helix; and
the implant comprises a helical band defined between the first and second helixes, wherein successive turns of the helical band are spaced apart along the longitudinal axis of the implant when the implant is in the expanded unconstrained state.

25. The implant of claim 24, wherein the wire occupies between about 5% and about 30% of a total area of the helical band when the implant is in the expanded unconstrained state.

26. The implant of claim 20, wherein the implant comprises a continuous opening extending between the turns of the wire path and forming a mucociliary clearance region having an average width at least 10 times greater than an average cross-sectional diameter of the wire, wherein the average width is measured parallel to the longitudinal axis of the implant.

27. The implant of claim 20, wherein an average pitch of the wire path when the implant is in the expanded unconstrained state is between about 50% and about 110% of an average diameter of the implant when the implant is in the expanded unconstrained state.

28. The implant of claim 20, wherein a ratio of a radial spring constant of the implant to a longitudinal spring constant is between about 10:1 to about 80:1.

29. The implant of claim 20, wherein a ratio of a radial spring constant of the implant in Newton-meters to a longitudinal shear modulus of the implant in Pascals is between about 0.005 and about 0.100.

30. The implant of claim 20, wherein a ratio of a longitudinal spring constant of the implant in Newton-meters to a longitudinal shear modulus of the implant in Pascals is between about 0.5 and about 5.0.

\* \* \* \* \*

UNITED STATES PATENT AND TRADEMARK OFFICE
CERTIFICATE OF CORRECTION

| | | |
|---|---|---|
| PATENT NO. | : 12,285,345 B2 | Page 1 of 1 |
| APPLICATION NO. | : 18/544215 | |
| DATED | : April 29, 2025 | |
| INVENTOR(S) | : Mayse et al. | |

It is certified that error appears in the above-identified patent and that said Letters Patent is hereby corrected as shown below:

On the Title Page

On Page 2, item (57), in Column 1, in "ABSTRACT", Line 9, delete "while the in" and insert -- while the implant is --, therefor.

Signed and Sealed this
Twenty-seventh Day of January, 2026

John A. Squires
*Director of the United States Patent and Trademark Office*